(12) United States Patent
Khuri-Yakub et al.

(10) Patent No.: US 12,353,531 B2
(45) Date of Patent: Jul. 8, 2025

(54) SYSTEM WITH ULTRASOUND SENSOR

(71) Applicant: Orchid Sound Technologies, LLC, Stamford, CT (US)

(72) Inventors: Butrus T. Khuri-Yakub, Palo Alto, CA (US); Gerard Touma, Sunnyvale, CA (US); Arif Sanli Ergun, Sunnyvale, CA (US); George Quintin Stedman, Mountain View, CA (US); Morten F. Rasmussen, San Francisco, CA (US); Chunfu Lin, Redwood City, CA (US); Paul Khuri-Yakub, Palo Alto, CA (US); Priscilla Marie Babb, Walnut, CA (US); Andre T. Khoury-Yacoub, Purchase, NY (US); John N. Irwin, III, Greenwich, CT (US); R. Maxwell Flaherty, Topsfield, MA (US); J. Christopher Flaherty, Nottingham, NH (US)

(73) Assignee: Orchid Sound Technologies, LLC, Stamford, CT (US)

( * ) Notice: Subject to any disclaimer, the term of this patent is extended or adjusted under 35 U.S.C. 154(b) by 149 days.

(21) Appl. No.: 18/272,965

(22) PCT Filed: Jan. 21, 2022

(86) PCT No.: PCT/US2022/013299
§ 371 (c)(1),
(2) Date: Jul. 18, 2023

(87) PCT Pub. No.: WO2022/159692
PCT Pub. Date: Jul. 28, 2022

(65) Prior Publication Data
US 2024/0346120 A1    Oct. 17, 2024

Related U.S. Application Data

(60) Provisional application No. 63/242,657, filed on Sep. 10, 2021, provisional application No. 63/186,567, (Continued)

(51) Int. Cl.
*G06F 15/16* (2006.01)
*G06F 9/54* (2006.01)
(Continued)

(52) U.S. Cl.
CPC ............ *G06F 21/32* (2013.01); *A61B 5/1172* (2013.01); *A61B 5/14552* (2013.01); *G06V 40/1306* (2022.01); *G06V 40/1365* (2022.01)

(58) Field of Classification Search
CPC ... G06F 21/32; A61B 5/1172; A61B 5/14552; G06V 40/1306; G06V 40/1365
(Continued)

(56) References Cited

U.S. PATENT DOCUMENTS 7,597,250 B2   10/2009  Finn
8,724,859 B2   5/2014   Schneider et al.
(Continued)

FOREIGN PATENT DOCUMENTS

WO   WO-2017132517 A1 *  8/2017  ............... A61B 8/14
WO   2020082164           4/2020
WO   2024191896           9/2024

OTHER PUBLICATIONS

International Preliminary Report on Patentability dated Aug. 3, 2023 issued in International Application No. PCT/US22/13299.
(Continued)

*Primary Examiner* — Hamza N Algibhah
(74) *Attorney, Agent, or Firm* — Onello & Mello, PC

(57) ABSTRACT

A user classification system is provided. The system includes a sensor for producing a sensor signal and a user
(Continued)

device. The system classifies a user of the system based on the sensor signal.

26 Claims, 48 Drawing Sheets

Related U.S. Application Data filed on May 10, 2021, provisional application No. 63/174,516, filed on Apr. 13, 2021, provisional application No. 63/140,647, filed on Jan. 22, 2021.

(51) Int. Cl.
*G06F 21/32* (2013.01)
*H04L 29/06* (2006.01)
*A61B 5/1172* (2016.01)
*A61B 5/1455* (2006.01)
*G06V 40/12* (2022.01)
*G06V 40/13* (2022.01)

(58) Field of Classification Search
USPC .......................................................... 726/18
See application file for complete search history.

(56) References Cited

U.S. PATENT DOCUMENTS

| | | | |
|---|---|---|---|
| 9,396,402 B2 | 7/2016 | Vardy | |
| 9,424,456 B1 | 8/2016 | Kamath Koteshwara et al. | |
| 9,453,822 B2 | 9/2016 | Schneider et al. | |
| 9,509,690 B2 | 11/2016 | Carter et al. | |
| 9,922,235 B2 | 3/2018 | Cho et al. | |
| 10,095,907 B2 | 10/2018 | Hinger | |
| 10,670,716 B2 * | 6/2020 | Apte | G01S 15/06 |
| 10,693,872 B1 | 6/2020 | Larson et al. | |
| 10,712,444 B1 * | 7/2020 | Kline | G01S 15/66 |
| 11,209,961 B2 | 12/2021 | Pope et al. | |
| 11,216,632 B2 * | 1/2022 | Chau | G06V 40/1306 |
| 11,243,300 B2 * | 2/2022 | Jennings | G06V 40/1306 |
| 11,328,165 B2 * | 5/2022 | Hall | G06F 21/32 |
| 11,392,789 B2 * | 7/2022 | Hall | G06F 21/32 |
| 11,460,957 B2 * | 10/2022 | Jennings | G06V 40/1306 |
| 11,526,018 B2 * | 12/2022 | Senkal | G01S 15/8915 |
| 11,719,671 B2 * | 8/2023 | Akhbari | G06F 3/043 |
| | | | 73/627 |
| 12,197,681 B2 * | 1/2025 | Baldasarre | H10N 30/87 |
| 2005/0163353 A1 | 7/2005 | Schneider et al. | |
| 2006/0219776 A1 | 10/2006 | Finn | |
| 2014/0090473 A1 | 4/2014 | Schneider et al. | |
| 2015/0135108 A1 | 5/2015 | Pope et al. | |
| 2015/0269452 A1 | 9/2015 | Vardy | |
| 2016/0224823 A1 | 8/2016 | Cho et al. | |
| 2016/0269402 A1 | 9/2016 | Carter et al. | |
| 2018/0046836 A1 | 2/2018 | Hinger | |
| 2020/0124412 A1 * | 4/2020 | Tamura | G01B 17/02 |
| 2021/0367004 A1 * | 11/2021 | Gao | H10K 59/40 |
| 2022/0178882 A1 * | 6/2022 | Bruch | G06F 3/14 |
| 2022/0342061 A1 * | 10/2022 | Pampus | G01S 15/10 |
| 2023/0350999 A1 * | 11/2023 | Irwin, III | H04W 12/55 |

OTHER PUBLICATIONS

International Search Report and Written Opinion dated Jun. 10, 2022 issued in International Application No. PCT/US22/13299.
International Search Report and Written Opinion dated Jul. 9, 2024 issued in International Application No. PCT/US2024/019359.

\* cited by examiner

SYSTEM WITH ULTRASOUND SENSOR

RELATED APPLICATIONS

This application claims priority to: U.S. Provisional Patent Application Ser. No. 63/140,647, titled "Ultrasound Signal-Processing System and Associated Methods", filed Jan. 22, 2021; U.S. Provisional Patent Application Ser. No. 63/174,516, titled "Multi-Platen Ultrasound Fingerprint Sensors and Associated Methods", filed Apr. 13, 2021; U.S. Provisional Patent Application Ser. No. 63/189,567, titled "System Including User Classification", filed May 17, 2021; and U.S. Provisional Patent Application Ser. No. 63/242,657, titled "System Including User Classification", filed Sep. 10, 2021; the content of each of which is incorporated herein by reference in its entirety for all purposes.

TECHNICAL FIELD

The embodiments disclosed herein relate generally to systems which include one or more ultrasound sensors, such as to receive commands from a user or identify or assess a condition of a user.

BACKGROUND

Numerous commercial devices include a sensor for collecting user information. These systems can include a user identification function, such as a function that identifies a user via fingerprint or face recognition. There is a need for improved systems, devices, and methods for classifying a user of the system.

BRIEF SUMMARY

According to an aspect of the present inventive concepts, a user classification system comprises a sensor configured to produce a sensor signal and a user device. The system can be configured to classify a user of the system based on the sensor signal.

In some embodiments, the user comprises a single user.

In some embodiments, the user comprises multiple users.

In some embodiments, classifying the user comprises determining and/or confirming an identity of the user. The system can determine and/or confirm the identity of the user via at least one of: user fingerprint data; an image of the user's face; a recording of the user's voice, and/or recorded physiologic data of the user.

In some embodiments, classifying the user comprises identifying and/or confirming a health condition of the user. The system can characterize the health condition of the user via at least one of: fingerprint data; facial image data; voice recording data; and/or physiologic data. The system can characterize the health condition of the user via physiologic data collected by the sensor and selected from the group consisting of: pulse oximetry data; blood glucose data; EEG; LFP; neuronal firing patterns and/or other brain data; heart rate data; respiration data; perspiration data; blood gas data; and combinations thereof.

In some embodiments, the system is configured to perform a calibration routine. The calibration routine can be configured to calibrate the sensor. The calibration routine can be performed after a portion of the system has been damaged and/or is otherwise functioning improperly. The calibration routine can be performed to accommodate a cracked screen of the user device and allow for successful identification of the user. The calibration routine can comprise at least two calibration routines. The calibration routine can comprise a first calibration routine that can be performed to modify the user device and a second calibration routine that can be subsequently performed. The calibration routine can be performed multiple times during use of the user device. The calibration routine can be configured to confirm the user has not changed. The calibration routine can be configured to confirm the user's health condition has not changed. The calibration routine can be configured to prevent one or more of: switching of users; prolonged use by a single user; and/or use by a user whose health condition has become unacceptable.

In some embodiments, the system is configured to perform a confirmation routine. The confirmation routine can be performed to confirm multiple fingerprints of a user. The multiple fingerprints can be collected according to a pre-assigned collection sequence. The system can provide feedback to the user as to which fingerprint is to be collected next.

In some embodiments, the sensor comprises one or more sensors positioned in and/or on another component of the system. The sensor can comprise one or more sensors positioned in and/or on the user device.

In some embodiments, the sensor comprises one, two, or more sensors selected from the group consisting of: ultrasound-based sensor; capacitive touch sensor; optical sensor; electrical sensor; magnetic sensor; force sensor; pressure sensor; strain gauge; physiologic sensor; a microphone, such as a microphone for recording the voice of a user; a camera, such as a camera for recording the face of a user; and combinations thereof.

In some embodiments, the system further comprises an interface for providing drive signals to the sensor and/or for receiving the sensors signals from the sensor.

In some embodiments, the sensor comprises one or more sensors integral to one or more other components of the system. At least one sensor can be integral to the user device. The system can further comprise a fob, and at least one sensor can be integral to the fob. The system can further comprise an accessory device, and at least one sensor can be integral to the accessory device.

In some embodiments, the sensor comprises two or more sensors. Multiple sensors can comprise similar sensors. Multiple sensors can comprise dissimilar sensors.

In some embodiments, the sensor comprises an ultrasound-based sensor. The sensor can comprise an array including one, two, or more ultrasound transducers configured to transmit and/or receive ultrasound energy.

In some embodiments, the sensor is configured to function when operating in wet and/or submersed in fluid conditions. The sensor can be configured to have improved performance when operating in wet and/or submersed conditions. The sensor can comprise a mass-loaded ultrasound transducer, such as a Langevin transducer.

In some embodiments, the sensor comprises an array including an arrangement of row electrodes and column electrodes. The row and column electrodes can comprise two sets of conductors. The two sets of conductors can be arranged orthogonal to each other. The two sets of conductors can be aligned at an angle of less than 90°, an angle of no more than 89°, and/or an angle of at least 45°. At least one of the row and/or column electrodes can comprise a non-uniform width. The non-uniform width can be configured to allow light to pass through the arrangement of row and column electrodes. The row and column electrodes can comprise two sets of conductors, and the conductors can comprise a thickness configured to achieve a resistance comparable to electrodes comprising a uniform width.

In some embodiments, the sensor is configured to provide a minimum resolution of the user's fingerprint. The minimum resolution can comprise at least 100 pixels per inch, at least 200 pixels per inch, at least 350 pixels per inch, at least 500 pixels per inch, and/or at least 1000 pixels per inch. The minimum resolution can comprise a resolution of at least 200 µm, such as a resolution of at least 100 µm, 75 µm, 50 µm, 25 µm, and/or 10 µm. The sensor can be configured to capture a minimum number of pixels of the fingerprint. The minimum number of pixels can comprise at least 15,000 pixels, at least 25,000 pixels, at least 35,000 pixels, at least 50,000 pixels, and/or at least 100,000 pixels.

In some embodiments, the sensor comprises a touch sensor configured to detect a tap and/or other touch of a user.

In some embodiments, the sensor comprises a light sensor configured to assess the aliveness of the user and/or assess another physiologic parameter of the user.

In some embodiments, the sensor is configured to provide thermal and/or mechanical feedback to the user. The system can further comprise a user device including a user interface, and the user device can be configured to operate in a dark mode and provide communication to the user via the feedback. The system can comprise a battery and/or other energy source, and the form and/or level of feedback can be based on an amount of energy remaining in the battery and/or other energy source. The system can be configured to provide the thermal feedback by increasing tissue temperature of the user by at least 0.2° C., at least 0.5° C., and/or at least 1.0° C. The increase in user tissue temperature can be no more than 4° C., no more than 10° C., no more than 20° C., and/or no more than 30° C. The system can be configured to operate in a no-look mode and provide communication to the user via the feedback without requiring visual attention of the user. The feedback can comprise thermal, mechanical, and/or other haptic feedback.

In some embodiments, the user device comprises a housing, and the sensor is integrated into the housing of the user device. The sensor can be configured to produce and/or receive sound waves, and the sound waves produced by and/or received by the sensor travels through at least a portion of the housing of the user device.

In some embodiments, the sensor comprises a fingerprint sensor and a pulse oximetry sensor. The sensor can further comprise a collimator comprising light-absorbing material configured to absorb light at the frequency range of the pulse oximetry sensor, and the collimator can be positioned between the fingerprint sensor and a pulse oximetry sensor to reduce clutter signals in recordings produced by the pulse oximetry sensor. The collimator can comprise height and width ratios configured to provide optimal transmit and acceptance angles.

In some embodiments, the sensor comprises a focusing lens.

In some embodiments, the sensor comprises multiple electronic attachment points. The sensor can comprise at least 100 electronic attachment points, at least 200 electronic attachment points, or at least 300 electronic attachment points. The sensor can further comprise input and output channels to which the electronic attachment options connect. The user device can further comprise a front-end ASIC configured to convert multiple sensor channels into fewer sensor channels.

In some embodiments, the sensor is configured to provide signals used by the system to identify the user based on an image of their palm and/or fingerprint.

In some embodiments, the sensor comprises an ultrasound-based sensor and a capacitive touch sensor. The ultrasound-based sensor can be positioned under the capacitive touch sensor. User contact with the capacitive touch sensor can be configured to change a current state of the system selected from the group consisting of: off to on; standby mode to awake mode; low power mode to a non-low power mode; silent mode to non-silent mode; and combinations thereof. User contact along a top surface of the capacitive touch sensor can be configured to define a zone of operation to be used by the system in a subsequent event.

In some embodiments, the sensor comprises an ultrasound-based sensor that includes a layer of ZnO.

In some embodiments, the sensor comprises a Langevin transducer-based sensor.

In some embodiments, the sensor comprises multiple sensors in a close-proximity arrangement and configured to operate as a single sensor. At least two of the multiple sensors can be configured to rotate relative to each other. The multiple sensors can comprise multiple ultrasound-based sensors.

In some embodiments, the user device comprises one, two, or more devices selected from the group consisting of: cell phone; smartwatch; computer device; user protection device; transportation device; construction equipment; card device; memory storage device; crypto wallet device; lock; storage container; lab equipment; medical device; and combinations thereof.

In some embodiments, the user device comprises a smart card and the sensor comprises an ultrasound-based sensor constructed of PVDF, and the sensor is positioned at a select depth from a first surface of the smart card.

In some embodiments, the system further comprises one or more interfaces configured to interface two or more components of the system to each other. The one or more interfaces can comprise at least one interface that is integral to the user device. Each interface can be configured to electrically, mechanically, acoustically, fluidically, optically, and/or otherwise operably connect two or more system components. The one or more interfaces can comprise at least one interface configured to operably connect the sensor to another component of the system. The sensor can be operably connected to the user device.

In some embodiments, the system further comprises a fob comprising one, two, or more fobs. The fob can comprise the sensor. The sensor can comprise an ultrasound-based sensor configured to provide a signal used to identify a fingerprint of the user. The fob can comprise an interface configured to interface the sensor with another portion of the fob. The fob can comprise a user interface. The fob can be configured to transmit information to the user device via a wired and/or wireless connection. The fob can comprise at least a portion of the sensor and can be configured to identify one or more fingerprints of the user. The fob can be configured to identify the user and transfer confirmation of the user's identity to the user device. The user can be identified via a fingerprint identified via a signal provided by the at least a portion of the sensor of the fob. The fob can comprise a first portion of the sensor and can be configured to collect confidential data of a user, and the user device can comprise a second portion of the sensor configured to collect non-confidential data of the user, and the system can be configured to perform a user confirmation routine using both the confidential data and the non-confidential data.

In some embodiments, the system further comprises one or more algorithms. The one or more algorithms can comprise a machine learning, neural network, and/or other artificial intelligence algorithm. The system can be configured to perform a user confirmation routine, and the one or more algorithms comprise an algorithm that can be configured to detect an attempt at spoofing of the user confirmation routine performed by the system. The algorithm can be configured to analyze physiologic data of the user. The analysis can be configured to identify and/or characterize the user. The algorithm can be configured to analyze fingerprint data to identify the user. The algorithm can further analyze other data selected from the group consisting of: facial image data; voice recording data; physiologic data; and combinations thereof.

In some embodiments, the system further comprises an accessory device comprising one, two, or more accessory devices that are configured to function in cooperation with another component of the system. The accessory device can comprise all or a portion of the sensor. The accessory device can comprise all or a portion of an interface configured to interface a sensor with another portion of the accessory device. The accessory device can be positioned proximate the user device. The accessory device can comprise a protective screen and/or case. The sensor can be configured to transmit and/or receive energy through the protective screen and/or case. The sensor can be integrated into the accessory device. The sensor can be configured to receive power from the user device via a wired and/or wireless connection. The sensor can be configured to communicate with the user device via a wired and/or wireless connection.

In some embodiments, the system further comprises a network comprising one, two, or more computer networks. The network can be selected from the group consisting of: cellular and/or other wireless network; LAN; WAN; VPN; the Internet; and combinations thereof. User information and/or other information collected and/or produced by a component of the system can be transferred via the network to one or more central locations. The system can comprise an algorithm that is configured to analyze the transferred information, such as to improve performance of the system. The algorithm can comprise an artificial intelligence algorithm.

According to another aspect of the present inventive concepts, an ultrasound signal-processing method comprises determining a time shift between a signal arrival time of a signal echo sensed by an ultrasound transducer and a baseline arrival time of a baseline echo sensed by the ultrasound transducer.

In some embodiments, the signal echo is generated by a platen surface, of a platen, with an object contacting the platen surface. The baseline echo can be generated by the platen surface without the object. The ultrasound transducer can be a pixel element of an ultrasound transducer array and the ultrasound signal-processing method can further comprise repeating said determining for each pixel element of the ultrasound transducer array to generate an array of time shifts and generating, for the array of time shifts, a time-shift image. The method can further comprise outputting the time-shift image. The ultrasound transducer array can have a number of rows and a number of columns and the time-shift image can have the same number of rows and the number of columns. The object can be a finger and the time-shift image can be a fingerprint of the finger. The method can further comprise determining, based on the time-shift image, an area of contact between the finger and the platen surface. The area of contact can be an area of ridges of the finger in contact with the platen surface. The method can further comprise determining, based on the area of contact, an applied force of the finger on the platen surface. The method can further comprise repeating said determining the time shift and said determining the area of contact to generate a temporal sequence of contact areas, determining an oscillation period of the temporal sequence of contact areas, and calculating a pulse rate based on the oscillation period. The method can further comprise applying, to the time-shift image, one or more of: Wiener filtering, steerable filtering, histogram equalization, and binarization. The method can further comprise identifying the signal echo from a signal waveform obtained from the ultrasound transducer while the object contacts the platen surface and identifying the baseline echo from a baseline waveform obtained from the ultrasound transducer while the object is not contacting the platen surface. The signal echo can be an initial echo of the signal waveform and the baseline echo can be an initial echo of the baseline waveform. Determining can comprise processing the signal waveform to identify the signal arrival time, processing the baseline waveform to identify the baseline arrival time, and subtracting the baseline arrival time from the signal arrival time. Processing of the signal waveform can include filtering the signal waveform and processing the baseline waveform can include filtering the baseline waveform. Processing the signal waveform can include: identifying a signal zero crossing of the signal waveform and calculating the signal arrival time based on a time of the signal zero crossing; and processing the baseline waveform can include: identifying a baseline zero crossing of the baseline waveform and calculating the baseline transit time based on a time of the baseline zero crossing. The method can further comprise subtracting a mean of the signal waveform from the signal waveform to obtain a mean-corrected signal waveform and subtracting a mean of the baseline waveform from the baseline waveform to obtain a mean-corrected baseline waveform, such that the signal zero crossing is a zero crossing of the mean-corrected signal waveform, and the baseline zero crossing is a zero crossing of the mean-corrected baseline waveform. The method can further comprise calculating the mean of the signal waveform and calculating the mean of the baseline waveform. Processing of the signal waveform can further include: selecting, from the signal waveform, a signal sub-waveform of the signal echo and subtracting, from the signal sub-waveform, a mean of the signal sub-waveform to obtain a mean-corrected signal sub-waveform, such that the signal zero crossing is a zero crossing of the mean-corrected signal sub-waveform. Processing the baseline waveform can further include: selecting, from the baseline waveform, a baseline sub-waveform of the baseline echo and subtracting, from the baseline sub-waveform, a mean of the baseline sub-waveform to obtain a mean-corrected baseline sub-waveform, such that the baseline zero crossing is a zero crossing of the mean-corrected baseline sub-waveform. The method can further comprise calculating the mean of the signal sub-waveform and calculating the mean of the baseline sub-waveform. Processing the signal waveform can further include interpolating the mean-corrected signal sub-waveform to obtain a signal best-fit curve, identifying the signal zero crossing can include identifying the signal zero crossing in the signal best-fit curve, processing the baseline waveform can further include interpolating the mean-corrected baseline sub-waveform to obtain a baseline best-fit curve, and identifying the baseline zero crossing can include identifying the baseline zero crossing in the baseline best-fit curve. The signal zero crossing can be one of a sequence of signal zero crossings and the baseline zero crossing can be one of a sequence of baseline zero crossings. A position of the baseline zero crossing in the sequence of baseline zero crossings can be the same as a position of the signal zero crossing in the sequence of signal zero crossings. Processing the signal waveform can include: identifying a signal maximum of the signal waveform and calculating the signal arrival time based on a time of the signal maximum, and processing the baseline waveform can include: identifying a baseline maximum of the baseline waveform and calculating the baseline arrival time based on a time of the baseline maximum. Processing the signal waveform can further include selecting, from the signal waveform, a signal sub-waveform of the signal echo such that the signal maximum is a local maximum, and processing the baseline waveform can further include selecting, from the baseline waveform, a baseline sub-waveform of the baseline echo such that the baseline maximum is a local maximum. Processing the signal waveform can further include interpolating the signal sub-waveform to obtain a signal best-fit curve; identifying the signal maximum can include identifying the signal maximum in the signal best-fit curve; processing the baseline waveform can further include interpolating the baseline sub-waveform to obtain a baseline best-fit curve; and identifying the baseline maximum can include identifying the baseline maximum in the baseline best-fit curve. The signal maximum can be one of a sequence of signal local maxima and the baseline maximum can be one of a sequence of baseline local maxima. A position of the baseline maximum in the sequence of baseline local maxima can be the same as a position of the signal maximum in the sequence of signal local maxima. Processing the signal waveform can include: transforming, with a Hilbert transform, at least part of the signal waveform into a sequence of signal phases; identifying a signal zero crossing of the sequence of signal phases; and calculating the signal transit time based on a time of the signal zero crossing. Processing the baseline waveform can include: transforming, with the Hilbert transform, at least part of the baseline waveform into a sequence of baseline phases; identifying a baseline zero crossing of the sequence of baseline phases; and calculating the baseline transit time based on a time of the baseline zero crossing. Processing the signal waveform can further include transforming, with the Hilbert transform, the at least part of the signal waveform into a sequence of signal envelope values; and calculating the signal transit time can be further based on the sequence of signal envelope values. Processing the baseline waveform can further include transforming, with the Hilbert transform, the at least part of the baseline waveform into a sequence of baseline envelope values; and calculating the baseline transit time can be further based on the sequence of baseline envelope values. Determining can comprise transforming the baseline and signal waveforms into a cross-correlation signal and calculating, based on the cross-correlation signal, the time shift. The method can further comprise transmitting, with the ultrasound transducer, a signal ultrasound pulse into the platen such that a portion of the signal ultrasound pulse reflects off of the platen surface to form the signal echo; and sensing the signal echo with the ultrasound transducer. The ultrasound transducer can be a pixel element of an ultrasound transducer array; and the transmitting and sensing use row-column addressing of the ultrasound transducer array. Transmitting can use only one row of the ultrasound transducer array and said sensing can use only one column of the ultrasound transducer array. One or both of said transmitting and said sensing can use beamforming. The method can further comprise transmitting, with the ultrasound transducer, a baseline ultrasound pulse into the platen such that a portion of the baseline ultrasound pulse reflects off of the platen surface to form the baseline echo and sensing the baseline echo with the ultrasound transducer. The ultrasound transducer can be a pixel element of an ultrasound transducer array; and transmitting the signal ultrasound pulse, receiving the signal echo, transmitting the baseline ultrasound pulse, and receiving the baseline echo can use row-column addressing of the ultrasound transducer array. The method can further comprise identifying, based on the time shift, a presence of the object contacting the platen surface. Identifying can include comparing the time shift to a threshold. The method can further comprise outputting an indication of the presence of the object. The ultrasound transducer can comprise a pixel element of an ultrasound transducer array. The object can comprise human tissue. The human tissue can comprise a finger.

According to another aspect of the present inventive concepts, an ultrasound signal-processing method comprises determining, for each pixel element of an ultrasound transducer array, a time shift between an arrival time of an echo sensed by said each pixel element and a baseline arrival time.

In some embodiments, the baseline arrival time is based on the arrival time determined for at least one pixel element. The baseline arrival time can equal the arrival time of one pixel element. In some embodiments, the arrival time can be one of an array of arrival times and the baseline arrival time can equal an average of the array of arrival times.

In some embodiments, the echo is generated from an object contacting a platen surface of a platen. The method can further comprise generating, based on the time shift for each pixel, a time-shift image. The method can further comprise outputting the time-shift image. The object can be a finger and the time-shift image can be a fingerprint of the finger. The method can further comprise for each pixel element of the ultrasound transducer array: transmitting, with the ultrasound transducer array, an ultrasound pulse into the platen such that a portion of the ultrasound pulse reflects off of the platen surface to form the echo; and sensing the echo with the ultrasound transducer array.

According to another aspect of the present inventive concepts, an object detection method comprises determining, for each pixel element of an ultrasound transducer array, an arrival time of an echo sensed by said each pixel element; and calculating, based on the arrival time for said each pixel element, a deviation; and determining, based on the deviation, the presence of an object.

In some embodiments, the deviation comprises standard deviation.

In some embodiments, determining the presence of the object includes comparing the deviation to a threshold.

In some embodiments, the method further comprises outputting an indication of the presence of the object.

In some embodiments, the echo being generated from the object is contacting a platen surface of a platen. The method can further comprise transmitting, with the ultrasound transducer array, an ultrasound pulse into the platen such that a portion of the ultrasound pulse reflects off of the platen surface to form the echo; and sensing the echo with the ultrasound transducer array. The object can comprise human tissue. The human tissue can comprise a finger.

According to another aspect of the present inventive concepts, an object detection method comprises: determining, for each pixel element of an ultrasound transducer array, a time shift between: a signal arrival time of a signal echo sensed by said each pixel element; and a baseline arrival time of a baseline echo sensed by said each pixel element; calculating, based on the time shift for said each pixel element, a deviation; and determining, based on the deviation, the presence of an object.

In some embodiments, the deviation comprises a standard deviation.

In some embodiments, determining the presence of the object includes comparing the deviation to a threshold.

In some embodiments, the method further comprises outputting an indication of the presence of the object.

In some embodiments, the signal echo being generated from the object is contacting a platen surface of a platen. The method can further comprise transmitting, with the ultrasound transducer array, a signal ultrasound pulse into the platen such that a portion of the signal ultrasound pulse reflects off of the platen surface to form the signal echo; and sensing the signal echo with the ultrasound transducer array. The method can further comprise transmitting, with the ultrasound transducer array, a baseline ultrasound pulse into the platen such that a portion of the baseline ultrasound pulse reflects off of the platen surface to form the baseline echo; and sensing the baseline echo with the ultrasound transducer array.

In some embodiments, the object comprises human tissue. The human tissue can comprise a finger.

According to another aspect of the present inventive concepts, an ultrasound signal-processing system, comprises: a processor and a memory storing machine-readable instructions that, when executed by the processor, control the ultrasound signal-processing system to determine a time shift between: a signal arrival time of a signal echo sensed by an ultrasound transducer; and a baseline arrival time of a baseline echo sensed by the ultrasound transducer.

In some embodiments, the signal echo is being generated by a platen surface, of a platen, with an object contacting the platen surface. The baseline echo can be generated by the platen surface without the object. The ultrasound transducer can be a pixel element of an ultrasound transducer array; and the memory stores additional machine-readable instructions that, when executed by the processor, can control the ultrasound signal-processing system to: determine, for each pixel element of the ultrasound transducer array, the time shift for said each pixel to generate an array of time shifts, and generate, based on the array of time shifts, a time-shift image. The memory storing additional machine-readable instructions that, when executed by the processor, can control the ultrasound signal-processing system to output the time-shift image. The ultrasound transducer array can have a number of rows and a number of columns; and the time-shift image can have the same number of rows and the number of columns. The object can be a finger and the time-shift image can be a fingerprint of the finger. The memory storing additional machine-readable instructions that, when executed by the processor, can control the ultrasound signal-processing system to determine, based on the time-shift image, an area of contact between the finger and the platen surface. The area of contact can be an area of ridges of the finger in contact with the platen surface. The memory storing additional machine-readable instructions that, when executed by the processor, can control the ultrasound signal-processing system to determine, based on the area of contact, an applied force of the finger on the platen surface. The memory storing additional machine-readable instructions that, when executed by the processor, can control the ultrasound signal-processing system to: repeatedly determine the time shift and determine the area of contact to generate a temporal sequence of contact areas; determine an oscillation period of the temporal sequence of contact areas; and calculate a pulse rate based on the oscillation period.

The memory storing additional machine-readable instructions that, when executed by the processor, can control the ultrasound signal-processing system to apply, to the time-shift image, one or more of: Wiener filtering, steerable filtering, histogram equalization, and binarization. The memory storing additional machine-readable instructions that, when executed by the processor, can control the ultrasound signal-processing system to: identify the signal echo from a signal waveform obtained from the ultrasound transducer while the object contacted the platen surface, and identify the baseline echo from a baseline waveform obtained from the ultrasound transducer while the object was not contacting the platen surface. The signal echo can be an initial echo of the signal waveform; and the baseline echo can be an initial echo of the baseline waveform. The machine-readable instructions that, when executed by the processor, can control the ultrasound signal-processing system include machine-readable instructions that, when executed by the processor, can control the ultrasound signal-processing system to: process the signal waveform to identify the signal arrival time, process the baseline waveform to identify the baseline arrival time, and subtract the baseline arrival time from the signal arrival time. The machine-readable instructions that, when executed by the processor, can control the ultrasound signal-processing system to process the signal waveform including machine-readable instructions that, when executed by the processor, can control the ultrasound signal-processing system to filter the signal waveform; and the machine-readable instructions that, when executed by the processor, can control the ultrasound signal-processing system to process the baseline waveform including machine-readable instructions that, when executed by the processor, can control the ultrasound signal-processing system to filter the baseline waveform. The machine-readable instructions that, when executed by the processor, can control the ultrasound signal-processing system to process the signal waveform including machine-readable instructions that, when executed by the processor, can control the ultrasound signal-processing system to: identify a signal zero crossing of the signal waveform, and calculate the signal arrival time based on a time of the signal zero crossing; and the machine-readable instructions that, when executed by the processor, can control the ultrasound signal-processing system to process the baseline waveform including machine-readable instructions that, when executed by the processor, can control the ultrasound signal-processing system to: identify a baseline zero crossing of the baseline waveform, and calculate the baseline transit time based on a time of the baseline zero crossing. The memory storing additional machine-readable instructions that, when executed by the processor, can control the ultrasound signal-processing system to: subtract a mean of the signal waveform from the signal waveform to obtain a mean-corrected signal waveform, and subtract a mean of the baseline waveform from the baseline waveform to obtain a mean-corrected baseline waveform, such that the signal zero crossing is a zero crossing of the mean-corrected signal waveform, and the baseline zero crossing is a zero crossing of the mean-corrected baseline waveform. The memory storing additional machine-readable instructions that, when executed by the processor, can control the ultrasound signal-processing system to: calculate the mean of the signal waveform, and calculate the mean of the baseline waveform. The machine-readable instructions that, when executed by the processor, can control the ultrasound signal-processing system to process the signal waveform including machine-readable instructions that, when executed by the processor, can control the ultrasound signal-processing system to: select, from the signal waveform, a signal sub-waveform of the signal echo, and subtract, from the signal sub-waveform, a mean of the signal sub-waveform to obtain a mean-corrected signal sub-waveform, such that the signal zero crossing is a zero crossing of the mean-corrected signal sub-waveform; and the machine-readable instructions that, when executed by the processor, can control the ultrasound signal-processing system to process the baseline waveform including machine-readable instructions that, when executed by the processor, can control the ultrasound signal-processing system to: select, from the baseline waveform, a baseline sub-waveform of the baseline echo, and subtract, from the baseline sub-waveform, a mean of the baseline sub-waveform to obtain a mean-corrected baseline sub-waveform, such that the baseline zero crossing is a zero crossing of the mean-corrected baseline sub-waveform. The memory storing additional machine-readable instructions that, when executed by the processor, can control the ultrasound signal-processing system to: calculate the mean of the signal sub-waveform, and calculate the mean of the baseline sub-waveform. The machine-readable instructions that, when executed by the processor, can control the ultrasound signal-processing system to process the signal waveform including machine-readable instructions that, when executed by the processor, can control the ultrasound signal-processing system to interpolate the mean-corrected signal sub-waveform to obtain a signal best-fit curve; the machine-readable instructions that, when executed by the processor, can control the ultrasound signal-processing system to identify the signal zero crossing include machine-readable instructions that, when executed by the processor, can control the ultrasound signal-processing system to identify the signal zero crossing in the signal best-fit curve; the machine-readable instructions that, when executed by the processor, can control the ultrasound signal-processing system to process the baseline waveform including machine-readable instructions that, when executed by the processor, can control the ultrasound signal-processing system to interpolate the mean-corrected baseline sub-waveform to obtain a baseline best-fit curve; the machine-readable instructions that, when executed by the processor, can control the ultrasound signal-processing system to identify the baseline zero crossing include machine-readable instructions that, when executed by the processor, can control the ultrasound signal-processing system to identify the baseline zero crossing in the baseline best-fit curve. The signal zero crossing can be one of a sequence of signal zero crossings; and the baseline zero crossing can be one of a sequence of baseline zero crossings. A position of the baseline zero crossing in the sequence of baseline zero crossings can be the same as a position of the signal zero crossing in the sequence of signal zero crossings. The machine-readable instructions that, when executed by the processor, can control the ultrasound signal-processing system to process the signal waveform including machine-readable instructions that, when executed by the processor, can control the ultrasound signal-processing system to: identify a signal maximum of the signal waveform, and calculate the signal arrival time based on a time of the signal maximum; and the machine-readable instructions that, when executed by the processor, can control the ultrasound signal-processing system to process the baseline waveform including machine-readable instructions that, when executed by the processor, can control the ultrasound signal-processing system to: identify a baseline maximum of the baseline waveform, and calculate the baseline arrival time based on a time of the baseline maximum. The machine-readable instructions that, when executed by the processor, can control the ultrasound signal-processing system to process the signal waveform including additional machine-readable instructions that, when executed by the processor, can control the ultrasound signal-processing system to select, from the signal waveform, a signal sub-waveform of the signal echo such that the signal maximum is a local maximum; and the machine-readable instructions that, when executed by the processor, can control the ultrasound signal-processing system to process the baseline waveform including additional machine-readable instructions that, when executed by the processor, can control the ultrasound signal-processing system to select, from the baseline waveform, a baseline sub-waveform of the baseline echo such that the baseline maximum is a local maximum. The machine-readable instructions that, when executed by the processor, can control the ultrasound signal-processing system to process the signal waveform including machine-readable instructions that, when executed by the processor, can control the ultrasound signal-processing system to interpolate the mean-corrected signal sub-waveform to obtain a signal best-fit curve; the machine-readable instructions that, when executed by the processor, can control the ultrasound signal-processing system to identify the signal maximum including machine-readable instructions that, when executed by the processor, can control the ultrasound signal-processing system to identify the signal maximum in the signal best-fit curve; the machine-readable instructions that, when executed by the processor, can control the ultrasound signal-processing system to process the baseline waveform including machine-readable instructions that, when executed by the processor, can control the ultrasound signal-processing system to interpolate the mean-corrected baseline sub-waveform to obtain a baseline best-fit curve; and the machine-readable instructions that, when executed by the processor, can control the ultrasound signal-processing system to identify the baseline maximum including machine-readable instructions that, when executed by the processor, can control the ultrasound signal-processing system to identify the baseline maximum in the baseline best-fit curve. The signal maximum can be one of a sequence of signal local maxima; and the baseline maximum can be one of a sequence of baseline local maxima. A position of the baseline maximum in the sequence of baseline local maxima can be the same as a position of the signal maximum in the sequence of signal local maxima. The machine-readable instructions that, when executed by the processor, can control the ultrasound signal-processing system to process the signal waveform including machine-readable instructions that, when executed by the processor, can control the ultrasound signal-processing system to: transform, with a Hilbert transform, at least part of the signal waveform into a sequence of signal phases, identify a signal zero crossing of the sequence of signal phases, and calculate the signal transit time based on a time of the signal zero crossing; and the machine-readable instructions that, when executed by the processor, can control the ultrasound signal-processing system to process the baseline waveform including machine-readable instructions that, when executed by the processor, can control the ultrasound signal-processing system to: transform, with the Hilbert transform, at least part of the baseline waveform into a sequence of baseline phases, identify a baseline zero crossing of the sequence of baseline phases, and calculate the baseline transit time based on a time of the baseline zero crossing. The machine-readable instructions that, when executed by the processor, can control the ultrasound signal-processing system to process the signal waveform including machine-readable instructions that, when executed by the processor, can control the ultrasound signal-processing system to transform, with the Hilbert transform, the at least part of the signal waveform into a sequence of signal envelope values; the machine-readable instructions that, when executed by the processor, can control the ultrasound signal-processing system to calculate the signal transit time including machine-readable instructions that, when executed by the processor, can control the ultrasound signal-processing system to calculate the signal transit time based on the sequence of signal envelope values; the machine-readable instructions that, when executed by the processor, can control the ultrasound signal-processing system to process the baseline waveform including machine-readable instructions that, when executed by the processor, can control the ultrasound signal-processing system to transform, with the Hilbert transform, the at least part of the baseline waveform into a sequence of baseline envelope values; and the machine-readable instructions that, when executed by the processor, can control the ultrasound signal-processing system to calculate the baseline transit time including machine-readable instructions that, when executed by the processor, can control the ultrasound signal-processing system to calculate the baseline transit time based on the sequence of baseline envelope values. The machine-readable instructions that, when executed by the processor, can control the ultrasound signal-processing system include machine-readable instructions that, when executed by the processor, can control the ultrasound signal-processing system to: transform the baseline and signal waveforms into a cross-correlation signal, and calculate, based on the cross-correlation signal, the time shift. The system can further comprise the ultrasound transducer. The ultrasound transducer can be an ultrasound transducer array. The system can further comprise the platen. The platen can have a thickness greater than 100 microns. The platen can have a thickness less than 5 millimeters. The platen can be formed from glass. The ultrasound transducer array can be affixed to the platen. The memory storing additional machine-readable instructions that, when executed by the processor, can control the ultrasound signal-processing system to: transmit, with the ultrasound transducer, a signal ultrasound pulse into the platen such that a portion of the signal ultrasound pulse reflects off of the platen surface to form the signal echo, and sense the signal echo with the ultrasound transducer. The ultrasound transducer can be a pixel element of an ultrasound transducer array; and the machine-readable instructions that, when executed by the processor, can control the ultrasound signal-processing system to transmit and to sense including machine-readable instructions that, when executed by the processor, can control the ultrasound signal-processing system to use row-column addressing of the ultrasound transducer array. The machine-readable instructions that, when executed by the processor, can control the ultrasound signal-processing system to transmit including machine-readable instructions that, when executed by the processor, can control the ultrasound signal-processing system to transmit using only one row of the ultrasound transducer array; and the machine-readable instructions that, when executed by the processor, can control the ultrasound signal-processing system to sense including machine-readable instructions that, when executed by the processor, can control the ultrasound signal-processing system to sense using only one column of the ultrasound transducer array. The machine-readable instructions that, when executed by the processor, can control the ultrasound signal-processing system to transmit including machine-readable instructions that, when executed by the processor, can control the ultrasound signal-processing system to transmit using beamforming. The machine-readable instructions that, when executed by the processor, can control the ultrasound signal-processing system to sense including machine-readable instructions that, when executed by the processor, can control the ultrasound signal-processing system to sense using beamforming. The memory storing additional machine-readable instructions that, when executed by the processor, can control the ultrasound signal-processing system to: transmit, with the ultrasound transducer, a baseline ultrasound pulse into the platen such that a portion of the baseline ultrasound pulse reflects off of the platen surface to form the baseline echo, and sense the baseline echo with the ultrasound transducer. The ultrasound transducer can be a pixel element of an ultrasound transducer array; and the machine-readable instructions that, when executed by the processor, can control the ultrasound signal-processing system to transmit the signal ultrasound pulse, receive the signal echo, transmit the baseline ultrasound pulse, and receive the baseline echo including machine-readable instructions that, when executed by the processor, can control the ultrasound signal-processing system to transmit the signal ultrasound pulse, receive the signal echo, transmit the baseline ultrasound pulse, and receive the baseline echo using row-column addressing. The memory storing additional machine-readable instructions that, when executed by the processor, can control the ultrasound signal-processing system to identify, based on the time shift, a presence of an object contacting the platen surface. The machine-readable instructions that, when executed by the processor, can control the ultrasound signal-processing system to identify machine-readable instructions that, when executed by the processor, can control the ultrasound signal-processing system to compare the time shift to a threshold. The machine-readable instructions that, when executed by the processor, can control the ultrasound signal-processing system to identify machine-readable instructions that, when executed by the processor, can control the ultrasound signal-processing system to output an indication of the presence of the object. The system can further comprise an indicator that displays the indication. The ultrasound transducer can comprise a pixel element of an ultrasound transducer array. The object can comprise human tissue. The human tissue can comprise a finger.

According to another aspect of the present inventive concepts, an ultrasound signal-processing system, comprises: a processor and a memory storing machine-readable instructions that, when executed by the processor, control the ultrasound signal-processing system to determine, for each pixel element of an ultrasound transducer array, a time shift between: an arrival time of an echo sensed by said each pixel element; and a baseline arrival time.

In some embodiments, the baseline arrival time is based on the arrival time determined for at least one pixel element. The baseline arrival time can equal the arrival time of one pixel element. The arrival time can be one of an array of arrival times and the baseline arrival time can equal an average of the array of arrival times.

In some embodiments, the echo is being generated from an object contacting a platen surface of a platen. The memory storing additional machine-readable instructions that, when executed by the processor, can control the ultrasound signal-processing system to generate, based on the time shift for each pixel, a time-shift image. The memory storing additional machine-readable instructions that, when executed by the processor, can control the ultrasound signal-processing system to output the time-shift image. The object can be a finger and the time-shift image can be a fingerprint of the finger. The system can further comprise the ultrasound transducer array and the platen; and the memory can store additional machine-readable instructions that, when executed by the processor, can control the ultrasound signal-processing system to: transmit, with the ultrasound transducer array, an ultrasound pulse into the platen such that a portion of the ultrasound pulse reflects off of the platen surface to form the echo; and sense the echo with the ultrasound transducer array. The ultrasound transducer array can be affixed to the platen.

According to another aspect of the present inventive concepts, an object detector comprises: a processor and a memory storing machine-readable instructions that, when executed by the processor, control the object detector to: determine, for each pixel element of an ultrasound transducer array, an arrival time of an echo sensed by said each pixel element, calculate, based on the arrival time for said each pixel element, a deviation, and identify, based on the deviation, the presence of an object.

In some embodiments, the deviation comprises a standard deviation.

In some embodiments, the machine-readable instructions that, when executed by the processor, control the object detector to identify machine-readable instructions that, when executed by the processor, control the object detector to compare the deviation to a threshold.

In some embodiments, the memory storing additional machine-readable instructions that, when executed by the processor, control the object detector to output an indication of the presence of the object.

In some embodiments, the echo is being generated from the object contacting a platen surface of a platen. The object detector can further comprise the ultrasound transducer array and the platen; and the memory stores additional machine-readable instructions that, when executed by the processor, can control the object detector to: transmit, with the ultrasound transducer array, an ultrasound pulse into the platen such that a portion of the ultrasound pulse reflects off of the platen surface to form the echo; and sense the echo with the ultrasound transducer array. The ultrasound transducer array can be affixed to the platen.

In some embodiments, the object comprises human tissue. The human tissue can comprise a finger.

According to another aspect of the present inventive concepts, an object detector comprises: a processor and a memory storing machine-readable instructions that, when executed by the processor, control the object detector to: determine, for each pixel element of an ultrasound transducer array, a time shift between (i) a signal arrival time of a signal echo sensed by said each pixel element, and (ii) a baseline arrival time of a baseline echo sensed by said each pixel element, calculate, based on the time shift for said each pixel element, a deviation, and identifying, based on the deviation, the presence of an object.

In some embodiments, the deviation comprises a standard deviation.

In some embodiments, the machine-readable instructions that, when executed by the processor, control the object detector to identify machine-readable instructions that, when executed by the processor, control the object detector to compare the deviation to a threshold.

In some embodiments, the memory storing additional machine-readable instructions that, when executed by the processor, control the object detector to output an indication of the presence of the object.

In some embodiments, the echo is being generated from the object contacting a platen surface of a platen. The object detector can further comprise the ultrasound transducer array and the platen; and the memory stores additional machine-readable instructions that, when executed by the processor, can control the object detector to: transmit, with the ultrasound transducer array, an ultrasound pulse into the platen such that a portion of the ultrasound pulse reflects off of the platen surface to form the echo; and sense the echo with the ultrasound transducer array. The ultrasound transducer array can be affixed to the platen.

In some embodiments, the object comprises human tissue. The human tissue can comprise a finger.

According to another aspect of the present inventive concepts, a fingerprint sensor comprises: an ultrasound transducer array having a plurality of pixel elements; a platen affixed to the ultrasound transducer array, the platen having a platen surface for contact with a finger; a processor communicably coupled to the ultrasound transducer array; and a memory storing machine-readable instructions that, when executed by the processor, control the fingerprint sensor to: for each pixel element of the ultrasound transducer array: (i) transmit, with the ultrasound transducer array, a signal ultrasound pulse into the platen such that a portion of the signal ultrasound pulse reflects off of the platen surface to form a signal echo, (ii) sense, with the ultrasound transducer array, the signal echo, (iii) transmit, with the ultrasound transducer, a baseline ultrasound pulse into the platen such that a portion of the baseline ultrasound pulse reflects off of the platen surface to form a baseline echo, (iv) sense, with the ultrasound transducer array, the baseline echo, and (v) determine a time shift between a signal arrival time of the signal echo, and a baseline arrival time of the baseline echo, determine, based on the time shift determined for at least one of the pixel elements, if the finger was in contact with the platen surface while the signal ultrasound pulse was transmitted and the signal echo was sensed, and generate, based on the time shift for each pixel element, a fingerprint image of the finger.

According to another aspect of the present inventive concepts, a multi-platen ultrasound fingerprint sensor comprises: a first platen having a first round-trip propagation time; an array of first pixel transducers adjacent to the first platen; a second platen having a second round-trip propagation time different from the first round-trip propagation time; and an array of second pixel transducers adjacent to the second platen; each of the first pixel transducers being electrically-paired with a corresponding one of the second pixel transducers.

In some embodiments, a first ultrasound pulse, when emitted into a first rear face of the first platen by one of the first pixel transducers, reflects off a first front face of the first platen to generate a first echo that said one of the first pixel transducers converts into a first electronic pulse; a second ultrasound pulse, when emitted into a second rear face of the second platen simultaneously with the first ultrasound pulse by the corresponding one of the second pixel transducers, reflects off a second front face of the second platen to generate a second echo that the corresponding one of the second pixel transducers converts into a second electronic pulse; and the first and second electronic pulses are temporally distinguishable.

In some embodiments, the first pixel transducers and the second pixel transducers are individually addressable.

In some embodiments, the first pixel transducers and the second pixel transducers are row-column addressable. Each of the first pixel transducers can comprise piezoelectric material located between one of a plurality of first transmit electrodes and one of a plurality of first receive electrodes; each of the second pixel transducers can comprise piezoelectric material located between one of a plurality of second transmit electrodes and one of a plurality of second receive electrodes; each of the plurality of first transmit electrodes can be electrically connected to a corresponding one of the plurality of second transmit electrodes; and each of the plurality of first receive electrodes can be electrically connected to a corresponding one of the plurality of second receive electrodes. Each of the plurality of first transmit electrodes and the plurality of second transmit electrodes can be a row electrode; and each of the plurality of first receive electrodes and the plurality of second receive electrodes can be a column electrode. Each of the plurality of first transmit electrodes and the corresponding one of the plurality of second transmit electrodes can form a single linear electrode extending underneath both the first and second platens. Each of the plurality of first receive electrodes and the corresponding one of the plurality of second receive electrodes can form a single linear electrode extending underneath both the first and second platens. The sensor can further comprise a transmit multiplexer having a plurality of outputs, each of the plurality of outputs can be electrically connected to one of the plurality of first transmit electrodes and the corresponding one of the plurality of second transmit electrodes; and a receive multiplexer having a plurality of inputs, each of the plurality of inputs can be electrically connected to one of the plurality of first receive electrodes and the corresponding one of the plurality of second receive electrodes.

In some embodiments, the first platen comprises a first material with a first sound velocity; the first round-trip propagation time is determined by the first sound velocity and a first thickness of the first platen; the second platen comprises a second material with a second sound velocity; and the second round-trip propagation time is determined by the second sound velocity and a second thickness of the second platen. The first and second materials can be similar. The first and second thicknesses can be different. The first and second sound velocities can be different. The first and second thicknesses can be similar.

In some embodiments, the first platen forms a first acoustic waveguide adjacent to each of the first pixel transducers, the first round-trip propagation time being determined by a first sound velocity of the first acoustic waveguide; and the second platen forms a second acoustic waveguide adjacent to each of the second pixel transducers, the second round-trip propagation time being determined by a second sound velocity of the second acoustic waveguide.

In some embodiments, a first rear face of the first platen is co-planar with a second rear face of the second platen.

In some embodiments, a first front face of the first platen is co-planar with a second front face of the second platen.

In some embodiments, a first rear face of the first platen faces a second rear face of the second platen.

According to another aspect of the present inventive concepts, a fingerprint-sensing method, comprises: driving electrically-paired first and second pixel transducers to emit (i) a first ultrasound pulse from the first pixel transducer into a first rear face of a first platen and (ii) a second ultrasound pulse from the second pixel transducer into a second rear face of a second platen; converting, with the first pixel transducer and into a first electronic pulse, a first echo generated when the first ultrasound pulse reflects off a first front face of the first platen; converting, with the second pixel transducer and into a second electronic pulse, a second echo generated when the second ultrasound pulse reflects off a second front face of the second platen; and outputting the first and second electrical pulses on a single electrode, the first and second electrical pulses being temporally distinguishable.

In some embodiments, the first platen has a first round-trip propagation time between the first rear face and the first front face; the second platen has a second round-trip propagation time between the second rear face and the second front face; and the first and second round-trip propagation times are different.

According to another aspect of the present inventive concepts, a multi-platen ultrasound fingerprint sensor, comprises: a first platen; an array of first pixel transducers adjacent to the first platen; a second platen; and an array of second pixel transducers adjacent to the second platen. Each of the first pixel transducers has a first frequency response and is electrically paired with a corresponding one of the second pixel transducers having a second frequency response different from the first frequency response.

In some embodiments, a first ultrasound pulse, when emitted into a first rear face of the first platen by one of the first pixel transducers, reflects off a first front face of the first platen to generate a first echo that said one of the first pixel transducers converts into a first electronic pulse; a second ultrasound pulse, when emitted into a second rear face of the second platen simultaneously with the first ultrasound pulse by the corresponding one of the second pixel transducers, reflects off a second front face of the second platen to generate a second echo that the corresponding one of the second pixel transducers converts into a second electronic pulse; and the first electronic pulse has a first center frequency; and the second electronic pulse has a second center frequency different from the first center frequency.

In some embodiments, the first pixel transducers and the second pixel transducers are individually addressable.

In some embodiments, the first pixel transducers and the second pixel transducers are row-column addressable. Each of the first pixel transducers can comprise piezoelectric material located between one of a plurality of first transmit electrodes and one of a plurality of first receive electrodes; each of the second pixel transducers can comprise piezoelectric material located between one of a plurality of second transmit electrodes and one of a plurality of second receive electrodes; each of the plurality of first transmit electrodes can be electrically connected to a corresponding one of the plurality of second transmit electrodes; and each of the plurality of first receive electrodes can be electrically connected to a corresponding one of the plurality of second receive electrodes. Each of the plurality of first transmit electrodes and the plurality of second transmit electrodes can be a row electrode; and each of the plurality of first receive electrodes and the plurality of second receive electrodes can be a column electrode. Each of the plurality of first transmit electrodes and the corresponding one of the plurality of second transmit electrodes can form a single linear electrode extending underneath both the first and second platens. Each of the plurality of first receive electrodes and the corresponding one of the plurality of second receive electrodes can form a single linear electrode extending underneath both the first and second platens. Each of the first pixel transducers can have a first piezoelectric thickness; and the corresponding one of the second pixel transducers can have a second piezoelectric thickness different from the first piezoelectric thickness. One side of the first platen can directly abut one side of the second platen. The first and second platens can comprise one integral piece of a common platen material. A first rear face of the first platen can face a second rear face of the second platen.

According to another aspect of the present inventive concepts, a fingerprint-sensing method, comprises: driving electrically-paired first and second pixel transducers to emit (i) a first ultrasound pulse with a first frequency from the first pixel transducer into a first rear face of a first platen, and (ii) a second ultrasound pulse with a second frequency, different from the first frequency, from the second pixel transducer into a second rear face of a second platen; converting, with the first pixel transducer and into a first electronic pulse, a first echo generated when the first ultrasound pulse reflects off a first front face of the first platen; converting, with the second pixel transducer and into a second electronic pulse, a second echo generated when the second ultrasound pulse reflects off a second front face of the second platen; and outputting the first and second electrical pulses on a single electrode.

According to another aspect of the present inventive concepts, a multi-platen ultrasound fingerprint sensor, comprises: a first platen having a first round-trip propagation time between a first front face and a first rear face; an array of transmit electrodes located underneath the first rear face; a second platen having a second round-trip propagation time, different from the first round-trip propagation time, between a second front face and a second rear face; an array of receive electrodes located underneath the second rear face; and piezoelectric material located between the array of receive electrodes and the array of transmit electrodes.

In some embodiments, a first ultrasound pulse, when emitted into the first platen by one of the column electrodes, reflects off the first front face to generate a first echo that one of the row electrodes senses; a second ultrasound pulse, when emitted into the second platen by said one of the column electrodes, reflects off the second front face to generate a second echo that said one of the row electrodes senses; and the first and second ultrasound pulses are temporally distinguishable.

In some embodiments, the first platen comprises a first material with a first sound velocity; the first round-trip propagation time is determined by the first sound velocity and a first thickness between the first rear face and the first front face; the second platen comprises a second material with a second sound velocity; and the second round-trip propagation time is determined by the second sound velocity and a second thickness between the second rear face and the second front face. The first and second materials can be similar. The first and second thicknesses can be different. The first and second sound velocities can be different. The first and second thicknesses can be similar. The first and second rear faces can be co-planar. The first and second front faces can be co-planar.

In some embodiments, the method comprises driving a single column electrode of a multi-platen ultrasound fingerprint sensor to emit (i) a first ultrasound pulse into a first rear face of a first platen and (ii) a second ultrasound pulse into a second rear face of a second platen; sensing, with a single row electrode of the multi-platen ultrasound fingerprint sensor, a first echo generated when the first ultrasound pulse reflects off a first front face of the first platen, and a second echo generated when the second ultrasound pulse reflects off a second front face of the second platen; and sensing, on the single row electrode, a first electrical pulse of the first echo and a second electrical pulse of the second echo.

In some embodiments, the first platen has a first round-trip propagation time between the first rear face and the first front face; the second platen has a second round-trip propagation time between the second rear face and the second front face; and the first and second round-trip propagation times are different such that the first and second electrical pulses are temporally distinguishable.

The technology described herein, along with the attributes and attendant advantages thereof, will best be appreciated and understood in view of the following detailed description taken in conjunction with the accompanying drawings in which representative embodiments are described by way of example.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE DRAWINGS

Figure 1:
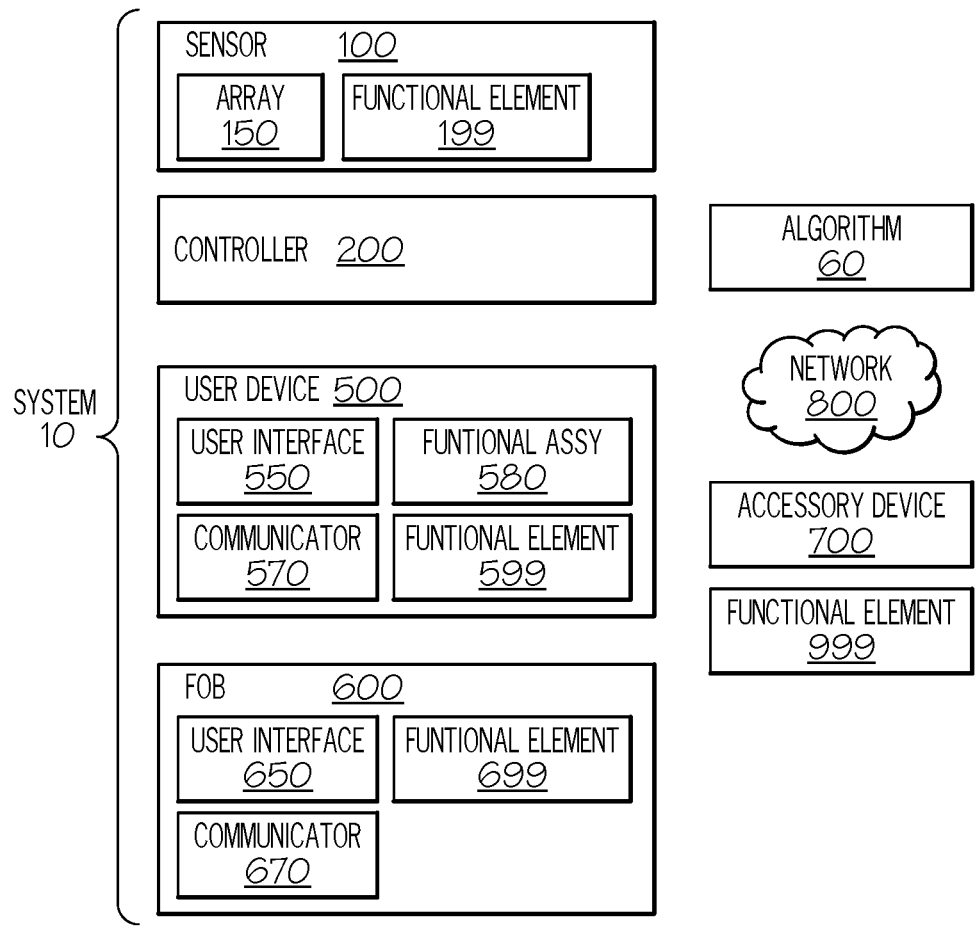
FIG. 1 illustrates a block diagram system for performing a function and classifying a user of the system, consistent with the present inventive concepts.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention.

However, because such elements are well known in the art, and because they do not necessarily facilitate a better understanding of the invention, a description of such elements is not provided herein.

Terms defined in the present disclosure are only used for describing specific embodiments of the present disclosure and are not intended to limit the scope of the present disclosure. Terms provided in singular forms are intended to include plural forms as well, unless the context clearly indicates otherwise. All of the terms used herein, including technical or scientific terms, have the same meanings as those generally understood by an ordinary person skilled in the related art, unless otherwise defined herein. Terms defined in a generally used dictionary should be interpreted as having meanings that are the same as or similar to the contextual meanings of the relevant technology and should not be interpreted as having ideal or exaggerated meanings, unless expressly so defined herein. In some cases, terms defined in the present disclosure should not be interpreted to exclude the embodiments of the present disclosure.

It will be understood that the words "comprising" (and any form of comprising, such as "comprise" and "comprises"), "having" (and any form of having, such as "have" and "has"), "including" (and any form of including, such as "includes" and "include") and/or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third, etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of two or more of these.

As used herein, the term "proximate", when used to describe proximity of a first component or location to a second component or location, is to be taken to include one or more locations near to the second component or location, as well as locations in, on and/or within the second component or location. For example, a component positioned proximate an anatomical site (e.g. a target tissue location), shall include components positioned near to the anatomical site, as well as components positioned in, on and/or within the anatomical site.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence. Correspondingly, the terms "prevent", "preventing", "prevention" and the like, where used herein, shall include the acts of "reduce", "reducing", and "reduction", respectively.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "one or more", where used herein can mean one, two, three, four, five, six, seven, eight, nine, ten, or more, up to any number.

The terms "and combinations thereof" and "and combinations of these" can each be used herein after a list of items that are to be included singly or collectively. For example, a component, process, and/or other item selected from the group consisting of: A; B; C; and combinations thereof, shall include a set of one or more components that comprise: one, two, three or more of item A; one, two, three or more of item B; and/or one, two, three, or more of item C.

In this specification, unless explicitly stated otherwise, "and" can mean "or", and "or" can mean "and". For example, if a feature is described as having A, B, or C, the feature can have A, B, and C, or any combination of A, B, and C. Similarly, if a feature is described as having A, B, and C, the feature can have only one or two of A, B, or C.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

As used herein, the term "threshold" refers to a maximum level, a minimum level, and/or range of values correlating to a desired or undesired state. In some embodiments, a system parameter is maintained above a minimum threshold, below a maximum threshold, within a threshold range of values, and/or outside a threshold range of values, such as to cause a desired effect (e.g. a successful function is performed as intended) and/or to prevent or otherwise reduce (hereinafter "prevent") an undesired event (e.g. performance of a function by an undesired or impaired user). In some embodiments, a system parameter is maintained above a first threshold and below a second threshold. In some embodiments, a threshold value is determined to include a safety margin, such as to account for user variability, system variability, tolerances, and the like. As used herein, "exceeding a threshold" relates to a parameter going above a maximum threshold, below a minimum threshold, within a range of threshold values and/or outside of a range of threshold values.

As described herein, "room pressure" shall mean pressure of the environment surrounding the systems and devices of the present inventive concepts. "Positive pressure" includes pressure above room pressure or simply a pressure that is greater than another pressure, such as a positive differential pressure across a fluid pathway component such as a valve. "Negative pressure" includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereinabove.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross-sectional area as the cross section of the component being described.

The terms "major axis" and "minor axis" of a component where used herein are the length and diameter, respectively, of the smallest volume hypothetical cylinder which can completely surround the component.

As used herein, the term "fluid" can refer to a liquid, gas, gel, or any flowable material, such as a material which can be propelled through a lumen and/or opening.

As used herein, the term "material" can refer to a single material, or a combination of two, three, four, or more materials.

As used herein, the term "transducer" is to be taken to include any component or combination of components that receives energy or any input and produces an output. In some configurations, a transducer converts an electrical signal into any output, such as: light (e.g. a transducer comprising a light emitting diode or light bulb), sound (e.g. a transducer comprising one or more piezoelectric transducers and/or capacitive micromachined ultrasound transducers (CMUTs) configured to deliver and/or receive ultrasound energy); pressure (e.g. an applied pressure or force); heat energy; cryogenic energy; chemical energy; mechanical energy (e.g. a transducer comprising a motor or a solenoid); magnetic energy; and/or a different electrical signal (e.g. different than the input signal to the transducer). Alternatively or additionally, a transducer can convert a physical quantity (e.g. variations in a physical quantity) into an electrical signal. Alternatively or additionally, a transducer can comprise a mechanism, such as: a valve; a grasping element; an anchoring mechanism; an electrically-activated mechanism; a mechanically-activated mechanism; and/or a thermally activated mechanism.

As used herein, the term "functional element" is to be taken to include one or more elements constructed and arranged to perform a function. A functional element can comprise one or more sensors and/or one or more transducers. A functional element (e.g. comprising one or more sensors) can be configured to record one or more parameters. In some embodiments, a functional element is configured to perform a function. A "functional assembly" can comprise an assembly constructed and arranged to perform a function. Alternatively or additionally, a functional assembly can be configured to record one or more parameters, such as a user parameter; a user environment parameter; and/or a system parameter. A functional assembly can comprise one or more functional elements.

As used herein, the term "system parameter" comprises one or more parameters of the system of the present inventive concepts.

As used herein, the term "user parameter", or "operator parameter", comprises one or more parameters associated with a user (also referred to as an "operator") of the system of the present inventive concepts. A user parameter can comprise a user physiologic parameter, such as a physiologic parameter selected from the group consisting of: temperature (e.g. tissue temperature); pressure such as blood pressure or other body fluid pressure; pH; a blood gas parameter; blood glucose level; hormone level; heart rate; respiration rate; and combinations of these. Alternatively or additionally, a user parameter can comprise a user environment parameter, such as an environment parameter selected from the group consisting of: user geographic location; temperature; pressure; humidity level; light level; time of day; and combinations of these.

As used herein, the term "transmitting a signal" and its derivatives shall refer to the transmission of power and/or data between two or more components, in any direction.

As used herein, the term "conduit" or "conduits" can refer to an elongate component that can include one or more flexible and/or non-flexible filaments selected from the group consisting of: one, two or more wires or other electrical conductors (e.g. including an outer insulator); one, two or more wave guides; one, two, or more hollow tubes, such as hydraulic, pneumatic, and/or other fluid delivery tubes; one or more optical fibers; one two or more control cables and/or other mechanical linkages; one, two or more flex circuits; and combinations of these. A conduit can include a tube including multiple conduits positioned within the tube. A conduit can be configured to electrically, fluidically, sonically, optically, mechanically, and/or otherwise operably connect one component to another component.

As used herein, an "ultrasound transducer" (also referred to as "ultrasound element") can refer to one or more components configured to transmit ultrasound energy (e.g. based on a delivered electrical signal) and/or one or more components configured to receive ultrasound energy (e.g. and convert it to an electrical signal). An ultrasound transducer can comprise a set of one or more ultrasound transducers, such as a 1D or 2D array of ultrasound transducers. An ultrasound transducer can refer to: a set of one or more piezoelectric transducers (also referred to as "piezo" transducers or elements); a set of one or more capacitive micromachine ultrasound transducers (CMUTs), or a set of one or more of both.

As used herein, an "optical transducer" (also referred to as "optical element") can refer to one or more components configured to transmit light (e.g. a diode such as a laser diode) and/or one or more components configured to receive and/or facilitate the travel of light (e.g. a lens, prism, optical fiber, and the like).

The systems, devices, and methods of the present inventive concepts include one, two, or more sensors (e.g. ultrasound-based sensors, capacitive sensors, and/or light-based sensors) that are configured to collect data of a user. The data collected (e.g. fingerprint data, pulse oximetry data, and/or other physiologic and anatomic data) can be used to verify that a proper user is present for use of a device or system.

Referring now to FIG. 1, a schematic view of a system for performing a function for a user is illustrated, consistent with the present inventive concepts. System 10 can be configured to perform a function, such as to perform one or more functions associated with: a cellular phone, a computer such as a tablet or laptop computer, a vehicle, a piece of equipment, a storage device such as a secure storage device, and/or other user-accessible device or system. System 10 can be configured to perform an identification routine (e.g. to determine the identity of a user), and/or a confirmation routine (e.g. to confirm the identity of a user). System 10 can be configured to perform a classification routine, such as to classify one or more users of system 10, such as a classification comprising identifying a user (e.g. determining and/or confirming the identity of a user), and/or characterizing a health or other condition of a user (e.g. confirming and/or identifying a health or other condition of a user). A user identification and/or confirmation routine (either or both referred to as "identification routine" or "confirmation routine" herein), can be performed in various ways, such as via a fingerprint, via an image of the user's face, via a recording of the person's voice, and/or via recorded life signs (e.g. current physiologic parameters) of a user. In some embodiments, two, three or more forms of data (e.g. fingerprint, facial image, voice recording, and/or physiologic data) are used to establish the identify and/or provide other status information (e.g. current health status) of a user. In some embodiments, physiologic data of a user (e.g. physiologic data such as: pulse oximetry data; blood glucose data; EEG, LFP, neuronal firing patterns, and/or other brain data; heart rate data; respiration data; perspiration data; and/or blood gas data) can be characterized (e.g. patterns recognized) in a classification routine, such as to identify, confirm, and/or otherwise characterize a health condition of the user. Alternatively or additionally, physiologic data collected by system 10 can be used to identify and/or confirm ("identify" or "confirm" herein) a user in a similar arrangement to that performed using fingerprint, facial images, and/or voice recordings.

System 10 includes one, two, or more sensors, sensor 100 shown. Sensor 100 can comprise one or more sensors that are positioned proximate (e.g. within and/or on) another component of system 10. Sensor 100 can comprise an ultrasound-based sensor, such as a piezo-based, CMUT-based, and/or other ultrasound-based sensor such as is described herein. In some embodiments, sensor 100 comprises one, two, or more sensors selected from the group consisting of: ultrasound-based sensor; capacitive touch sensor; optical sensor; electrical sensor; magnetic sensor; force sensor; pressure sensor; strain gauge; physiologic sensor; a microphone (e.g. for recording the voice of a user); camera (e.g. for recording the face of a user); and combinations of these. Sensor 100 can comprise a "detection area" which includes one or more 2D or 3D surfaces from which user input can be recorded, such as user input including: contact of a finger or other body portion of a user (e.g. to select an icon, type on a keyboard, and/or otherwise enter data into a user interface); an image of the user's tissue such as an image of a fingerprint or other tissue surface; temperature of tissue of a user; pulse oximetry and/or other physiologic information of a user; and combinations of these. In some embodiments, sensor 100 comprises an ultrasound-based sensor as described hereinbelow in reference to any one or more of FIGS. 2 through 19, FIGS. 20 through 28, FIGS. 29 through 45.

System 10 can include one, two, or more user devices, user device 500 shown. In some embodiments, sensor 100 is integral to user device 500. Each user device 500 can comprise a user interface, user interface 550 shown. User interface 550 can comprise one or more user input components and/or user output components, such as one or more components selected from the group consisting of: display; touchscreen display; a light such as an LED; switch; button; knob; a keypad such as a membrane keypad; keyboard; lever; joystick; speaker; microphone; vibrational transducer and/or other haptic transducer; a capacitive sensor or switch; an ultrasound-based sensor or switch; and combinations of these. Each user device 500 can comprise a communicator, such as communicator 570 shown, which can be configured to transfer information between user device 500 and another component of system 10, such as to transfer information between the components. Communicator 570 can comprise a wired communication assembly, such as when communicator 570 comprises a cable configured to operably (e.g. electrically) attach user device 500 to another component of system 10. Alternatively or additionally, communicator 570 can comprise a wireless communication module, such as an NFC and/or Bluetooth module configured to transfer information between user device 500 and another component of system 10. Each user device 500 can comprise one or more assemblies, functional assembly 580 shown, which can be configured to provide an output and/or otherwise perform a function for user device 500. Functional assembly 580 can comprise one or more assemblies which provide a function selected from the group consisting of: a cell phone function such as a communication function and/or a smartphone function; a transportation function; a storage function; a gaming function; a medical device function (e.g. a therapeutic and/or diagnostic function); a testing function such as a laboratory testing function; a manipulation function (e.g. an excavation function); a recreational function; a storage function such as a secure storage function; a data processing function; a computer function; a financial transaction function; and combinations of these.

In some embodiments, user interface 550 includes sensor 100, such as when user interface 550 comprises a multi-layer construction, and all or at least a portion of sensor 100 is integrated into one or more layers of interface 550, such as is described in reference to FIGS. 35 through 40 and otherwise herein. In these embodiments, user interface 550 can comprise a touch screen, and the integrated sensor 100 can comprise an ultrasound-based sensor (e.g. as described in reference to FIGS. 2 through 19, 20 through 28). In some embodiments, user interface 550 includes such an ultrasound-based sensor, but interface 550 is void of either or both of a capacitance-based sensor and/or an optical sensor (e.g. the ultrasound-based sensor 100 is configured to provide all user touch-based input to the user interface 550 and associated device 500). Alternatively, user interface 550 can comprise a sensor 100 that includes an ultrasound-based sensor, as well as either or both of a capacitive sensor and an optical sensor.

User interface 550 can comprise an integrated sensor 100 that can be constructed and arranged to receive user input from a majority of the "surface" of user interface 550 (e.g. the user-accessible surface portion of interface 550), such as when the detection area of sensor 100 (e.g. an ultrasound-based sensor as described herein) is at least 51%, at least 70%, at least 80%, and/or at least 90% of the visualizable portion of user interface 550.

In some embodiments, the detection area of sensor 100 (e.g. an ultrasound-based sensor as described herein) has an area of at least 10,000 mm$^2$, 40,000 mm$^2$, and/or 1,000,000 mm$^2$ and/or has a major axis of at least 20 cm, 40 cm, and/or 80 cm.

As described herein, user interface 550 and/or sensor 100 (e.g. a sensor 100 that is integral to interface 550 as described herein) can comprise a first sensor that is configured to operate at a first power level, and a second sensor that operates at a second power level that is greater than the first power level. In these embodiments, system 10 (e.g. controller 200 described herein) can be configured to operate in a lower power mode in which power is provided to the first sensor but not the second sensor (e.g. the second sensor is off or in a standby state). Contact and/or other activation by a user with the first sensor causes system 10 to provide power to the second sensor (e.g. to turn on or otherwise make the second sensor active). The second sensor can comprise an ultrasound-based sensor comprising multiple pixel elements as described herein, such as a sufficient number of pixel elements to identify one or more users via one or more fingerprints of the user. The first sensor can comprise a mechanical switch, a pressure sensor, a capacitive sensor, a low-resolution ultrasound-based pixel transducer array, and/or other low power sensor. In some embodiments, the first sensor and the second sensor comprise a sensor 100a and 100b, respectively, that are integrated into a user interface 550 of a device 500 (e.g. a cell phone, tablet, or other battery-operated device). Similar to sensor 100a, second sensor 100b can be constructed and arranged to receive user input from a majority of the "surface" of user interface 550 (e.g. the user-accessible surface portion of interface 550), such as when the detection area of sensor 100b (e.g. an ultrasound-based sensor as described herein) is at least 51%, at least 70%, at least 80%, and/or at least 90% of the visualizable portion of user interface 550. In some embodiments, the detection area of sensor 100b (e.g. an ultrasound-based sensor as described herein) has an area of at least 10,000 mm$^2$, 40,000 mm$^2$, and/or 1,000,000 mm$^2$. and/or has a major axis of at least 20 cm, 40 cm, and/or 80 cm.

System 10 can include one or more control modules, controller 200 shown, which can be configured to transmit signals to, and/or receive signals from, sensor 100.

Alternatively or additionally, controller 200 can be configured to interface two or more components of system 10 to each other. Controller 200 can comprise one or more electronic elements, electronic assemblies, and/or other electronic components, such as components selected from the group consisting of: memory storage components; analog-to-digital converters; rectification circuitry; state machines; microprocessors; microcontrollers; filters and other signal conditioners; sensor interface circuitry; transducer interface circuitry; and combinations thereof. In some embodiments, controller 200 comprises a memory storage component that includes instructions, such as instructions used by controller 200 to perform an algorithm, such as algorithm 60 described herein. In some embodiments, controller 200 is integral to a user device 500 (e.g. a user device 500 that comprises a sensor 100). Controller 200 can be configured to electrically, mechanically, acoustically, fluidically, optically, and/or otherwise operably connect two components of system 10 to each other, such as to operably connect sensor 100 to another component of system 10, such as to connect sensor 100 to user device 500 as described herein. Controller 200 can comprise various electronic components and circuitry that are configured to operably interface with one or more components of system 10, and/or to facilitate operably interfacing any component of system 10 with another component of system 10. In some embodiments, controller 200 comprises one or more application specific integrated circuits (ASICs), such as one, two, or more ASICs configured to transmit signals to and/or receive signals from one or more pixel elements of an ultrasound-based sensor 100 as described herein. In some embodiments, a single ASIC is configured to drive at least 250 transmit lines and at least 250 receive lines, as described herein. In other embodiments, multiple ASICs are configured to drive (e.g. in a parallel arrangement) at least 500, at least 1000, and/or at least 5000 pairs of transmit and receive lines.

System 10 can comprise FOB 600 shown. FOB 600 can comprise one, two, or more fobs and/or other handheld devices ("fobs" herein), such as a device configured to fit in a user's pocket, purse, wallet, and/or other user location such that fob 600 can easily be carried by the user in daily life activities. In some embodiments, FOB 600 comprises sensor 100 (e.g. and also controller 200). For example, FOB 600 can comprise at least an ultrasound-based sensor, as described herein, such as to identify the fingerprint of a user.

FOB 600 can comprise user interface 650 shown. In some embodiments, user interface 650 is of similar construction and arrangement as user interface 550 described herein.

FOB 600 can comprise an assembly, communicator 670 shown, which can be configured to transfer information between FOB 600 and another component of system 10, such as to transfer information between FOB 600 and user device 500 (e.g. when FOB 600 comprises sensor 100 and user information recorded by sensor 100 is transferred to user device 500 via communicator 670). Communicator 670 can comprise a wired communication assembly, such as when communicator 670 comprises a cable configured to operably (e.g. electrically) attach FOB 600 to device 500 and/or another component of system 10. Alternatively or additionally, communicator 670 can comprise a wireless communication module, such as an NFC and/or Bluetooth module that is configured to transfer information between FOB 600 and communicator 570 of user device 500 and/or a similar wireless module of another system 10 component.

System 10 can comprise one, two, or more accessory devices, accessory device 700 shown. Accessory device 700 can comprise one or more devices that function in cooperation with another system 10 component. In some embodiments, accessory device 700 comprises all or a portion of sensor 100 and/or all or a portion of controller 200.

System 10 can include one or more algorithms, algorithm 60 shown. Algorithm 60 can comprise a machine learning, neural network, and/or other artificial intelligence algorithm ("AI algorithm" herein).

Algorithm 60 can comprise an algorithm configured to detect an attempt at spoofing of a user confirmation routine performed by system 10.

Algorithm 60 can comprise an algorithm configured to analyze life signs of a user (e.g. pulse oximetry, blood glucose, heart rate, blood pressure, respiration, EKG, EEG, LFP, and/or neuronal firing), such as to identify and/or characterize a user via the analysis (e.g. an analysis of a single physiologic parameter or multiple physiologic parameters in combination).

Algorithm 60 can comprise an algorithm that analyzes fingerprint data to identify a user. In some embodiments, algorithm 60 comprises an algorithm that analyzes fingerprint data and another form of user data to identify a user, such as other data including: facial images (e.g. images produced by a camera of system 10); voice recordings (e.g. recordings produced by a microphone of system 10); physiologic data (also referred to as life sign data herein); and combinations of these.

System 10 can comprise one, two, or more computer networks, network 800 shown, such as a cellular and/or other wireless network, LAN, WAN, VPN, the Internet, and/or other computer network. In some embodiments, user information and/or other information collected and/or produced by a system 10 component is transferred via network 800 to one or more central locations, such as when this information comprises information related to use of system 10 by multiple users (e.g. of multiples of system 10) that is analyzed by system 10, such as by an algorithm 60 of system 10 as described herein. Such analysis of information from multiple users of system 10 can be used to improve the performance of system 10 with one or more users of system 10. In some embodiments, algorithm 60 comprises an AI algorithm that analyzes information from multiple users as collected via network 800.

System 10 can comprise one, two, or more functional elements, such as functional element 199 of sensor 100, functional element 599 of user device 500, functional element 699 of FOB 600, and/or functional element 999, each as shown. Each functional element 199, 599, 699, and/or 999 can comprise one, two, or more functional elements, such as one or more sensors and/or one or more transducers, such as are described herein.

Sensor 100 can comprise one, two or more sensors. Sensor 100 can comprise multiple sensors that are similar, and/or multiple sensors that are dissimilar (e.g. two or more different fingerprint sensors). Sensor 100 can comprise one or more sensors that are integral to (e.g. positioned on and/or within, and operably attached to) another component of system 10 (e.g. integral to user device 500), as well as one or more sensors that are integral to a different component of system 10 (e.g. integral to FOB 600, accessory device 700, and/or a different user device 500).

As described herein, sensor 100 can comprise at least an ultrasound-based sensor, such as a sensor comprising an array 150 including one, two, or more ultrasound transducers (e.g. piezo and/or CMUT elements) configured to transmit, receive, or both transmit and receive, ultrasound energy. In some embodiments, controller 200 is configured to drive array 150 (e.g. a 1D or 2D array of ultrasound transducers)

at a frequency of at least 1 MHz, 5 MHz, 10 MHz, 25 MHz, or 50 MHz, such as when controller 200 drives array 150 at a frequency between 50 MHz and 500 MHz, or between 12.5 MHz and 100 MHz. In some embodiments, controller 200 is configured to drive this ultrasound-based array 150 at a frequency of no more than 500 MHz, or no more than 750 MHz. Sensor 100 can be configured in a phase and/or delay measurement arrangement (e.g. and operate without a frequency limit). In some embodiments, sensor 100 is configured to perform transmit and receive beamforming of ultrasound transmissions.

In some embodiments, sensor 100 is configured to function, and have significant repeatability, specificity, or both, when operating in wet and/or "underwater" (e.g. submersed in fluid) conditions. System 10 and sensor 100 can be configured to operate under a wide variety of wet conditions. In some embodiments, sensor 100 is configured to have improved performance during wet conditions, such as when sensor 100 comprises a fingerprint detector that transmits ultrasound signals deeper into a finger when the finger is wet (e.g. when system 10 is configured to perform low frequency banking transaction confirmations and/or other high security scans). For operation in these wet conditions, and/or other conditions, sensor 100 can comprise a mass-loaded ultrasound transducer, such as a Langevin transducer. Sensor 100 can drive the center frequency of ultrasound delivery at a low level, such as a level low enough to pass through patient tissue.

In some embodiments, sensor 100 comprises an ultrasound array (e.g. a piezoelectric ultrasound array) including an arrangement of row electrodes and column electrodes as described herein. The row and column electrodes can comprise two sets of conductors (or "wires" or "traces") that are relatively orthogonal to each other, such as is described in U.S. Pat. No. 9,953,205. Alternatively, the two sets of conductors can be aligned at an angle of less than 90°, such as at an angle of no more than 89°, an angle between 1° and 89°, and/or at an angle of at least 45°. In some embodiments, the row and column electrodes have a uniform width along their length (e.g. a rectangular geometry). Alternatively or additionally, one or more of these electrodes of sensor 100 can comprise a non-uniform width, such as when the conductors narrow between the locations of the ultrasound transducers (e.g. a narrowing that allows more light to pass through the arrangement of conductors forming the set of row electrodes and column electrodes). In these non-uniform arrangements, the thickness of the conductors can be increased to achieve a similar resistance to that which would be present in a uniform arrangement (e.g. an increase in conductor thickness that can correlate to a change in the backing of the piezo transducer and/or the drive frequency of the transducer).

In some embodiments, sensor 100 comprises an ultrasound array (e.g. a piezoelectric ultrasound array) that provides a minimum resolution of a user's fingerprint (and/or other tissue surface of the user such as the palm or other tissue surface), such as a resolution of at least 100 pixels per inch, at least 200 pixels per inch (PPI), at least 350 PPI, at least 500 PPI, and/or at least 1000 PPI. In some embodiments, system 10 is configured to provide a resolution of at least 200 µm, such as a resolution of at least 200 µm, 75 µm, 50 µm, 25 µm, and/or 10 µm of a fingerprint or other image captured by sensor 100. In some embodiments, system 10 is configured to capture a minimum number of pixels of a fingerprint or other image captured by sensor 100, such as at least 15,000 pixels, at least 25,000 pixels, at least 35,000 pixels, at least 50,000 pixels, and/or at least 100,000 pixels.

In some embodiments, sensor 100 is configured as a touch sensor (e.g. to detect a tap or other touch by a user). In these embodiments, sensor 100 can be further configured as a fingerprint sensor or other sensor that identifies a particular user.

In some embodiments, sensor 100 comprises an ultrasound-based sensor 100*a* and a light-based sensor 100*b* positioned behind sensor 100*a* such that light delivered and/or received by sensor 100*b* passes through sensor 100*a*, such as is described in U.S. Pat. No. 10,691,912.

In some embodiments, sensor 100 comprises at least a light sensor configured to assess the aliveness of a user and/or to assess another physiologic parameter of the user.

In some embodiments, sensor 100 is configured to provide feedback to a user of system 10, such as thermal and/or mechanical feedback as described herein. For example, sensor 100 can comprise an ultrasound-based sensor that is configured to provide thermal (e.g. heating) and/or mechanical (e.g. force) feedback to a user. In these embodiments, a user device 500 including both a user interface 550 (e.g. a touchscreen or other display) as well as sensor 100, can be configured to operate in a "dark mode" where communication to the user can be provided via the thermal, mechanical, and/or other haptic feedback, without the need for the user to visualize user interface 550 (e.g. providing the ability to "stay dark" such as in a military or policing operation, and/or when device 500 is in the user's pocket or other personal hidden storage location). In some embodiments, the form and/or level of feedback changes based on the amount of "battery life" remaining (e.g. the energy remaining in a battery and/or other energy source of system 10, such as an energy source of user device 500), such as when the changes in form and/or level of feedback are determined by algorithm 60.

As described hereinabove, sensor 100 can be configured to provide feedback, instructions, and/or information ("feedback" herein) to a user of system 10. For example, feedback provided to a user can comprise a vibration, thermal sensation, audio signal (e.g. a beep) and/or other non-textually provided feedback that indicates to a user (e.g. via training) that an action is to be taken by the user (e.g. applying a different finger to user interface 550, moving a currently contacting finger to a new location, and/or performing another physical activity). The feedback provided can comprise at least a thermal sensation, such as when sensor 100 causes an increase in temperature of the patient's finger or other tissue of the patient. For example, sensor 100 can comprise a platen (e.g. a glass platen), as described herein, and controller 200 can be configured to provide a drive signal to array 150 of sensor 100 that matches the platen's resonance frequency, resulting in a power transmission into tissue (e.g. the finger) of the user in contact with sensor 100 that causes a thermal haptic sensation. In some embodiments, controller 200 provides enough power to cause a tissue temperature increase associated with "thermal touch" feedback, such as a tissue temperature increase of at least 0.2° C., such as at least 0.5° C., at least 1.0° C., at least 5.0° C., and/or at least 10.0° C. In some embodiments, controller 200 is configured to cause a tissue temperature increase of no more than 4° C., no more than 10° C., no more than 20° C., and/or no more than 30° C. In these embodiments, the platen can comprise a uniform thickness, such that the platen creates a resonant acoustic cavity. When controller 200 provides a drive signal with a frequency that matches the resonance of this cavity, multiple reflections within the platen can sum in a constructive way while transmitting into the finger. In these embodiments, the drive signal provided by controller 200 can comprise a continuous wave/tone burst signal (e.g. not pulse excitation). The resonant based feedback described above can be configured to provide a mechanical sensation to the user (e.g. as an alternative to, or in addition to thermal feedback, such as by modulating the drive signal, such as at a frequency of 300 Hz). In some embodiments, controller 200 is configured to provide a chirp signal that causes an ultrasound-based array 150 to transmit ultrasound waves at different frequencies (e.g. as a way of adjusting the frequency to match the platen resonant frequency). In some embodiments, the mechanical, thermal, and/or other feedback provided by sensor 100 to the user is adjustable and/or calibratable.

In some embodiments, system 10 is configured in a "no-look mode", such as to provide feedback and/or any information (e.g. text provided in braille) without requiring sight of the user, or visual attention of the user to user interface 550, user interface 650, and/or other display portion of system 10 (e.g. such as when the user is blind, or user device 500 is in a pocket, purse, or other non-line of sight location relative to the user). In these embodiments, system 10 can be configured to provide thermal, mechanical, and/or other haptic feedback to the user representing various forms of information.

In some embodiments, system 10 is configured in an "enhanced feedback mode", such as to provide haptic feedback (e.g. thermal or mechanical feedback as described herein) as well as visual feedback. This enhanced feedback mode can be used to improve the experience of using a gaming and/or other application of user device 500. In some embodiments, device 500 is capable of receiving (e.g. downloading) third-party applications, and sensor 100 is configured to provide haptic feedback that is used by these applications. In some embodiments, system 10 comprises a calibration function that is configured to adjust the feedback provided to a third-party application.

In some embodiments, sensor 100 comprises multiple sensors (e.g. multiple similar sensors) that are arranged in a close-proximity arrangement (e.g. the periphery of each sensor borders the periphery of a neighboring sensor), where these multiple sensors can be collectively configured (e.g. in an interface arrangement) to function as a single sensor (e.g. via electronic "stitching" via controller 200). For example, sensor 100 can comprise: 3 sensors in a 1 by 3 array; 4 sensors arranged in a 1 by 4 array, or in a 2 by 2 array; 6 sensors arranged in a 1 by 6 array, or in a 2 by 3 array; and the like. These multiple sensors of sensor 100 can be constructed and arranged (e.g. attached to a flexible or hinged substrate) to rotate relative to each other (e.g. at least two sensors rotate relative to each other), such as when included in a device configured to flex (e.g. a smart card or other device in which flexibility or at least flexing provides an advantage). Each of the multiple sensors of sensor 100 can comprise an array of one, two, or more ultrasound transducers, (e.g. multiple piezo and/or CMUT transducers), such that the multiple arrays of ultrasound transducers can pivot relative to each other, yet otherwise function as a single array of transducers (e.g. multiple arrays that collectively provide a larger effective sensing area than any of the individual arrays, yet can pivot relative to a neighboring array to provide more flexibility as compared to a single area of similar area). In some embodiments, sensor 100, and/or another component of system 10, is configured to monitor and/or otherwise determine the relative positions between multiple sensors (e.g. multiple individual and/or multiple sets of two or more pixel transducers and/or other piezoelectric sensors as described herein). The relative positions of the sensors can be used for one or more purposes, such as to perform beamforming across the sensors, stitching together of images (e.g. fingerprint images or other tissue images), and other functions associated with the relative position of multiple sensors. In some embodiments, delivering and/or receiving ultrasound energy (e.g. by the multiple sensors of sensor 100) is used to determine the position of those sensors and/or other sensors of sensor 100.

In some embodiments, user device 500 comprises all or a portion of sensor 100, and/or all or a portion of controller 200.

In some embodiments, user device 500 comprises one, two, or more devices for which access to the user device 500 and/or user operation of the user device 500 is provided after a confirmation routine (also referred to as an "identification routine) is performed by system 10. A confirmation routine can comprise one, two, or more confirmation routines selected from the group consisting of: identification of a user, such as via one or more fingerprints of the user (e.g. as described herein); recognition of the user's face; confirmation of acceptable "health condition" of the user (e.g. the user is alive, and/or the user is in a safe physical and/or mental state); confirmation that the user is not under significant influence of alcohol and/or drugs (e.g. the user is not intoxicated per applicable standards); and combinations of these.

User device 500 can comprise a cell phone, such as a smartphone.

User device 500 can comprise a device that is worn by a user, such as a smartwatch or other watch device.

User device 500 can comprise a computer device, such as a laptop or a tablet.

User device 500 can comprise a user protection device, such as a gun or a taser.

User device 500 can comprise a transportation device, such as a car, motorcycle, bus, boat (e.g. a yacht), airplane, helicopter, and/or other vehicle.

User device 500 can comprise a piece of equipment (e.g. construction equipment), such as a bulldozer, crane, and/or excavation device. User device 500 can comprise a piece of lab equipment.

User device 500 can comprise a "card device", such as a credit card, personal ID card, passport, and/or driver's license.

User device 500 can comprise a memory storage device such as a USB drive.

User device 500 can comprise a crypto wallet device.

User device 500 can comprise a user device selected from the group consisting of: a door lock; a medicine cabinet lock; a storage device such as a gun storage container and/or a storage facility; child lock; and combinations of these.

User device 500 can comprise a medical device. For example, user device 500 can comprise a medical device configured to provide a therapy, such as when system 10 is configured (e.g. via data provided by sensor 100) to confirm the identity of a healthcare professional that, once confirmed, sets and/or modifies the therapy provided by the medical device. User device 500 can comprise a medical device that allows input of medical information, such as when system 10 is configured (e.g. via data provided by sensor 100) to confirm the identity of a healthcare professional that, once confirmed, can enter and/or modify the medical information. In some embodiments, system 10 can be configured to be used by multiple healthcare workers (e.g. doctors, nurses, and/or other healthcare workers), where different users have different levels of authority, where the different levels of authority correlate to different levels of permissions in changing or accessing medical information of a patient, and/or changing settings of a user device 500 (e.g. changing therapeutic parameters of a user device 500 comprising a medical device).

User device 500 can comprise two, three, or more devices selected from the group consisting of: a phone such as a smartphone or other cell phone ("smartphone" or "cell phone" herein); a computer device; a user protection device; a transportation device; a piece of equipment; a card-based device; a memory storage device; a crypto wallet device; and combinations of these.

As described herein, system 10 can comprise fob 600. In some embodiments, fob 600 comprises all or a portion of sensor 100, and/or all or a portion of controller 200. Fob 600 can be configured to transmit information to user device 500, such as via a wired and/or wireless connection. In some embodiments, fob 600 comprises at least a portion of sensor 100 (e.g. and at least a portion of controller 200) and is configured to identify one or more fingerprints of a user and/or otherwise perform a confirmation routine on a user, as described herein. In these embodiments, once the user can be confirmed by fob 600 (e.g. it is an acceptable user and/or the user is in an acceptable health condition), this confirmation can be transmitted to user device 500 (e.g. a user device that otherwise is not configured to perform a fingerprint scan and/or other user confirmation). In some embodiments, fob 600 comprises a sensor 100 that comprises an ultrasound-based fingerprint sensor 100a, and a light-based sensor 100b (e.g. a light-based sensor configured as a pulse oximeter such as a reflective oximeter), such as when sensor 100a is transmissive of the light sent by sensor 100b (e.g. when sensor 100b is positioned behind the sensor 100a).

FOB 600 can comprise sensor 100, such as when sensor 100 comprises at least an ultrasound-based sensor as described herein. Alternatively or additionally, FOB 600 can comprise a sensor 100 comprising a physiologic sensor (e.g. a pulse oximeter or other light-based physiologic sensor). For example, FOB 600 can comprise a sensor 100 comprising a first sensor 100a that comprises an ultrasound-based sensor (e.g. a fingerprint sensor) and a second sensor 100b that comprises a light-based sensor whose light transmissions pass through sensor 100a (e.g. when sensor 100a is configured to pass light therethrough), such as is described in U.S. Pat. No. 10,691,912.

FOB 600 can be configured to identify the fingerprint of a user, and/or perform another user identification as described herein, and transfer the confirmation of the user to user device 500 (e.g. when user device 500 does not include a fingerprint sensor or other sensor to identify a user).

In some embodiments, system 10 is configured to identify a user using two, three, or more identification routines (e.g. as described herein) selected from the group consisting of: ultrasound-based fingerprint identification; capacitive sensor-based fingerprint identification; life-sign recognition (e.g. using a pulse oximeter or other light-based physiologic sensor); life sign identification; and combinations of these, such as are described herein.

In some embodiments, system 10 is configured to perform a calibration routine, such as a calibration routine configured to calibrate a sensor 100 comprising a single sensor, and/or a sensor 100 comprising multiple sensors (e.g. multiple similar and/or dissimilar sensors). In some embodiments, system 10 is configured to perform a calibration routine after a portion of system 10 is damaged (e.g. a portion of sensor 100 and/or a portion of user device 500 proximate sensor 100 is damaged) or otherwise is functioning improperly, such as to allow use of system 10 after this calibration is performed. For example, sensor 100 can comprise an array of elements (e.g. ultrasound elements), and after damage to some of the elements is detected, a calibration routine can be performed in which the non-damaged portions of sensor 100 are used, the damaged portions are no longer used, and an identification routine of the present inventive concepts can successfully be performed using the non-damaged portions of sensor 100. In another example, user device 500 can comprise a cell phone that has a cracked portion of a screen of user interface 550 through which sensor 100 sends and/or receives transmissions, and the calibration routine can be performed to accommodate the cracked screen and allow successful completion of a user identification routine. In some embodiments, a device 500 can be modified after an initial calibration routine, after which a second calibration routine is performed (e.g. must be performed). For example, user device 500 can comprise a cell phone upon which a protective case, screen protector, or other covering is added, and system 10 can be configured to perform a calibration routine (e.g. a second calibration routine) to compensate for the added covering.

System 10 can be configured to authenticate a user or group of multiple users in a financial transaction, such as a bank transfer. In some embodiments, multiple devices 500 (e.g. multiple cell phones), each including a sensor 100, are used to authenticate a single user and/or multiple users.

In some embodiments, system 10 is configured to perform a confirmation routine multiple times during the use of device 500, such as to confirm the user hasn't changed, and/or the user's health condition hasn't changed. For example, system 10 can require successful completion of a confirmation routine on a periodic and/or random basis, such as when the user device 500 comprises a car, plane, and/or piece of equipment, and repeated confirmations are required to prevent one or more of: switching of users; prolonged use by a single user; and/or use by a user whose health condition has become unacceptable.

In some embodiments, system 10 comprises a first component C1 (e.g. FOB 600) that comprises a first sensor 100a, and a second component C2 (e.g. device 500) that comprises a second sensor 100b. Sensor 100a can be configured to collect two different forms of data from a user, such as data classified as "confidential data" (e.g. fingerprint data, facial recognition data, voice recording data, and/or other data the user may wish to remain confidential), data CD herein, and data classified as "non-confidential data" (e.g. facial recognition data, voice recording data, physiologic data such as current physiologic data), data NCD herein. Sensor 100b can be configured to at least collect non-confidential data NCD. In an authentication procedure, C1 can collect both confidential and non-confidential data from a user, $CD_1$ and $NCD_1$ respectively, and C2 can collect non-confidential data (e.g. similar non-confidential data) from the user, $NCD_2$. Data $NCD_1$ and $NCD_2$ can be collected at the same time (e.g. the user interfaces with C1 and C2 simultaneously or at least within a short time period, such as within minutes). The data $NCD_2$ can be transmitted from C2 to C1. C1 can perform a confirmation routine of the user via first confirming the user based on the confidential information $CD_1$ collected by C1. Once that confirmation is successfully completed, C1 can perform a comparison of $NCD_1$ and $NCD_2$, in order to confirm the non-confidential data $NCD_2$ collected by C2 is from the same user. If the comparison indicates the same user interfaced with each device, data representing a confirmation of the user can be transmitted from C1 to C2. In these embodiments, confirmation of a user can be provided to a device (e.g. C2 as described hereinabove), without C2 ever receiving the confidential information of the user (i.e. the user can use their fingerprint, facial image, voice data, and/or other data that the user wants to remain confidential in a confirmation routine for the user, without having to share that confidential data with a device separate from FOB 600). In some embodiments, C2 can be configured to perform a confirmation routine comprising receiving $NCD_1$ from C1 (e.g. after C1 confirms $CD_1$ is associated with the correct user), where C2 compares the received $NCD_1$ to the $NCD_2$ collected by C2. In some embodiments, C1 comprises FOB 600, and C2 comprises a user device 500 (e.g. cell phone, computer, an ATM or other financial transaction device, and the like). In some embodiments, $NCD_1$ and $NCD_2$ comprise data input by a user (e.g. not recorded by the associated sensor 100). For example, $NCD_1$ can comprise an alphanumeric or other code that is presented to the user (e.g. via C1) and entered by the user into C2 as $NCD_2$, such as when configured as a 2-factor authentication routine. In some embodiments, data CD and/or data NCD is collected from multiple users of system 10, such as when a first user confirms the identity of a second user, or confirmation from multiple users is required in order to perform an event (e.g. a financial transaction). In some embodiments, component C1 described hereinabove (e.g. FOB 600) is configured for single use (e.g. a single confirmation of the user), and FOB 600 can be destroyed or otherwise disposed of after its use. In some embodiments, FOB 600 is configured for use (e.g. and provided) by an accredited agency (e.g. a notary, a government authority, or the like) to a user. For example, the agency can identify the user via one or more means (e.g. driver's license, passport, fingerprint, facial recognition, and/or voice recognition), and then configure FOB 600 to be assigned to the user (e.g. via collecting and storing in FOB 600 data representing the user's fingerprint, face, voice, or other data collectable by an integrated sensor 100), such as to perform future confirmation routines for that user (e.g. to provide confirmed electronic digital signatures such as those provided by service providers such as DocuSign, provide an alternative to a notary, and the like).

In some embodiments, a confirmation routine performed by system 10 can be configured to confirm multiple fingerprints from a user (e.g. as pre-assigned by the user and/or system 10), such as at least one from each hand of the user. During a confirmation routine, the multiple fingerprints are collected (e.g. by sensor 100) and confirmed (e.g. by algorithm 60). In some embodiments, a particular sequence of collecting the fingerprints is also required for proper confirmation (e.g. a sequence pre-assigned by the user and/or by system 10). In some embodiments, system 10 provides feedback to the user (e.g. via user interface 550, and/or 650) as to which fingerprint is to be collected next (e.g. via a graphical image of the user's left and/or right hands).

In some embodiments, user device 500 comprises a housing, such as a metal or plastic housing surrounding at least a portion of each of user interface 550, communicator 570, functional assembly 580, and/or functional element 599. For example, user device 500 can comprise a smartphone including user interface 550 comprising a touch screen defining the front of the phone and a housing surrounding the back and sides of the phone. In some embodiments, as described herein, sensor 100 can be integrated into user interface 550, such that sound produced by and received by sensor 100 travels through at least a portion of user interface 550. Alternatively or additionally, sensor 100 can be integrated into a housing of user device 500, such that sound produced by and received by sensor 100 travels through at least a portion of the housing (e.g. when the user places their finger on a portion of the housing).

In some embodiments, accessory device 700 comprises a device configured to be positioned proximate (e.g. surround at least a portion of) user device 500, for example a protective device, such as a screen protector and/or a phone case. Sensor 100 can be integrated into accessory device 700. In some embodiments, sensor 100 (e.g. a sensor 100 positioned within a cover-based accessory device 700 and/or a sensor 100 positioned within user device 500) is configured to receive power from user device 500, such as wirelessly transmitted power provided via inductive coupling. Alternatively or additionally, sensor 100 can receive power from a wired connection of user device 500, such as when sensor 100 (e.g. sensor 100 integrated into accessory device 700) connects to user device 500 via a USB connection. In some embodiments, sensor 100 is configured to communicate with user device 500, such as via a wired or wireless communication (e.g. via NFC, Bluetooth, or other short-range wireless communication methods).

In some embodiments, user interface 550 has an integrated ultrasound-based sensor 100, such as a sensor comprising an array of conductors (also referred to as "wires", "lines" and/or "electrodes" herein) in an orthogonal and/or other X-Y arrangement. The sensor 100 can be constructed and arranged to have a relatively thin profile, such as a sensor 100 with a thickness less than or equal to 40 μm, and/or 20 μm. The user interface 550 can comprise an "exposed surface area" (e.g. a user viewable, contactable, and/or otherwise accessible surface area) that is at least 25 $mm^2$ in area, such as at least 10,000 $mm^2$, and/or at least 40,000 $mm^2$. In some embodiments, sensor 100 is configured to record swiping motion of a user's finger, and a user interface 550 into which sensor 100 is integrated can comprise an area of at least 5 $mm^2$ and/or 10 $mm^2$. An ultrasound-based sensor 100 can be integrated into a user interface 550 such as when the sensor 100 is adhesively attached to or directly deposited onto (e.g. without the use of adhesives) a display (e.g. an OLED, microLED, LCD, and/or other display) of user interface 550. An ultrasound-based sensor 100 can include a detection area that is at least 50% of the exposed surface area of the interface 550 (e.g. at least 50% of the viewable portion of the integrated OLED or other display). In some embodiments, an ultrasound-based sensor 100 can have a detection area that is at least 75%, 85%, and/or 95% of the interface 550 exposed surface area. In some embodiments, the detection area of the ultrasound-based-sensor 100 has an area of at least 10,000 $mm^2$, 40,000 $mm^2$, and/or 1,000,000 $mm^2$ and/or has a major axis of at least 20 cm, 40 cm, and/or 80 cm. The ultrasound-based sensor 100 can be configured to detect contact of a user (e.g. contact via one or more fingers of a user), record fingerprints and/or other physiologic information of a user, or both. The ultrasound-based sensor 100 can comprise an X-Y arrangement of conductors (e.g. as described herein) that are positioned at varied densities, such as varied separation distances between conductors. For example, at least one portion of a detection area can have a density sufficient to identify a fingerprint of a user, while at least one other portion can be at a lower density, such as a density sufficient to detect contact of a user. In some embodiments, the ultrasound-based sensor 100 is relatively transparent, or includes one or more relatively transparent portions, such that light passes through the sensor 100, such as to allow a user to visualize a display positioned beneath the sensor 100 and/or to allow diagnostic light (e.g. for pulse oximetry) to pass through the sensor 100. As described herein, a user interface 550 comprising an integrated sensor 100 can comprise a multi-layer (e.g. laminate) construction. In these embodiments, the thickness of one or more layers can be based on the acoustic wavelength of ultrasound transmitted and/or received by the sensor 100 of the user interface 550. For example, the user interface 550 can comprise an adhesive layer that has a thickness that is configured to maximize ultrasound transmission through that layer.

Sensor 100 can comprise an ultrasound-based sensor comprising one or more portions (e.g. layers) that are deposited (e.g. sputtered onto, spun onto, printed onto, baked on, thin film deposited, vapor deposited, lithography deposited, and/or otherwise directly deposited) onto a layer of one or more materials selected from the group consisting of: a platen or other substrate layer (e.g. a glass or plastic platen as described herein); a surface of a display (e.g. an OLED or other display); a previously deposited layer of sensor 100; any layer of material (e.g. a substrate layer of a user interface 550); and combinations of these. In these embodiments, sensor 100 can be relatively fixed to another component (e.g. a layer of interface 550 as described herein), without the need for any adhesive.

In some embodiments, a user interface 550 comprises a first ultrasound-based sensor 100, and a second ultrasound-based sensor 100. In these embodiments, the first sensor 100 and the second sensor 100 can be positioned on opposite sides of a display (e.g. an OLED or other display) of interface 550, such as is described in reference to FIGS. 38A-B herein. The first sensor 100 can be relatively transparent (e.g. include at least one relatively transparent portion) such that the first sensor 100 can be positioned above the display (e.g. without obstructing a user's view of the display). In these embodiments, the user interface 550 can be integrated into a device 500 (e.g. a cell phone, tablet, and/or other handheld electronic device) and user input (e.g. commands and/or images such as fingerprints) can be captured via user contact (e.g. finger contact) on either or both sides of the device.

Figure 38A:
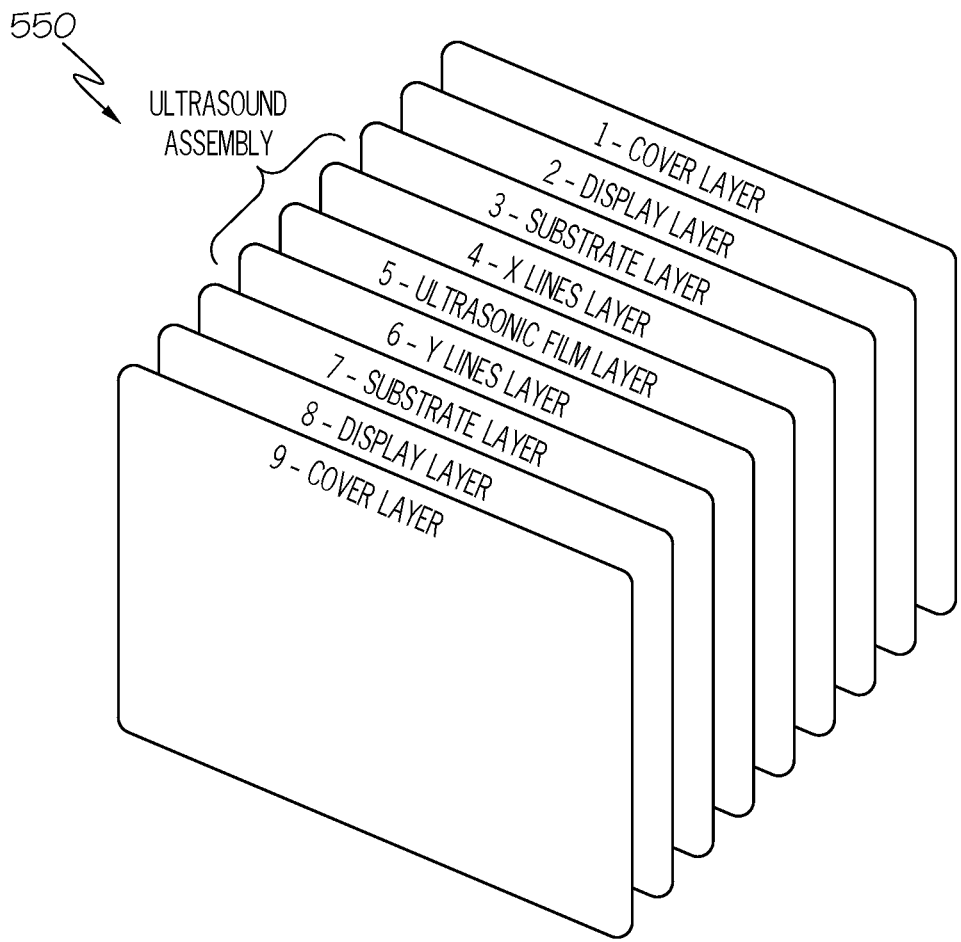
Figure 38B:
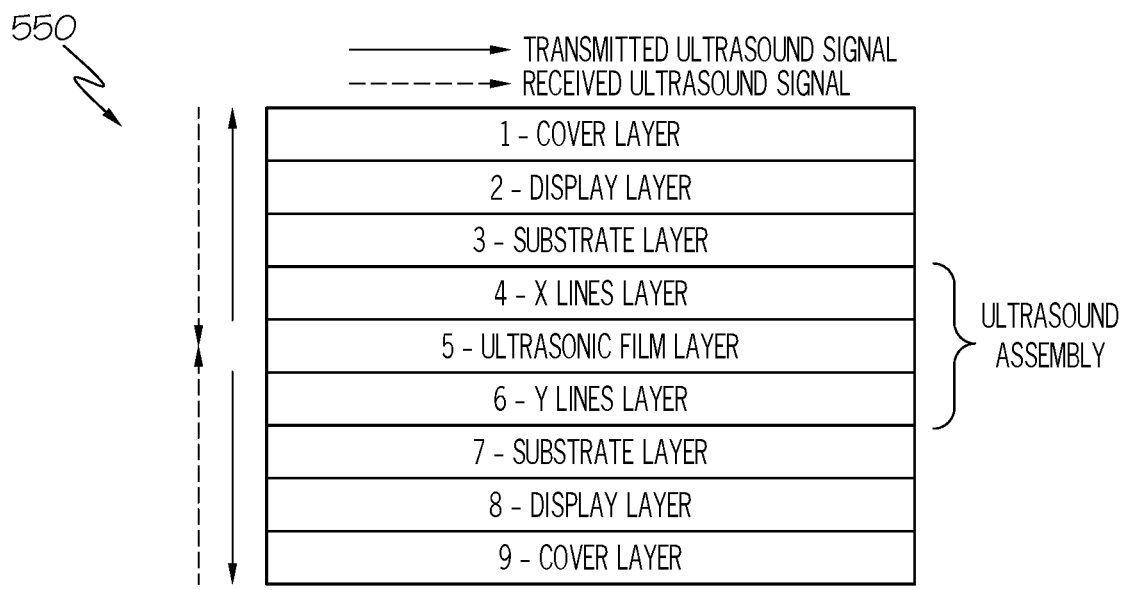

In some embodiments, a user interface 550 comprises two displays that are positioned on either sensor of an ultrasound-based sensor 100, such as is described herein in reference to FIGS. 38A-B.

In some embodiments, device 500 (e.g. including a user interface 550 with an integrated ultrasound-based sensor 100) comprises a controller for a gaming device (e.g. a gaming table or other gaming device including a user-interface portion with a detection area comprising a major axis or a major diameter of at least 20", 30", and/or 40"). For example, user interface 550 can comprise a sufficient detection area and be configured to allow use by multiple users, such as multiple users that are sitting in chairs and/or standing in an arrangement that allows a comfortable space between the users. In some embodiments, user interface 550 is configured to differentiate touch between different users (e.g. via fingerprint recognition) as described herein.

In some embodiments, sensor 100 is flexible, such as when sensor 100 comprises wires (e.g. transmit and/or receive wires) that are directly deposited onto a layer of piezoelectric material.

In some embodiments, sensor 100 comprises a set of wires (e.g. transmit and/or receive wires), wherein at least a portion of the set of wires are positioned at varied density (e.g. varied separation distances between pairs of wires).

System 10, via sensor 100, can be constructed and arranged to identify, characterize, and/or differentiate contact by multiple fingers, simultaneously or sequentially, such as at least 2, 3, 4, 5, 6, and/or 11 fingers. In some embodiments, the multiple fingers are fingers of multiple users, such as at least 2, 3, 4, 5, 6, and/or 11 fingers. In some embodiments, sensor 100 comprises a first sensor 100*a* positioned on a first user interface 550*a* and a second sensor 100*b* positioned on a second user interface 550*b*, and system 10 (e.g. a system being used by multiple users to play video games or other multi-user programs) is configured to detect one or more fingerprints of each of one or more users, via each sensor 100. Alternatively or additionally, system 10 can be configured to identify (e.g. via algorithm 60) one or more fingerprints from multiple users via a single sensor 100 (e.g. a single sensor 100 integrated into a single display of a user interface 550, such as a single display which is accessed by the fingers of multiple users). For example, device 500 or another system 10 component can be configured to detect multiple fingerprints such as to differentiate one user from another (e.g. to control an application based on the particular user providing the input), and/or to differentiate one finger from another finger of a single user (e.g. to control an application by which particular finger of a particular user is providing the input). In some embodiments, sensor 100 comprises at least one high-density sensing area, and at least one low-density sensing area, such as when the high-density sensing area comprises sets of X and Y conductors that are closer together than those of the low-density sensing area. In these embodiments, the high-density sensing area can comprise one, two, or more areas that are configured to detect fingerprints from two or more users. In these embodiments, a multi-user confirmation can be required to perform a task, such as to initiate a medical procedure, a weapon strike, a large financial transaction, and/or other event in which agreement to initiate from multiple users is required. In some embodiments, device 500 comprises a vehicle (e.g. a plane) and/or a piece of equipment, in which multiple users control device 500, such as when confirmation of the identify of both users is performed by device 500 via sensor 100 (e.g. fingerprint detection and/or other confirmation as described herein as detected by one, two, or more sensors 100). In these embodiments, after user identification, certain functions of the device may be available to one user (e.g. one of two pilots, or one of two equipment operators) that are not available to the other user, and/or vice versa. In some embodiments, device 500 comprises a large-scale user interface device that can be positioned in a public place (e.g. an airport or town square) and accessed by multiple users (e.g. at least 3, 5, or 10) simultaneously. For example, the device 500 can comprise a user interface 550 with a large aspect ratio (e.g. large width as compared to height), such as to be used by multiple users simultaneously to: request transportation, order a meal, make a reservation, and the like. In this configuration, system 10 can be configured to differentiate one user from another based on fingerprint data obtained via sensor 100, such as if users change their position when accessing the device 500.

In some embodiments, sensor 100 comprises an ultrasound-based sensor 100 that is configured to capture (e.g. image) the majority of a user's hand (e.g. palm), where a particular user can be identified by the captured data.

In some embodiments, sensor 100 comprises an ultrasound-based sensor 100 that comprises sets of X and Y conductors as described herein. The thickness, width, and/or length of these conductors can be based on the layer (e.g. a plate) on which the conductors are located. In some embodiments, the piezoelectric layer comprises PVDF (e.g. applied as large sheets or spun on similar to a photoresist process), and the sensor 100 can be operated in the 25 MHz to 50 MHz frequency range. In some embodiments, the piezo layer comprises a layer with a thickness of between 9 μm and 10 μm. For a resolution of 1 mm, the conductors can be positioned with a periodicity of 1 mm (e.g. 0.5 mm conductor width with 0.5 mm spacing). For a sensor 100 with larger resolution, the periodicity can be increased accordingly. The length of the X and Y conductors can be based on the particular use (e.g. application) of sensor 100, such as to accommodate a large display (e.g. a display with a major axis or major diameter of at least 20", 30", and/or 40") for a gaming device (e.g. a gaming table) and/or public display application, or a relatively small display applicable to a cell phone. Longer conductors will tend to have an increased thickness, such as to reduce overall resistance of the conductor. Thickness of the conductors can be at least 0.1 μm, such as at least 0.2 μm, 0.5 μm, 1.0 μm, and/or 2.0 μm. In some embodiments, conductor thickness is chosen based on power requirements of the system.

In some embodiments, system 10 is configured to capture a fingerprint of a user at an accelerated rate. System 10 can identify a user's fingerprint in two steps, a fingerprint "data acquisition" step, and a fingerprint "data processing" step. The data acquisition step includes acquiring the user's fingerprint information and converting analog data produced by sensor 100 (e.g. an ultrasound-based sensor as described herein), to digital data that can be processed by controller 200. Subsequently, the data processing step can be performed in which controller 200 processes the sensor 100 data, such as processing which occurs in several steps in order to determine whether or not a particular user is confirmed via the fingerprint data.

The duration of the data acquisition step is dependent on the number of transmit and receive events (TR-RX events) performed by sensor 100, which are dependent on the numbers of X and Y conductors that are used to transmit and receive (e.g. all conductors present and/or a subset of those), and the number of parallel read-outs (e.g. signal acquisition of all the X or Y conductors). The data acquisition time $T_{DA}$, can be determined by the following:

$$T_{DA}=(\text{Number of } TX\text{-}RX \text{ events})\times(\text{Duration of a single } TX\text{-}RX \text{ event})\times(\text{Number of Averages})$$

In some embodiments, sensor 100 comprises 250 transmit conductors (e.g. 250× conductors) and 250 receive conductors (e.g. 250 Y conductors), where a single conductor is used to transmit and a single conductor is used to receive in each TR-RX event. In this configuration the total number of TR-RX events is equal to: 250 times 250 divided by 2, or 31,250.

The duration of a single TX-RX event is the minimum wait time that is needed between sequential TX-RX events. This wait time is based on the time it takes for the ultrasound echoes reverberating inside the sensor 100 platen to die down (to avoid an overlap of echoes before consecutive TX-RX events), and the wait time is determined by parameters that include the sensor 100 platen material speed of sound, thickness, and associated attenuation. In some embodiments, sensor 100 comprises a ZnO sensor, and the wait time is 1 μs.

Averaging is the process of acquiring a set of replicate measurements from the same TX-RX location, then taking the average of all these measurements. Averages reduce the noise and increase the signal-to-noise ratio by filtering out uncorrelated noise that usually exists in electronic systems. Higher numbers of averages yield higher SNR values, and system 10 can be configured to perform a minimum number of averages (e.g. 16 or more). In some embodiments, system 10 does not perform averaging.

In some embodiments, sensor 100 comprises 250 transmit conductors and 250 receive conductors, as described hereinabove, and the current total data acquisition time without averaging equals 31.25 ms, and with averaging equals 500 ms. In some embodiments, system 10 includes additional (e.g. more than two) parallel read-out circuits (e.g. includes more electronic circuitry and its associated power drain and product volume). For example, system 10 can include 16 read-out circuits, and the associated data acquisition times will be reduced to 3.9 ms and 62.5 ms (without and with averaging, respectively). In some embodiments, sensor 100 is configured to reduce data acquisition time.

In some embodiments, sensor 100 can comprise an ultrasound-based sensor comprising a deposition of a piezoelectric on a platen (e.g. a glass platen), along with conductors (e.g. metal lines) above and below the piezo layer. The piezoelectric (e.g. zinc oxide, ZnO) can be deposited directly onto a display (e.g. an OLED or other display) of user interface 550. The sensor 100 can be of relatively thin construction, such as when comprising a thickness of no more than 40 μm, 30 μm, and/or 20 μm. As described herein, sensor 100 can be integrated into user interface 550 without the need for an adhesive bond (e.g. without the need for an epoxy layer and/or other adhesive attachment of sensor 100 to a display or other layer component of interface 550). Sensor 100 and user interface 550 can be manufactured in a single process. In some embodiments, sensor 100 and user interface 550 are tested (e.g. manufacturing quality tested) as a single assembly (e.g. a user interface 550 comprising an integrated sensor 100). In some embodiments, sensor 100 comprises an ultrasound-based sensor comprising X and Y conductors as described herein, and at least one set of the conductors is deposited onto a substrate (e.g. glass) portion of a display (e.g. an OLED or other display) of user interface 550, prior to the entire display being manufactured (i.e. one or more portions of the display are assembled to the display after the depositing of the X and/or Y conductors). The conductors can be deposited onto a portion of a display via sputtering, lithography, and/or other depositing process (e.g. as described herein). Manufacture of an interface 550 with an integrated sensor 100 can be performed in an assembly line (e.g. one after the other) manufacturing process, and/or in a batch mode (e.g. a mode in which multiples, such as at least 10 at a time are manufactured, such as when conductors of at least 10 sensors 100 are simultaneously deposited onto a corresponding at least 10 displays of 10 user interfaces 550.

In some embodiments, sensor 100 comprises a "flexible sensor" such as a sensor that includes one or more flexible portions or is relatively flexible in its entirety. Sensor 100 can comprise an ultrasound-based flexible sensor including a flexible layer of polyvinylidene fluoride (PVDF). In these embodiments, device 500 can comprise a "flexible device" such as a device that comprises one or more flexible portions that support some level of bending, such as a credit card configured to support slight bending (e.g. when located in a wallet) without being damaged. Sensor 100 can comprise a flexible sensor that is attached to (e.g. directly deposited onto or adhesively attached) to a display (e.g. an OLED or other display), such as a display of user interface 550.

In some embodiments, sensor 100 comprises an ultrasound-based sensor comprising X and Y conductors, as described herein, and the sensor 100 can be further configured as a capacitive-touch sensor (e.g. detect contact of a user based on a measured capacitance change). In these embodiments, sensor 100 can be configured to transfer between a low power capacitive touch sensing mode and a higher power ultrasound transmitting and receiving mode (e.g. a mode in which at least two sets of at least 128 conductors, or at least 256 conductors actively transmit and receive ultrasound waves). In these embodiments, sensor 100 can comprise a detection area that occupies a majority (e.g. at least 50%, 75%, 85%, and/or 95%) of the exposed surface area of a user interface 550 into which sensor 100 is integrated. In some embodiments, the detection area of sensor 100 (e.g. an ultrasound-based sensor as described herein) has an area of at least 10,000 mm$^2$, 40,000 mm$^2$, and/or 1,000,000 mm$^2$. and/or has a major axis of at least 20 cm, 40 cm, and/or 80 cm.

In some embodiments, sensor 100 comprises an ultrasound-based sensor (e.g. comprising X and Y conductors as described herein) that is configured to be integrated into a user interface 550 comprising a relatively thick glass layer through which ultrasound waves are transmitted and received. The relatively thick glass layer can be configured to reduce breakage, and/or to avoid the need for a screen protector (e.g. a screen protector commonly attached to a cell phone screen for protection). The user interface 550 (e.g. the device 500 into which the user interface 550 and sensor 100 is integrated) can be configured to operate in harsh environments, such as when used in military applications, outdoor use, and/or water-based activities.

A user interface 550 comprising an ultrasound-based sensor 100 can be configured to detect touch of one or more fingers of a user while the finger is covered by a fabric or other flexible material (e.g. gloves or finger cots). In these embodiments, a user may apply one or more fingers to a surface imageable by sensor 100 (e.g. after removing a covering of the one or more fingers), such that the user's identity can be confirmed (e.g. via one or more fingerprints and/or other physiologic confirming information of the user). After the confirmation, the user's fingers can be covered (e.g. recovered) and sensor 100 can receive various forms of user input (e.g. icon selection, and the like) while the one or more fingers used remain covered.

A user interface 550 comprising an ultrasound-based sensor 100 can be integrated into a device 500 comprising an automated teller machine (ATM).

As described herein, a user interface 550 comprising an ultrasound-based sensor 100 can be flexible (e.g. include one or more flexible portions), such as when the device 500 comprising user interface 550 comprises a wearable device including a flexible "smart screen". The device 500 can comprise a wearable computer device, and/or an article of clothing, that includes user interface 550. The device 500 can include a first portion (e.g. a watch or article of clothing) that includes sensor 100, and a second portion (e.g. a cell phone, laptop, tablet, and/or other electronic user device) that receives information from the first portion (e.g. via wireless communication). In some embodiments, the first portion is configured to perform a user confirmation routine, such as to allow one or more functions (e.g. "smart functions") provided by the first portion to only be enabled after access by an allowed user is confirmed (e.g. via fingerprint detection performed by the first portion and/or the second portion).

User device 500 can comprise a medical device, as described herein. In some embodiments, a user interface 550 comprising an integrated sensor 100 (e.g. an ultrasound-based sensor 100) is configured to confirm the identity of a nurse, doctor, and/or other authorized caregiver (e.g. via fingerprint identification) prior to allow setting and/or changing of any parameters of the medical device (e.g. turning on, turning off, and/or modifying any setting of the device 500). Alternatively or additionally, the device 500 can be configured, via the sensor 100, to detect and/or measure ("detect" or "measure" herein) life signs and/or other physiologic parameters of the user (e.g. including fingerprints), such as to confirm proper use and/or adjust therapy provided by the device 500 based on the physiologic parameter measurements.

In some embodiments, user interface 550 comprises an alphanumeric keypad and/or other keyboard. In these embodiments, an integrated ultrasound-based sensor 100 can detect one or more fingerprints of one, two, or more users, such as while the associated one or more users are typing (e.g. entering data via typing) into the user interface 550. In some embodiments, system 10 (e.g. via algorithm 60) is configured to repeatedly confirm a user's identity during data entry (e.g. to avoid a permitted user to initiate data entry after which a second, non-permitted user continues to enter data). The repeated confirmation can be continuously repeated based on a time interface (e.g. every XX seconds), and/or based on the amount of data entered (e.g. repeatedly after YY characters are entered). Alternatively or additionally, system 10 can be configured to confirm an identify of a user via capture of a fingerprint (e.g. one or more fingerprints), and as long as the finger remains in contact (e.g. continued contact at a pressure level above a threshold) with the portion of system 10 (e.g. user interface 550) used to capture the fingerprint, it can be assumed that the particular user is providing input to system 10 (e.g. to device 500). However, if the finger "loses contact", system 10 can be configured to require the repeating of a user confirmation routine (e.g. again record and identify the user via their fingerprint or other method), such as to allow continued control of device 500 by that user (e.g. continued control that is also dependent on continuous contact of the user with the associated device).

In some embodiments, sensor 100 comprises an assembly comprising a first ultrasound-based sensor 100a and a second ultrasound-based sensor 100b arranged in a stacked arrangement. In these embodiments, the first sensor 100a can be configured to detect a first set of one or more forms of user input, and the second sensor 100b can be configured to detect a second set of one or more forms of user input. In these embodiments, the first set of one or more forms of user input can include at least one form of user input that is not included in the second set of one or more forms of user input, and/or vice versa. For example, the first sensor 100a can be configured to detect a fingerprint of one or more users, while the second sensor 100b may not have the resolution to perform a proper detection. The first sensor 100a can be configured to transition from a sleep state to an awake state based on detection of user contact by the second sensor 100b. Controller 200 can comprise a single electronic module for interfacing (e.g. for transmitting and/or receiving signals) with both sensor 100a and 100b, or it can comprise a distinct separate electronic module for each.

In some embodiments, at least a portion of a detection area of a sensor 100 is positioned along an edge of user device 500 (e.g. along an edge of user interface 550). For example, a first portion of sensor 100 (e.g. a set of X and Y conductors, a magnetic switch, and/or other touch-based sensor) positioned along an edge of device 500 can be configured, when contacted (e.g. activated) by a user, to cause a second portion of sensor 100 (e.g. a high-density portion) to transition from a sleep state to an active state. In some embodiments, the first portion of sensor 100 is configured to measure a force applied by a user (e.g. one or more user's fingers, such as when a tapping and/or squeezing force is applied to one or more edges of device 500), such as when the transition in states only occurs when the applied force exceeds a threshold. In some embodiments, the first portion determines the level of force applied by measuring the amount of the user's skin in contact with the first portion, as described herein.

In some embodiments, sensor 100 comprises an ultrasound-based sensor comprising sets of X and Y conductors, as described herein. In these embodiments, sensor 100 can comprise a portion $P_V$ that includes one or more portions (e.g. all) of sensor 100, where each portion $P_V$ comprises sets of X and Y conductors that are positioned in a high-density layout, such that these portions can operate in a low-density, medium-density, and/or high-density mode of operation (e.g. providing low, medium, and/or high resolution, respectively, based on the quantity of conductors used to transmit and/or receive). For example, when a portion $P_V$ is operated in a low-density mode, every other, every third, or every "$n^{th}$" conductor (e.g. every $n^{th}$ X conductor) is used to transmit ultrasound waves (e.g. and a corresponding subset of Y conductors is configured to receive reflected ultrasound waves). Medium-density and high-density modes involve increasing numbers of conductors being used to transmit and receive. When portion $P_V$ is operated in a low-density mode (e.g. a low power mode of device 500) and contact is made by a user (e.g. a user's finger) to a location proximate portion $P_V$ (e.g. contact is made to a portion of user interface 550 directly above portion $P_V$ of sensor 100), at least portion $P_V$ (e.g. portion $P_V$ and one or more portions of sensor 100 proximate portion $P_V$) transitions to a medium-density or high-density mode of operation, in which at least more (or all) of the X and Y conductors are used in a transmit and receive fashion as described herein. In these embodiments, device 500 can normally (e.g. most of the time) operate in a low power mode (e.g. due to the low-density transmit and receive mode of portion $P_V$), but transition to a higher power mode in which portion $P_V$ operates in the medium-density or high-density modes of operation described hereinabove. This configuration of portion $P_V$ allows the user to, on demand, transition sensor 100 (e.g. as an integrated part of user interface 550) from a low power, low-density mode, to a higher power, medium-density and/or high-density mode (e.g. at least portion $P_V$ of sensor 100 operates in the greater density mode). This arrangement of portion $P_V$ has numerous advantages, such as: saving battery life of a device 500, where the high-power usage of the high-density mode is only encountered when needed (e.g. as initiated by a user and/or by system 10 on a relatively infrequent basis); and/or faster image (e.g. fingerprint) acquisition time and lower data storage needs (e.g. associated with scanning only the reduced portion $P_V$). In some embodiments, a first "contact" (e.g. through one or more layers of user interface 550) of portion $P_V$ causes portion $P_V$ to transition from a low-density mode of operation to a medium-density mode of operation, and a second contact of portion $P_V$ causes portion $P_V$ to transition from a medium-density mode of operation to a high-density mode of operation. In some embodiments, a user causes the transition to high-density mode in order to have their fingerprint detected (e.g. have their identity confirmed). In some embodiments, portion $P_V$ transitions automatically to a low-resolution mode after a time period has elapsed (e.g. a time period in which no user contact and/or no other user input is received). In some embodiments, portion $P_V$ transitions from a low-density mode to a medium-density and/or a high-density mode on an event selected from the group consisting of: user interface 550 is touched (e.g. touched by the user); a particular time of day is reached; a user physiologic parameter reaches a threshold; device 500 is manipulated (e.g. rotated or shaken) in one or more ways, such as when detected by a sensor-based functional element 999; when a particular application (e.g. gaming application or other application) is being used on device 500; and combinations of these. In some embodiments, portion $P_V$ is operated in a high-density mode and confirms a user via their fingerprint, after which portion $P_V$ enters a low-density mode. Portion $P_V$ can remain in the low-density mode as long as the finger providing the fingerprint remains in contact with device 500 (e.g. with user interface 550). If loss of contact (e.g. with sensor 100 via interface 550) is detected, portion $P_V$ can transition to a high-density mode (e.g. and require the user to confirm their fingerprint an additional time).

In some embodiments, sensor 100 and/or other components of system 10 are configured to create an image of a biological material such as blood, such as biological material that is positioned (e.g. directly and/or on a slide) proximate a user interface 550 comprising an integrated sensor 100. In these embodiments, system 10 can be configured (e.g. via algorithm 60) to perform an analysis of the biological material (e.g. blood, plasma, and/or cells), such as to determine blood type, the presence of a pathogen, and/or another detectable parameter of a substance within the biological material. Analysis of the blood can be performed using a time-shift image, an amplitude-shift image, or both, such as are described herein. In some embodiments, sensor 100 and/or other components of system 10 are configured to create an image of an inorganic substance, such as to perform an analysis of the inorganic substance.

Referring collectively to FIGS. 2 through 19, various configurations of a sensor 100 and system 10 are illustrated, such as ultrasound-based systems and sensors that utilize a time-shift image as described herein.

Many security systems and electronic devices use biometric sensing for user authentication. Compared to other authentication methods (e.g., text-based passwords, cognitive passwords, graphical passwords, passphrases, public key cryptography), biometric authentication uses a person's unique biological, physiological, or behavioral characteristics to verify their identity. These biological characteristics can be found as patterns in a person's fingerprints, facial expressions, irises, speech patterns, and other features. Due to their uniqueness, biological characteristics are typically harder to spoof than passwords, and therefore biometric authentication can be advantageously combined with other authentication methods to improve overall security.

Fingerprint-based authentication is one type of biometric authentication that records the ridges and valleys that make up a person's fingerprints. Compared to other types of biometric authentication, fingerprint-based authentication benefits from sensors that are small, robust, and manufacturable at high volumes and low cost. As a result, fingerprint-based authentication has become widespread, finding use in mobile devices, automated teller machines (ATMs), and door locks, among other devices and applications.

To implement fingerprint-based authentication, a digital image of a candidate's fingerprint is recorded, typically using an ultrasound, capacitive, optical, or thermal scanner. Regardless of which scanning technology is used, the fingerprint must be recorded with a spatial resolution high enough to differentiate between the ridges and valleys. For example, the Federal Bureau of Investigation (FBI) and the National Institutes of Standards and Technology (NIST) established a standard resolution of 500 pixels per inch for automatic fingerprint identification systems (AFISs), corresponding to a pixel imaging size of 50 microns. A pattern-matching algorithm can then compare the digital image to a database of fingerprints of "allowed" individuals. If a match is found, the security system infers that the candidate is one of the allowed individuals. In this case, the security system can then grant access to the candidate.

Many ultrasound scanners use an ultrasound transducer array that can both transmit and sense ultrasound. For example, consider a two-dimensional transducer array forming rows and columns of pixel elements ("pixel elements" or "pixel transducers" herein). The transducer array can be affixed to a bottom face of a platen, and each pixel element can be driven to emit an ultrasound pulse into the platen. Part of the ultrasound pulse reflects off the top face of the platen and propagates back to the transducer array as an echo. One or more pixel elements sense the echo, and the resulting waveform can be processed to obtain a pixel of a corresponding image. When a finger contacts the top face of the platen, the resulting image will reveal the fingerprint of the finger.

Prior-art ultrasound scanners measure the change in echo energy caused by ridges contacting the top face of the platen. For example, consider a valley of a finger contacting the top face. In this case, a pocket of air is formed between the top face and the skin, and therefore no skin directly contacts the top face. An ultrasound pulse emitted into this region of the platen will reflect off the top face with a large reflection coefficient due to the relatively large difference between the mechanical impedances of the platen (typically glass or plastic) and air. The resulting valley echo will have a relatively high energy. However, where a ridge directly contacts the top face, the difference between the mechanical impedances of the platen and skin is smaller. In this region of the platen, the ultrasound pulse will reflect off the top face with a smaller reflection coefficient, resulting in a ridge echo with a relatively low energy. Therefore, a fingerprint image can be obtained by mapping echo energy across the two-dimensional top face of the platen. Additional details about fingerprint imaging based on echo energy can be found in International Publication No. WO 2019/032590, titled "Interactive Biometric Touch Scanner", and Gerard Touma, "A row-column addressed acoustic biometric scanner integrated with pulse oximetry" (Ph.D. Dissertation, Stanford University, 2020); each of these references is incorporated herein by reference in its entirety for all purposes.

The present inventive concepts can use ultrasound to image fingerprints by recording the spatial variation in echo phase, or time delay, as an alternative to, or in addition to the spatial variation in echo energy. Specifically, a ridge echo is phase-shifted with respect to a valley echo, and therefore the transducer array will detect, for a ridge echo, a round-trip pulse travel time that is different from that of a valley echo. A fingerprint image can be obtained by mapping echo phase, and/or pulse travel time, across the two-dimensional top face of the platen.

Figure 9:
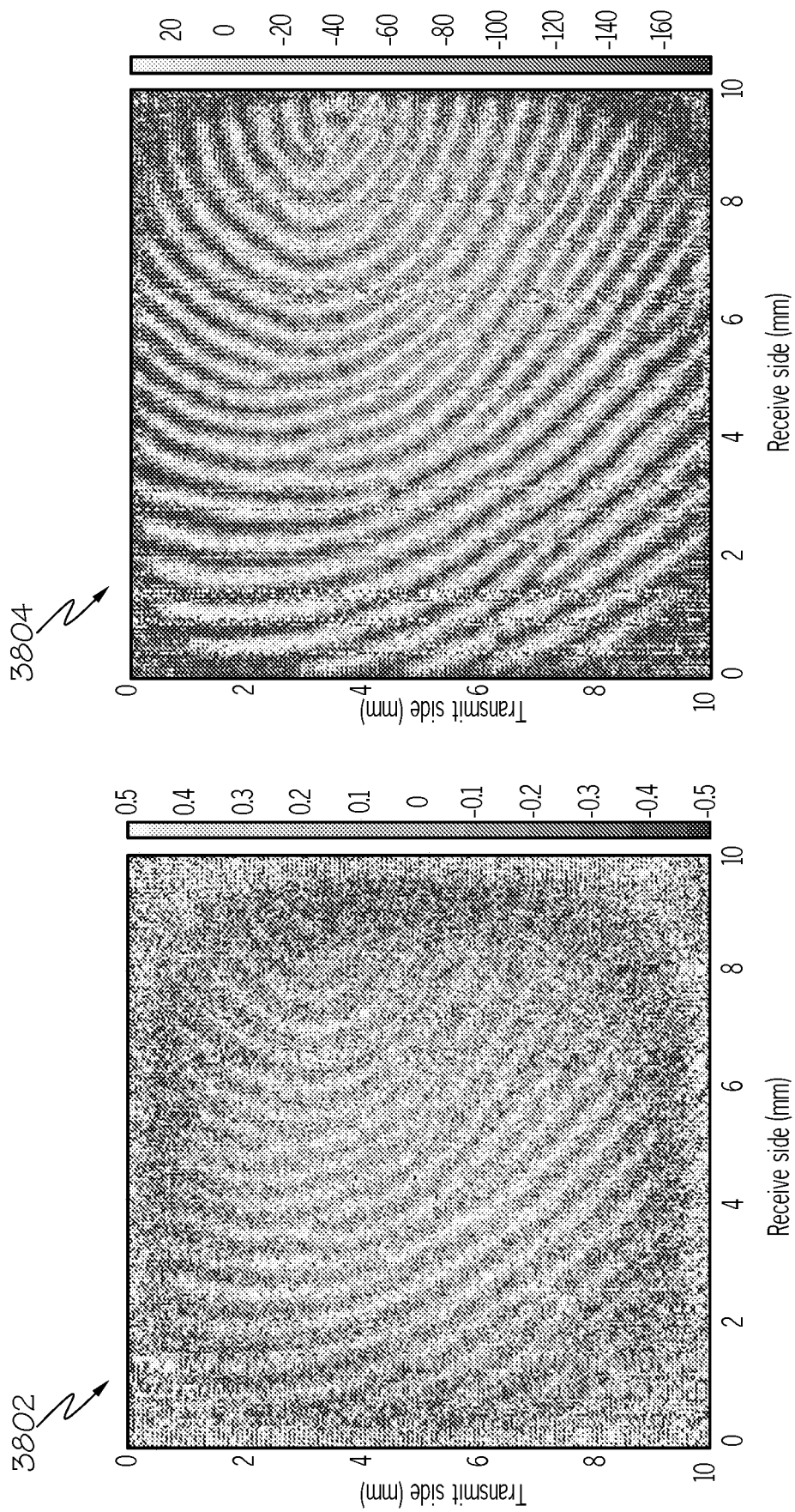
FIG. 9 compares a time-shift image of a fingerprint with a conventional amplitude-shift image of the same fingerprint, consistent with the present inventive concepts.

Advantageously, fingerprint images obtained with the present inventive concepts have a higher signal-to-noise ratio (SNR) than images obtained with prior-art energy-based techniques (see FIG. 9). As described in more detail below, the higher SNR likely arises from the fact that echoes have less phase noise relative to their amplitude noise.

Accordingly, phase can be measured with higher precision than amplitude. This relatively less phase noise may be due to: ultrasound pulses being generated with less phase noise, as compared to amplitude noise; and/or receive electronics having less electronics phase noise.

Accordingly, the present inventive concepts utilize time-based, rather than amplitude-based, signal processing techniques to process waveforms of sensed echoes. For example, each pixel element can be used to record a baseline waveform when no finger contacts the platen, and a signal waveform when a finger does contact the platen. The baseline waveform can be processed to determine a baseline arrival time of a baseline echo, and the signal waveform can be processed to determine a signal arrival time of a signal echo. The baseline arrival time can then be subtracted from the signal arrival time (or vice versa) to obtain a time shift for the pixel element. The time shift will be relatively closer to zero for pixel elements near valleys, and relatively farther from zero for pixel elements near ridges.

As described in more detail below, there are many ways to process a waveform to determine an echo arrival time, some of which originate from the field of ultrasound time-domain reflectometry. For example, many ultrasound transducers are excited with a tone burst, i.e., an integer number of continuous cycles of a single-frequency sinusoid. In this case, the echo will also have the form of a tone burst, and the arrival time can be defined as the time at which any node or anti-node in the recorded waveform occurs. Signal-processing techniques involving Hilbert transforms or cross-correlations can then be used to determine the time shift. However, other signal processing techniques can be used without departing from the scope hereof. In addition, the present inventive concepts can be used with any type of pulse excitation, and are therefore not limited to tone bursts.

The present inventive concepts extend to operation of a single ultrasound transducer in contact with the platen. For example, a single ultrasound transducer can be used to determine the presence of a finger contacting the top face of the platen by comparing the measured time shift to a threshold. An indication of the presence can then be outputted, such as a binary indication (e.g., "0" or "1") or a value between 0 and 1 indicating the probability that a finger is present. The single ultrasound transducer can be one pixel element of a transducer array. Alternatively, several pixel elements of the array can be operated to obtain several time shifts, which can be aggregated (e.g., by calculating a mean or variance) to determine the indication. In any case, when the resulting indication indicates the presence of a finger, the transducer array can be controlled to obtain an image of the fingerprint. In this way, the transducer array is only used to image a finger once it is known that a finger is, in fact, present on the platen.

While the above discussion describes fingerprint sensing, the present inventive concepts can be used to detect any object contacting the platen, provided that the presence of the object induces a measurable phase shift in an echo. Furthermore, while the above discussion describes two-dimensional transducer arrays whose pixel elements are arranged linearly in rows and columns, the present embodiments can be implemented with any type of transducer array, including one-dimensional pixel arrangements (e.g., pixel elements arranged linearly or circularly), two-dimensional pixel arrangements (e.g., pixel elements arranged in concentric circles), and/or three-dimensional pixel arrangements.

When used for fingerprint sensing, the present inventive concepts can be integrated with other physical, physiological, and biological measurements, such as when included as part of a multi-function biometric system. For example, the above referenced documents (i.e., International Publication No. WO 2019/032590, and the Ph.D. dissertation by Gerard Touma) show how a pulse oximeter can be incorporated with an ultrasound transducer array when at least part of the transducer array is at last partially optically transparent (e.g., in the near-infrared). As another example, the present inventive concepts can be used to determine an area of contact between the finger ridges and platen. This area of contact can be measured over time to identify periodic changes indicative of a pulse. In this way, the biometric system can distinguish between living tissue and inanimate matter. The present inventive concepts can be combined with other sensors and/or biometric functionality without departing from the scope hereof.

Figure 2:
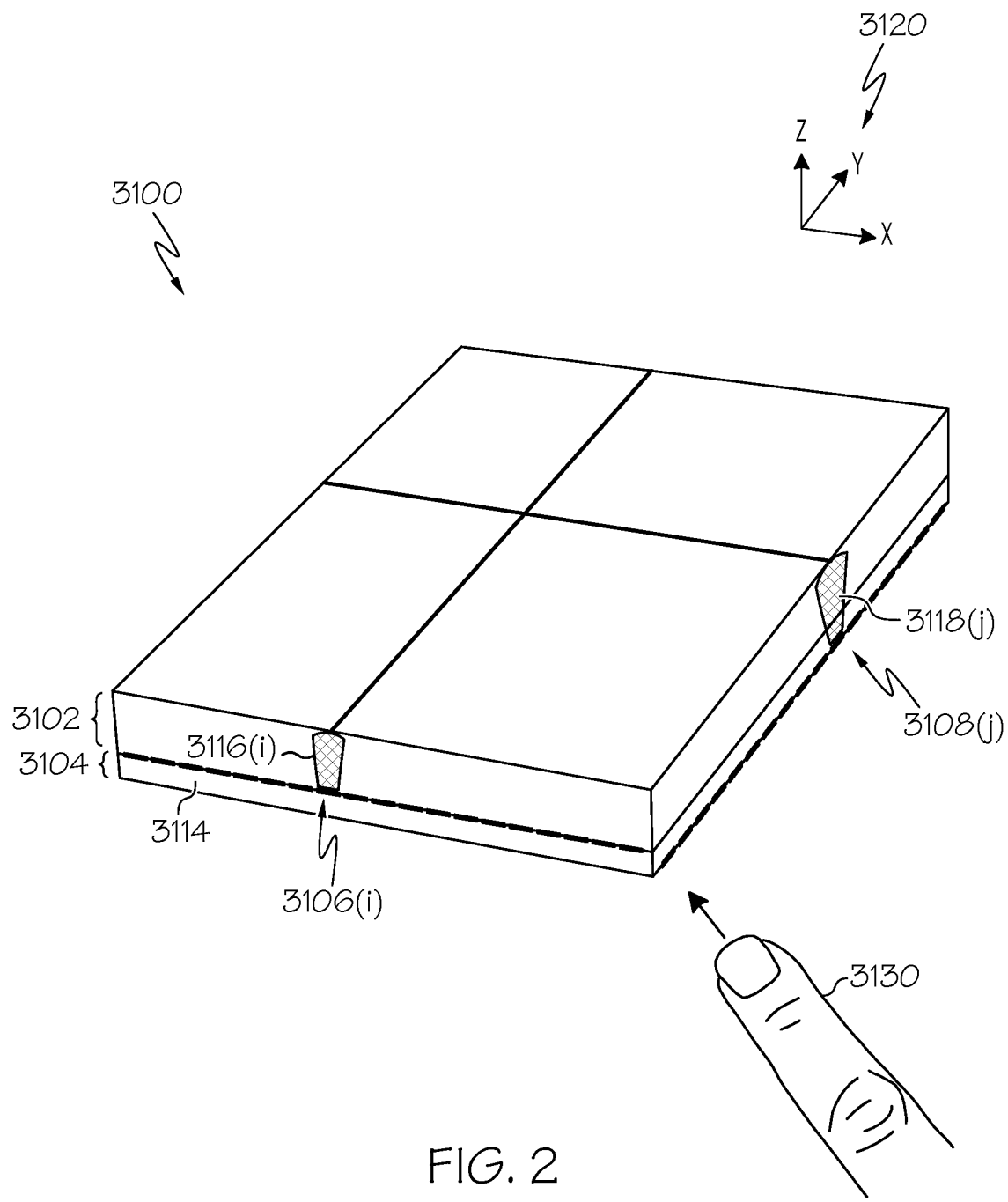
FIG. 2 is a perspective view of an ultrasound sensor that combines an ultrasound transducer array with a platen, consistent with the present inventive concepts.
Figure 3:
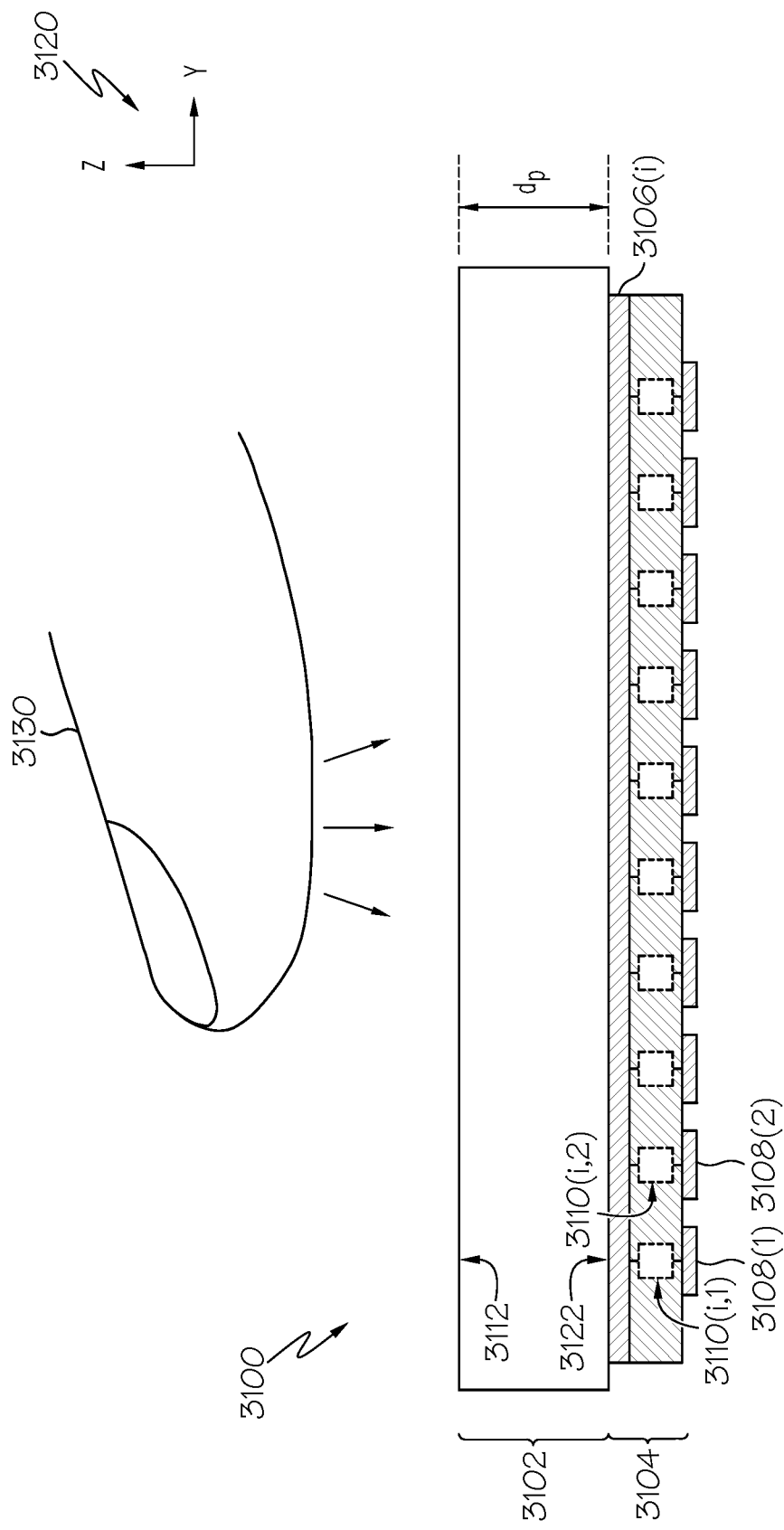
FIG. 3 is a cut-away side view of the ultrasound sensor of FIG. 2, consistent with the present inventive concepts.

FIG. 2 is a perspective view of an ultrasound sensor 3100 that combines an ultrasound transducer array 3104 with a platen 3102. FIG. 3 is a cut-away side view of the ultrasound sensor 3100. The ultrasound transducer array 3104 is bonded to, or fabricated on, a bottom face 3122 of the platen 3102 so that an ultrasonic pulse emitted by the transducer array 3104 propagates through the platen 3102 in the +z direction (see right-handed coordinate system 3120) toward a top surface 3112 of the platen 3102. The top surface 3112 is a boundary between materials with different mechanical impedances (e.g. densities and/or stiffnesses). Therefore, the ultrasonic pulse will reflect off the top surface 3112, and the resulting reflection will propagate through the platen 3102 in the −z direction toward the bottom face 3122, where it is detected by the transducer array 3104. This reflection is also referred to as an echo.

The ultrasound transducer array 3104 is row-column addressable. Specifically, the transducer array 3104 has a plurality of row electrodes 3106 that extend in the y direction, and a plurality of column electrodes 3108 that extend in the x direction. Between the row electrodes 3106 and column electrodes 3108 in the z direction is a piezoelectric layer 3114 that can be electrically actuated, via the row electrodes 3106 and column electrodes 3108, to mechanically oscillate, thereby emitting ultrasound waves into the platen 3102. Similarly, the piezoelectric layer 3114, when mechanically actuated by ultrasound waves, produces a time-varying electrical signal that can be subsequently detected and processed. The piezoelectric layer 3114 can be formed from a crystal (e.g., lithium niobate, lithium tantalate, quartz, etc.), ceramic (e.g., zinc oxide, lead zirconium titanate, potassium niobate, barium titanate, etc.), III-V or II-VI semiconductor (e.g., aluminum nitride, gallium arsenide, etc.), polymer, and/or any other piezoelectric material.

FIG. 2 shows the $i^{th}$ row electrode 3106($i$) causing piezoelectric layer 3114 to emit an ultrasound pulse 3116($i$) into the platen 3102. Since the row electrode 3106($i$) extends across the entire length (in the y direction) of the ultrasound sensor 3100, the ultrasound pulse 3116($i$) similarly extends across the entire length of the platen 3102. Alternatively, the $j^{th}$ column electrode 3108($j$) can cause piezoelectric layer 3114 to emit an ultrasound pulse 3118($j$) into the platen 3102. Since the column electrode 3108($j$) extends across the entire width (in the x direction) of the ultrasound sensor 3100, the ultrasound pulse 3118($j$) similarly extends across the entire width of the platen 3102. In operation, either the row electrode 3106($i$) or the column electrode 3108($j$) causes an ultrasound pulse to be emitted (e.g. via a signal applied to the electrode), and the other of electrodes 3106($i$) or 3108($j$) is configured to record the received ultrasound pulse. The transverse area (i.e., in the x-y plane) where the row electrode 3106($i$) and column electrode 3108($j$) overlap is referred to herein as a pixel element (e.g., see pixel elements 3110 in FIG. 3). While FIG. 2 shows the transducer array 3104 with 19 row electrodes 3106 and 17 column electrodes 3108 (corresponding to 19×17=323 pixel elements), the transducer array 3104 can alternatively have any number of row electrodes 3106 and column electrodes 3108 without departing from the scope hereof. For example, the transducer array 3104 can have 512 row electrodes 3106 and 512 column electrodes 3108, corresponding to 512×512=262,144 pixel elements. It should be understood that there is no applicable minimum and/or maximum quantity of row electrodes 3106 and/or column electrodes 3108 applicable to the sensors of the present inventive concepts.

As shown in FIG. 3, the platen 3102 has a thickness $d_p$ in the z direction. Since pixel elements 3110 are used to both emit and sense ultrasound waves, the thickness $d_p$ can be chosen such that the duration of an emitted pulse is less than the round-trip propagation time $t_p$ in the platen 3102. This requirement ensures that pixel elements 3110 do not emit and sense at the same time, and that electrical leakage (e.g., see leakage 3502 in FIG. 6) does not contaminate an output signal. For example, the platen 3102 can be fabricated from glass with a sound velocity $v_s$ of 6000 m/s. A pulse with a bandwidth of 45 MHz has a bandwidth-limited duration of 22 ns, corresponding to sound travel in the z direction of 132 μm (e.g. forward and back travel in a platen 3102 with a thickness of 66 μm). However, the pulse can have a greater spatial extent, which can simplify signal processing (e.g., see FIG. 6). In some embodiments, the platen 3102 has a thickness $d_p$ of 0.5 mm. However, the platen 3102 can have a different thickness $d_p$ without departing from the scope hereof. Similarly, the platen 3102 can be fabricated from a material other than glass (e.g., plastic, metal, crystal, semiconductor, etc.) without departing from the scope hereof.

When a finger and/or other tissue of one or more users, finger 3130 shown, physically contacts the top surface 3112 of the platen 3102, the ultrasound sensor 3100 can be used to (i) detect the presence of the finger 3130, (ii) image a fingerprint of the finger 3130, (iii) measure a force with which the finger 3130 pushes against the top surface 3112, (iv) measure time variation of the force to determine that the finger 3130 is from a living being (as opposed to a prosthetic), and/or any combination thereof. Accordingly, the ultrasound sensor 3100 can be used as a biometric touch sensor (e.g., see finger sensor system 3700 in FIG. 8). To detect a full fingerprint, the ultrasound sensor 3100 can have an area (i.e., in the x and y direction) of at least 0.1 cm², 0.3 cm², 0.5 cm², 0.7 cm² and/or 1 cm². For clarity, the finger 3130 is not drawn to scale in FIGS. 2 and 3, and finger 3130 can comprise a finger, palm, other body part, and/or any other tissue of one, two, or more users of the systems, devices, and methods of the present inventive concepts.

Figure 4:
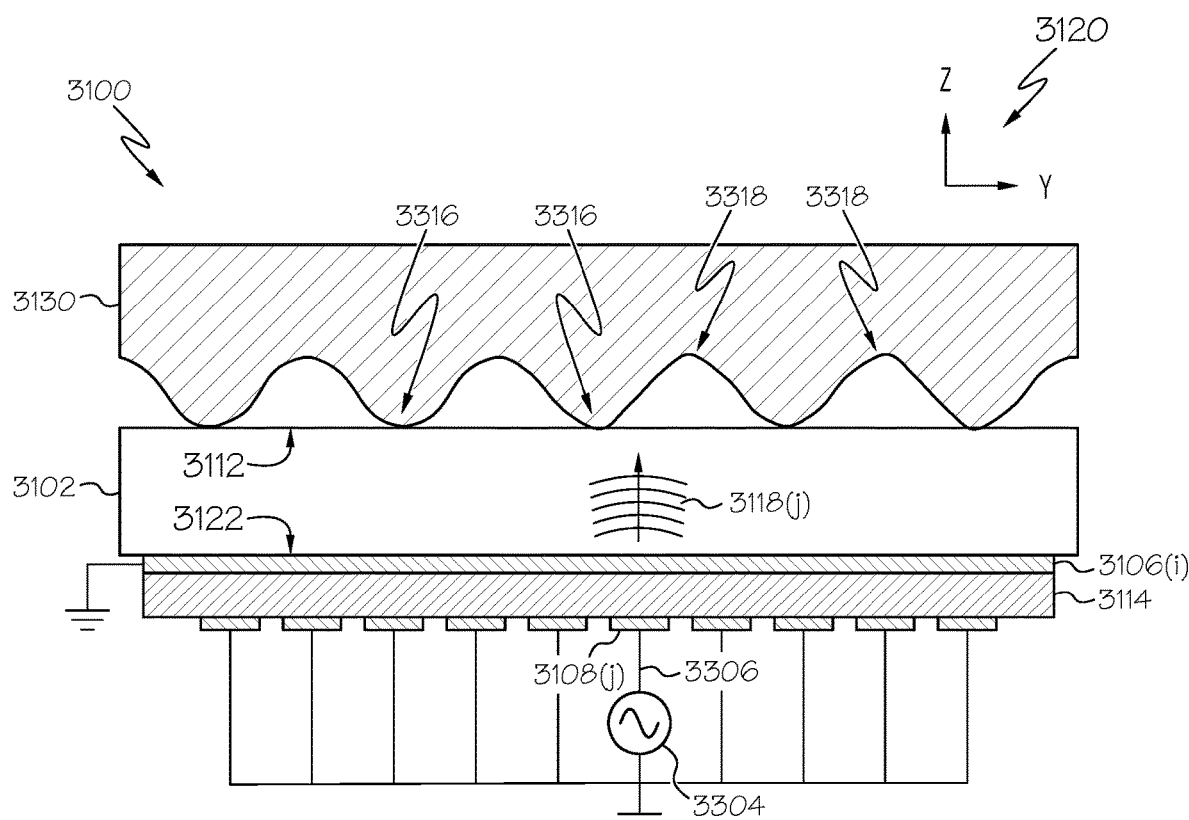
FIG. 4 shows a column electrode emitting an ultrasound pulse into the platen of FIGS. 2 and 3, consistent with the present inventive concepts.
Figure 5:
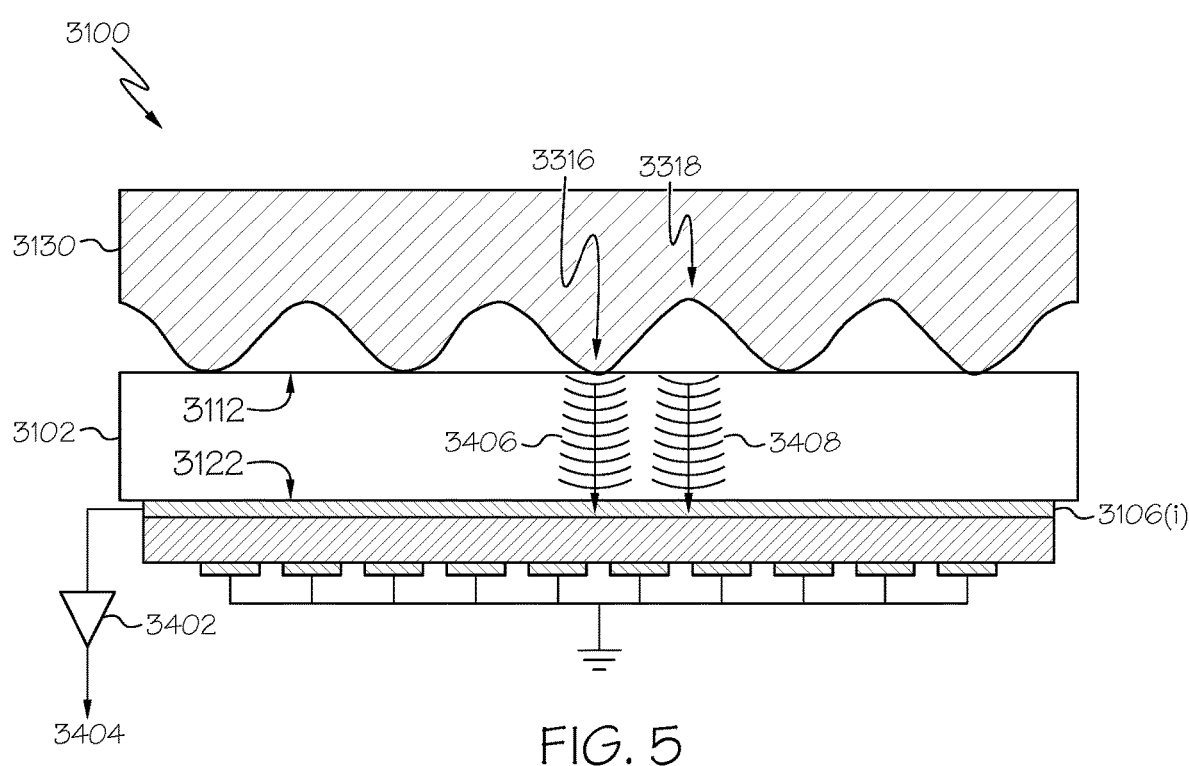
FIG. 5 shows a row electrode sensing echoes generated when the ultrasound pulse of FIG. 4 reflects off a top surface of the platen of FIGS. 2 and 3, consistent with the present inventive concepts.

FIGS. 4 and 5 illustrate row-column addressing of the ultrasound sensor 3100 with the finger 3130 contacting the platen 3102. In FIG. 4, a column electrode 3108($j$) emits an ultrasound pulse 3118($j$) into the platen 3102. In FIG. 5, a row electrode 3106($i$) senses echoes 3406, 3408 generated when the ultrasound pulse 3118($j$) reflects off the top surface 3112. FIGS. 4 and 5 are both side cut-away views through the row electrode 3106($i$). For clarity in FIGS. 4 and 5, only ten column electrodes 3108 are shown. FIGS. 4 and 5 are best viewed together with the following description.

The bottom surface of the finger 3130 forms an alternating sequence of ridges 3316 (also referred to as "friction ridges" or "epidermal ridges") and valleys 3318. The ridge 3316 directly contacts the top surface 3112 of the platen 3102, while the valleys 3318 do not directly contact the top surface 3112. Thus, beneath each valley 3318, air contacts the top surface 3112. Accordingly, the reflection coefficient at the top surface 3112 is larger at the valleys 3318 and smaller at the ridges 3316, and therefore the amplitude of the echo 3408 is larger than the amplitude of the echo 3406.

During emission, a signal source 3304 applies a drive signal 3306 to the column electrode 3108(j) while all other column electrodes 3108 and all row electrodes 3106 are grounded, thereby establishing a voltage difference across the piezoelectric layer 3114. For clarity, only the row electrode 3106(i) is shown in FIG. 4 as being grounded. During sensing, an amplifier 3402 amplifies the electrical output of the row electrode 3106(i) into an amplified output 3404 that is subsequently digitized and processed. Emitting with the column electrode 3108(j) and sensing with the row electrode 3106(i) is equivalent to imaging the finger 3130 with a single pixel element 110(i,j). Accordingly, an image of the finger 3130 can be captured by repeating emission and sensing for all combinations of the row electrodes 3106 and column electrodes 3108. Alternatively, emission can be performed with row electrodes 3106, and sensing can be performed with column electrodes 3108.

Figure 6:
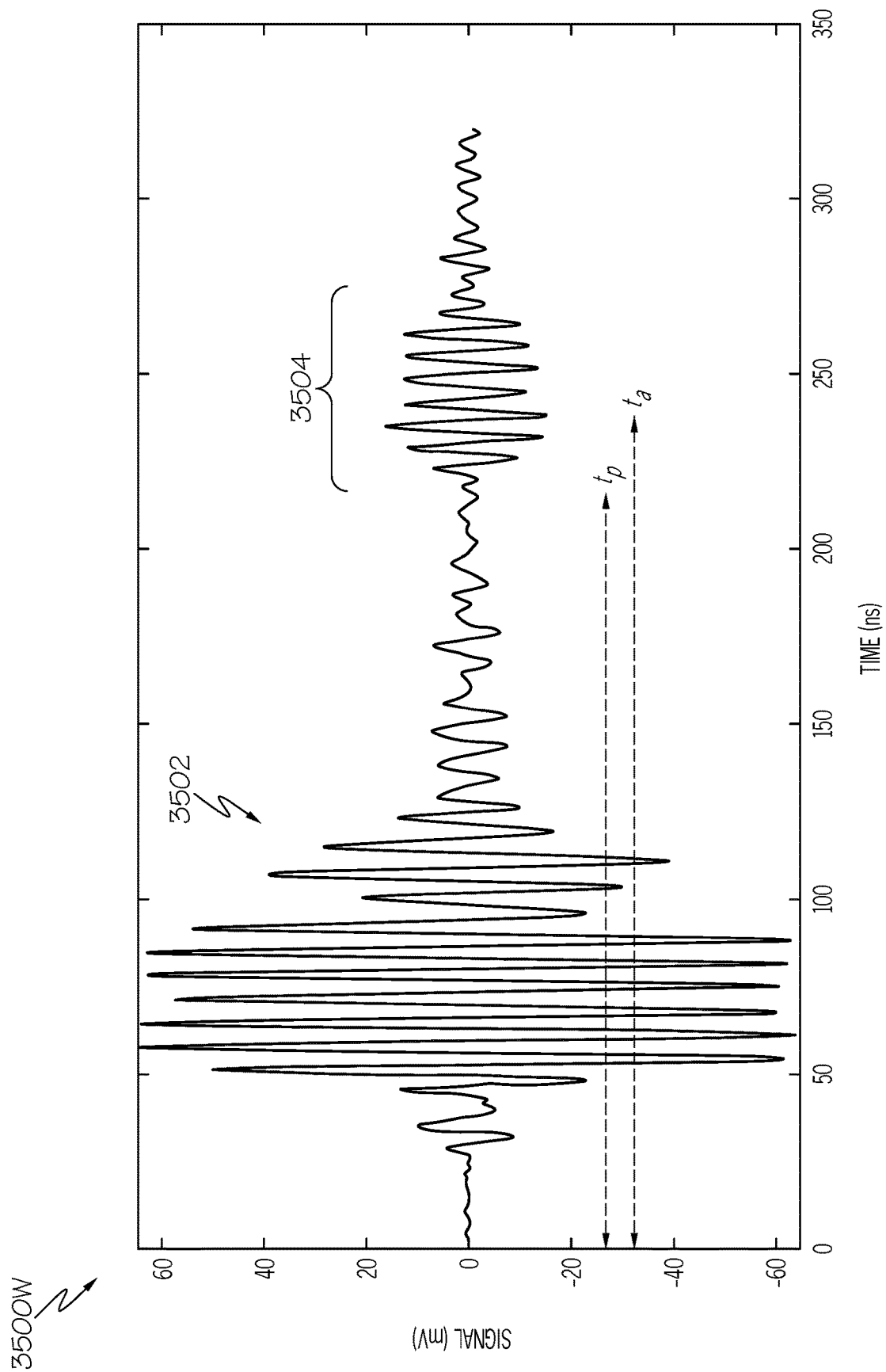
FIG. 6 shows a waveform recorded from a row electrode during emission and sensing of one pixel element of the ultrasound sensor of FIGS. 2 through 5, consistent with the present inventive concepts.

FIG. 6 shows a waveform 3500W recorded from the row electrode 3106(i) during emission and sensing of one pixel element 3110. The waveform 3500W is a digital sequence of signal values obtained by digitizing the amplified output 3404 (e.g., see analog-to-digital converter 3706 in FIG. 8). The signal values are also time-tagged. At an emission start time of t=0, the drive signal 3306 was applied to the column electrode 3108(j) to generate the ultrasound pulse 3118(j). In the example of FIG. 6, the drive signal 3306 was a pulse with a center frequency of 150 MHz, and a duration of eight cycles of the center frequency (i.e., approximately 53 ns). The emission start time t=0 serves as a reference time for all temporal measurements of the waveform 3500W.

While the drive signal 3306 was applied to the column electrode 3108(j), RF leakage 3502 appeared on the waveform 3500W due to capacitive coupling between the electrodes 3106(i) and 3108(j). The RF leakage 3502 died out by 150 ns, after which an echo appeared (e.g., one of the echoes 3406 and 3408 in FIG. 5). The portion of the waveform 3500W with the echo is referred to herein as a "sub-waveform" and is shown in FIG. 6 as a sub-waveform 3504. The ultrasound sensor array 3100 and drive signal 3306 is designed so that the propagation time of the pulse 3118(i) through the platen 3102 is larger than the time required for the RF leakage 3502 to die out. This requirement allows the sub-waveform 3504 to be distinguished from the RF leakage 3502 and prevents the RF leakage 3502 from contaminating or affecting the sub-waveform 3504. Note that RF leakage 3502 does not always occur, depending on the particular implementation of the ultrasound sensor array 3100. Where RF leakage 3502 does not occur, or where RF leakage 3502 occurs but dies out faster than shown in FIG. 6, the platen 3102 can be made even thinner.

FIG. 6 shows that the sub-waveform 3504 occurs at an arrival time $t_a$ that is measured with respect to the emission reference time t=0. The arrival time $t_a$ can be defined relative to any feature of the sub-waveform 3504, such as a beginning or end of the sub-waveform 3504, a peak of an envelope calculated from the sub-waveform 3504 (e.g., via a Hilbert transform applied to the sub-waveform 3504), a zero-crossing of an instantaneous phase calculated from the sub-waveform 3504, and/or a peak or zero-crossing of any oscillation of the sub-waveform 3504. The arrival time $t_a$ can alternatively or additionally be defined with respect to any phase of any oscillation of the sub-waveform 3504. Another definition of the arrival time $t_a$ can be used without departing from the scope hereof. Methods to process the waveform 3500W to determine the arrival time $t_a$ depend on the chosen definition and are described in more detail below.

Some of the definitions of the arrival time $t_a$ are based on a zero-crossing of the waveform 3500W. To facilitate the determination of $t_a$ in these cases, a mean of the waveform 3500W can be calculated and subtracted from the waveform 3500W. The result is referred to herein as a "mean-corrected waveform". The waveform 3500W is one example of a mean-corrected waveform, as evidenced by the fact that the waveform 3500W is generally centered at a signal of 0 mV. Furthermore, since a zero-crossing need only be detected near or within the sub-waveform 3504, the waveform 3500W can be windowed to extract the sub-waveform 3504. The mean of the sub-waveform 3504 can be calculated and subtracted from the sub-waveform 3504. The result is referred to herein as a "mean-corrected sub-waveform", of which the sub-waveform 3504 is one example. Windowing eliminates a large portion of the waveform 3500W, advantageously speeding up signal processing and reducing the required memory of the associated device or system. In some embodiments, the recording of a waveform begins after the emission start time, in which case some or all of the waveform 3500W prior to the sub-waveform 3504 can be ignored.

In FIG. 6, the echo represented by the sub-waveform 3504 is an initial echo of the ultrasound pulse 3118(j). Specifically, the time delay between the beginning of pulse emission (i.e., t=0) and the beginning of the sensed echo (i.e., the beginning of the sub-waveform 3504) is approximately the round-trip propagation time $t_p=2d_p/v_s$. The echo reflects off the bottom face 3122 to create another upward-traveling pulse, which in turn reflects off the top surface 3112 to create a second downward-traveling echo that is sensed starting at $2t_p$. This process repeats, giving rise to a sequence of sensed echoes that are temporally spaced by $t_p$, and that decrease in amplitude with each reflection (i.e., position in the sequence). The sub-waveform 3504 of the initial echo has the largest amplitude (i.e., highest SNR). Accordingly, it is assumed herein that the sub-waveform 3504 represents an initial echo. However, the present embodiments can be readily adapted to record and process a second echo, third echo, etc.

Figure 7:
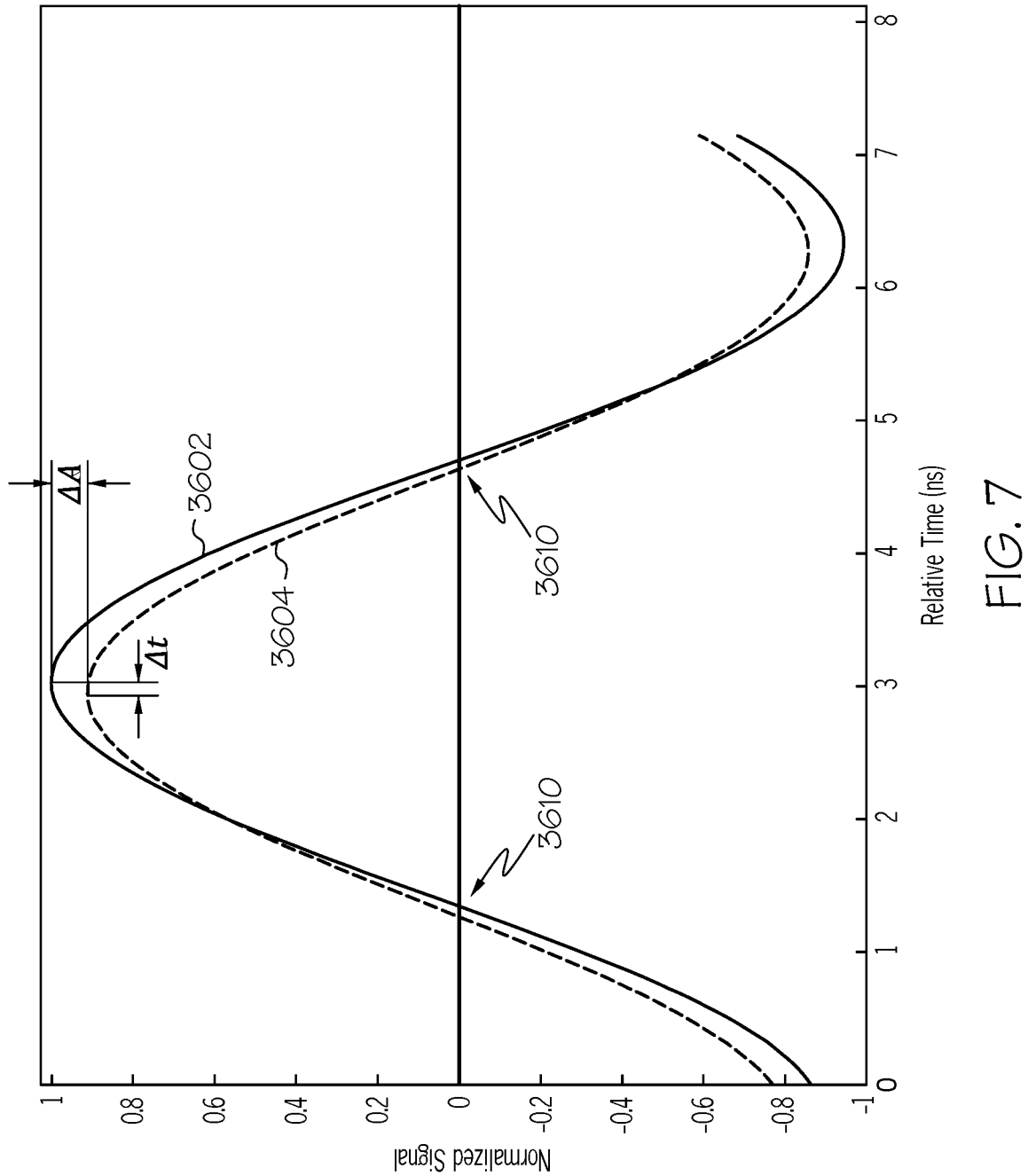
FIG. 7 illustrates a time shift between a baseline sub-waveform and a signal sub-waveform, in embodiments, consistent with the present inventive concepts.

FIG. 7 illustrates a time shift Δt between a baseline sub-waveform 3602 and a signal sub-waveform 3604. Each of the sub-waveforms 3602 and 3604 is an example of a mean-corrected sub-waveform 3504. For clarity in FIG. 7, the sub-waveforms 3602 and 3604 are normalized and overlapped on the same plot. To enhance visibility of the time shift Δt, only a 7-ns-wide portion of the sub-waveforms 3602 and 3604 is plotted.

The baseline sub-waveform 3602 was recorded by a pixel element 3110 with air contacting the top surface 3112 of the platen 3102 in the region directly over the pixel element 3110 (e.g., under a valley 3318 of the finger 3130, or with the finger 3130 completely removed from the platen 3102). By contrast, the signal sub-waveform 3604 was recorded when a ridge 3316 of the finger 3130 contacted the top surface 3112 in the region directly over the pixel element 3110. As shown in FIG. 7, the presence of a ridge 3316 on the top surface 3112 not only reduces the normalized amplitude of the baseline sub-waveform 3604 by AA, but also shifts the baseline sub-waveform 3604 by Δt.

Therefore, the presence or absence of a ridge 3316 can be determined from Δt.

In some embodiments, the drive signal 3306 has the form of a tone pulse, i.e., several consecutive cycles of a single-frequency sinusoid. The sub-waveform 3504 will also have the form of the tone pulse, and therefore can be described using phase rather than time. In these cases, the arrival time $t_a$ is equivalent to an arrival phase, and the time shift $\Delta t$ is therefore equivalent to a phase shift $\Delta\phi$. That is, the presence of a ridge 3316 of the top surface 3112 shifts the phase of the baseline sub-waveform 3604 by $\Delta\phi=f\Delta t\times 360°$, where f is the frequency of the sinusoid and 360° converts the result into degrees. Accordingly, in the present disclosure, any reference to the time shift $\Delta t$ is equivalent to the phase shift $\Delta\phi$ (and vice versa) when the sub-waveform 3504 has a well-defined phase and frequency. However, the drive signal 3306 need not be a tone pulse, and can instead be a different type of pulse and/or excitation waveform.

The time delay $\Delta t$ can be either positive or negative. In fact, the sign of $\Delta t$ can be used to identify whether the material contacting the platen 3102 is either softer or harder than the material of the platen 3102. As such, the sign of $\Delta t$ can also be used to determine what type of object is contacting the platen 3102.

Figure 8:
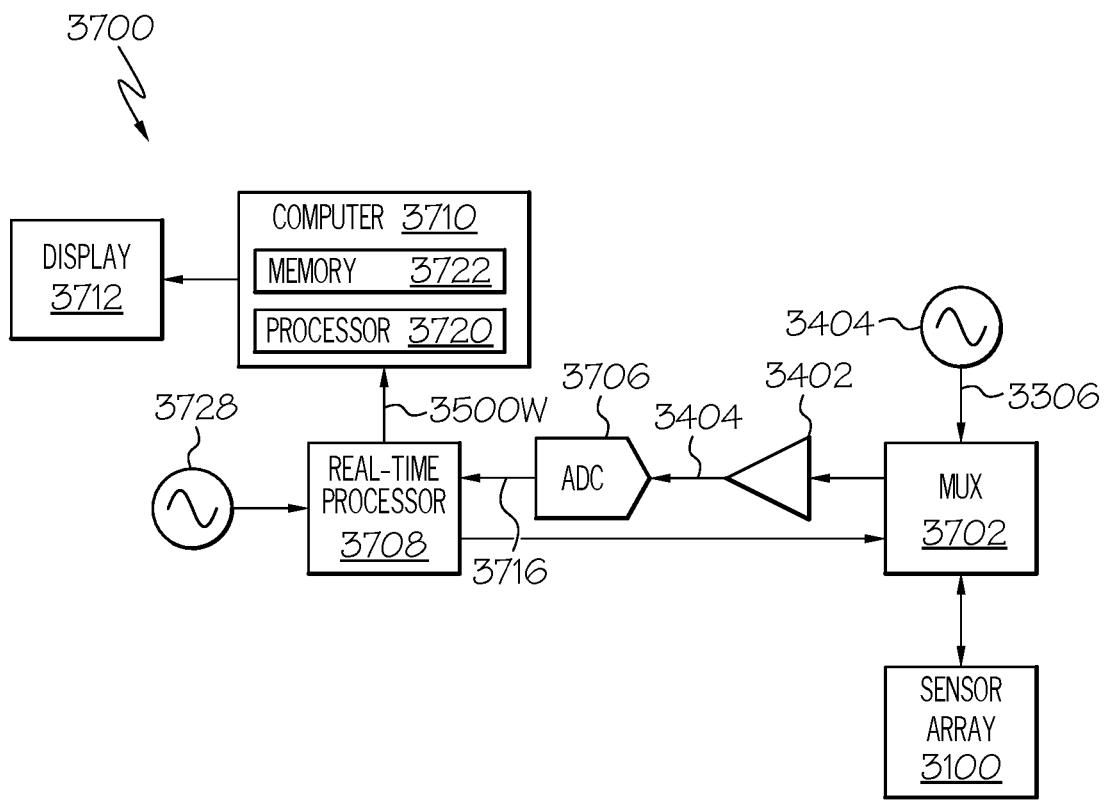
FIG. 8 is a block diagram of a finger sensor system that uses the ultrasound sensor array of FIGS. 2 through 5 to image a finger based on time shifts, in an embodiment, consistent with the present inventive concepts.

FIG. 8 is a block diagram of a finger sensor system 3700 that uses the ultrasound sensor array 3100 to image the finger 3130 based on time shifts $\Delta t$. The finger sensor system 3700 can also determine the presence or absence of the finger 3130 on the platen 3102 and determine a force with which the finger 3130 pushes against the platen 3102.

The finger sensor system 3700 includes a real-time processor 3708 that controls a multiplexer (MUX) 3702 to select which of the column electrodes 3108 is driven by the signal source 3304. The real-time processor 3708 also controls the MUX 3702 to select which of the row electrodes 3106 is connected to the input of the amplifier 3402. The amplified output 3404 of the amplifier 3402 is digitized with an analog-to-digital converter (ADC) 3706, whose output is sensor data 3716 that the real-time processor 3708 then time-stamps to create the waveform 3500W. The real-time processor 3708 is referenced to a time base 3728 that references all timing of the waveform 3500W, thereby ensuring that all waveforms 3500 are time-stamped with accuracy and stability. Although not shown in FIG. 8, the time base 3728 can also be used as a time/frequency reference for one or both of the ADC 3706 and the signal source 3304.

The processor 3708 comprises a "real-time" processor in that the time it requires to complete an operation is deterministic, and therefore predictable (i.e., does not change based on external factors or unforeseen events). Real-time control of the MUX 3702 and processing of the amplified output 3404 ensures time-stamping is implemented consistently for all waveforms 3500. This consistency is important since each time shift $\Delta t$ is determined from two waveforms 3500 recorded at different times. A sporadic or unpredictable delay in signal processing, control of the MUX 3702, or both, could result in an erroneous value of the time shift $\Delta t$, i.e., the time shift $\Delta t$ will be erroneously attributed to the presence or absence of the finger 3130 on the platen 3102. Examples of the real-time processor 3708 include a field-programmable gate array (FPGA), digital signal processor (DSP), and a system-on-chip (SoC). However, the real-time processor 3708 can be another type of circuit and/or chip, provided that it operates deterministically. After a waveform 3500W is generated, it can be non-deterministically processed to determine a time shift $\Delta t$. As such, the processor 3720 need not be a real-time processor (e.g., it can be a central processing unit).

The real-time processor 3708 transmits the waveform 3500W to a computer 3710 that processes the waveform 3500W to determine the time shift $\Delta t$. The computer 3710 includes a processor 3720 and a memory 3722 that stores the waveform 3500W. The memory 3722 also stores machine-readable instructions that, when executed by the processor 3720, process the waveform 3500W to determine the time shift $\Delta t$ from sensor data 3716. The signal-processing methods used by the computer 3710 to determine the time shift $\Delta t$ are discussed in more detail below. Additional details about the computer 3710 are described below in relation to FIG. 19.

In some embodiments, the finger sensor system 3700 generates a time-shift image (e.g., see time-shift image 3804 in FIG. 9) from the time shift $\Delta t$ determined for each pixel element 3110 of the sensor array 3100. Each pixel of the time-shift image uniquely corresponds to one pixel element 3110, and the pixels of the time-shift image are arranged identically to the pixel elements 3110. The computer 3710 can display the time-shift image to a user via a display 3712 that can be integrated with the computer 3710 (e.g., a tablet or laptop computer) or be separate from the computer 3710 (e.g., a desktop monitor or high-definition television). Although not shown in FIG. 8, the computer 3710 can alternatively or additionally communicate with another computer system (e.g., via a wide area network, a local area network, the internet, Wi-Fi, and the like) that uses the time-shift image, such as a biometric security system that processes the time-shift image to determine access to a room, computer system, files, etc. In some embodiments, the real-time processor 3708 and computer 3710 are combined as a single computer system.

A waveform 3500W recorded by the finger sensor system 3700 when the finger 3130 contacts the platen 3102 is referred to herein as a "signal waveform". The finger sensor system 3700 can sequentially record one signal waveform 3500W for each pixel element 3110 of the ultrasound sensor array 3100. In some embodiments, the finger sensor system 3700 determines the time shift $\Delta t$ for each pixel element 3110 using a waveform 3500W that was obtained when the finger 3130 was not contacting the platen 3102 (i.e., air completely contacted the top surface 3112 of the platen 3102). Such a waveform 3500W is referred to herein as a "baseline waveform".

The finger sensor system 3700 processes the signal and baseline waveforms 3500 for each pixel element 3110 to determine the time shift $\Delta t$ for that pixel element 3110. For example, the finger sensor system 3700 can process the signal waveform 3500W to determine a signal arrival time $t_a^{(s)}$ of a signal echo, and the baseline waveform 3500W to determine a baseline arrival time $t_a^{(b)}$ of a baseline echo. The finger sensor system 3700 can then subtract the baseline arrival time $t_a^{(b)}$ from the signal arrival time $t_a^{(s)}$ to obtain the time shift $\Delta t = t_a^{(s)} - t_a^{(b)}$. In other embodiments, the finger sensor system 3700 transforms the signal and baseline waveforms 3500 into a cross-correlation waveform.

The finger sensor system 3700 then processes the cross-correlation waveform (e.g., by identifying a peak) to determine the time shift $\Delta t$.

Subtracting the baseline arrival time $t_a^{(b)}$ from the signal arrival time $t_a^{(s)}$ for each pixel element 3110 of the ultrasound sensor 3100 is referred to as time (or phase) compensation. Advantageously, time compensation improves accuracy by ensuring that detected spatial variations of time shifts $\Delta t$ are correctly attributed to ridges 3316 and valleys 3318 of the finger 3130 on the platen 3102. Specifically, baseline time compensation corrects for spatial variability of the round-trip propagation time $t_p=2d_p/v_s$ across the sensor 3100, i.e., that $t_p$ can vary for different pixel elements 3110 due to spatial variations in the sound velocity $v_s$, the thickness $d_p$, or both. Spatial variability in $d_p$ can be caused by manufacturing limitations, such as when the platen 3102 is fabricated with the top and bottom faces 3112, 3122 not flat or not parallel to each other, or when the piezoelectric layer 3114 has a frequency/phase response that spatially varies across the platen 3102. Spatial variability in $d_p$ can also be caused by differential thermal expansion of the platen 3102, which may arise from a transverse temperature gradient across the platen 3102. Such a temperature gradient may be caused by heat that conducts from the finger 3130 into the platen 3102. Thermal gradients can also cause spatial variations in the density of the platen 3102, thereby causing the sound velocity $v_s$ to spatially vary as well. Spatial variability of the round-trip propagation time $t_p$ may also be caused by electronics, such as different latencies for different circuit components, different lengths of metallic traces, variations in channel impedances, and/or other inconsistencies within the electronics that may cause spatial variability.

Since many sources of spatial variability of $t_p$ are time-dependent, the most accurate values of $\Delta t$ can be determined from signal and baseline waveforms 3500 that are recorded temporally close to each other (e.g., within one second). However, many sources of spatial variability change slowly enough over time that the baseline arrival times $t_a^{(b)}$ are essentially constant for extended time periods (e.g., minutes or more). In this case, it may not be necessary to record a full set of baseline waveforms 3500 (i.e., one for each pixel element 3110) for each time-shift image. For example, the baseline waveforms 3500 can be recorded once, saved in the memory 3722, and retrieved from the memory 3722 as needed. In this case, the finger sensor system 3700 can periodically (e.g., once every minute) record new baseline waveforms 3500 and overwrite the baseline waveforms 3500 stored in the memory 3722 with the new baseline waveforms 3500. Alternatively, only the baseline arrival times $t_a^{(b)}$ are stored in the memory 3722 and retrieved from the memory 3722 as needed to determine a time delay $\Delta t$. Storing only the baseline arrival times $t_a^{(b)}$ uses less memory than storing the baseline waveforms 3500, thereby reducing the computational resources needed to generate the time-shift image. It is also possible to correct the stored baseline waveforms 3500 for temperature variations that have occurred since the baseline waveforms 3500 were recorded, thereby increasing the amount of time that can elapse before recording new baseline waveforms 3500.

FIG. 9 compares a time-shift image 3804 of a fingerprint with a conventional amplitude-shift image 3802 of the same fingerprint. To improve signal-to-noise ratio (SNR), each of the images 3802 and 3804 was averaged over sixteen scans. The ultrasound sensor 3100 had 250×250=62,500 pixel elements 3110 covering an area of 1×1 cm². The images 3802 and 3804 were obtained from the same signal and baseline waveforms 3500. To generate the amplitude-shift image 3802, the signal and baseline waveforms 3500 for each pixel element 3110 were processed to determine the average amplitude shift therebetween (e.g., see the amplitude shift $\Delta A$ in FIG. 7). Each average amplitude shift was mapped to a grayscale value of a corresponding pixel of the image 3802. For the time-shift image 3804, the average time shift $\Delta t$ determined for each pixel element 3110 was mapped to a grayscale value of a corresponding pixel of the image 3804.

Subtracting the baseline amplitude from the signal amplitude for each pixel element 3110 of the ultrasound sensor 3100 is referred to as baseline amplitude (or power) compensation. Similar to baseline time compensation, baseline amplitude compensation is used to correct for spatial variability of the sensed amplitude (or power) of the echoes, thereby ensuring that spatial variation in AA is correctly attributed to the finger 3130. In fact, baseline-echo amplitude can spatially vary by more than the amplitude shift $\Delta A$, in which case baseline amplitude compensation is critical for obtaining a clear fingerprint image. Spatial amplitude variability can be caused by any of several factors, including spatial variations in the piezoelectric properties of the piezoelectric layer 3114, electrical variations in the electrodes 3106 and 3108, and readout electronics.

The time-shift image 3804 has a noticeably higher SNR than the amplitude-shift image 3802, as evidenced by the visibly improved contrast of the ridges. This improved SNR likely indicates that ultrasound pulses 3116 are generated with less phase noise than amplitude noise, and thus phase (or time delay) can be measured with better sensitivity than amplitude. The higher SNR achievable with the present inventive concepts can be used to improve image clarity, as shown in FIG. 9. However, higher SNR can also be used to advantageously decrease data acquisition time by reducing the number of averages needed to meet a target SNR. For example, a time period of at least 1 µs can be used to scan each pixel element 3110, and therefore a full scan of all 62,500 pixel elements 3110 would take place over a time period of at least 62.5 ms. However, for amplitude-shift imaging, up to 64 scans can be performed and averaged to obtain an image with sufficient SNR, resulting in a total scan time of at least 4 s. By contrast, with time-shift imaging, sufficient SNR can be obtained by averaging over less than 64 scans, such as less than 16 scans, less than 8 scans, such as only four scans. The resulting total scan time for four scans of 0.25 s is a factor of sixteen less than what is needed for amplitude-shift imaging. In some embodiments, time-shift imaging is implemented with any positive integer number of scans that are averaged together. These embodiments include time-shift imaging with one scan, in which case no averaging is needed.

The time-shift image 3804 and amplitude-shift image 3802 can be combined to obtain a hybrid time-amplitude-shift image having a higher SNR than either of the images 3802 and 3804. Specifically, each pixel of the hybrid image can be obtained by processing the corresponding signal and baseline waveforms 3500 to obtain both the time shift $\Delta t$ and the amplitude shift $\Delta A$. These shifts can then be transformed into a single value (e.g., a weighted sum) that is then mapped to a grayscale value. Other techniques to combine the time shift $\Delta t$ and amplitude shift $\Delta A$ can be used without departing from the scope hereof. In some embodiments, either or both a time-shift image 3804 and an amplitude-shift image 3802 can be obtained, a device (e.g. user device 500 described herein) can be configured to first create one or more time-shift images or amplitude-shift images to identify the location of a finger (e.g. on a sensor), and then create one or more amplitude-shift images or time-shift images, respectively, that are used by the device to create a fingerprint of the finger. Alternatively or additionally, the device can be configured to create either or both of time-shift images and/or amplitude-shift images based on a user entered configuration, or a condition identified (e.g. automatically identified) by the device. For example, if one type of image (e.g. of a fingerprint) is not providing sufficient and/or appropriate data (e.g. for user identification), the device can automatically switch to obtaining the other type of image. For example, indications that one or more fingerprint ridges and/or valleys are missing can cause a transition from one type of image capture (e.g. time-shift image or amplitude-shift image) to the other type of image capture (e.g. amplitude-shift image or time-shift image, respectively), and/or to transition from a single type of image capture (e.g. time-shift image or amplitude-shift image) to a combination of multiple types of image capture (e.g. a combination of time-shift image and amplitude-shift image). In another example, one type of image (e.g. time-shift image or amplitude-shift image) is used to identify the periphery of a finger placed proximate sensor 3100, and the other type of image (e.g. amplitude-shift image or time-shift image, respectively) is used to capture the fingerprint of the finger (e.g. to improve response time of fingerprint identification).

Figure 10:
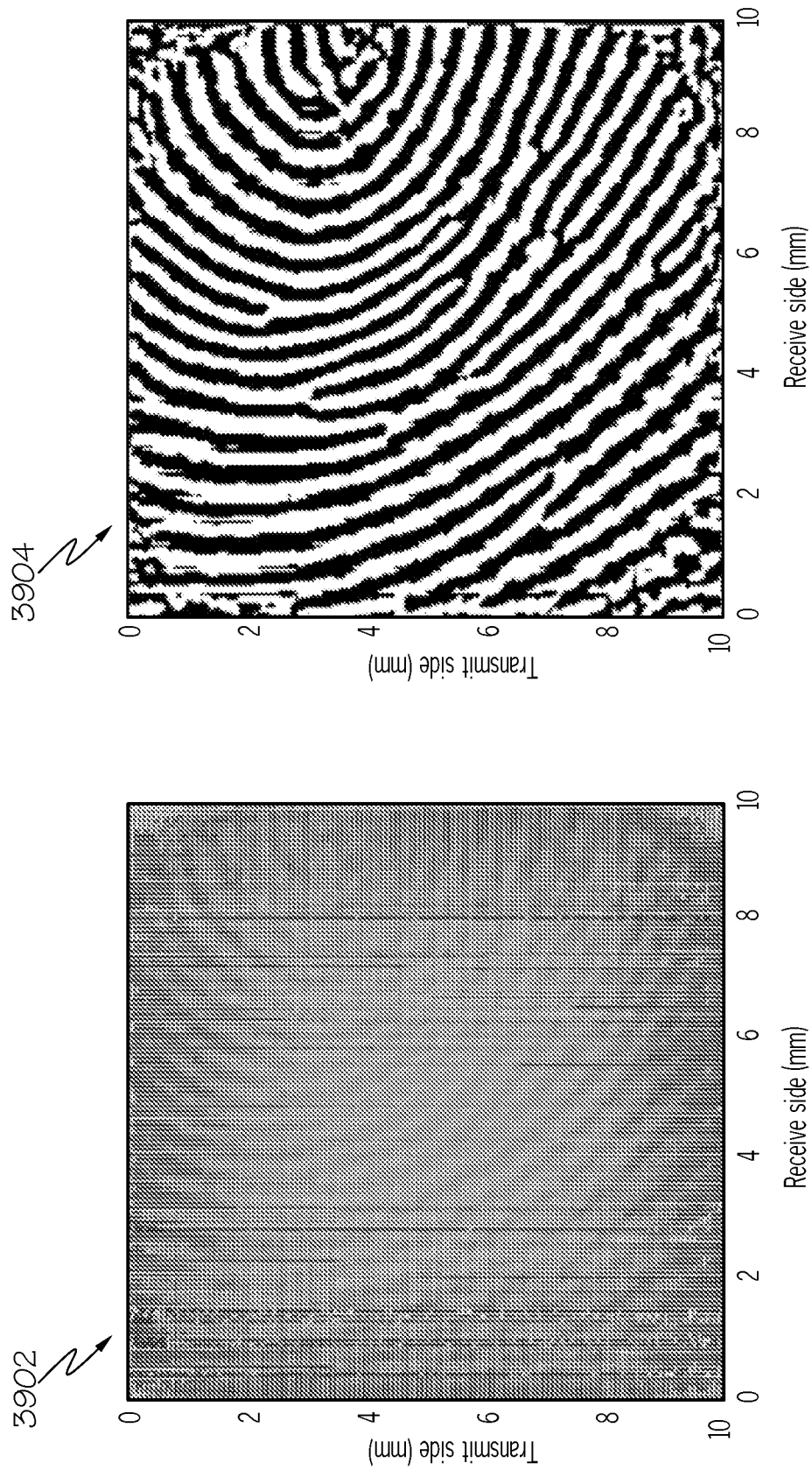
FIG. 10 shows a fingerprint image generated using only signal arrival times of signal waveforms, in an embodiment, consistent with the present inventive concepts.

FIG. 10 shows a fingerprint image 3902 generated using only the signal arrival times $t_a^{(b)}$ of the signal waveforms 3500. Thus, the fingerprint image 3902 of FIG. 10 was generated without baseline compensation (i.e., baseline waveforms 3500). Specifically, the signal arrival time $t_a^{(b)}$ determined for each pixel element 3110 of the ultrasound sensor 3100 was mapped to a grayscale value of a corresponding pixel of the fingerprint image 3902. The fingerprint image 3902 was created from the same signal waveforms 3500 used to generate the images 3802, 3804 of FIG. 9.

FIG. 10 also shows a binarized image 3904 obtained by applying binarization to the fingerprint image 3902. The binarized image 3904 shows almost all of the same features that appear in the time-shift image 3804. Accordingly, the spatial variability of the round-trip propagation time $t_p$ may be small enough that baseline time compensation is not needed. For example, the thickness $d_p$ of the platen 3102 may have sufficient spatial uniformity that the baseline arrival times $t_a^{(b)}$ are essentially identical for all of the pixel elements 3110. In this case, the baseline waveforms 3500 are not needed, advantageously reducing data acquisition time, speeding up signal processing, and reducing memory storage requirements.

Figure 11:
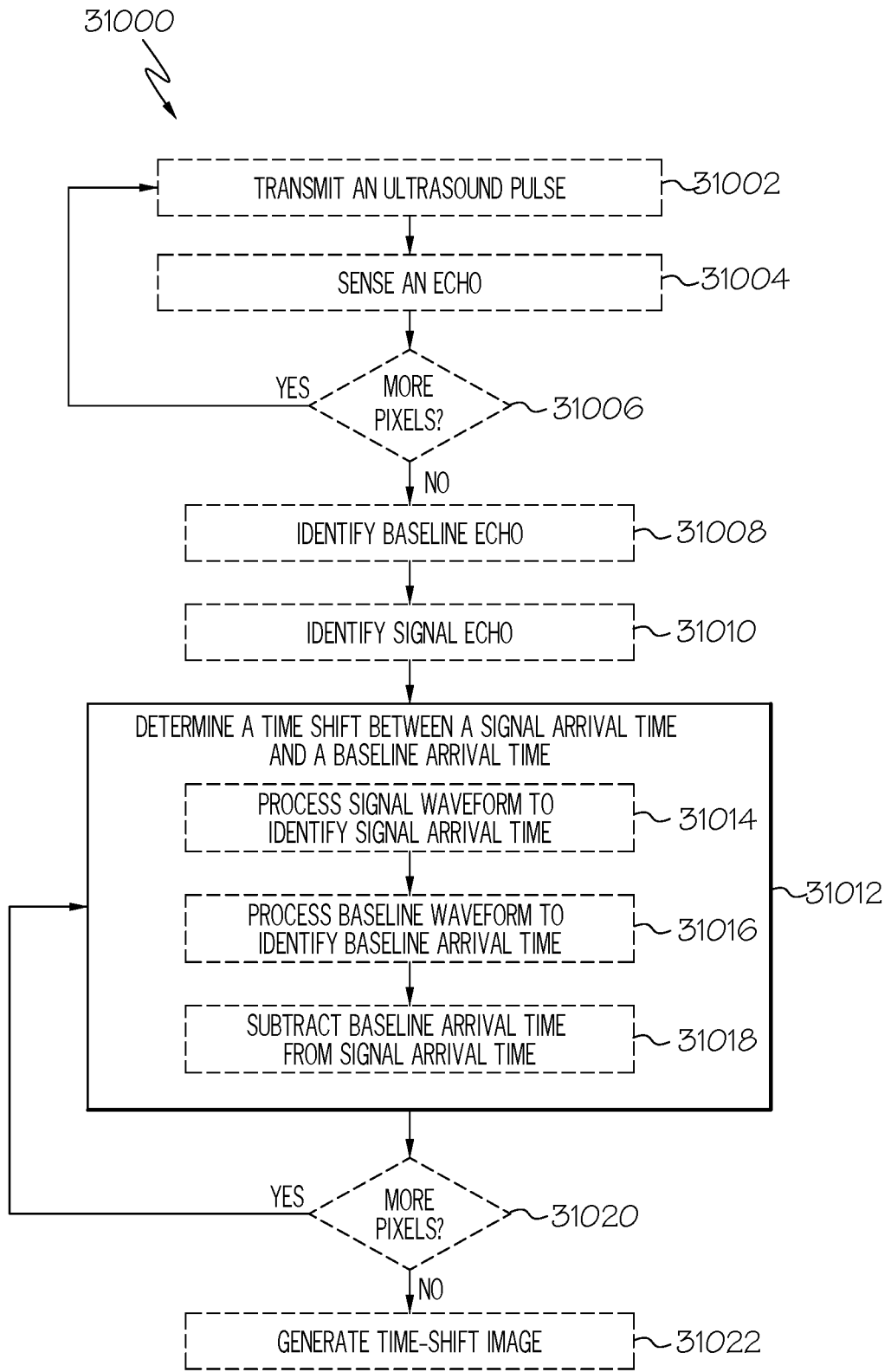
FIG. 11 is a flow chart of an ultrasound signal-processing method that uses baseline time compensation, in embodiments, consistent with the present inventive concepts.

FIG. 11 is a flow chart of an ultrasound signal-processing method 31000 that uses baseline time compensation. Method 31000 can be performed using the systems and devices of the present inventive concepts, and it is described using the various components described herein. In the block 31012, a time shift is determined between (i) a signal arrival time of a signal echo sensed by an ultrasound transducer, and (ii) a baseline arrival time of a baseline echo sensed by the ultrasound transducer. In one example of the block 31012, the ultrasound transducer is one pixel element 3110(i, j) of the ultrasound sensor 3100, and the computer 3710 of FIG. 8 processes signal and baseline waveforms 3500 to determine the time shift Δt. The signal echo may have been generated by a platen surface, of a platen, with an object contacting the platen surface. Similarly, the baseline echo may have been generated by the platen surface without the object. For example, the signal and baseline echoes may have been generated by the platen top surface 3112 of the platen 3102, as shown in FIGS. 2 to 5.

In some embodiments, the ultrasound transducer is a pixel element of an ultrasound transducer array. In these embodiments, the method 31000 includes the decision block 31020, which repeats the block 31012 for each pixel element of the ultrasound transducer array to generate an array of time shifts. The method 31000 also includes the block 31022 in which a time-shift image is generated for the array of time shifts. In one example of the blocks 31020 and 31022, the computer 3710 processes signal and baseline waveforms 3500 to determine one time shift Δt for each pixel element 3110 of the ultrasound sensor array 3100. The one-time shift Δt is one of an array of time shifts corresponding to the two-dimensional array of pixel elements 3110. The computer 3710 then processes the array of time shifts to create a time-shift image (e.g., the time-shift image 3804 of FIG. 9). Although not shown in FIG. 9, the time-shift image can then be outputted (e.g., to the display 3712, or to another computer system for additional processing or storage).

In some embodiments, the ultrasound transducer array has a number of rows (rows of conductors) and a number of columns (columns of conductors), and the time-shift image has the same numbers of rows and columns. For example, the numbers of rows and columns in the time-shift image 3804 can equal the numbers of rows and columns of the ultrasound sensor 3100. In this case, the pixels of the time-shift image can have a one-to-one correspondence with the pixel elements 3110 of the sensor 3100.

In some embodiments, the method 31000 further includes post-processing of the time-shift image (e.g. post-processing of the time-shift image data). For example, post-processing can include applying, to the time-shift image, one or more of: Wiener filtering, steerable filtering, histogram equalization, and/or binarization. In some embodiments, binarization is applied to the fingerprint image 3902 to generate the binarized image 3904. However, any type of image post-processing can be implemented without departing from the scope hereof. Details about various post-processing techniques can be found in Gerard Touma in "A row-column addressed acoustic biometric scanner integrated with pulse oximetry" (Ph.D. Dissertation, Stanford University, 2020).

In some embodiments, the method 31000 includes one or both of the blocks 31008 and 31010. In the block 31008, the baseline echo is identified from a baseline waveform obtained from the ultrasound transducer while the object contacted the platen surface. In the block 31010, the signal echo is identified from a signal waveform obtained from the ultrasound transducer while the object was not contacting the platen surface. The signal echo may be an initial echo of the signal waveform, and the baseline echo may be an initial echo of the baseline waveform. The waveform 3500W is one example of a waveform that may be either the signal waveform or the baseline waveform. The sub-waveform 3504 is one example of an initial echo.

In some embodiments, the block 31012 of the method 31000 includes the blocks 31014, 31016, and 31018. In the block 31014, the signal waveform is processed to identify the signal arrival time. In the block 31016, the baseline waveform is processed to identify the baseline arrival time. In the block 31018, the baseline arrival time is subtracted from the signal arrival time to determine the time shift. The signal waveform can be filtered prior to identifying the signal arrival time. Similarly, the baseline waveform can be filtered prior to identifying the baseline arrival time.

The preceding embodiments of the method 31000 can be performed on a computer system (e.g., see the ultrasound signal-processing system 31800 of FIG. 19), such as a computer system that receives signal and baseline waveforms 3500 recorded by the finger sensor system 3700. A third party may operate the finger sensor system 3700 and transmit the recorded waveforms 3500 to the computer system for processing. Thus, the ultrasound sensor is not required to perform the method 31000. However, the following discussion presents additional embodiments of the method 31000 that include operation of the ultrasound sensor to obtain waveforms.

Accordingly, some embodiments of the method 31000 include the blocks 31002 and 31004. In the block 31002, a signal ultrasound pulse is transmitted, by the ultrasound transducer, into the platen such that a portion of the signal ultrasound pulse reflects off of the platen surface to form the signal echo. In the block 31004, the signal echo is sensed with the ultrasound transducer. The output of the ultrasound sensor can then be processed into a signal waveform. For example, in FIG. 8 the amplifier 3402 amplifies the output of the sensor array 3100 into the amplified output 3404, the ADC 3706 digitizes the amplified output 3404 into sensor data 3716, and the real-time processor processes the sensor data 3716 into the waveform 3500W. While the ultrasound transducer in this example is an array of multiple pixel elements, the ultrasound transducer can alternatively be a single ultrasound transducer.

In some embodiments, the ultrasound transducer includes one or more pixel elements of an ultrasound transducer array. In these embodiments, the method 31000 can include the decision block 31006 that repeats the block 31002 and 31004 for each pixel element of the transducer array. If the pixel elements of the transducer array are row-column addressable, then the signal ultrasound pulse can be transmitted, and the signal echo can be sensed, by controlling the ultrasound transducer array via row-column addressing. The signal ultrasound pulse can be transmitted using only one row of the sensor array, and the echo pulse can be sensed using only one column of the sensor array. In one example of these embodiments, the column electrode 3108($j$) of the ultrasound sensor 3100 is excited to transmit the ultrasound pulse 3118($j$) into the platen 3102. The ultrasound pulse 3118($j$) reflects off the top surface 3112 of the platen 3102 to generate echoes 3406, 3408 that are then sensed by the row electrode 3106($i$).

In other embodiments, the ultrasound transducer array has individually addressable pixel elements. In these embodiments, the signal ultrasound pulse can be transmitted, and the signal echo can be sensed, by addressing the individual pixel elements. In some embodiments, the signal ultrasound pulse can be transmitted using beamforming, i.e., multiple pixel elements can be excited simultaneously, and with appropriately selected complex-valued weights, such that the signal ultrasound pulse is focused onto the top face of the platen. Similarly, the signal echo can be sensed using beamforming, i.e., multiple pixel elements can be sensed simultaneously, and with appropriate complex-values weights applied to the electrical outputs of the pixel elements. Beamforming can be implemented with both row-column addressable sensor arrays and individually addressable sensor arrays. Beamforming can also be realized in software on the detected data once it is digitized and stored in a computer (e.g., see the ultrasound-signal processing system 31800 of FIG. 19), as an alternative to beamforming using hardware for both or either transmit and receive operations.

In the preceding embodiments of the method 31000 that include the blocks 31002 and 31004, baseline waveforms can be stored in memory, and retrieved from the memory, as part of the block 31012. However, in other embodiments, the method 31000 iterates twice over the blocks 31002 and 31004. Specifically, the method 31000 performs a first iteration over the blocks 31002 and 31004 to measure the signal waveform, as described above. In the second iteration over the blocks 31002 and 31004, a baseline ultrasound pulse is transmitted, by the ultrasound transducer, into the platen such that a portion of the baseline ultrasound pulse reflects off of the platen surface to form the baseline echo. The baseline echo is then sensed with the ultrasound transducer. The output of the ultrasound sensor can then be processed into the baseline waveform, similarly to the signal waveform. The baseline waveform can be generated before or after the signal waveform.

In embodiments where the ultrasound transducer is a pixel element of an ultrasound transducer array, the method 31000 includes the block 31006 to repeat the blocks 31002 and 31004 for each pixel element of the transducer array. Specifically, the method 31000 performs a first iteration of the blocks 31002, 31004, and 31006 to measure a signal waveform for each pixel element. The method 31000 then performs a second iteration of the blocks 31002, 31004, and 31006 to measure a baseline waveform for each pixel element. The transducer array can be controlled to transmit the baseline ultrasound pulse similarly to how it is controlled to transmit the signal ultrasound pulse (e.g., row-column or individual-pixel addressing, beamforming or single-row transmitting, etc.). Similarly, the transducer array can be used to sense the baseline echo similarly to how it is used to sense the signal echo (e.g., row-column or individual-pixel addressing, beamforming or single-column sensing, etc.). The signal and baseline waveforms can be obtained in any temporal order. For example, all of the signal waveforms can be obtained before all of the baseline waveforms, or vice versa.

Signal Processing to Determine Time Shifts

Figure 12:
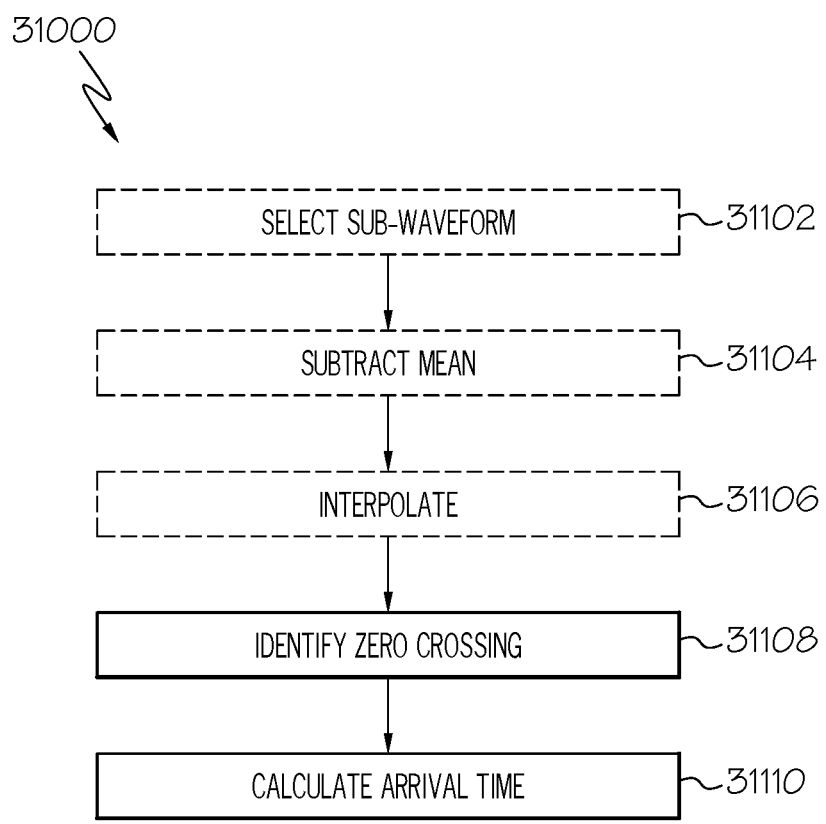
FIG. 12 is a flow chart of a method for processing a waveform to identify an arrival time of an echo, in embodiments, consistent with the present inventive concepts.

FIG. 12 is a flow chart of a method 31100 for processing a waveform to identify an arrival time of an echo. When the method 31100 is performed with the signal waveform to identify the signal arrival time, the method 31100 can substitute for the block 31014 of the method 31000. Similarly, when the method 31100 is performed with the baseline waveform to identify the baseline arrival time, the method 31100 can substitute for the block 31016 of the method 31000.

In the block 31108 of the method 31100, the waveform is processed to identify a zero crossing of the echo. In the block 31110, the arrival time of the echo is calculated based on a time of the zero crossing. The blocks 31108 and 31110 can be performed with the signal waveform to calculate the signal arrival time $t_a^{(s)}$. The blocks 31108 and 31110 can also be performed with the baseline waveform to calculate the baseline arrival time $t_a^{(b)}$. The signal arrival time $t_a^{(s)}$ can be determined before or after the baseline arrival time $t_a^{(b)}$ is determined.

Some embodiments of the method 31100 include the block 31104, in which a mean of the waveform is subtracted from the waveform to obtain a mean-corrected waveform. In these embodiments, the blocks 31108 and 31110 are performed with the mean-corrected waveform, i.e., the identified zero crossing is a zero crossing of the mean-corrected waveform. In some of these embodiments, the method 31100 includes calculating the mean of the waveform.

Some embodiments of the method 31100 include the block 31102, in which a sub-waveform of the echo is selected from the waveform. The sub-waveform 3504 of FIG. 6 is one example of a sub-waveform. In this case, the block 31104 is performed with the sub-waveform (i.e., the mean of the sub-waveform is subtracted from the sub-waveform) to obtain a mean-corrected sub-waveform. The blocks 31108 and 31110 are then performed with this mean-corrected sub-waveform (i.e., the zero-crossing is a zero-crossing of the mean-corrected sub-waveform). The mean-corrected sub-waveforms 3602 and 3604 of FIG. 7 are examples of a mean-corrected baseline sub-waveform and a mean-corrected signal sub-waveform, respectively. In one of these embodiments, the method 31100 includes calculating the mean of the sub-waveform.

Some embodiments of the method 31100 include the block 31106, in which the mean-corrected sub-waveform is interpolated to obtain a best-fit curve. In these embodiments, the blocks 31108 and 31110 are performed with the best-fit curve (i.e., the zero crossing is a zero crossing in the best-fit curve). Either the entire mean-corrected sub-waveform can be interpolated, or a portion thereof. For example, a portion of the mean-corrected sub-waveform 3602 near a zero crossing 3610 can be selected for linear interpolation, while other portions (e.g., near the neighboring anti-nodes) are excluded. Excluding these other portions advantageously speeds up interpolation by reducing the amount of data that needs to be processed.

As shown in FIG. 6, the sub-waveform 3504 lasts for several cycles, and therefore forms a sequence of zero crossings. Any one or more of these zero crossings can be used to determine a singular arrival time of the echo. The sequence of zero crossings can include only those zero crossings with a positive slope, only those zero crossings with a negative slope, or both. In some embodiments, a sequence of signal zero crossings is processed to determine the signal arrival time, and a sequence of baseline zero crossings is processed similarly to determine the baseline arrival time. Processing these two sequences similarly ensures that the definition of arrival time is the same for the baseline and signal echoes. For example, in embodiments where only one baseline zero crossing is used to determine the baseline arrival time $t_a^{(b)}$, and where only one signal zero crossing is used to determine the signal arrival time $t_a^{(s)}$, the position of the baseline zero crossing in the sequence of baseline zero crossings can be the same as the position of the signal zero crossing in the sequence of signal zero crossings.

In some embodiments of the method 31000, the signal waveform is processed, in the block 31014, to identify the signal arrival time by applying a Hilbert transform to at least part of the signal waveform (e.g., a portion or all of the signal sub-waveform). The output of the Hilbert transform includes a temporal sequence of instantaneous signal phases that can be processed to identify a signal zero crossing. The signal transmit time can then be calculated based on the time when the signal zero crossing occurred. The same steps can be implemented in the block 31016, but with the baseline waveform instead of the signal waveform, to calculate the baseline arrival time. Any of the techniques described above for the method 31100 can be implemented with the sequence of instantaneous signal phases and the sequence of instantaneous baseline phases, such as selecting a sub-waveform, interpolating, subtracting a mean, etc.

The Hilbert transform can also output a temporal sequence of envelope values that can also be used to determine an echo arrival time. For example, an extremum can be identified in the sequence of envelope values and the time at which the extremum occurred can be selected as the arrival time. The sequence of envelope values can be interpolated to more precisely identify the time at which the extremum occurred. A sequence of envelope values can be used either with or without the corresponding sequence of instantaneous phase values outputted by the Hilbert transform. Examples of techniques to identify an echo arrival time based on both phase and envelope outputs of a Hilbert transform can be found in Mario Kupnik, Edwin Krasser, and Martin Groschl, "Absolute Transit Time Detection for Ultrasonic Gas Flowmeters Based on Time and Phase Domain Characteristics" (2007 IEEE Ultrasonics Symposium Proceedings, New York, NY, 2007, pp. 142-145). However, those trained in the art will recognize that there are a host of techniques to use the Hilbert transform to determine the arrival time of echo, any of which can be used without departing from the scope hereof.

In some embodiments of the method 31000, the time shift is determined by transforming the baseline and signal waveforms into a cross-correlation signal and calculating the time shift based on the cross-correlation signal. In these embodiments, the block 31012 can exclude the blocks 31014, 31016, and 31018, as the peak of the cross-correlation signal will directly indicate the time shift Δt without having to separately determine the signal and baseline arrival times. Those trained in the art will recognize that there are a host of techniques to use cross-correlation to determine a time shift, any of which can be used without departing from the scope hereof.

Figure 13:
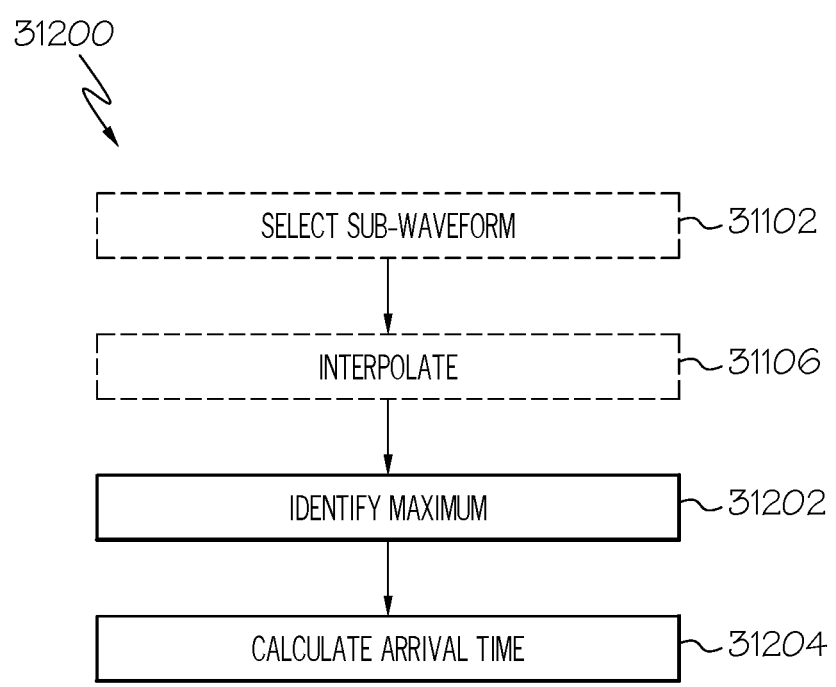
FIG. 13 is a flow chart of a method for processing a waveform to identify an arrival time of an echo, in embodiments, consistent with the present inventive concepts.

FIG. 13 is a flow chart of a method 31200 for processing a waveform to identify an arrival time of an echo. Like the method 31100, the method 31200 can be performed with the signal waveform to identify a signal arrival time, in which case the method 31200 can substitute for the block 31014 of the method 31000. Similarly, the method 31200 can be performed with the baseline waveform to identify a baseline arrival time, in which case the method 31200 can substitute for the block 31016 of the method 31000. The method 31200 is similar to the method 31100 except that arrival times are determined from extrema (i.e., maxima or minima) of sub-waveforms. For clarity in the following discussion, maxima are used for the extrema. However, minima can be used instead without departing from the scope hereof.

In the block 31202 of the method 31200, the waveform is processed to identify a maximum of the echo. In the block 31204, the arrival time of the echo is calculated based on a time of the maximum. The blocks 31202 and 31204 can be performed with the signal waveform to calculate the signal arrival time $t_a^{(s)}$. Similarly, the blocks 31202 and 31204 can also be performed with the baseline waveform to calculate the baseline arrival time $t_a^{(b)}$. The signal arrival time $t_a^{(s)}$ can be determined before or after the baseline arrival time $t_a^{(b)}$ is determined.

Some embodiments of the method 31200 include the block 31102, in which a sub-waveform of the echo is selected from the waveform. In these embodiments, the blocks 31202 and 31204 are performed with this sub-waveform. The resulting amplitude can be a local maximum of the sub-waveform. Some embodiments of the method 31200 include the block 31106, in which the sub-waveform is interpolated to obtain a best-fit curve. In these embodiments, the blocks 31202 and 31204 are performed with the best-fit curve. Either the entire sub-waveform can be interpolated, or a portion thereof.

As shown in FIG. 6, the sub-waveform 3504 lasts for several cycles, and therefore forms a sequence of extrema. Any one or more of these extrema can be used to determine a singular arrival time of the echo. The sequence of extrema can include only maxima, only minima, or both. In some embodiments, a sequence of signal extrema is processed to determine the signal arrival time, and a sequence of baseline extrema is processed similarly to determine the baseline arrival time. Processing these two sequences similarly ensures that the definition of arrival time is the same for the baseline and signal echoes. For example, in embodiments where only one baseline maximum is used to determine the baseline arrival time $t_a^{(b)}$, and where only one signal maximum is used to determine the signal arrival time $t_a^{(s)}$, the position of the baseline maximum in the sequence of baseline extrema can be the same as the position of the signal maximum in the sequence of signal extrema.

Figure 14:
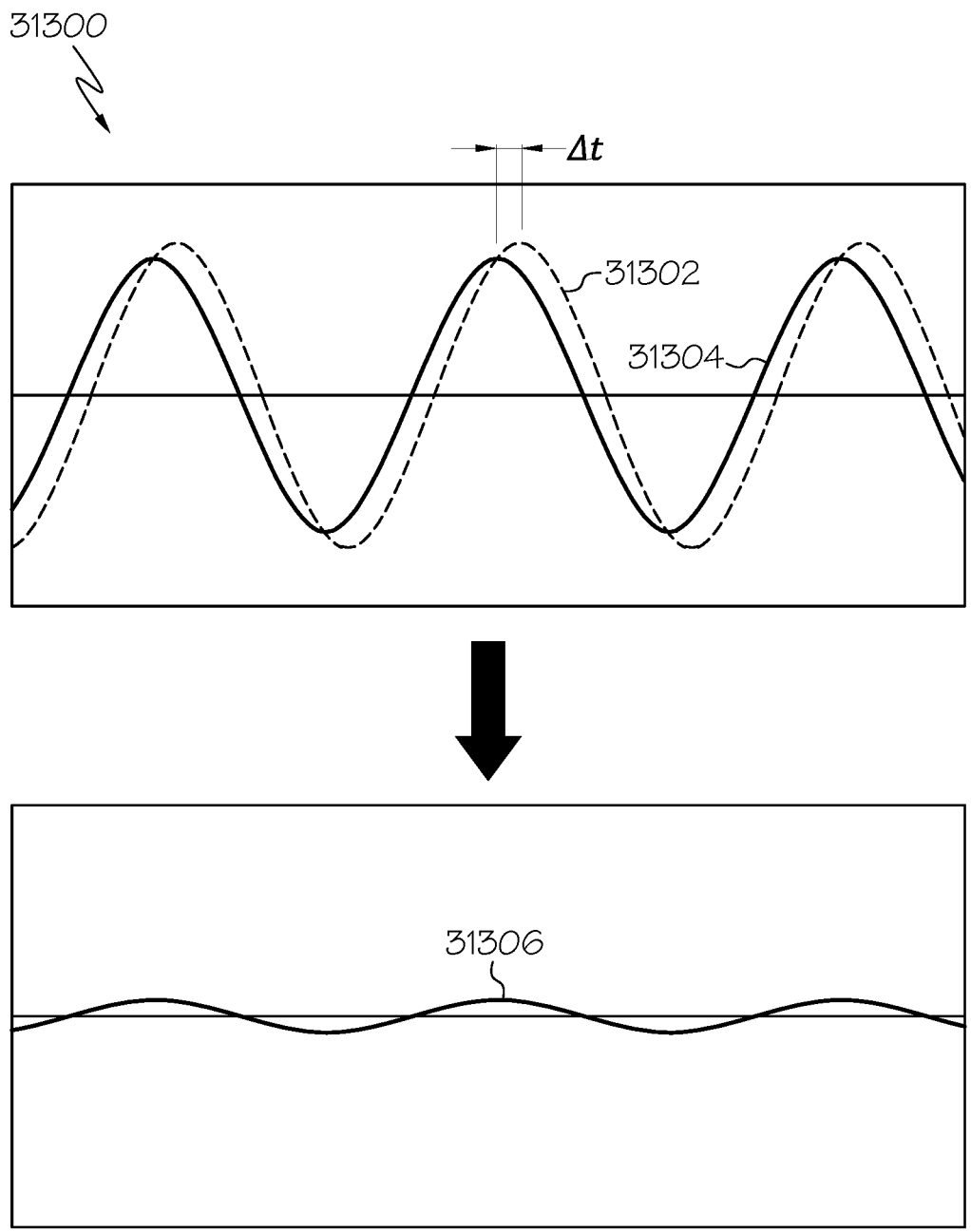
FIG. 14 illustrates a method for processing signal and baseline waveforms to identify a time shift, in an embodiment, consistent with the present inventive concepts.

FIG. 14 illustrates a method 31300 for processing the signal and baseline waveforms to identify the time shift Δt. Similar to cross-correlation, the method 31300 combines the signal and baseline waveforms to directly determine Δt, as opposed to separately processing the signal and baseline waveforms to determine $t_a^{(s)}$ and $t_a^{(b)}$. Accordingly, the method 31300 can be used for the block 31012 of the method 31000. The method 31300 is based on excitation of a pixel element with several continuous cycles of a single-frequency waveform, also referred to as a "tone burst". For example, the tone burst can be formed from eight consecutive cycles of a sine wave whose frequency is 150 MHz. The tone burst can be unipolar or bipolar. Furthermore, the tone burst can be low-pass filtered to smooth out its envelope. It can be assumed that the echo resulting from the tone burst has the same fixed number of continuous cycles of the center frequency. Specifically, any time shift Δt resulting from an object is constant across the entire echo. In this case, a signal sub-waveform 31304 can be subtracted from a baseline sub-waveform 31302 to obtain a difference waveform 31306. The frequency of the difference waveform 31306 is the same as that of the sub-waveforms 31302 and 31304, and the amplitude of the difference waveform 31306 depends on the time shift Δt. Accordingly, the difference waveform 31306 can be processed to determine the time shift Δt.

For small values of the time shift Δt, the amplitude of the difference waveform 31306 will be smaller than that of the sub-waveforms 31302 and 31304. In this case, the difference waveform 31306 will have a lower SNR than the sub-waveforms 31302 and 31304. This reduced SNR can limit how well the time shift Δt can be determined. One way to preserve SNR is to fit each of the sub-waveforms 31302 and 31304 to a sine wave with variable phase and amplitude (but fixed frequency), and then calculate the difference waveform 31306 from the best-fit sine waves. Other techniques to preserve SNR can be used without departing from the scope hereof.

Figure 15:
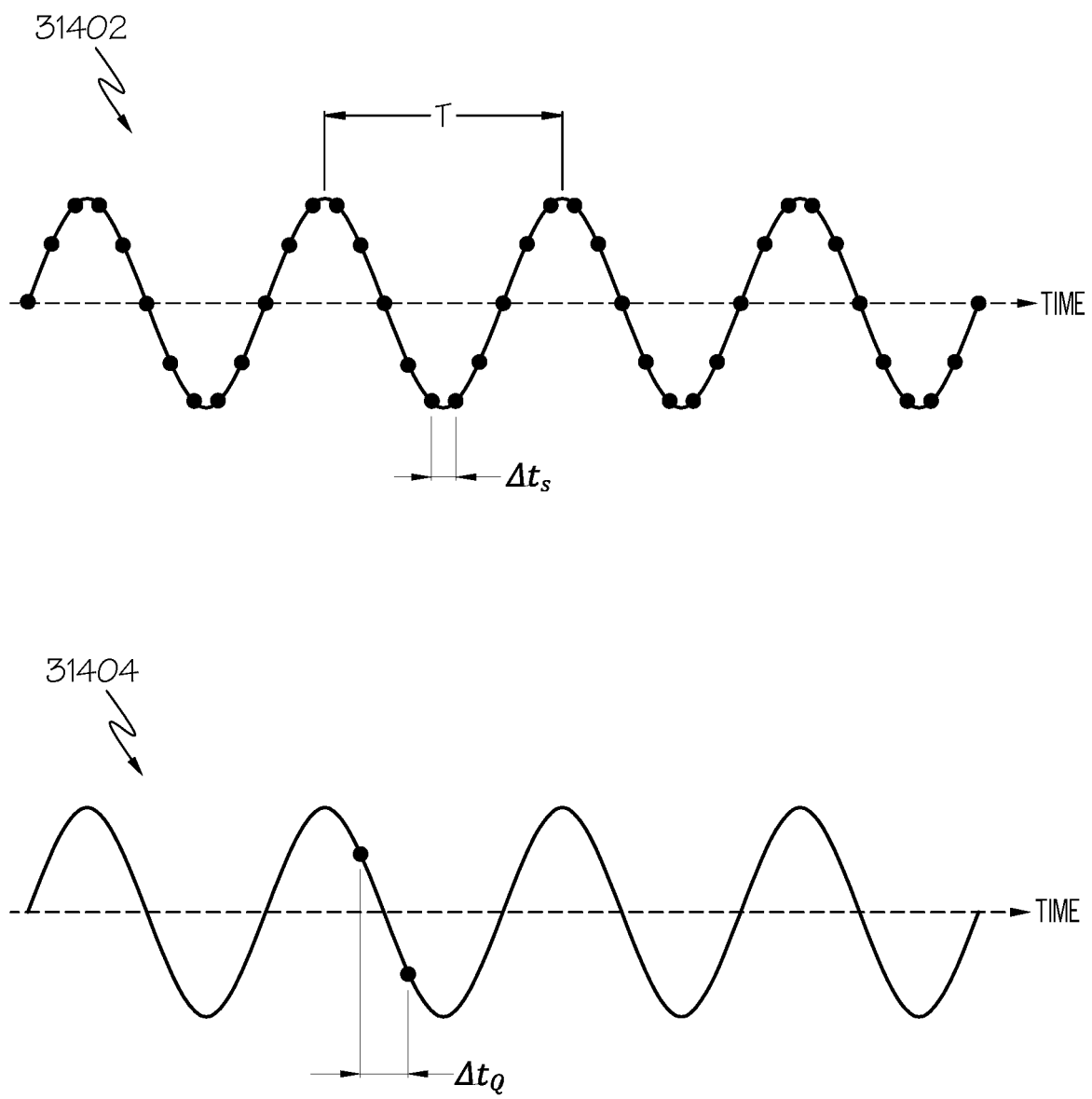
FIG. 15 illustrates a method for processing a waveform to identify an arrival time of an echo, in an embodiment, consistent with the present inventive concepts.

FIG. 15 illustrates two sampling methods 31402 and 31404 for processing a waveform to identify an arrival time of an echo. In method 31402, an echo comprising a sinusoidal waveform is sampled by system 10 at a sampling rate of 10 samples per each cycle of a sinusoid. System 10 can analyze the collected 10 samples per cycle in order to create an estimation of the echo (e.g. an estimation of amplitude and/or phase). In method 31404, an echo (e.g. the same echo as in method 31402) is sampled at 2 samples per each cycle of the sinusoid. System 10, knowing the parameters of the transmitted signal from which the echo is based, can similarly provide an estimation of the echo (e.g. an estimation of amplitude and/or phase). The reduced sampling of method 31402 provides numerous advantages, such as processing speed, data storage and transfer, and other advantages. Similar to the methods 31100 and 31200, the methods 31402 and/or 31404 can be performed with a signal waveform to calculate a signal arrival time $t_a^{(s)}$, in which case the methods 31402 and/or 31404 can be used for the block 31014 of the method 31000. Similarly, the methods 31402 and/or 31404 can be performed with a baseline waveform to calculate a baseline arrival time $t_a^{(b)}$, in which case the methods 31402 and/or 31404 can be used for the block 31016 of the method 31000. The signal arrival time $t_a^{(s)}$ can be determined before or after the baseline arrival time $t_a^{(b)}$ is determined.

The methods 31402 and/or 31404 can implement quadrature sampling of sensed echoes, which advantageously reduces the amount of data to be recorded and processed, as compared to uniform sampling. For example, the sub-waveforms 3602, 3604 in FIG. 7 can be uniformly sampled (e.g., by the ADC 3706 of FIG. 8) at a sampling rate of 1.25 Gbps (i.e., 0.8 ns between sequentially sampled points). At this sampling rate, approximately eight data points can be sampled for each cycle of waveform whose center frequency $f_0$ is 150 MHz. However, since the center frequency $f_0$ is known, only two data points need to be sampled for each cycle in order to determine the phase. These two data points must be separated in time by one-quarter of the period (i.e., in quadrature), but may occur anywhere within a single cycle. Specifically, consider first and second quadrature data points $(t_1, a_1)$ and $(t_2, a_2)$ recorded from one cycle of a baseline waveform. These two data points constrain the baseline waveform to a sinusoid of the mathematical form $y(t) = A \cos \cos (2\pi f_0 t + \phi_b)$, where $A = \sqrt{a_1^2 + a_2^2}$ and the baseline phase $\phi_b$ can be determined by solving either $a_1 = A \cos \cos (2\pi f_0 t_1 + \phi_b)$ or $a_2 = A \cos \cos (2\pi f_0 t_2 + \phi_b)$. This process can be repeated for two quadrature data points from the signal waveform to obtain a signal phase $\phi_s$. The resulting time shift is then $\Delta t = (\phi_s - \phi_b)/(2\pi f_0)$, where $\phi_s$ and $\phi_b$ are in radians and $f_0$ is in hertz. Alternatively, the phase shift $\phi_s - \phi_b$ can be used directly to create the time-shift image (e.g., by mapping the phase shift to a corresponding grayscale value of a pixel of the time-shift image).

Exemplary Pseudocode

The following pseudocode is an exemplary implementation of the method 31000 in which the method 31200 is used for each of the blocks 31014 and 31016. Comments are preceded by the symbol "#".

```
# Define constants
    n_tx = 250 # number of transmitting electrodes
    n_rx = 250 # number of sensing electrodes
    wfm_size = 100 # number of data points within each waveform
    interp_factor = 25 # interpolation factor
    fc = 150 MHz # center frequency of the transmitted pulse and sensed
echo
    fs = 1.25 GSPS # ADC sampling rate
    Ts = fs x interp_factor # sample period after interpolation
# Retrieve a three-dimensional (3D) array of baseline waveforms. The first
index
# of the array runs from 1 to n_tx, and identifies one corresponding row of
the
# sensor. The second index of the array runs from 1 to n_rx, and identifies
one
# corresponding column of the sensor. The third index runs from 1 to
wfm_size
# and identifies one data point of each waveform.
    input_data_baseline = echo_array_baseline(n_tx, n_rx, wfm_size)
# Retrieve a similar 3D matrix of signal waveforms
    input_data_signal = echo_array_signal(n_tx, n_rx, wfm_size)
```

```
# Pre-process each waveform to remove the mean. The parameter "3" indicates
# which dimension of the 3D arrays corresponds to the time of the
waveforms.
    input_data_baseline = mean_removal(input_data_baseline, 3)
    input_data_signal = mean_removal(input_data_signal, 3)
# Interpolate each waveform to achieve a sample period << expected time
delay
    input_data_baseline = interpolation(input_data_baseline,
interp_factor)
    input_data_signal = interpolation(input_data_signal, interp_factor)
# Bandpass filter each waveform between 120 and 180 MHz. The parameter BW
is
# bandwidth, and the parameter N_order is the filter order.
    Input_data_baseline = FIR_filter(input_data_baseline,
       BW = [120 180]MHz, N_order = 100)
    Input_data_signal = FIR_filter(input_data_signal,
       BW = [120 180]MHz, N_order = 100)
# Process each waveform peak to identify the time at which the waveform
peaks
    [max_val_baseline, max_idx_baseline] =
       max(input_data_baseline(sub_window), 3)
    [max_val_signal, max_idx_signal] =
       max(input_data_signal(sub_window), 3)
# Generate a two-dimensional 2D map of the time shifts. Multiply each pixel
of
# the map by 1e12 to express results in picoseconds
    Raw_image = (max_idx_signal - max_idx_baseline) x Ts x 1e12
```

Embodiments with a Single Ultrasonic Transducer

As described hereabove, the method 31000 can be performed with a single ultrasound transducer (e.g. not part of an array of multiple transducers). In this case, the method 31000 can be used to detect the presence of an object contacting the platen surface of the platen. For example, the object may be human tissue, such as the finger 3130, contacting the top surface 3112 of the platen 3102 of FIGS. 2 to 5. The presence of the object can be determined from the time shift, such as by comparing the time shift to a threshold. If the time shift is less than the threshold, the time shift can be assumed to be zero, and therefore the signal and baseline arrival times are the same. In this case, it can be inferred that there is no object contacting the platen. On the other hand, if the time shift is greater than the threshold, it can be inferred that an object was contacting the platen while recording the signal waveform. The threshold can be large enough to ensure that statistical fluctuations of echo arrival times do not lead to erroneous indications of the object's presence. An indication of the presence of the object can then be outputted.

Embodiments with Biometric Sensing

The method 31000 can also be used for biometric sensing. For example, in some embodiments the object is a finger and the time-shift image is a fingerprint of the finger.

The time-shift image 3804 is one example of a time-shift image of a fingerprint. The method 31000 can further include determining, based on the time-shift image, an area of contact between the finger and the platen surface. The area of contact can be an area of ridges of the finger in contact with the platen surface (e.g., see ridges 3316 of the finger 3130 in FIGS. 4 and 5). The method 31000 can further include determining, based on the area of contact, an applied force of the finger and/or other human tissue on the platen surface. The method 31000 can further include (i) repeating said determining the time shift (i.e., the block 31012) and said determining the area of contact to generate a temporal sequence of contact areas, (ii) determining an oscillation period of the temporal sequence of contact areas, and (iii) calculating a pulse rate based on the oscillation period. More details about using two-dimensional ultrasound transducer arrays to measure the area of contact of a finger, and determine a pulse rate therefrom, is described by Gerard Touma in "A row-column addressed acoustic biometric scanner integrated with pulse oximetry" (Ph.D. Dissertation, Stanford University, 2020). This reference also describes how an ultrasound transducer array that is at least partially transparent can be combined with a pulse oximeter.

Embodiments without Baseline Waveforms

Figure 16:
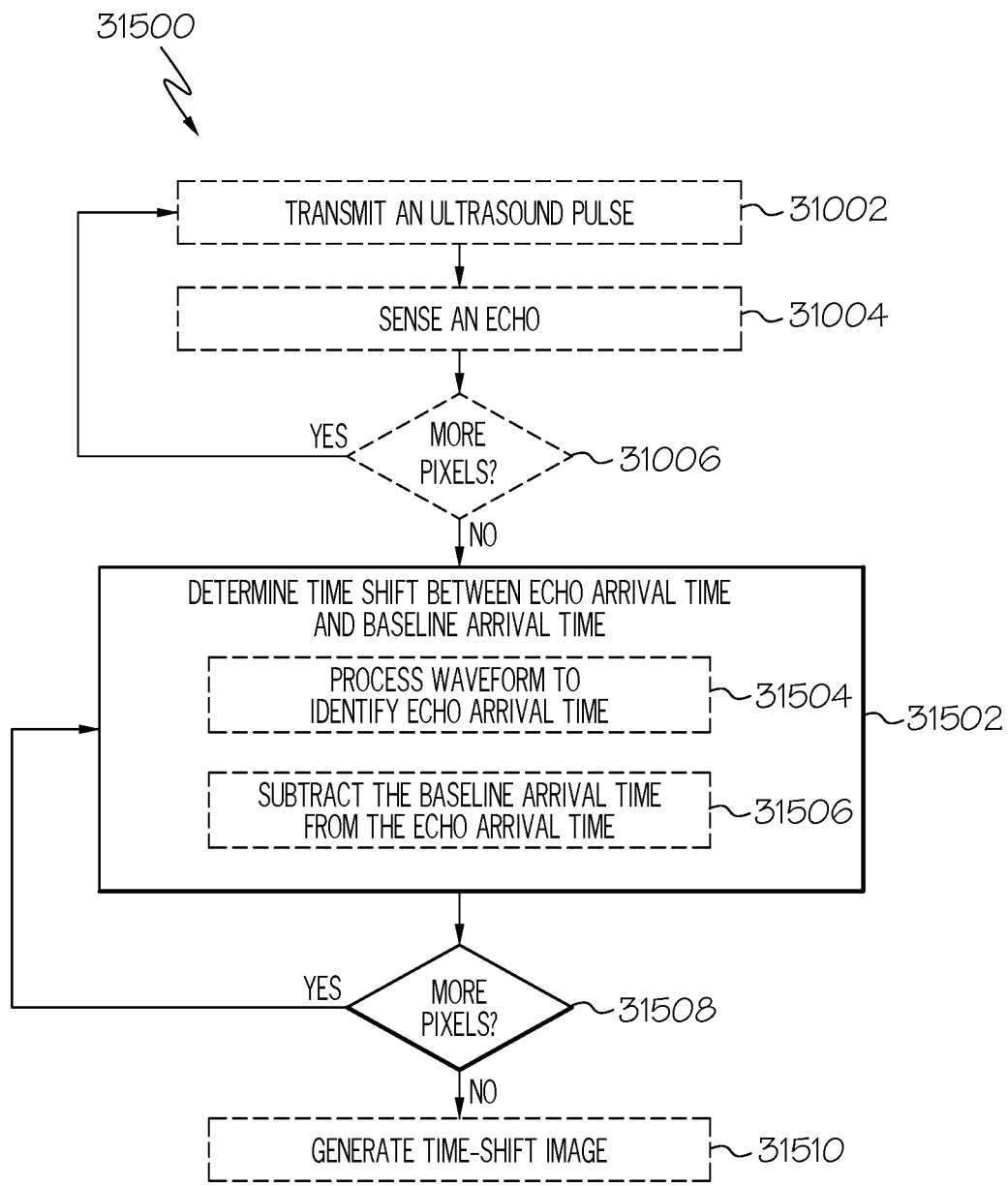
FIG. 16 is a flow chart of an ultrasound signal-processing method that generates a time-shift image without baseline waveforms, in embodiments, consistent with the present inventive concepts.

FIG. 16 is a flow chart of an ultrasound signal-processing method 31500 that generates a time-shift image without baseline waveforms. In the block 31502, a time shift is determined between (i) an arrival time of an echo sensed by a pixel element of an ultrasound transducer array, and (ii) a baseline arrival time. Any technique or method described herein to determine an echo arrival time can be used as part of the block 31502. For example, the method 31100 or the method 31200 can be used to determine the arrival time from a waveform recorded from the pixel element. With the block 31504, the method 31500 repeats the block 31502 for each pixel element of the ultrasound sensor array. The echo can be generated by an object contacting a platen surface of a platen (e.g., the top surface 3112 of the platen 3102 in FIGS. 2 to 5). The object can be a finger (e.g., the finger 3130), and/or other human tissue.

In the block 31510, a time-shift image is generated based on the time shifts determined for the pixel element. Similar to the method 31000, the pixels of the time-shift image can have a one-to-one correspondence with the pixel elements of the ultrasound transducer array. The time-shift image can then be outputted. When the object contacting the platen is a finger, the time-shift image can be a fingerprint of the finger.

Unlike the method 31000, where the baseline arrival time was determined separately for each pixel element, the baseline arrival time in the method 31500 is the same for all pixel elements. The baseline arrival time can be calculated based on arrival times of one or more of the pixel elements. For example, the baseline arrival time can be set equal to the arrival time of one of the pixel elements. Alternatively, the baseline arrival time can be set equal to the average of the arrival times of all the pixel elements. The baseline arrival time can also be set to zero.

The preceding embodiments of the method 31500 can be performed on a computer system (e.g., see the ultrasound signal-processing system 31800 of FIG. 19) that receives waveforms recorded by a sensor system (e.g., the finger sensor system 3700 of FIG. 8). A third party may operate the sensor system and transmit the recorded waveforms to the computer system, which processes the waveforms to determine the echo arrival times. Thus, the ultrasound transducer array is not required to perform the method 31500. However, in some embodiments the method 31500 includes the blocks 31002, 31004, and 31006, in which the ultrasound transducer array is operated to record one waveform for each pixel element. These waveforms can then be used by the block 31502 to determine the corresponding echo arrival times.

Object Detection Methods

Figure 17:
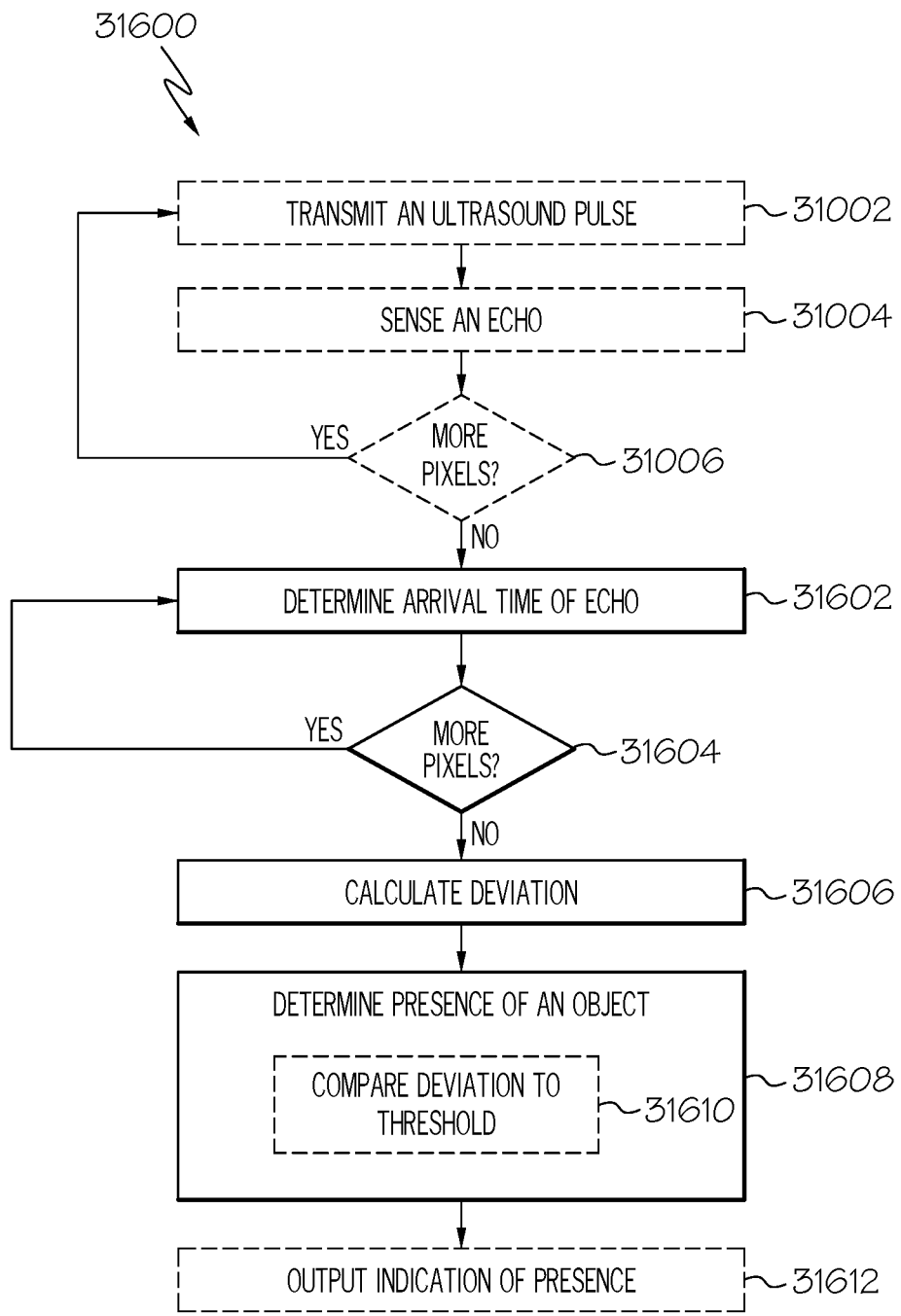
FIG. 17 is a flow chart of an object detection method that does not use baseline waveforms, in embodiments, consistent with the present inventive concepts.

FIG. 17 is a flow chart of an object detection method 31600 that does not use baseline waveforms. In the block 31602, an arrival time is determined for an echo sensed by a pixel element of an ultrasound transducer array. Any technique or method to determine an echo arrival time (e.g., the method 31100 or the method 31200) can be used as part of the block 31602. With the block 31604, the method 31600 repeats the block 31602 for each pixel element of the ultrasound transducer array. The echo can be generated from the object contacting a platen surface of the platen. The object can be human tissue, such as a finger (e.g., the finger 3130 contacting the top surface 3112 of the platen 3102 in FIGS. 2 to 5).

The method 31600 also includes the block 31606, in which a deviation is calculated based on the arrival time determined for one or more pixel elements (e.g. for each pixel element). This deviation is also referred to as the "arrival-time deviation". The method 31600 also includes the block 31608, in which the presence of an object is determined based on the arrival-time deviation. The arrival-time deviation can be a standard deviation, variance, median absolute deviation, and/or any other statistical measure of dispersion. In some embodiments, the method 31600 includes the block 31610, in which the arrival-time deviation is compared to a threshold. For example, if the arrival-time deviation is less than a threshold, it can be inferred that no object is contacting the platen surface. However, if the arrival-time deviation is greater than the threshold, it can be inferred that an object is contacting the platen surface. Specifically, the ridges 3316 and valleys 3318 of a finger (e.g. a finger and/or other body part) can cause the spread of arrival times to increase noticeably, as compared to the distribution of arrival times without the finger contacting the platen surface.

In some embodiments, the method 31600 includes the block 31612, in which an indication of the presence of the object is outputted. The indication can be binary (i.e., an object is indicated as being present or not present). Alternatively, the indication can be a value indicating a probability that an object is contacting the platen surface. The value can be calculated based on the arrival-time deviation, such that a higher arrival-time deviation results in a higher outputted value that indicates a greater likelihood of the object's presence on the platen.

The preceding embodiments of the method 31600 can be performed on a computer system (e.g., see the ultrasound signal-processing system 31800 of FIG. 19) that receives waveforms recorded by a sensor system (e.g., the finger sensor system 3700 of FIG. 8). A third party can operate the sensor system and transmit the recorded waveforms to the computer system, which processes the waveforms to determine the echo arrival times. Thus, the ultrasound transducer array is not required to perform the method 31600. However, in some embodiments the method 31600 includes the blocks 31002, 31004, and 31006, in which the ultrasound transducer array is operated to record one waveform for each pixel element. These waveforms can then be used by the block 31602 to determine the corresponding echo arrival times.

Figure 18:
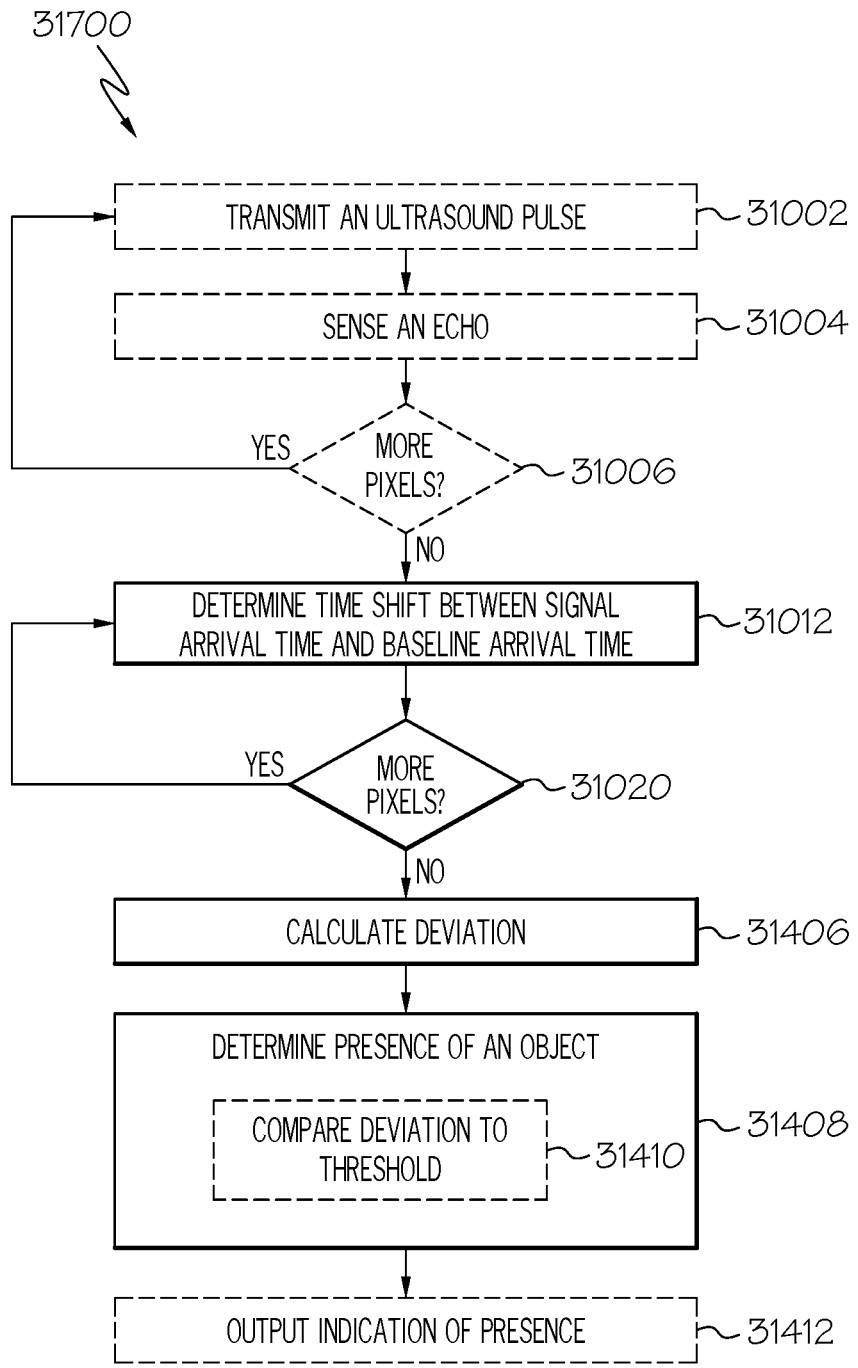
FIG. 18 is a flow chart of an object detection method that uses baseline waveforms, in embodiments, consistent with the present inventive concepts.

FIG. 18 is a flow chart of an object detection method 31700 that is similar to the method 31600 except that it uses baseline waveforms. Therefore, the method 31700 implements baseline time compensation by using the time shift for each pixel element, as opposed to a single echo arrival time. Accordingly, the method 31700 includes the blocks 31012 and 31020 of the method 31000. The method 31700 also includes the block 31406, in which a deviation is calculated based on the time shifts, and the block 31408 in which the presence of an object is determined based on the deviation (e.g., by comparing to a threshold). This deviation is also referred to as the "time-shift deviation". Similar to the method 31600, in method 31700 the signal echo can be generated from the object contacting a platen surface of the platen. The object can be human tissue, such as a finger (e.g., the finger 3130 contacting the top surface 3112 of the platen 3102 in FIGS. 2 to 5). The method 31700 can also include the block 31412 in which an indication of the presence of the object is outputted.

Compared to the method 31600, the method 31700 can advantageously improve the accuracy with which the object's presence is determined, especially when the deviation of round-trip propagation times across the platen is comparable to, or larger than, the arrival-time deviation. When no object contacts the platen, each time shift is near zero, and the resulting time-shift deviation can be smaller than the arrival-time deviation. When an object contacts the platen, some pixel elements will have time shifts that are no longer near zero. As a result, the time-shift deviation can increase significantly, especially for a fingerprint where ridges and valleys typically give rise to a wide spread of time shifts. This increase in the time-shift deviation can be significantly greater than the increase in the arrival-time deviation, advantageously helping to distinguish between the case when no object contacts the platen, and the case when an object does contact the platen.

The preceding embodiments of the method 31700 can be performed on a computer system (e.g., see the ultrasound signal-processing system 31800 of FIG. 19) that receives waveforms recorded by a sensor system (e.g., the finger sensor system 3700 of FIG. 8). A third party may operate the sensor system and transmit the recorded waveforms to the computer system, which processes the waveforms to determine the signal and baseline arrival times. Thus, the ultrasound transducer array is not required to perform the method 31700. However, in some embodiments the method 31700 includes the blocks 31002, 31004, and 31006, in which the ultrasound transducer array is operated to record waveforms for each pixel element. In some of these embodiments, the method 31700 repeats the blocks 31002, 31004, and 31006 twice, the first time to obtain signal waveforms and the second time to obtain baseline waveforms. These signal and baseline waveforms can then be used by the block 31012 to determine the time delays.

System Embodiments

Figure 19:
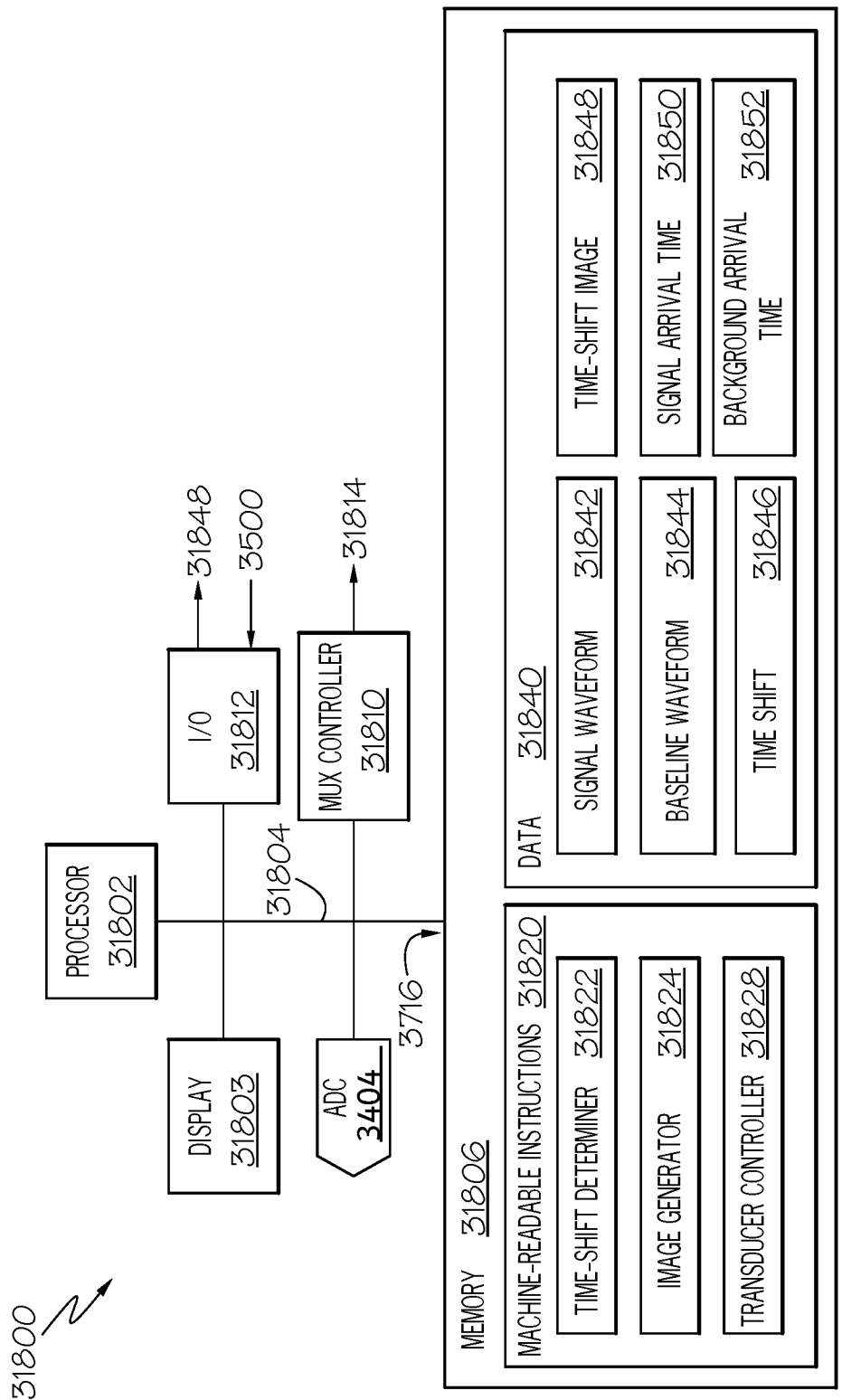
FIG. 19 is a block diagram of an ultrasound signal-processing system with which the present method embodiments may be implemented, in embodiments, consistent with the present inventive concepts.

FIG. 19 is a block diagram of an ultrasound signal-processing system 31800 with which the present method embodiments can be implemented. The ultrasound signal-processing system 31800 is a computer system that can form at least part of an ultrasound-based sensor system, such as the finger sensor system 3700 of FIG. 8. For example, the ultrasound signal-processing system 31800 can serve as one or both of the computer 3710 and the real-time processor 3708.

The ultrasound signal-processing system 31800 includes a processor 31802 and a memory 31806 that communicate with each other over a system bus 31804. The system 31800 can also include at least one I/O block 31812 for communicating with at least one peripheral device. While FIG. 19 shows the system 31800 with only one I/O block 31812, the system 31800 can contain any number of the I/O block 31812, as needed to implement the functionality described herein. For example, when the system 31800 serves as the computer 3710, the I/O block 31812 can be used to receive waveforms 3500 from the real-time processor 3708. In this case, the I/O block 31812 can be a serial port or parallel port that interfaces with the real-time processor 3708. Similarly, the I/O block 31812 can be a graphics card for outputting time-shift images to a display, display 31803 shown (e.g., a display similar to display 3712 of FIG. 8), or a host adapter that connects the system 31800 to a storage device (e.g., a hard disk drive, solid-state drive, memory card, memory stick, etc.) for storing and retrieving time-shift images and other data. The I/O block 31812 can also be a host adapter that connects the system 31800 to a network for communicating with another device or computer system (e.g., via a wide area network, a local area network, the internet, Wi-Fi, USB, and the like), such as a biometric security system that processes time-shift images to determine access to a room, computer system, files, etc. In some embodiments, the system 31800 implements at least some of the functionality of the biometric security system. Accordingly, the system 31800 is not limited to implementing only the functionality of the finger sensor system 3700.

The processor 31802 can be any type of circuit capable of performing logic, control, and input/output operations. For example, the processor 31802 can include one or more of a microprocessor with one or more central processing unit (CPU) cores, a graphics processing unit (GPU), a digital signal processor (DSP), an FPGA, a system-on-chip (SoC), and a microcontroller unit (MCU). The processor 31802 can also include a memory controller, bus controller, one or more co-processors, and/or other components that manage data flow between the processor 31802 and other devices communicably coupled to the system bus 31804. In embodiments where the system 31800 implements the functionality of the real-time processor 3708, the processor 31802 includes at least one circuit and/or chip (e.g. integrated circuit) that operates deterministically, as described previously. The processor 31802 can be one example of the processor 3720 of FIG. 8.

The memory 31806 stores machine-readable instructions 31820 that, when executed by the processor 31802, control the system 31800 to implement the functionality and methods described herein (e.g., one or more of the methods 31000 to 31700). The memory 31806 also stores data 31840 used by the processor 31802 when executing the machine-readable instructions 31820. In the example of FIG. 19, the machine-readable instructions 31820 include a time-shift determiner 31822 that determines a time shift 31846 between a signal arrival time of a signal echo sensed by an ultrasound transducer, and a baseline arrival time of a baseline echo sensed by the ultrasound transducer. In this case, the time-shift determiner 31822 implements the block 31012 of the method 31000. The memory 31806 can store additional machine-readable instructions 31820 than shown in FIG. 19 without departing from the scope hereof. Similarly, the memory 31806 can store additional data 31840 than shown in FIG. 19 without departing from the scope hereof. The memory 31806 can be one example of the memory 3722 of FIG. 8.

In some embodiments, the time-shift determiner 31822 identifies the signal echo from a signal waveform 31842 obtained from an ultrasound transducer while an object was contacting a platen surface of a platen, thereby implementing the block 31010 of the method 31000. Similarly, the time-shift determiner 31822 can identify the baseline echo from a baseline waveform 31844 obtained from the ultrasound transducer while the object was not contacting the platen surface, thereby implementing the block 31008 of the method 31000. The time-shift determiner 31822 can also implement the block 31014 of the method 31000 by processing the signal waveform 31842 to identify a signal arrival time 31850 of the signal echo, implement the block 31016 of the method 31000 by processing the baseline waveform 31844 to identify a baseline arrival time 31852 of the baseline echo, and implement the block 31016 of the method 31000 by subtracting the baseline arrival time 31852 from the signal arrival time 31850 to obtain the time shift 31846. Each of the waveforms 31842 and 31844 is an example of the waveform 3500W of FIG. 6, the time shift 31846 is an example of the time shift $\Delta t$ (see FIG. 7), the signal arrival time 31850 is an example of the signal arrival time $t_a^{(s)}$, and the baseline arrival time 31852 is an example of the baseline arrival time $t_a^{(b)}$.

The machine-readable instructions 31820 can also include an image generator 31824 that determines, for one or more pixel elements (e.g. all the pixel elements) of an ultrasound transducer array, the time shift for said each pixel to generate an array of time shifts. The image generator 31824 can then generate, based on the array of time shifts, a time-shift image 31848. Therefore, the image generator 31824 can implement the blocks 31020 and 31022 of the method 31000. Although not shown in FIG. 9, the memory 31806 can store additional machine-readable instructions 31820 that control the system 31800 to output the time-shift image 31848 (e.g., via the I/O block 31812 to a peripheral device or another computer system). Machine-readable instructions 31820 can include transducer controller 31828 shown, where transducer controller 31828 comprises data that provides instructions for the timing of transmissions of energy, and recording of reflected energy (echoes) for each of the pixel elements.

In some embodiments, the system 31800 includes an ADC 31808 that digitizes the amplified output 3404. As shown in FIG. 19, the ADC 31808 can be connected to the bus 31804 such that the sensor data 3716 outputted by the ADC 31808 can be stored in the memory 31806. Alternatively, the sensor data 3716 can be directly transmitted over the bus 31804 to the processor 31802 for time-stamping, thereby converting the sensor data 3716 into a waveform. The ADC 31808 is one example of the ADC 3706 of FIG. 8.

In some embodiments, the system 31800 includes a MUX controller 31810 that outputs one or more digital control lines 31814 to drive the MUX 3702. As shown in FIG. 19, the MUX controller 31810 can be connected to the bus 31804, and therefore the digital control lines 31814 can be controlled by the processor 31802. However, the MUX controller 31810 can be embedded within the processor 31802. In embodiments where the system 31800 implements real-time functionality (e.g., time-stamping, MUX control, ADC sampling, etc.), the system 31800 can further include the time base 3728.

While FIG. 19 shows the system 31800 as a computing device with a von Neumann architecture, in some embodiments system 31800 uses a Harvard architecture, or a modified Harvard architecture. In these embodiments, the machine-readable instructions 31820 can be stored as firmware in a separate memory (e.g., non-volatile flash memory) from the data 31840. Accordingly, the system 31800 can form part of an embedded system that includes one or more of the sensor array 3100, MUX 3702, amplifier 3402, and signal source 3304.

The systems of the present inventive concepts, can produce an image (e.g. an image of a fingerprint or other tissue surface) using amplitude-shift image creation or time-shift image creation, each as described herein. In some embodiments, system 10 is configured to use both amplitude-shift image creation, as well as time-shift image creation (e.g. in order to create an enhanced image of a fingerprint or other tissue surface). In these embodiments, system 10 can be configured to utilize beamforming, also as described herein, to further enhance the image quality achieved.

Referring collectively to FIGS. 20 through 28, various configurations of a sensor 100 and system 10 are illustrated, such as ultrasound-based systems and sensors that utilize a multi-platen configuration.

In some embodiments, sensor 100 is constructed and arranged as described in reference to FIGS. 25A-D described herein.

The present embodiments can include multi-platen ultrasound sensors (e.g. fingerprint sensors) that utilize two or more platens. These sensors can be used to sense one or more fingerprints. Advantageously, the present embodiments can drive and sense multiple pixel transducers simultaneously, thereby reducing the time needed to scan across a set of multiple pixel transducers and generate a fingerprint image. For example, a set of multiple pixel transducers of a multi-platen sensor with two platens can be operated in approximately half the time required to operate each of the pixel transducers of the set individually. Signals from electrically-paired pixel transducers (e.g. electrically connected sets of two, three, or more pixel transducers) can be distinguished and assigned to the platens using temporal discrimination, frequency discrimination, or a combination thereof. Furthermore, some of the present embodiments feature electrically-paired pixel transducers that share transmit electrodes and receive electrodes. In some embodiments, a multi-platen ultrasound sensor of the present inventive concepts comprises three, four, five, or more platens.

Advantageously, electrically-paired pixel transducers reduce the number of electrical connections to the fingerprint and/or other sensor ("sensor" or "fingerprint sensor" herein), thereby simplifying multiplexing circuitry that interfaces with the sensor. Another advantage of the present embodiments is reduced energy per scan. A portion of the energy consumed by an ultrasound fingerprint sensor system is proportional to the scan time. Such energy is typically consumed by amplifiers and other electronics that are maintained in an "active" state during scanning. Since the present embodiments reduce the scan time, these electronics can spend more time in a lower-energy "sleep" state. Reduced energy per scan can extend battery life, such as when the present embodiments are used for portable electronic devices (e.g., smartphones, laptops, and tablets) in which extended battery life is a significant advantage.

Another advantage of the present embodiments is that they can tolerate variations in platen topography that typically occur during fabrication. For example, when the platen is a glass display for a smartphone, tablet, or the like, the resulting platen topography can typically depend on the specific processes used to manufacture the display, the size of each display pixel, the overall size of the display, and/or other factors. In any case, pixel elements can be deposited on the rear face of the platen while still achieving all or at least a portion of the above benefits. Thus, while the present embodiments are shown with platens having perfectly flat surfaces, it should be understood that the platen surfaces can have some curvature, surface variations, digs, defects, and/or other topological features (e.g. topological nonuniformities), and that the presence of these topological features will have minimal, if any, impact on the manufacture and/or operation (e.g. performance) of the present embodiments.

While the present embodiments are described as fingerprint sensors, the present embodiments can be used to measure any object contacting the two, three, or more platens, provided that the presence of the object induces a measurable shift in the amplitude and/or phase of the echo. Examples of such objects include prosthetics, toes and other human tissue, and inanimate objects. The present embodiments can therefore be used to determine the binary presence of a single object contacting any one of the platens, or an integer number of objects (e.g., multiple fingers. from one or more users) contacting the platens. This ability to detect object presence can be combined with fingerprint sensing. For example, the present embodiments can be programmed to only perform fingerprint sensing after one or more objects contacting the platens (e.g. platens 4102 and 4103 described herein) are detected.

When used for fingerprint sensing, the present embodiments can be integrated with other physical, physiological, and biological measurements as part of a multi-function biometric system. For example, the documents (i) International Publication No. WO 2019/032590, titled "Interactive Biometric Touch Scanner", and (ii) Gerard Touma, "A row-column addressed acoustic biometric scanner integrated with pulse oximetry" (Ph.D. Dissertation, Stanford University, 2020) show how a pulse oximeter can be incorporated with an ultrasound transducer array when at least part of the transducer array is optically transparent (e.g., in the near-infrared). Each of these documents is incorporated herein by reference in its entirety for all purposes.

As another example of biometric measurements, the present embodiments can be used to determine an area of contact between finger ridges and one of the platens. This area of contact can be measured over time to identify periodic changes indicative of a pulse. In this way, the biometric system can distinguish between living tissue and inanimate matter. The present embodiments can be combined with other sensors and biometric functionality without departing from the scope hereof. Furthermore, multiple biometric functionalities can be implemented with different platens of one fingerprint sensor. For example, one platen can be used for pulse oximetry with one finger while another is used to measure pulse and/or other physiologic parameter of one or more users ("user" herein).

Figure 20:
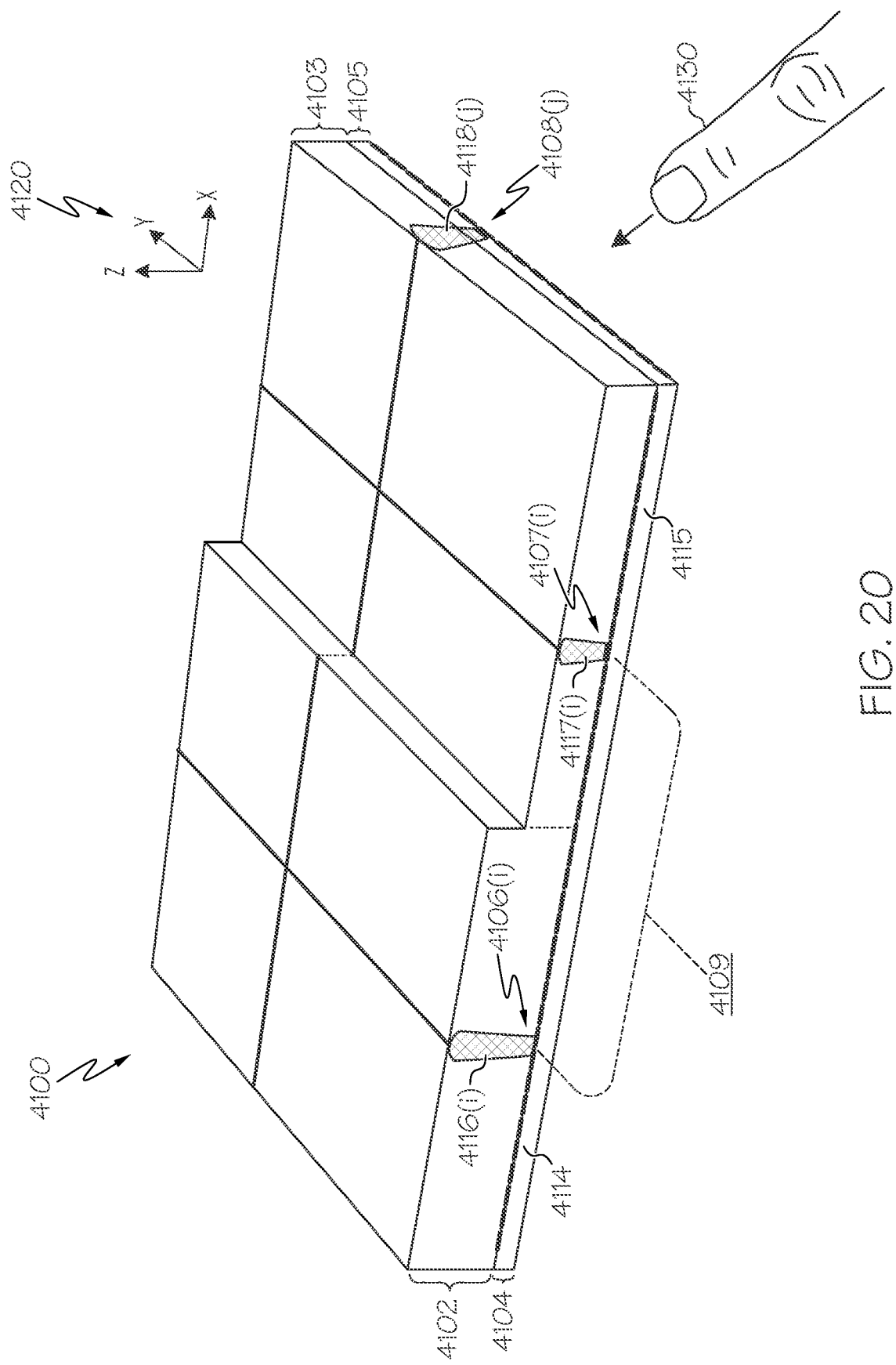
FIG. 20 is a perspective view of a multi-platen ultrasound fingerprint sensor having a first platen and a second platen with different round-trip propagation times, in an embodiment, consistent with the present inventive concepts.
Figure 21:
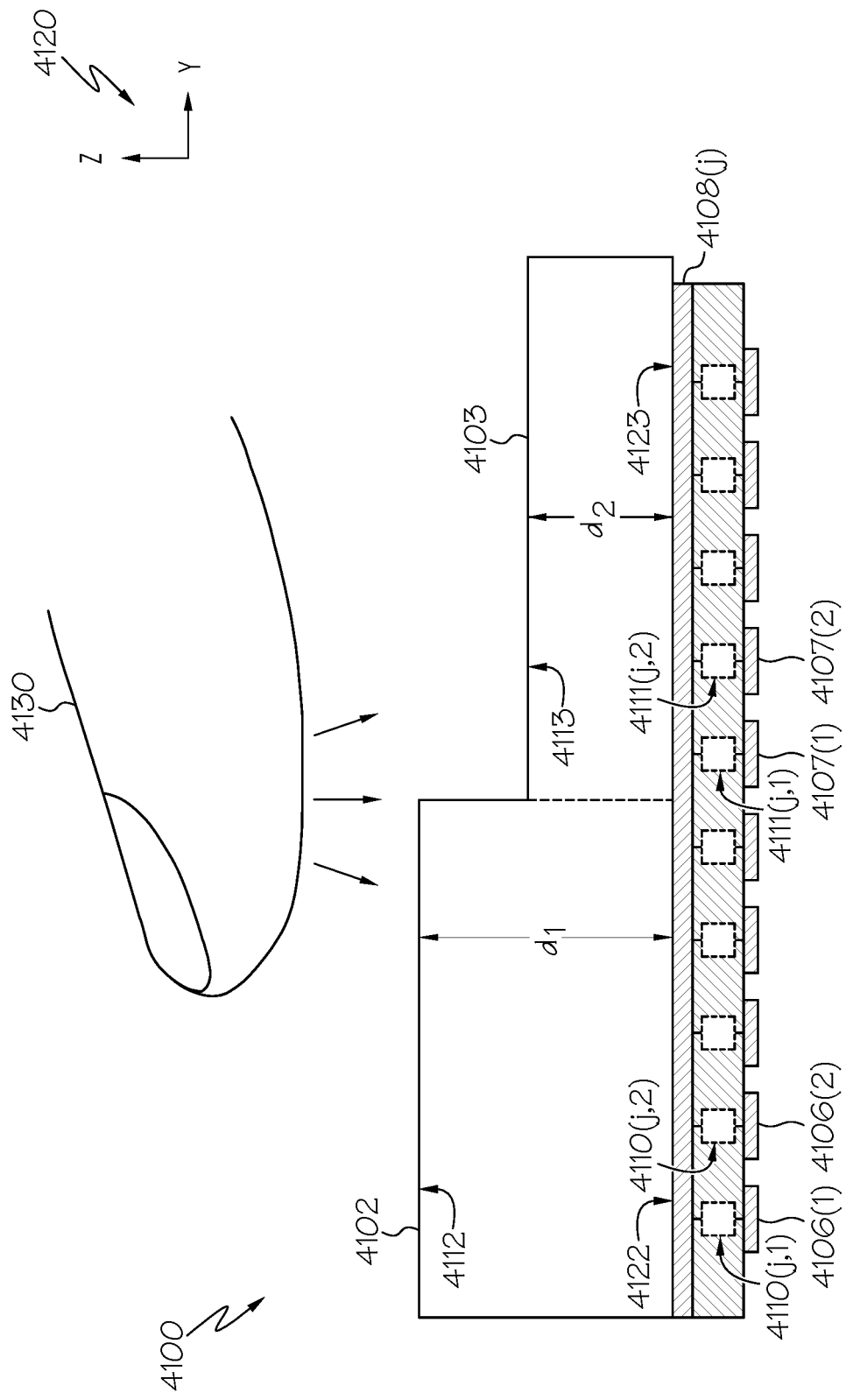
FIG. 21 is a side cross-sectional view of the multi-platen ultrasound fingerprint sensor of FIG. 20, consistent with the present inventive concepts.

FIG. 20 is a perspective view of a multi-platen ultrasound fingerprint sensor 4100 having a first platen 4102 and a second platen 4103 with different round-trip propagation times. FIG. 21 is a side cross-sectional view of the multi-platen ultrasound fingerprint sensor 4100 of FIG. 20. The fingerprint sensor 4100 also includes a first ultrasound transducer array 4104 that can be bonded to, and/or fabricated on, a first rear face 4122 of the first platen 4102. An ultrasound pulse emitted by the first ultrasound transducer array 4104 propagates through the first platen 4102 in the +z direction (see the right-handed coordinate system 4120) toward a first front face 4112 of the first platen 4102. The first front face 4112 is a boundary between materials with different mechanical impedances (e.g. different densities and/or stiffnesses). Therefore, the ultrasound pulse will reflect off the first front face 4112, and the resulting reflection will propagate through the first platen 4102 in the −z direction toward the first rear face 4122, where it is detected by the first ultrasound transducer array 4104. This reflection is also referred to as an echo.

Similarly, the multi-platen ultrasound fingerprint sensor 4100 also includes a second ultrasound transducer array 4105 that can be bonded to, and/or fabricated on, a second rear face 4123 of the second platen 4103. An ultrasound pulse emitted by the second ultrasound transducer array 4105 propagates through the second platen 4103 in the +z direction toward a second front face 4113 of the second platen 4103. Like the first front face 4112, the second front face 4113 is a boundary between materials with different mechanical impedances, and therefore the ultrasound pulse will reflect off the second front face 4113. The resulting reflection, or echo, will propagate through the second platen 4103 in the −z direction toward the second rear face 4123, where it is detected by the second ultrasound transducer array 4105. In some embodiments, faces 4112 and 4113 can be differentiated (e.g. tactilely differentiated) by a finger of a user, such that the user can place one or more fingers on a particular surface via the differentiation (e.g. to select one surface versus the other to perform a particular function associated with one surface versus the other).

In FIGS. 20 and 21, the first platen 4102 and second platen 4103 have different round-trip propagation times due to different thicknesses. Specifically, the first platen 4102 has a first thickness $d_1$ along the z direction while the second platen 4103 has a second thickness $d_2$ that is different than the first thickness $d_1$. The first thickness $d_1$ is measured between the first rear face 4122 and the first front face 4112. Similarly, the second thickness $d_2$ is measured between the second rear face 4123 and the second front face 4113. While FIGS. 20 and 21 shows the first thickness $d_1$ as being greater than the second thickness $d_2$, the first thickness $d_1$ can alternatively be less than the second thickness $d_2$. As described in more detail below, in some of the present embodiments the first thickness $d_1$ is the same as the second thickness $d_2$.

A finger or other body tissue, finger 4130 shown, physically contacts the front faces 4112 and 4113, such as to detect a fingerprint. While FIGS. 20 and 21 show the sensor 4100 being used to sense the fingerprint of only one finger 4130, the sensor 4100 can alternatively be used to simultaneously sense more than one finger (e.g. from a single user or from multiple users). For example, a first finger 4130(1) can physically contact the first front face 4112 at the same time that a second finger 4130(2) physically contacts the second front face 4113 (e.g., see FIGS. 22 and 23). To detect a full fingerprint, each of the platens 4102 and 4103 can have an area (i.e., in the x and y direction) of at least 0.1 cm², 0.3 cm², 0.5 cm², 0.7 cm² and/or 1 cm². For clarity, the finger 4130 is not drawn to scale in FIGS. 20 and 21.

The first ultrasound transducer array 4104 has a plurality of first pixel transducers 4110 that, in the example of FIGS. 20 and 21, are arranged in a linear two-dimensional array of rows and columns. Similarly, the second ultrasound transducer array 4104 has a plurality of second pixel transducers 4111 that are also shown as being arranged in a linear two-dimensional array. In FIGS. 20 and 21, the first pixel transducers 4110 are row-column addressable via a plurality of receive electrodes 4108 and a plurality of first transmit electrodes 4106. Similarly, the second pixel transducers 4111 are row-column addressable via the plurality of receive electrodes 4108 and a plurality of second transmit electrodes 4107. Thus, each of the first transmit electrodes 4106 extends in the y direction only across the first platen 4102, each of the second transmit electrodes 4107 extends in the y direction only across the second platen 4103, and each of the receive electrodes 4108 extends in the x direction across both the first platen 4102 and the second platen 4103.

The first ultrasound transducer array 4104 also includes a first piezoelectric layer 4114 that is located between the receive electrodes 4108 and the first transmit electrodes 4106. Similarly, the second ultrasound transducer array 4105 includes a second piezoelectric layer 4115 that is located between the receive electrodes 4108 and the second transmit electrodes 4107. Thus, each of the first pixel transducers 4110$(j,i)$ is spatially defined by the overlap, in the x-y plane, of the $j^{th}$ receive electrode 4108$(j)$ and the $i^{th}$ first transmit electrode 4106$(i)$, while each of the second pixel transducers 4111$(j,i)$ is spatially defined by the overlap, in the x-y plane, of the $j^{th}$ receive electrode 4108$(j)$ and the $i^{th}$ second transmit electrode 4107$(i)$.

For clarity, FIG. 20 only shows nineteen first transmit electrodes 4106, nineteen second transmit electrodes 4107, and seventeen receive electrodes 4108. Similarly, FIG. 21 only shows six first transmit electrodes 4106 and six second transmit electrodes 4107. However, the sensor 4100 can have any number of first transmit electrodes 4106, any number of second transmit electrodes 4107, and any number of receive electrodes 4108 without departing from the scope hereof. Typically, the fingerprint sensor 4100 will contain several hundred first transmit electrodes 4106, several hundred second transmit electrodes 4107, and several hundred receive electrodes 4108. For example, the first ultrasound transducer array 4104 can have 512 first transmit electrodes 4106 and 512 receive electrodes 4108, corresponding to 512×512=262,144 first pixel transducers 4110. The second ultrasound transducer array 4105 can be similarly configured, yielding a total of 524,288 pixel transducers 4110, 4111.

The first piezoelectric layer 4114 can be electrically actuated (e.g., via an ultrasound wave into the first platen 4102). The piezoelectric layer 4114, when mechanically actuated by an ultrasound wave, produces a time-varying electrical signal that can be subsequently detected and processed. The first piezoelectric layer 4114 can be formed from a crystal (e.g., lithium niobate, lithium tantalate, quartz, etc.), ceramic (e.g., zinc oxide, lead zirconium titanate, potassium niobate, barium titanate, etc.), III-V or II-VI semiconductor (e.g., aluminum nitride, gallium arsenide, etc.), polymer, and/or any other piezoelectric material. Similar materials of construction are applicable for the second piezoelectric layer 4115.

FIG. 20 shows the $i^{th}$ first transmit electrode 4106$(i)$ "emitting" an ultrasound pulse 4116$(i)$ into the first platen 4102 (i.e. the electrode-piezo-electrode transducer element emits an ultrasound pulse). Since each first transmit electrode 4106 extends across the entire length (in the y direction) of the first platen 4102, the ultrasound pulse 4116$(i)$ similarly extends across the entire length of the first platen 4102. FIG. 20 similarly shows the $i^{th}$ second transmit electrode 4107$(i)$ emitting an ultrasound pulse 4117$(i)$ into the second platen 4103. FIG. 20 also shows the receive electrode 4108(j) emitting an ultrasound pulse 4118(j) into both of the platens 4102 and 4103. The receive electrode 4108(j) extends across the entire width (in the x direction) of the fingerprint sensor 4100, and therefore the ultrasound pulse 4118(j) similarly extends across the entire width of both platens 4102 and 4103. While the electrodes 4106 and 4107 are referred to as "transmit" electrodes, it should be understood that these electrodes can alternatively or additionally be used for sensing echoes. Similarly, the electrodes 4108, while referred to herein as "receive" electrodes, can alternatively or additionally be used for emitting ultrasound pulses into the platens 4102 and 4103.

Figure 22:
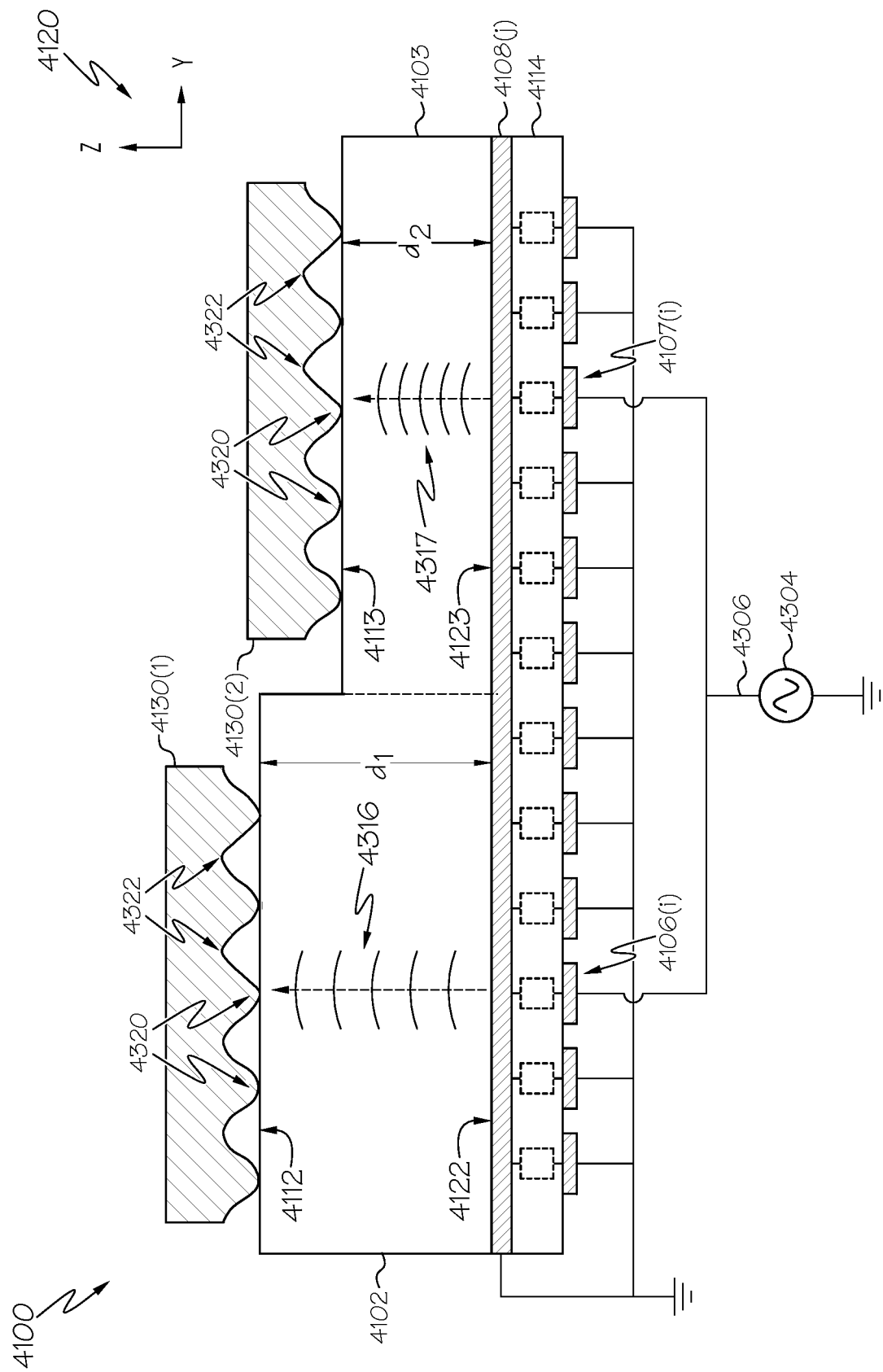
FIG. 22 shows the multi-platen ultrasound fingerprint sensor of FIGS. 20 and 21 being electrically driven to simultaneously emit a first ultrasound pulse into the first platen and a second ultrasound pulse into the second platen, in an embodiment, consistent with the present inventive concepts.
Figure 23:
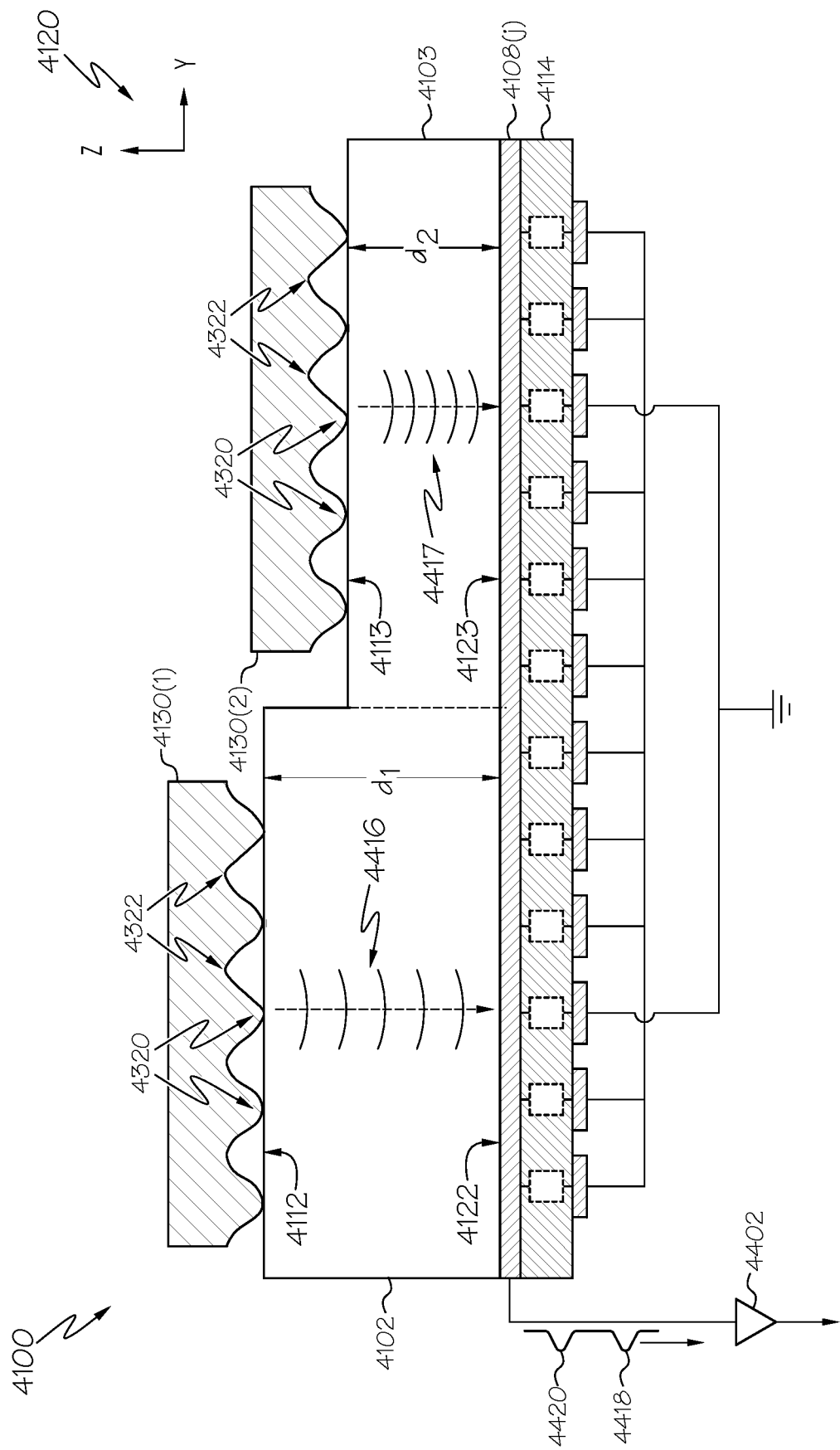
FIG. 23 shows the multi-platen ultrasound fingerprint sensor of FIG. 22 sensing a first echo and a second echo, in an embodiment, consistent with the present inventive concepts.

FIG. 22 shows the multi-platen ultrasound fingerprint sensor 4100 being electrically driven to simultaneously emit a first ultrasound pulse 4316 into the first platen 4102 and a second ultrasound pulse 4317 into the second platen 4103. FIG. 23 shows the fingerprint sensor 4100 sensing a first echo 4416 generated when the first ultrasound pulse 4316 reflects off the first front face 4112, and a second echo 4417 generated when the second ultrasound pulse 4317 reflects off the second front face 4113. FIGS. 22 and 23 are the same cross-sectional view as FIG. 21, but with a first finger 4130(1) contacting the first front face 4112 and a second finger 4130(2) contacting the second front face 4113. FIGS. 22 and 23 are best viewed together with the following description.

The bottom surface of each of the fingers 4130(1) and 4130(2) forms an alternating sequence of ridges 4320 (also referred to as "friction ridges" or "epidermal ridges") and valleys 4322. Each ridge 4320 of the first finger 4130(1) directly contacts the first front face 4112 of the first platen 4102 while the valleys 4322 do not directly contact the first front face 4112. Thus, beneath each valley 4322, air contacts the first front face 4112. Accordingly, the reflection coefficient at the first front face 4112 is larger at the valleys 4322 and smaller at the ridges 4320, and therefore the amplitude of the echo 4416 is larger when the reflection occurs at a ridge 4320, as opposed to a valley 4322. Similar arguments hold for at the second front face 4113.

In FIG. 22, a waveform generator 4304 outputs a drive signal 4306 to both the first transmit electrode 4106(i) and the second transmit electrode 4107(i), which are electrically connected. All of the other transmit electrodes 4106 and 4107 are grounded and all of the receive electrodes 4108 are grounded. In this configuration, the ultrasound pulses 4316 and 4317 are emitted at similar times (ignoring slight differences in electrical propagation times to the transmit electrodes 4106(i) and 4107(i)). In FIG. 23, the receive electrode 4108(j) outputs a first electrical pulse 4418 in response to sensing the first echo 4416, and a second electrical pulse 4420 in response to sensing the second echo 4417. Both of the electrical pulses 4418, 4420 are outputted on the same electrically conductor, and are both processed by an amplifier 4402 into an amplified output 4404 that is subsequently digitized and processed. For the sensing shown in FIG. 23, all of the transmit electrodes 4106 and 4107 are grounded. Although not shown in FIG. 23, all of the other receive electrodes 4108 are also grounded.

Since the platens 4102 and 4103 have different round-trip propagation times, the electrical pulses 4418 and 4420 are temporally distinguishable, i.e., the electrical pulses 4418 and 4420 can be unambiguously assigned to the echoes 4416 and 4417. Specifically, the first round-trip propagation time of the first platen 4102 is $t_1=2d_1/v_1$, where $v_1$ is the velocity of sound of the first platen 4102. Similarly, the second round-trip propagation time of the second platen 4103 is $t_2=2d_2/v_2$, where $v_2$ is the velocity of sound of the second platen 4103. Assuming that the platens 4102 and 4103 are fabricated from the same bulk material (i.e., $v_1=v_2$), the choice of $d_2<d_1$ means that $t_2<t_1$. Accordingly, the first electrical pulse 4418 is due to the second echo 4417 and the second electrical pulse 4420 is due to the first echo 4416.

The electrical pulses 4418 and 4420 can be partially overlapped (in time) while still being temporally distinguishable. For example, a tail of the first electrical pulse 4418 can overlap ahead of the second electrical pulse 4420 such that the peaks of the electrical pulses 4418 and 4420 are detected at different times. Thus, a delay $|t_2-t_1|$ between the peaks of the electrical pulses 4418 and 4420 can be less than the temporal widths of the electrical pulses 4418 and 4420.

In other embodiments, the platens 4102 and 4103 are fabricated from different materials such that $v_1 \neq v_2$. In these embodiments, the platens 4102 and 4103 can have the same thickness, i.e., $d_1=d_2$, in which case the platens 4102 and 4103 can be placed at corresponding sides such that the front faces 4112 and 4113 are coplanar, and such that the rear faces 4122 and 4123 are coplanar. In other embodiments, the platens 4102 and 4103 are fabricated from different materials, and have different thicknesses.

In other embodiments, the platens 4102 and 4103 form arrays of ultrasound waveguides, as opposed to a bulk material. In these embodiments, one waveguide is located directly over each of the pixel transducers 4110 and 4111. The velocity of the ultrasound pulse (and resulting echo) is determined by a dispersion equation of the waveguide, which typically depends on the geometry of the waveguide (e.g., transverse dimensions), frequency, the sound velocity in the core of the waveguide, and the sound velocity in the material surrounding the core. Accordingly, the first platen 4102 can contain a first array of waveguides sized to achieve a first velocity, while the second platen 4103 contains a second array of waveguides sized to achieve a second velocity different from the first velocity. In this case, the platens 4102 and 4103 can have the same thickness with different round-trip propagation times.

Each of the first pixel transducers 4110 is electrically-paired with one of the second pixel transducers 4111. Specifically, the first pixel transducers 4110 form a one-to-one correspondence with the second pixel transducers 4111. Here, "electrically-paired" means that the transmit electrodes of the paired pixel transducers are directly electrically connected to each other, and therefore can be driven by a single waveform generator or oscillator. Similarly, "electrically-paired" also means that the receive electrodes of the paired pixel transducers are directly electrically connected to each other, and therefore their electrical outputs can be processed by a single amplifier and digitized by a single analog-to-digital (A/D) converter or channel.

FIG. 20 shows how a single conductor 4109 is split into two "legs", one of which is routed to the first transmit electrode 4106(i) while the second is routed to the second transmit electrode 4107(i). In this case, the two legs are electrically in parallel. By contrast, the receive electrode 4108(j) does not need to be split, as it can extend as a single line (either straight, curved, or piece-wise) across both of the platens 4102 and 4103. While FIG. 20 shows only one single conductor 4109 for clarity, it should be understood that every first transmit electrode 4106 is similarly connected to a corresponding second transmit electrode 4107. Furthermore, while FIG. 20 shows the $i^{th}$ first transmit electrode 4106(i) paired with the $i^{th}$ second transmit electrode 4107(i), it is not required that pixel transducers 4110 and 4111 be paired in index order (e.g. column 1 electrode does not have to be paired with row 1 electrode).

In other embodiments, the fingerprint sensor 4100 has individually addressable pixel transducers 4110 and 4111. In this case, each of the pixel transducers 4110 and 4111 has its own receive electrode and transmit electrode (i.e., not shared with other pixel transducers in the same row or column), and the above definition of "electrically-paired" still applies.

Figure 24:
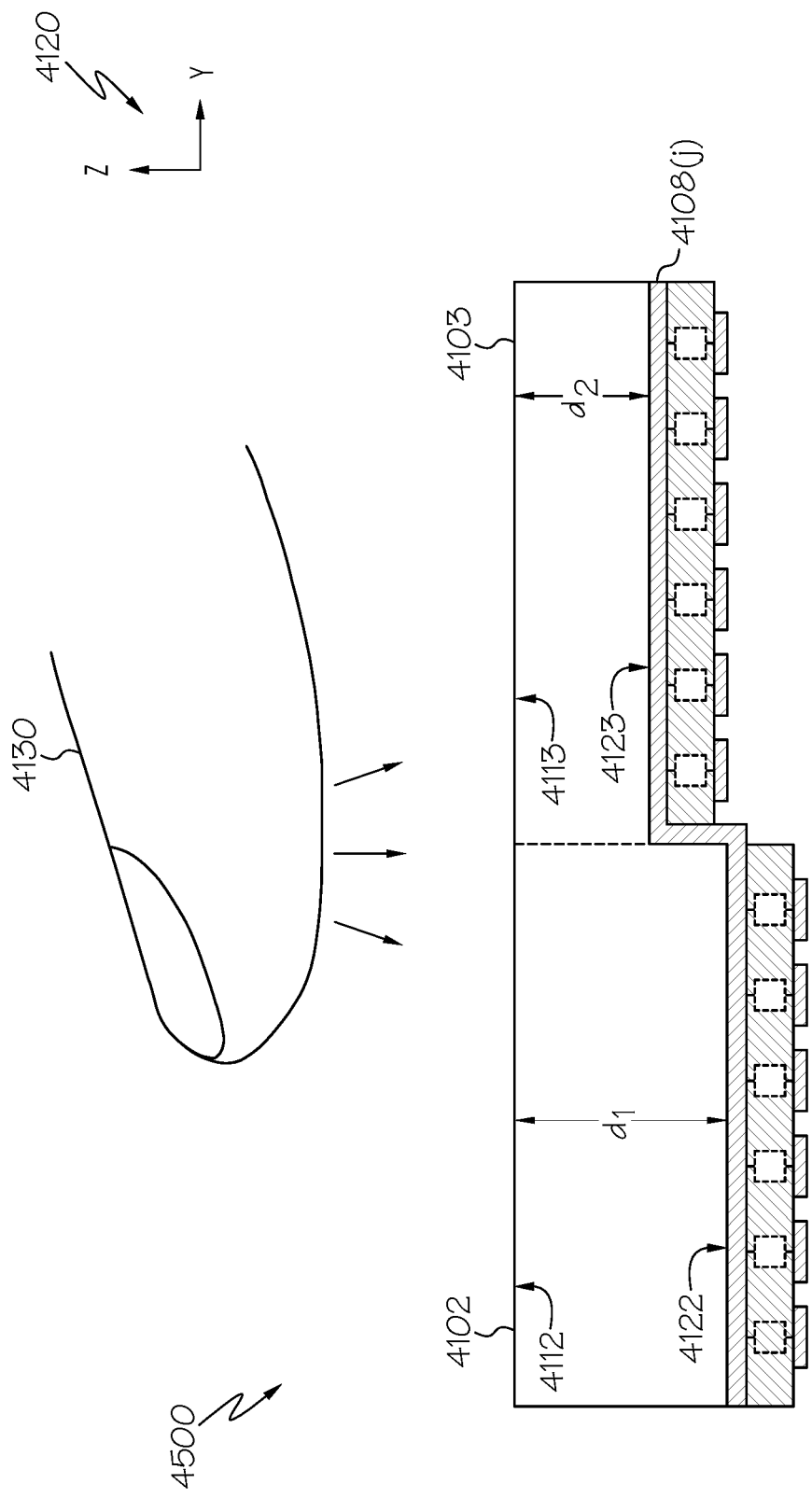
FIG. 24 is a side cross-sectional view of a multi-platen ultrasound fingerprint sensor that is similar to the multi-platen ultrasound fingerprint sensor of FIGS. 20 through 23 except that it has coplanar front faces, in an embodiment, consistent with the present inventive concepts.

FIG. 24 is a side cross-sectional view of a multi-platen ultrasound fingerprint sensor 4500 that is similar to the multi-platen ultrasound fingerprint sensor 4100 of FIGS. 20 to 23 except that the front faces 4112 and 4113 of FIG. 24 are coplanar. In FIGS. 20 to 23, the rear faces 4122 and 4123 of the fingerprint sensor 4100 are coplanar, thereby giving rise to a "step" (in the z direction) between the front faces 4112 and 4113. For the fingerprint sensor 4500 of FIG. 24, this step occurs between the rear faces 4122 and 4123. Therefore, each of the receive electrodes 4108 changes its z position at the step to ensure electrical continuity across both of the platens 4102 and 4103.

The platens 4102 and 4103 can be fabricated from one piece of bulk material (e.g., glass or plastic) to form a single integral component. Alternatively, the platens 4102 and 4103 can be separately fabricated and bonded along corresponding sides (e.g., via contact bonding, epoxy, anodic bonding with an intervening piece of silicon, etc.). In some embodiments, the platens 4102 and 4103 can be fabricated using spin on glass (SOG) and/or etching processes. In other embodiments, the first platen 4102 and first transducer array 4104 are physically disjoint from the second platen 4103 and second transducer array 4105. In these embodiments, the first pixel transducers 4110 are electrically-paired with the second pixel transducers 4111 (e.g., via a circuit board to which the transducer arrays 4104 and 4105 are soldered).

The above embodiments (e.g. as described in reference to FIGS. 20 to 23) can use temporal discrimination of the electrical pulses 4418 and 4420 to assign these electrical pulses to first pixel transducers 4110 and second pixel transducers 4111. In other embodiments, the electrical pulses 4418 and 4420 have different frequencies, in which case frequency discrimination can be used to assign these electrical pulses to pixel transducers 4110 and 4111. For example, the first pixel transducers 4110 and second pixel transducers 4111 can be fabricated with different frequency responses. Specifically, the first pixel transducers 4110 can all have a first resonance with a first center frequency and a first bandwidth. Similarly, the second pixel transducers 4111 can all have a second resonance with a second center frequency, different from the first center frequency, and a second bandwidth. The difference between the first and second center frequencies can be selected to be larger than the first and second bandwidths. In other embodiments, the first and second center frequencies are selected such that there is overlap between the first and second bandwidths, and electrical pulses 4418 and 4420 are differentiated using frequency discrimination as described hereinabove. Electrically-paired pixel transducers 4110 and 4111 can be driven with a two-frequency waveform having a first component at the first center frequency and a second component at the second center frequency. Each of the first and second components can be a tone burst (i.e., an integer number of periods of a single-frequency sinusoidal waveform). The first component will resonantly excite the first pixel transducer 4110(*i*) at the first center frequency, but without resonant excitation at the second center frequency. Conversely, the second component will resonantly excite the second pixel transducer 4111(*j*) at the second center frequency, but without resonant excitation at the first center frequency. In this case, the ultrasound pulses 4316 and 4317 will have different frequencies, which can be resolved electronically using signal-processing techniques known in the art.

One advantage of frequency discrimination over temporal discrimination is that the platens 4102 and 4103 can be made from a single bulk piece of material of uniform thickness (i.e., $d_1=d_2$). However, to achieve different frequency responses, the first pixel transducers 4110 may need to be fabricated separately from the second pixel transducers 4111. The frequency responses can be modified via a thickness of the piezoelectric layers. For example, the first piezoelectric layer 4114 can be fabricated with a different thickness (in the z direction) than that of the second piezoelectric layer 4115. Alternatively or additionally, the shape and thickness of the electrodes 4106, 4107, and 4108 can be modified to alter the frequency responses. More details about constructing pixel transducers with different frequency responses appear in Appendix A.

The present embodiments can be used to detect fingerprints or other imageable tissue or other patterns ("fingerprints" herein) by measuring amplitude shifts, e.g., by measuring the spatial variation of amplitude of the echoes. Alternatively or in combination with amplitude shift measurements, the present embodiment can be used to detect fingerprints by measuring time and/or phase shifts, e.g., by measuring the spatial variation of delay time, phase shift, or both. In some embodiments, beamforming techniques can be used to construct the image, for example while using amplitude shift measurements, phase shift measurements, or both. More details about fingerprint detection with time and/or phase shifts is described in U.S. Provisional Patent Application No. 63/140,647, filed Jan. 22, 2021 and titled "Ultrasound Signal-Processing System and Associated Methods". This provisional patent application is incorporated herein by reference in its entirety for all purposes.

Figure 25:
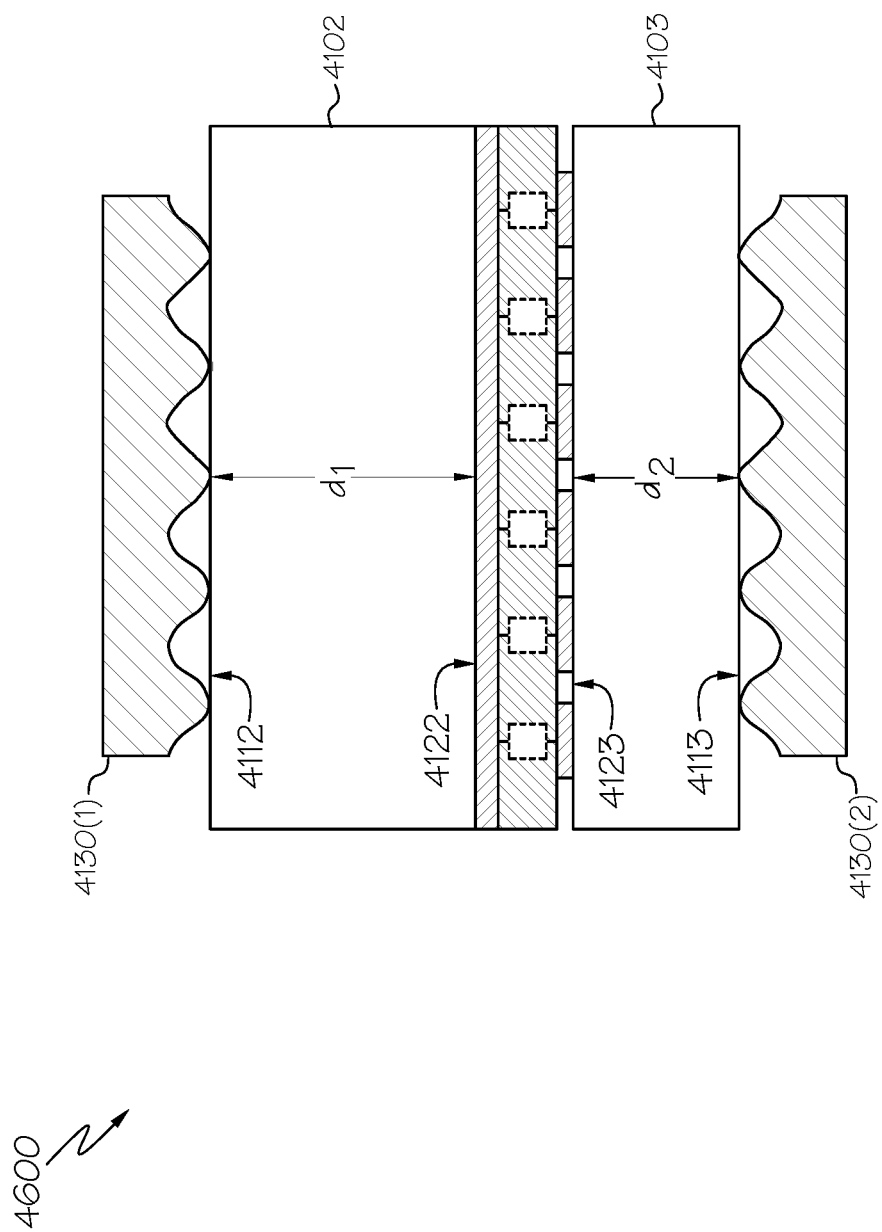
FIG. 25 is a side cross-sectional view of a multi-platen ultrasound fingerprint sensor in which one array of pixel transducers is used with both first and second platens, in an embodiment, consistent with the present inventive concepts.

FIG. 25 is a side cross-sectional view of a multi-platen ultrasound fingerprint sensor 4600 in which one array of pixel transducers is used with both the first platen 4102 and the second platen 4103. The fingerprint sensor 4600 is also referred to as a "double-sided" fingerprint sensor in that it can simultaneously detect fingerprints from the first finger 4130(1) and the second finger 4130(2) with the platens arranged in a back-to-back geometry (as opposed to the side-to-side geometry shown in FIGS. 20 to 24). The fingerprint sensor 4600 uses temporal discrimination to identify electrical pulses with platens, and therefore $d_1 \neq d_2$ when the platens 4102 and 4103 are fabricated from the same bulk material. Given the back-to-back geometry, the fingerprint sensor 4600 is particularly advantageous when one of the fingers 4130(1) and/or 4130(2) is a thumb. Alternatively, the fingerprint sensor 4600 can be used to detect one fingerprint from each of two of a person's hands (e.g., the finger 4130(1) is from the person's left hand while the finger 4130(2) is from the person's right hand), and/or when one finger is from one person and another finger is from another person.

While FIGS. 20 to 24 show the multi-platen ultrasound fingerprint sensors 4100 and 4500 with two platens 4102 and 4103, the concepts of temporal discrimination, frequency discrimination, and electrically-paired pixel transducers can be extended to more than two platens without departing from the scope hereof. For example, a fingerprint sensor similar to the fingerprint sensors 4100 and 4500 can be fabricated with three platens of three different thicknesses, and therefore three different round-trip propagation times. In this example, each pixel transducer for the first platen has a corresponding pixel transducer for the second platen and a corresponding pixel transducer for the third platen, giving rise to three pixel transducers forming an electrically connected triad that can be driven simultaneously with one waveform generator. The receive electrode will then output three electrical pulses that are temporally separated, each uniquely corresponding to one of the platens. This concept can be similarly extended to four or more platens.

In other embodiments, a multi-platen ultrasound fingerprint sensor combines time discrimination and frequency discrimination. For example, a fingerprint sensor can comprise four platens. The first and second platens have the same first round-trip propagation time, and the third and fourth platens have the same second round-trip propagation time that is different than the first round-trip propagation time. Furthermore, the first and third platens can be fabricated with pixel transducers having the same first frequency response, while the second and fourth platens can be fabricated with pixel transducers having the same second frequency response that is different than the first frequency response. In this case, the pixel transducers form electrically connected quadruples that can be simultaneously driven with a two-frequency waveform. The sensed echoes then give rise to two temporally distinguishable pulses, each of which contains two resolvable frequencies.

Referring additionally to FIGS. 25A-D, various electrical configurations of an ultrasound sensor are illustrated, consistent with the present inventive concepts. Both the double-sided sensor embodiment of FIG. 25 and large area sensor embodiments described herein can be implemented using "Time Division Multiplexing" (e.g. using the time axis in one scan to capture multiple reflections from different locations under the sensor). Alternatively or additionally, "Frequency Division Multiplexing" can be used on the same single time domain signal that provides interrogation at multiple locations under the sensor. These embodiments rely on receiving reflections from several locations under the sensor at different instances in time. These time differences can be accomplished in a variety of ways: different platen thickness at different sensor locations; different platen material at different sensor locations; and/or multiple different sensors (e.g. as with the double-sided sensor). In some embodiments, frequency division multiplexing (FDM) can be achieved by changing the thickness of the piezoelectric (e.g. a zinc oxide piezoelectric) and/or the thickness and/or type of metal layers below and above the piezoelectric. Signal processing of the received signals from different locations can then be applied to extract the amplitude and/or phase of the signals at different locations on the underside of the sensor.

As shown in FIG. 25, two fingers (e.g. a thumb and index finger) can be used to apply a compressing force (e.g. a squeeze) to a sensor made of two back-to-back ultrasound sensors, with platens of different thickness, that are attached to have common X-lines (e.g. transmit electrodes) and Y-lines (receive electrodes). Thus, each single X-line (transmit electrode) can be used to transmit two signals, a first signal in a first sensor, and a second signal in a second sensor. The two sensors can be constructed to have platens of slightly different thicknesses, such that the signals on a single Y-line (receive electrode) will arrive at different times (e.g. but on the same electrical connection). The measurement of the amplitudes and/or phases (arrival times) of the two signals would correspond to the fingerprints on the two sensors at the same X-Y location.

The coupling of the two sensors can be accomplished in a variety of ways: such as a solder bump attachment to a flexible printed circuit board thus carrying contacts to the X and Y lines in both sensors.

The two sensors can be of the same or different thickness, and the piezo material (e.g. ZnO film) can be a different thickness such that the phases of the reflected signals would be different, and hence processing of the signals in the frequency domain would allow extraction of the amplitude and phase (arrival time) of the two signals associated with the two fingers, with both arriving on the same electrical channel.

In FIGS. 20-24, a platen with various thicknesses at different sensor locations is shown with the same X-lines and different Y-lines. The Y-lines are connected electrically one by one to have the same channels 1 through n where n is the number of channels. In some embodiments, when exciting one Y-line, ultrasound energy is transmitted from different Y-lines to interrogate the platen at different locations. A receiving X-line would then receive signals on the same channel at different times because of the different thickness of the platen at the different locations. FIGS. 20-24 illustrate two steps (i.e. two different platen thicknesses) in one direction, however there is no limit to the number of steps as long as there is enough separation between the reflected pulses to allow the measurement of the amplitude and phase at different arrival times. In this arrangement, a very large area sensor can be achieved with a relatively low number of channels, thus making data acquisition and processing fast, such as to enable real time operation. Alternatively, this arrangement can be applied to sensors of any size, such as to achieve faster data acquisition.

Figure 25A:
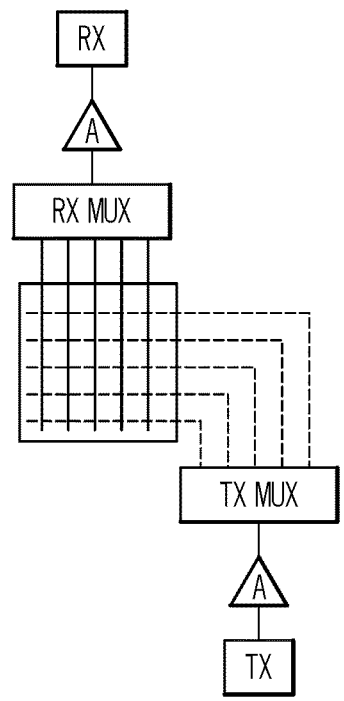
FIGS. 25A-D illustrate various electrical configurations of an ultrasound sensor, consistent with the present inventive concepts.
Figure 25B:
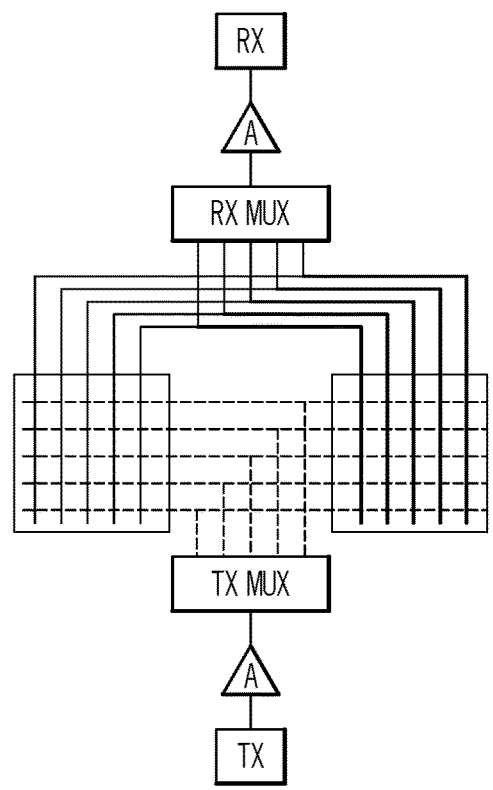
Figure 25C:
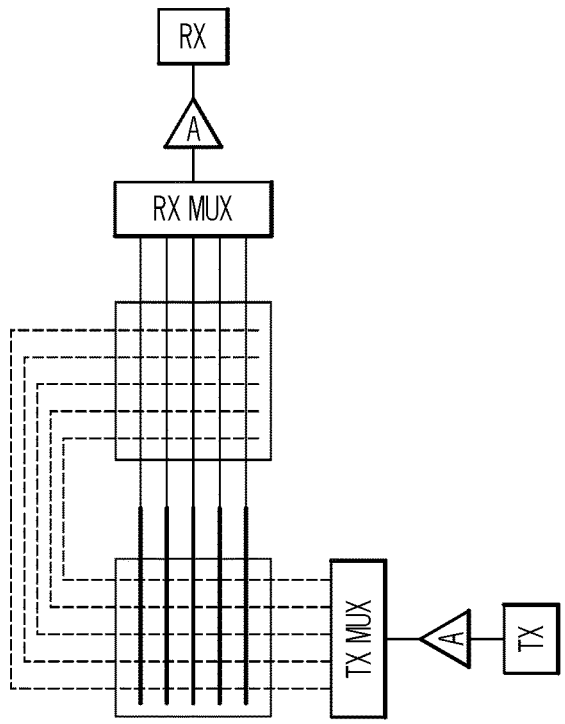

FIGS. 25A-D illustrate how resources can be shared compared to a single sensor approach. The illustrated hardware can be used to generate images from two or more sensors (essentially multiplying the sensor area) with appropriate connections and time-division multiplexing and/or frequency division multiplexing. Time division multiplexing and/or frequency division multiplexing can increase information density without increasing the hardware or the data acquisition time. FIG. 25A illustrates a single 5×5 sensor connected to imaging hardware. Dashed lines represent transmit lines and solid lines represent receive lines. FIG. 25B illustrates two 5×5 sensors connected to the same hardware as FIG. 25A. Dashed lines represent transmit lines. Solid lines represent receive lines with different time of flight (e.g. such as can be achieved with multiple different platen thicknesses as described above) and/or with different frequency responses (e.g. that can be achieved with different ZnO or other piezo material thickness), that can be combined together and can be separated by windowing in the time domain and/or filtering in the digital domain, respectively. FIG. 25C illustrates a variation in the connectivity between sensors.

These arrangements allow for a reduction in the hardware energy requirement per scan (e.g. important for portable applications), since multiple ultrasound channels can share the same electrical channels, and since the total data acquisition time (e.g. the time the hardware needs to be powered) is shorter. A variation of this arrangement can be used which impacts data acquisition time and hardware complexity and reduces digital processing requirements by avoiding time division or frequency division multiplexing. Hardware sharing remains where the transmit electronics and the receive chain, these being the main power drains, are shared.

Figure 25D:
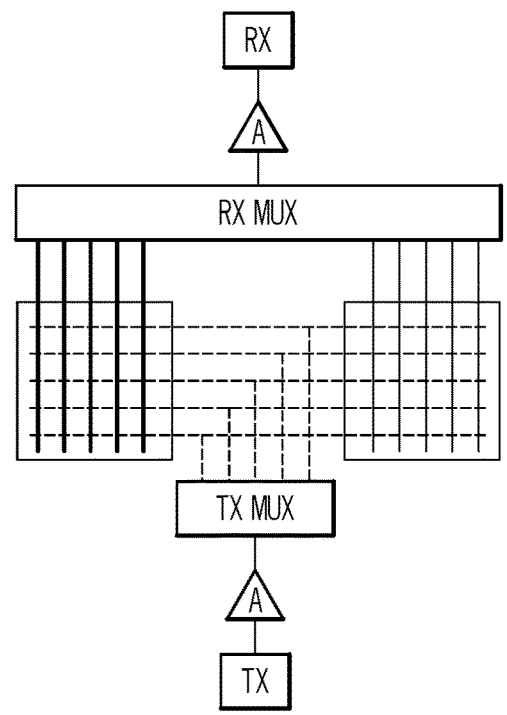

FIG. 25D illustrates identical 5×5 sensors that are connected to the same transmit lines. On the receiving side, aside from the increased number of multiplexers used to switch between lines, the hardware resources are shared between the two sensors.

Another arrangement for realizing different arrival times of multiple pulses is to use a platen made of different materials that are attached together (e.g. at the side). For instance, multiple glass square rods can be fused together, then sliced horizontally, to make flat disks (e.g. platens) with different material properties (e.g. speed of sound), such as to allow the realization of a large area fingerprint sensor in the manner described earlier. For frequency division multiplexing, system 10 can determine differences in phase in the signals excited at different locations while maintaining the type of electrical connections shown in FIGS. 20-24, in both X and Y directions. In some embodiments, the change in phase can be accomplished by changing the thickness of the piezo material (e.g. ZnO film).

Applicant has conducted simulations of the above arrangements where output pressure was measured at a fused quartz platen with a piezo ZnO film thickness changing from 16 μm to 19 μm in 1 μm steps. At an operating frequency of 150 MHz, there is a phase change of about 10° for every micron of ZnO film thickness change. Simulations were performed with arrangements including metal films (e.g. gold with a thickness of 0.2 m) above and below the ZnO film. Sufficient phase shift was present at different locations of the metal films that form the electrode of the sensor. An alternative way to achieve phase shift is by changing the metal over and under the piezoelectric film. A film of aluminum can be used at the interface between the ZnO and the quartz platen. In simulations, a large phase shift is achieved when the thickness of the aluminum film is changed from 0.2 μm to 1.0 μm.

Figure 26:
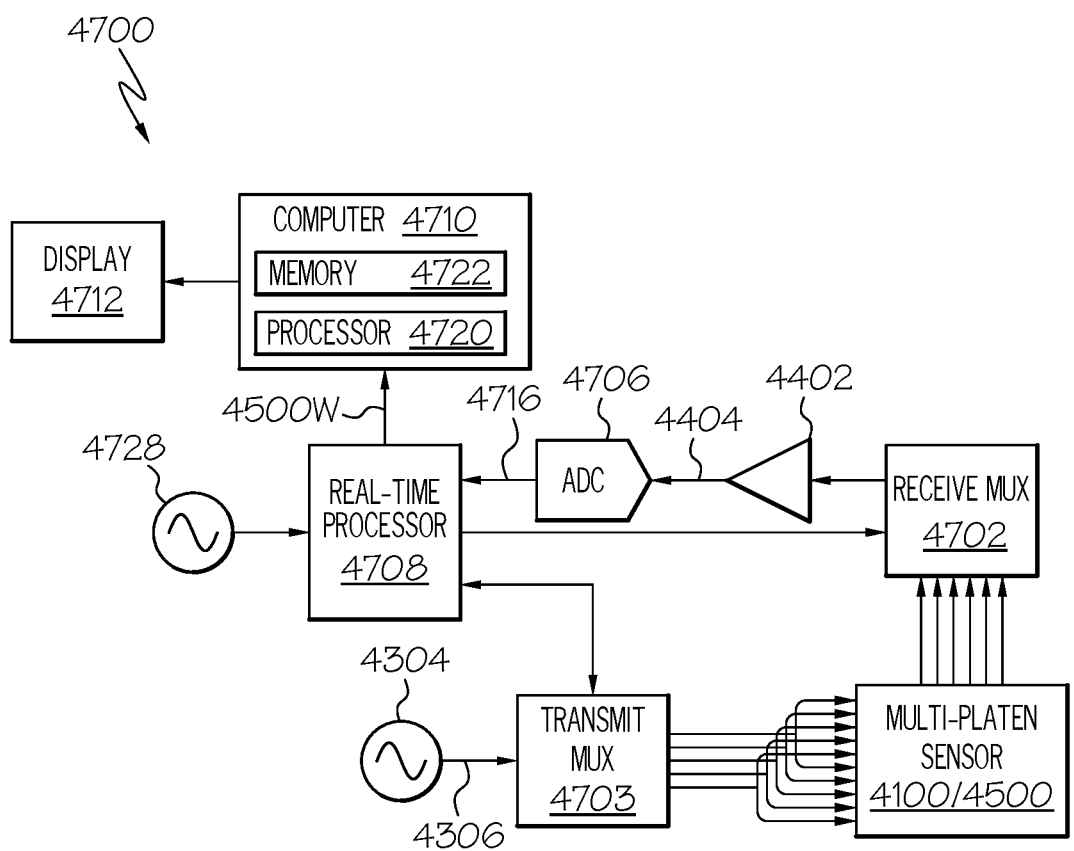
FIG. 26 is a block diagram of a fingerprint-sensing system that uses a multi-platen ultrasound fingerprint sensor, in an embodiment, consistent with the present inventive concepts.

FIG. 26 is a block diagram of a fingerprint-sensing system 4700 that uses the fingerprint sensor 4100 or 4500. The fingerprint-sensing system 4700 includes a real-time processor 4708 that controls a transmit multiplexer (MUX) 4703 to select which of the electrically-paired transmit electrodes 4106, 4107 is driven by the waveform generator 4304. The real-time processor 4708 also controls a receive MUX 4702 to select which of the receive electrodes 4108 is connected to the input of the amplifier 4402. The amplified output 4404 of the amplifier 4402 is digitized with an analog-to-digital converter (ADC) 4706, whose output is sensor data 4716 that the real-time processor 4708 then time-stamps. The real-time processor 4708 is referenced to a time base 4728 that references all timing. Although not shown in FIG. 26, the time base 4728 can also be used as a time and/or frequency reference for one or both of the ADC 4706 and the waveform generator 4304.

The processor 4708 is "real-time" in that the time it requires to complete an operation is deterministic, and therefore predictable (e.g. does not change based on external factors or unforeseen events). Examples of the real-time processor 4708 include a field-programmable gate array (FPGA), digital signal processor (DSP), and/or a system-on-chip (SoC). However, the real-time processor 4708 can be another type of circuit and/or chip, provided that it operates deterministically.

The real-time processor 4708 transmits the waveform 4500W to a computer 4710 that includes a processor 4720 and a memory 4722 that stores the waveform 4500W. The memory 4722 also stores machine-readable instructions that, when executed by the processor 4720, process the waveform 4500W to determine amplitude shifts and/or time shifts for the sensed pair of pixel transducers 4110, 4111. More details about the signal-processing methods used by the computer 4710 are described in reference to FIGS. 2 through 19 herein.

The fingerprint-sensing system 4700 processes a waveform 4500W for all of the pixel transducers 4110, 4111, from which it generates a fingerprint image. The computer 4710 can display the fingerprint image to a user via a display 4712 that can be integrated with the computer 4710 (e.g., a tablet or laptop computer) or can be separate from the computer 4710 (e.g., a desktop monitor or high-definition television). Although not shown in FIG. 26, the computer 4710 can alternatively or additionally communicate with another computer system (e.g., via a wide area network, a local area network, the internet, Wi-Fi, and the like) that uses the fingerprint image, such as a biometric security system that processes the fingerprint image to determine access to a room, computer system, files, and the like. In some embodiments, the real-time processor 4708 and computer 4710 are combined as one computer system.

Figure 27:
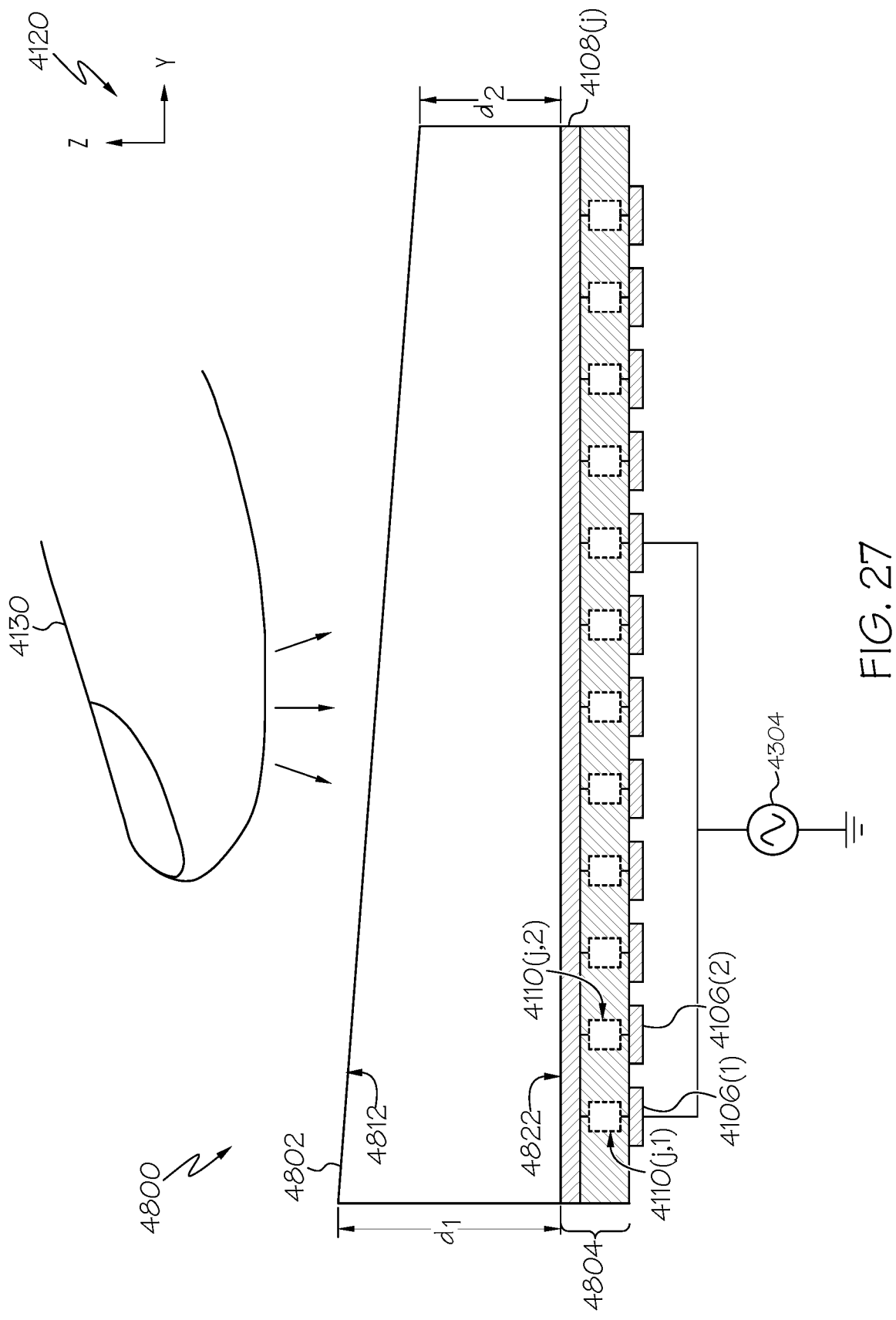
FIG. 27 is a side cross-sectional view of an ultrasound fingerprint sensor with a wedged platen, in an embodiment, consistent with the present inventive concepts.

FIG. 27 is a side cross-sectional view of an ultrasound fingerprint sensor 4800 with a wedged platen 4802. The fingerprint sensor 4800 includes an ultrasound transducer array 4804 that is similar to the transducer arrays 4104 and 4105 of FIG. 20, and that is located on a rear face 4822 of the wedged platen 4802. A front face 4812 of the wedged platen 4802 is not parallel to the rear face 4822, and therefore a thickness (in the z direction) of the wedged platen 4802 varies linearly (in the x direction) from $d_1$ to $d_2$. Due to this varying thickness, the round-trip propagation time of an ultrasound pulse emitted by transducer array 4804 will also vary linearly in the x direction.

The ultrasound fingerprint sensor 4800 can be operated similarly to the multi-platen ultrasound fingerprint sensor 4100, and therefore will have similar advantages. Specifically, and as shown in FIG. 27, a pair of transmit electrodes 4106 can be directly electrically connected to each other and driven simultaneously with a single waveform generator 4304. This arrangement will simultaneously emit two ultrasound pulses into the wedged platen 4802, similar to the operation of the multi-platen fingerprint sensor 4100 shown in FIG. 22. Thus, the pixel transducers 4110 in FIG. 27 can be electrically-paired, similar to the electrically-paired pixel transducers described above. Reflections off the front face 4812 will create two echoes that are sensed with a single receive electrode 4108(j), similar to the operation of the fingerprint sensor 4100 shown in FIG. 23. Due to the different round-trip propagation times, each detected echo can be correlated to its spatial location along the x direction.

Advantageously, the ultrasound fingerprint sensor 4800 offers the same benefits as the multi-platen fingerprint sensors described herein, but may be easier to fabricate because the wedged platen 4802 does not have a "step". While FIG. 27 shows the wedged platen 4802 as sloping only along the x direction, the wedged platen 4802 can be sloped along both x and y directions without departing from the scope hereof.

Embodiments with Anti-Reflection Coatings

Figure 28:
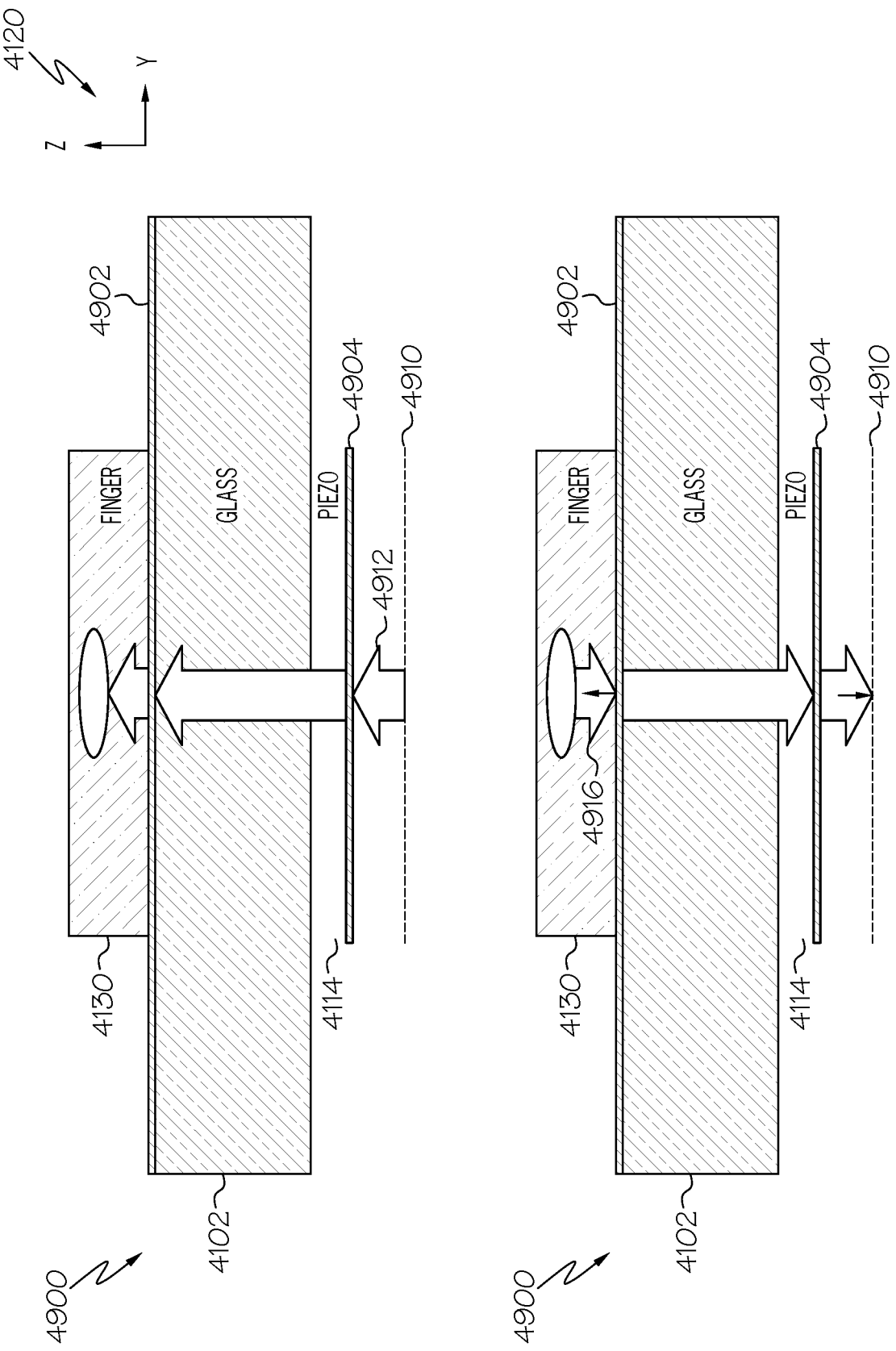
FIG. 28 shows two cross-sectional side views of an anti-reflection coated multi-platen ultrasound fingerprint sensor, in an embodiment, consistent with the present inventive concepts.

FIG. 28 shows two cross-sectional side views of an anti-reflection (AR) coated ultrasound fingerprint sensor 4900. The AR-coated ultrasound fingerprint sensor 4900 has a first AR coating 4902 deposited directly onto the front face 4112 of the platen 4102, which is shown in FIG. 28 as being made of glass. The AR-coated ultrasound fingerprint sensor 4900 has a second AR coating 4904 deposited directly onto the ultrasound transducer array (e.g. transducer array 4104 described herein). Thus, the second AR coating 4904 is deposited directly onto both electrodes (e.g., the electrodes 4106 in FIGS. 20 and 21) and regions of the piezoelectric layer 4114 between the electrodes.

The top diagram in FIG. 28 illustrates probing light 4912 propagating upward (i.e., in the +z direction) through the platen 4102 and into a finger 4130 physically contacting the first AR coating 4902. The probing light 4912 can be generated by a LED or laser (not shown) located underneath the AR-coated ultrasound fingerprint sensor 4900 at a plane 4910. The second AR coating 4904 increases transmission of the probing light 4912 into the piezoelectric layer 4114 (as opposed to the transmission without the second AR coating 4904) by reducing the magnitude of the reflection generated by the step-function change in refractive index between air and the piezoelectric layer 4114 (e.g., ZnO). The first AR coating 4902 increases transmission of the probing light 4912 into the finger 4130 (as opposed to the transmission without the first AR coating 4902) by reducing the magnitude of the reflection generated by the step-function change in refractive index between the platen 4102 and finger 4130.

The bottom diagram in FIG. 28 illustrates signal light 4916 transmitting downward (i.e., in the −z direction) from the finger 4130 and through the platen 4102. The first AR coating 4902 increases transmission of the signal light 4916 out of the finger and into the platen 4102 while the second AR coating 4904 increases transmission of the signal light 4916 out of the piezoelectric layer 4114 and into the underlying air. The signal light 4916, after exiting the piezoelectric layer 4114, can be detected by a photodiode (not shown) located on or near the plane 4910.

The AR-coated ultrasound fingerprint sensor 4900 can be used to increase signal-to-noise ratio (SNR) of a pulse oximeter. The above-referenced documents (i) International Publication No. WO 2019/032590 and (ii) Gerard Touma, "A row-column addressed acoustic biometric scanner integrated with pulse oximetry" (Ph.D. Dissertation, Stanford University, 2020) show how a pulse oximeter can be incorporated with an ultrasound transducer array when at least part of the transducer array is optically transparent. For pulse oximetry, the wavelength of the probing light 4912 is typically near 660 nm while the wavelength of the signal light 4916 is typically near 940 nm. In this case, the AR coatings 4902 and 4904 can be configured to enhance transmission at both of these wavelengths.

Since the probing light 4912 and signal light 4916 can propagate simultaneously, the second AR coating 4904 reduces the amount of probing light 4912 that is detected with the signal light 4916, thereby reducing the noise level when detecting the signal light 4916. The first AR coating 4902, by increasing the amount of probing light 4912 entering the finger 4130 and the amount of signal light 4916 exiting the finger 4130, increases the signal level when detecting the signal light 4916.

Each of the AR coatings 4902 and 4904 can be configured to increase transmission (i) at any wavelength in the infrared, optical, or ultraviolet regions of the electromagnetic spectrum, (ii) at a plurality of such wavelengths (e.g., 660 nm and 940 nm), and/or (iii) over a wavelength range (e.g., 660-940 nm). Each of the AR coatings 4902 and 4904 can be a multi-layer dielectric stack (e.g., formed from alternating layers of $SiO_2$ and $Ta_2O_5$, or other materials used for dielectric stacks) or a single-layer coating (e.g., $MgO_2$).

When the electrodes are made of metal, the probing light 4912 and signal light 4916 cannot pass through the electrodes. However, the electrodes can be made of an optically transparent, electrically conductive material (e.g., indium tin oxide). When the total area of the piezoelectric layer 4114 covered by electrodes is greater than the corresponding area that is uncovered, the second AR coating 4904 can be designed to maximize transmission of light at the interface between air and the electrode material, as opposed to the interface between air and the piezoelectric material, as this can result in an overall increase in transmission of light through the platen 4102 in both directions. Alternatively, the second AR coating 4904 can be designed to partially (but not maximally) increase transmission of light at the interface between air and the electrode material, and partially (but not maximally) at the interface between air and the piezoelectric material. This alternative design can result in maximal transmission of light, depending on the fraction of the area of the piezoelectric layer 4114 that is covered by electrodes, the refractive indices of the piezoelectric layer 4114 and the electrodes, the wavelengths of the probing light 4912 and signal light 4916, and/or other factors.

The AR coatings 4902 and 4904 can be used for an ultrasound fingerprint sensor having a single platen, such as those described in (i) International Publication No. WO 2019/032590 and (ii) Gerard Touma, "A row-column addressed acoustic biometric scanner integrated with pulse oximetry" (Ph.D. Dissertation, Stanford University, 2020). The AR coatings 4902 and 4904 can also be used with any one or more of the platens of any of the multi-platen ultrasound fingerprint sensors described herein (e.g., the first platen 4102 and second platen 4103 of the multi-platen ultrasound fingerprint sensor 4100 of FIGS. 20 and 21).

In other embodiments, a screen protector for a mobile device with a touch screen (e.g., a smartphone or tablet) includes a thin sheet of plastic (e.g., polyethylene terephthalate or thermoplastic polyurethane), glass, and/or another optically transparent material. A first side of the screen protector directly contacts an outward-facing surface of the touch screen (i.e., the side of the touch screen to be viewed by a user) to physically protect the outward-facing surface. Deposited directly onto a second side of the screen protector, opposite the first side, can be an AR coating similar to the second AR coating 4904 of FIG. 28. A light source and photodetector for pulse oximetry can be located behind an inward-facing surface of the touch screen, opposite the outward-facing surface, and pointing toward the touch screen. In this case, the touch screen acts like the platen 4102, and the AR coating on the second side increases transmission of light between the screen protector and a finger in direct physical contact with the AR coating. The AR coating can be designed to increase transmission of light used for pulse oximetry (e.g., 660 nm and 940 nm).

Referring collectively to FIGS. 29 through 45B, the reference numbers of FIG. 1 are used.

Figure 29:
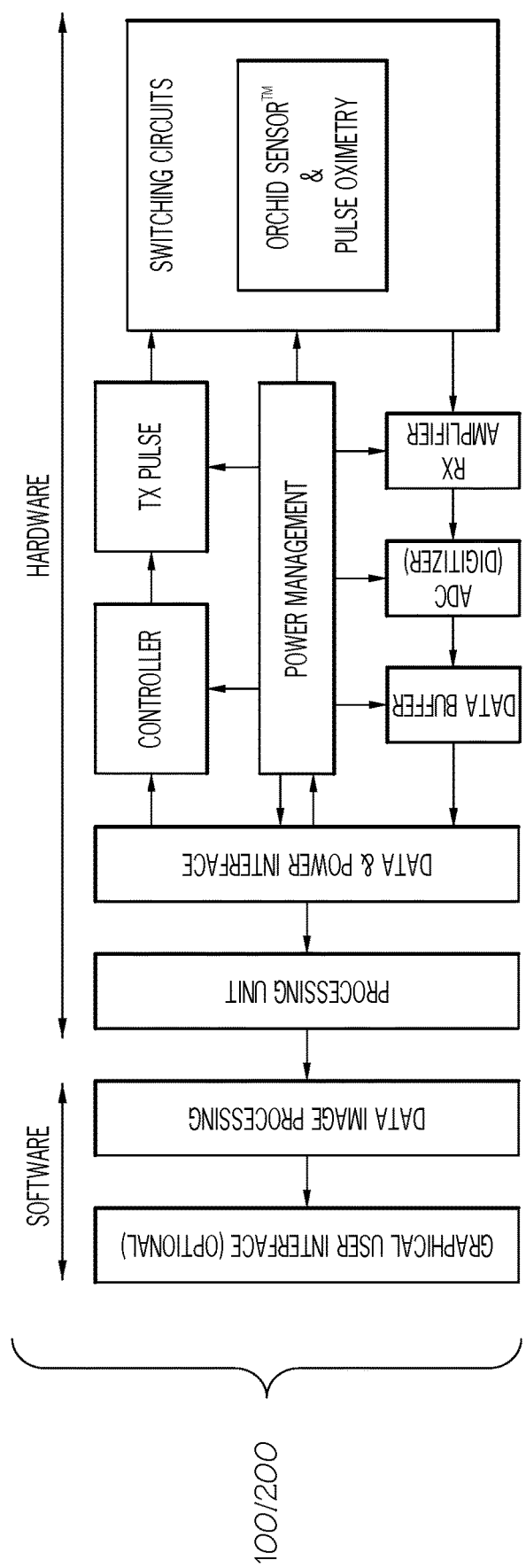
FIGS. 29 through 34G illustrate various schematics, sectional views, perspective views, exploded views, and graphs of simulated signals of a system including user classification, consistent with the present inventive concepts.

FIG. 29 is a block diagram of hardware and software portions of a system of the present inventive concepts. System 10 includes sensor 100 and controller 200. Sensor 100 and controller 200 can include various components such as those shown in FIG. 29.

Figure 30:
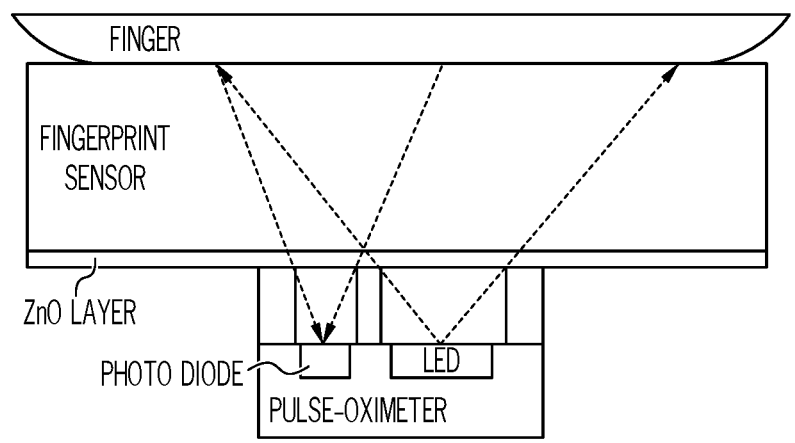

In some embodiments, system 10 is constructed and arranged as shown in FIG. 30. Sensor 100 of FIG. 30 comprises a fingerprint sensor 100a and a pulse oximetry sensor 100b. Sensor 100 of FIG. 30 further comprises a collimator comprising light-absorbing material at the frequency range of pulse oximetry sensor 100b, and positioned between sensor 100b and sensor 100a, such as to reduce clutter signals in the recordings produced by sensor 100b. The collimator can be used instead of, or in addition to, an anti-reflective coating. Height and width ratios of the collimator can be configured to provide optimal transmit and acceptance angles.

Figure 31:
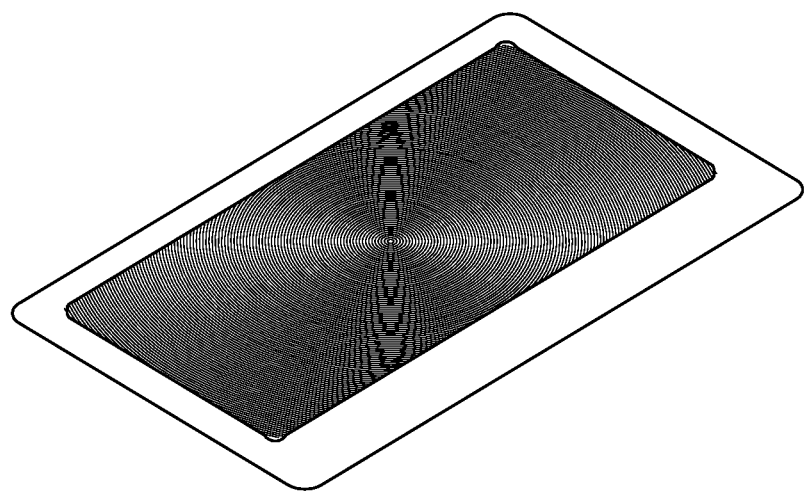

In some embodiments, sensor 100 comprises a focusing lens, such as is shown in FIG. 31. The focusing lens can be included to increase signal-to-noise ratio (SNR), reduce misalignment, and reduce clutter. In some embodiments, the lens comprises a Fresnel lens.

Figure 32:
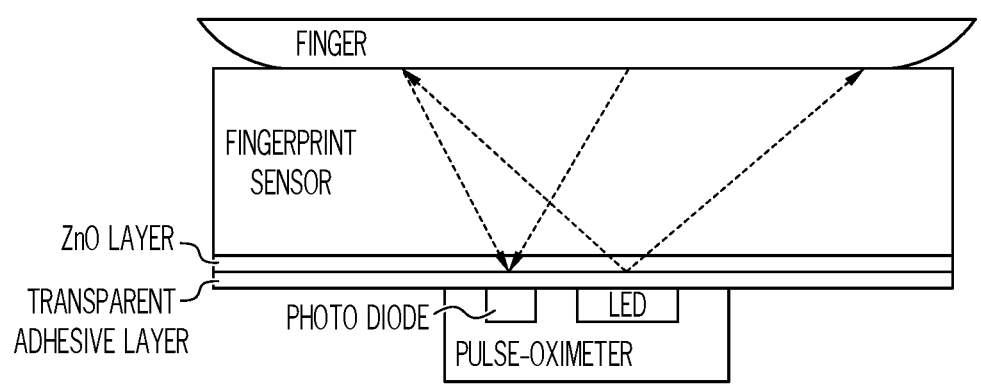

In some embodiments, system 10 is constructed and arranged as shown in FIG. 32. Sensor 100 of FIG. 30 comprises a fingerprint sensor 100a and a pulse oximetry sensor 100b. Sensor 100 of FIG. 30 further comprises a transparent, non-conductive adhesive layer to attach sensor 100b to sensor 100a. The adhesive layer provides permanent alignment while mechanically coupling sensors 100a and 100b.

Sensor 100 can comprise a relatively large number of electronic attachment points, or "pads", such as at least 100 pads, at least 200 pads, or at least 300 pads. These pads attach to the sensor's various input channels (e.g. power and control channels) and output channels. User device 500 can include a front-end ASIC (e.g. positioned close to sensor 100) that converts numerous channels (e.g. analog channels) of sensor 100 into fewer (e.g. one) channels (e.g. one or a few digital channels).

In some embodiments, user device 500 comprises a smart card, and sensor 100 comprises an ultrasound-based sensor constructed of PVDF, where the sensor 100 is positioned at a select depth from a first surface of the smart card, such that ultrasound transmissions travel through only a portion of the full thickness of the smart card.

In some embodiments, user device 500 comprises a smart card, and sensor 100 comprises an ultrasound-based sensor constructed of zinc oxide (ZnO) positioned on a small glass portion of the smart card. In some embodiments, the glass portion comprises a scratch-resistant coating.

In some embodiments, user device 500 comprises a cell phone, and sensor 100 comprises an ultrasound-based sensor that is positioned within a housing of the phone (e.g. a metal case that is acoustically transmissive), and ultrasound transmissions to and from sensor 100 are configured to travel through the housing.

In some embodiments, sensor 100 (e.g. an ultrasound-based sensor) is configured to identify a user based on an image of their palm (e.g. in addition to or as an alternative to a fingerprint).

Ultrasound Sensor Combined with Capacitive Sensor

In some embodiments, sensor 100 comprises a sensor 100a comprising an ultrasound-based sensor, and a sensor 100b comprising a capacitive touch sensor (e.g. operating at a DC level).

In some embodiments, sensor 100 comprises an ultrasound-based sensor (e.g. sensor 100a described hereinabove) that includes a layer of ZnO that is positioned on (e.g. sputtered onto) the back of a display (e.g. a display of a cell phone or other user device 500). In these embodiments, the sound produced by and received by sensor 100 travels through the display. In some embodiments, the display (e.g. user interface 550) includes: LCD, OLED, and/or microLED layers (e.g. including substrate, thin film transistors, liquid crystal, color filters, encapsulation, and the like); a capacitive sensor matrix (e.g. a sensor 100b, as described hereinabove, that includes electrodes, an insulator, thin film transistors, a passivation layer, and the like); one or more thin (e.g. approximately 1 μm, 2 μm, or 3 μm, such as up to 50 μm, or 75 μm) optically transparent adhesive layers (e.g. in between one or more other layers); and/or a glass cover layer. The display layers can be of uniform construction and arrangement, can be acoustically conductive, and can include minimal or no air gaps.

Similarly, in some embodiments, sensor 100 comprises an ultrasound-based sensor 100a that is positioned on (e.g. sputtered onto) the back of a sensor 100b comprising a capacitive touch sensor. In these embodiments, the sound produced by and received by sensor 100a travels through sensor 100b.

In some embodiments, sensor 100 can comprise an ultrasound-based sensor 100a that is positioned within layers of a sensor 100b and/or between layers of a display (e.g. a display of user interface 550 of device 500). In these embodiments, the sound produced by and received by sensor 100a travels through the various layers of sensor 100b and/or layers of the display (e.g. as described hereinabove) that are between sensor 100a and tissue of a user (e.g. finger tissue of the user). Sensor 100b and/or user interface 550 can comprise a transparent insulator film surrounded by two line-electrode layers (e.g. orthogonal line-electrode layers, or line-electrode layers in an angular arrangement between 1° and 89°) that are relatively transparent and can be constructed of indium tin oxide. This construction allows light to pass therethrough (e.g. having an optical transmittance of approximately 94%). Sensor 100a can be positioned within two of these line-electrode layers, such as by depositing a piezo film in place of the insulator film (e.g. such that sound passes through a reduced number of layers as compared to positioning on sensor 100a on the back of the mating component). This construction of an ultrasound-based sensor 100a in combination with a capacitive touch sensor (e.g. of sensor 100b and/or user interface 550) can provide a single assembly that can perform one, two, three, or more functions selected from the group consisting of: ultrasonic fingerprint detection; capacitive fingerprint detection; ultrasound touch sensing (e.g. location sensing); capacitive touch sensing; force sensing (e.g. via capacitive or ultrasound-based measurements); haptic feedback; acoustic feedback; and combinations of these.

Figure 33A:
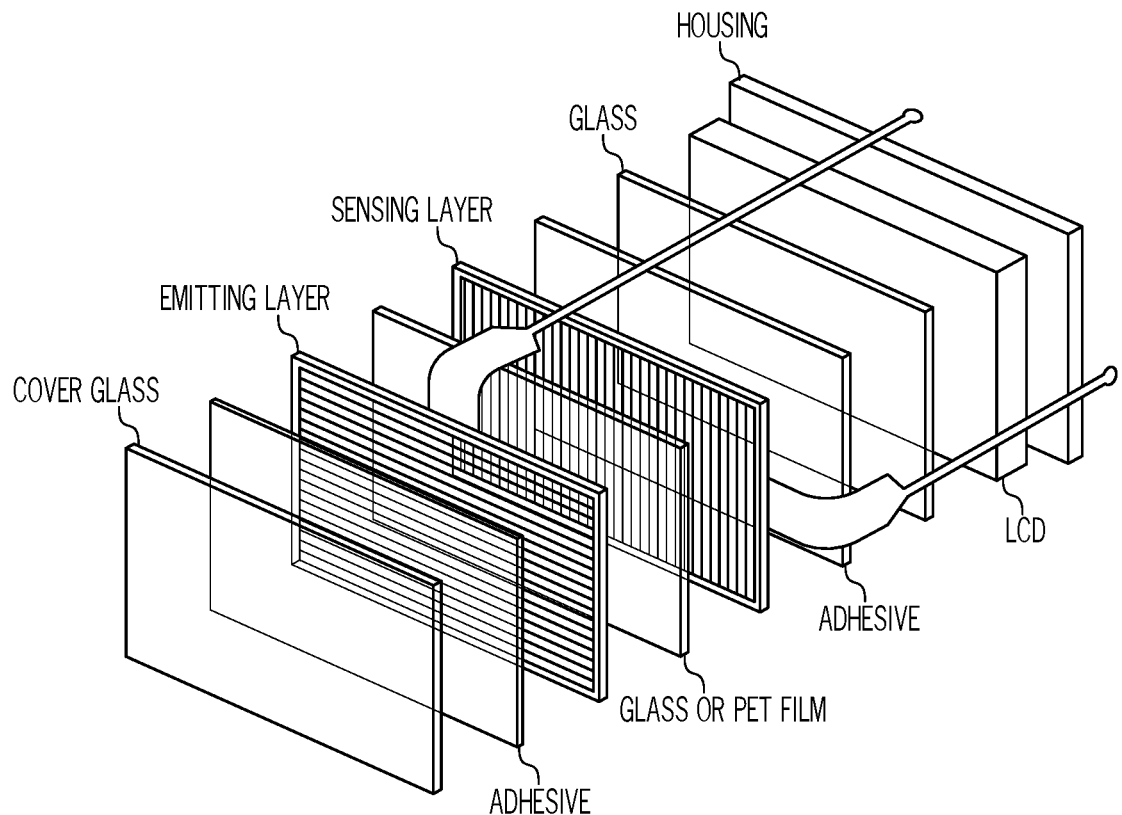
Figure 33B:
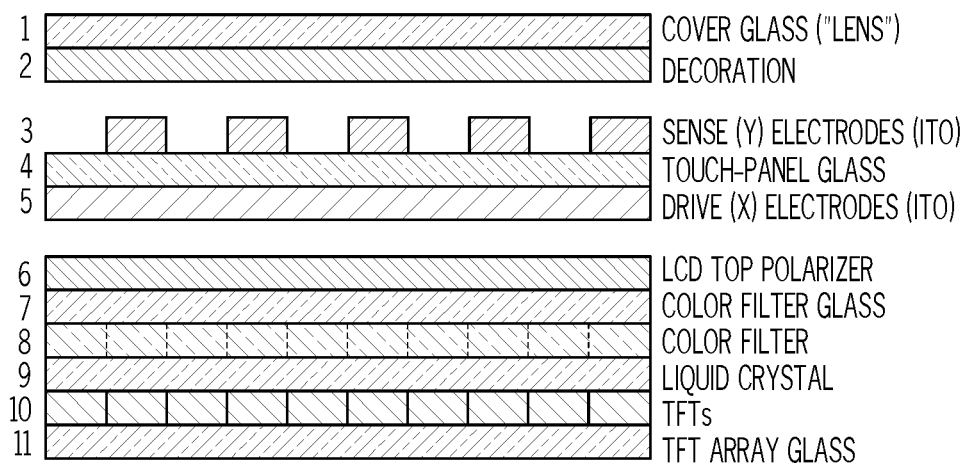

FIGS. 33A-B illustrate a construction of a user interface 550 including a capacitive touch sensor 100b (e.g. operating at a DC level), as described hereinabove. An ultrasound-based sensor 100a, not shown but including a piezo film and operating in the MHz range as described herein, can be positioned between two or more of the various layers shown. Alternatively or additionally, the sensor 100a can replace one of the layers shown in FIG. 33A.

Zones of Operation

In some embodiments, sensor 100 comprises a sensor 100a comprising an ultrasound-based sensor, and a sensor 100b comprising a capacitive touch sensor, as described hereinabove. Sensor 100a can be positioned under (e.g. from the viewpoint of a user) sensor 100b. System 10 can be configured such that user contact (e.g. contact via a finger of a user) with sensor 100b is used to change the current state of user device 500, such as to make a change in state selected from the group consisting of: off to on; standby mode to awake mode; low power mode to a non-low power mode; silent mode to non-silent mode; and combinations of these. In some embodiments, sensor 100 is configured such that contact (e.g. continuous finger contact) by a user along portions of the top surface of sensor 100 can be configured, via sensor 100b, to define a "zone of operation" to be used by system 10 in a subsequent event (e.g. a user can dynamically set one or more zones of operation as subsets of a relatively large sensor 100 surface area). For example, one or more of these user-defined zones of operation can correlate to one or more "active zones" for sensor 100a (e.g. one or more subsets of the entire area of sensor 100 in which sensor 100a will actively image contacting portions of the user). These limited area active zones can be used to reduce power consumption, and/or to reduce the amount of data collected by sensor 100*a* (e.g. for faster data collection, processing, and/or matching). Multiple active zones can be created, and each can be assigned to a similar and/or different function (e.g. to different functions of a gaming application of device 500 or other application), such that either or both sensor 100*a* and/or 100*b* can correlate a function to user contact with the particular active zone.

In some embodiments, device 500 is configured for use with multiple users, where each user controls a particular cursor of user interface 550. In these embodiments, system 10 can associate a particular cursor (e.g. from a set of cursors of different colors, shapes, emojis, and/or other varied graphical parameters) with a particular user by their fingerprint. Once detected, continuous contact by that user with their finger can continue the association with the cursor. If contact by the finger is lost, a re-association can be performed by the user (e.g. selecting the same cursor), and/or detection (e.g. an automatic detection) of the user can be performed by a repeat analysis of their fingerprint.

In some embodiments, an ultrasound-based sensor 100 (e.g. sensor 100*a* described hereinabove) is used to determine one or more zones of operation (e.g. with or without the use or even presence of a capacitive touch-based sensor, such as sensor 100*b* described immediately hereinabove). For example, an ultrasound-based sensor 100 can utilize pulse-echo on all of its ultrasound transducers (also referred to as "channels" herein) to rapidly detect a location of contact of a user (e.g. a finger of a user), and subsequently define a zone of operation around that contact location (e.g. including a buffer zone around the detected contact location). Alternatively or additionally, an ultrasound-based sensor 100 can provide a drive signal to a small subset of the total number of ultrasound sensors (e.g. an equally spaced distribution of less than 20% of the total number of sensors), and sensor 100 can use the reflections of these signals to locate a point of contact of a user, and use this point of contact as a zone of operation (e.g. with or without an accompanying buffer zone).

Langevin Transducer-Based Sensor

In some embodiments, sensor 100 comprises a Langevin transducer-based sensor (or its equivalent). In normal operation, a piezoelectric is resonant where the thickness of the piezo is one-half the wavelength of the drive signal, and resonance is also achieved at higher frequencies where the piezo thickness is an odd multiple of the one-half wavelength. Sensor 100 can comprise Langevin transducers comprising an assembly including a piezo element and an attached element of a particular mass. These Langevin transducers resonate at a frequency where the thickness of the assembly (piezo transducer thickness plus attached element thickness) is one-half the wavelength of the drive signal, and resonance is also achieved at high frequencies where the assembly thickness is an odd multiple of the one-half wavelength. Sensor 100 can comprise a Langevin transducer that includes an attached element that is much thicker than the piezo element, such as to create an assembly whose resonant frequencies are much lower than the resonant frequency of the piezo element without the connection to the attached element.

In some embodiments, sensor 100 comprises an ultrasound-based sensor comprising one or more piezo elements (e.g. zinc oxide piezo elements) with a particular thickness, such as 16 μm. Sensor 100 comprises a particular area (e.g. 1 mm by 1 mm, 5 mm by 5 mm, and the like), with all row electrodes connected together, and all column electrodes connected together. Controller 200 can drive a set of multiple piezo elements in unison (e.g. all or a portion of the total number of piezo elements of sensor 100), such as to have this set of piezo transducers function as a signal sensor (e.g. a low-frequency sensor), such as to send and receive ultrasound energy to and from tissue (e.g. a user's finger), to perform a Doppler ultrasound measurement (e.g. of blood flow, heart rate, and the like). For example, system 10 can comprise a system that includes multiple piezo elements which can be configured (e.g. via controller 200) as a Langevin transducer, where system 10 is capable of performing a function selected from the group consisting of: Doppler ultrasound; blood flow analysis; capillary mapping (e.g. of a finger and/or other tissue of a user); and combinations of these.

Figure 34A:
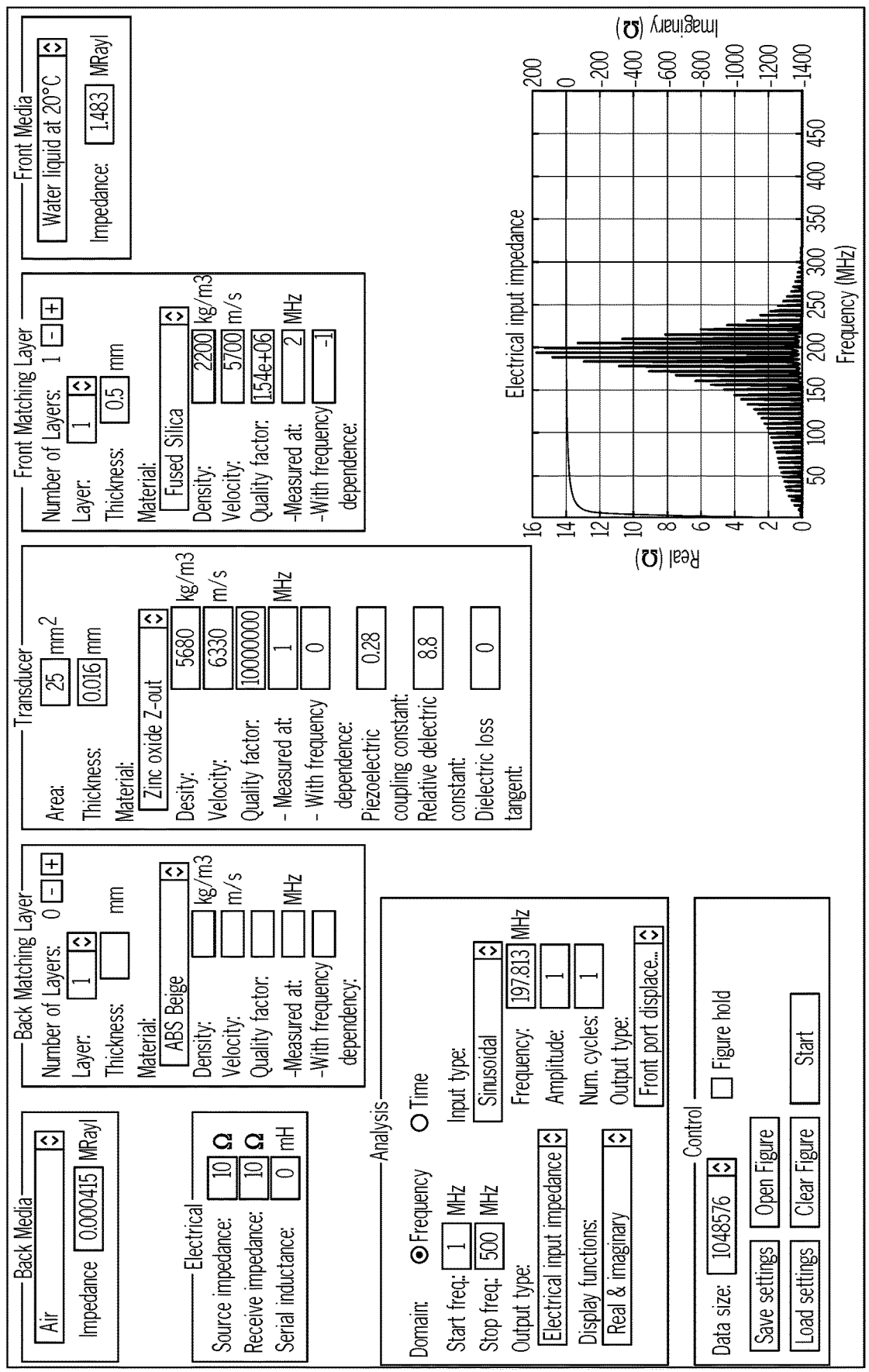

Applicant has performed simulations modeling a sensor 100 comprising multiple piezo elements configured as a Langevin transducer. FIG. 34A represents various parameters of the transducer.

Note that fused silica results in the multiple resonances seen in the input impedance, and shows that the silica acts as a mechanical matching layer that allows operation of sensor 100 at multiple frequencies that are well below the 200 MHz natural frequency of operation.

Figure 34B:
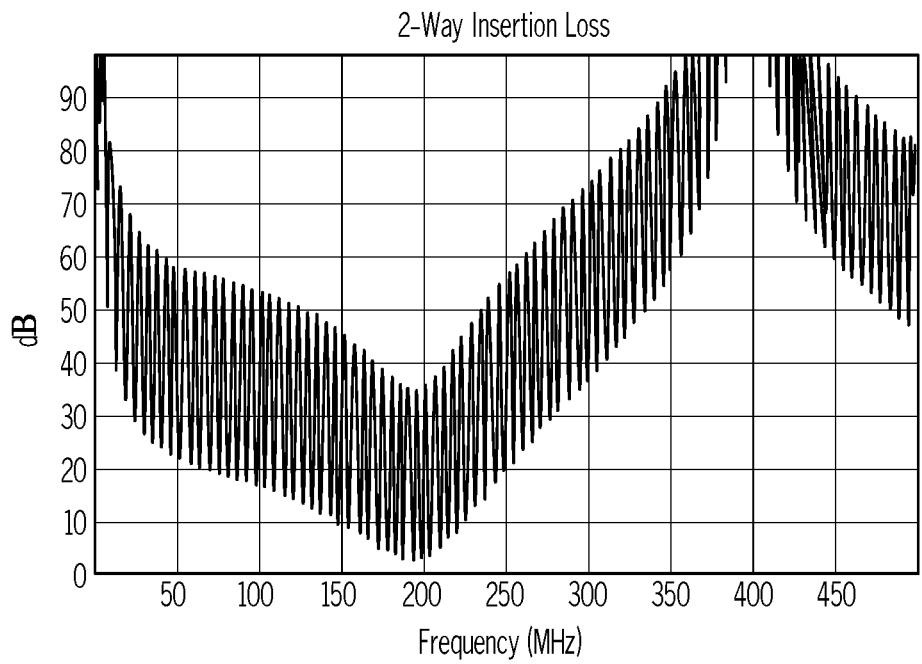

The insertion loss from a 50-Ohm system is shown in FIG. 34B.

Figure 34C:
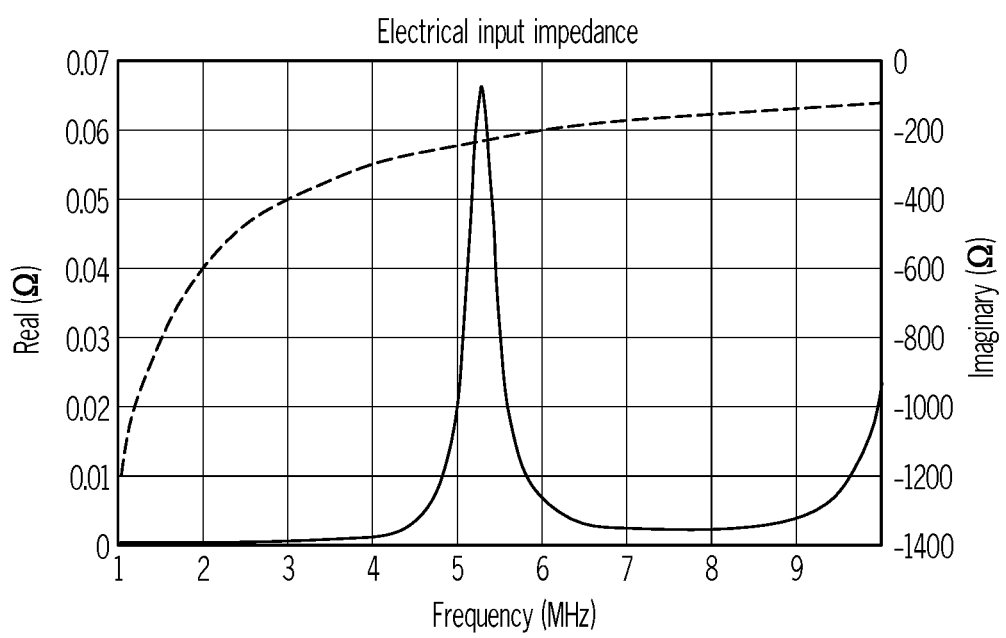

As the frequency decreases, the efficiency of the sensor 100 worsens. However, it is possible to operate at low frequency where the thickness of the silica and ZnO is one-half wavelength of the drive signal (e.g. 5 MHz as shown in FIG. 34C).

Figure 34D:

The real part of the impedance is quite low, so the insertion loss into a 50-Ohm system is rather high, as shown in FIG. 34D.

Figure 34E:
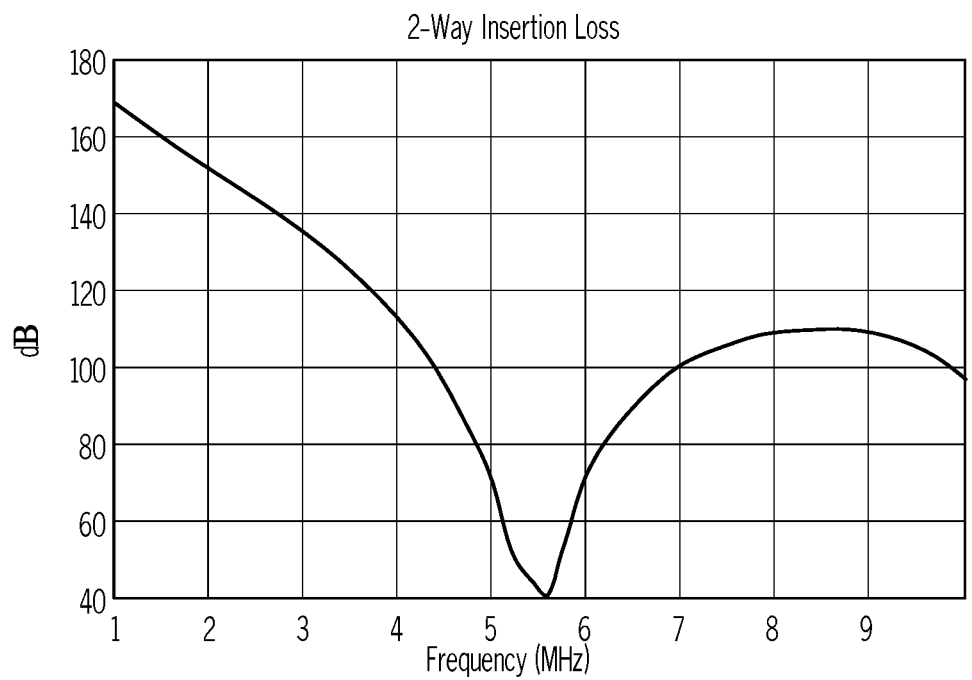

In FIG. 34E, insertion loss is shown when tuned with a 6.1 μHenry and using a 10-Ohm system (transformer 5:1).

Figure 34F:
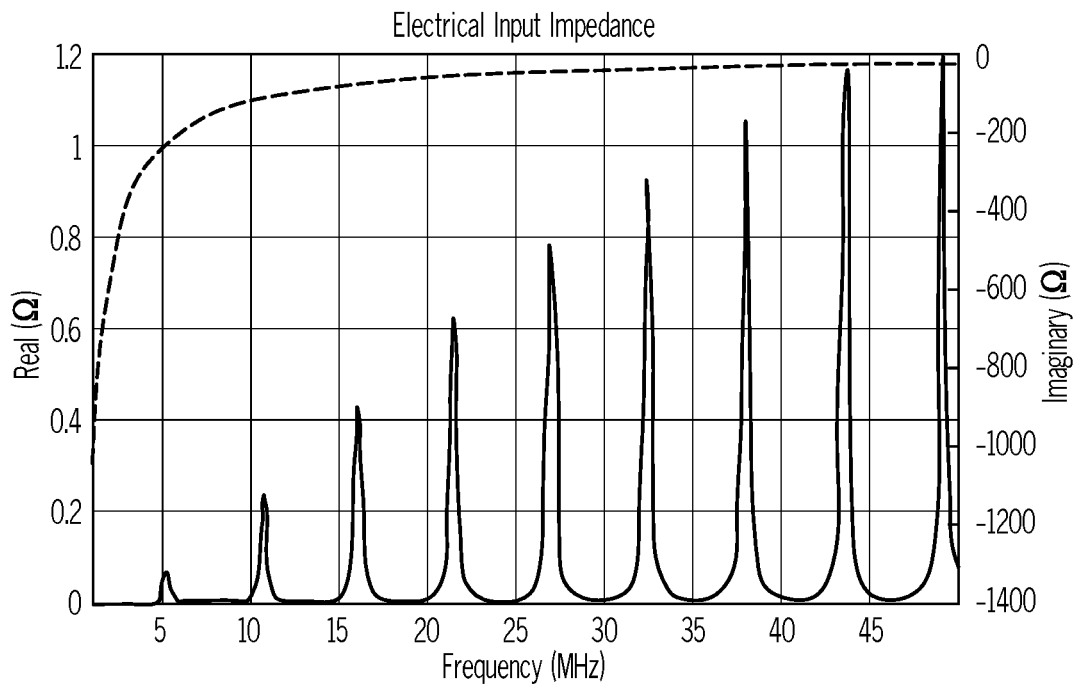

FIG. 34F shows use of higher frequencies (e.g. the peaks shown are frequencies at which sufficient energy can be delivered). Controller 200 can provide drive frequencies that are related to depth of penetration into the user's tissue (e.g. finger tissue), such as to provide a Doppler measurement for that user.

Figure 34G:
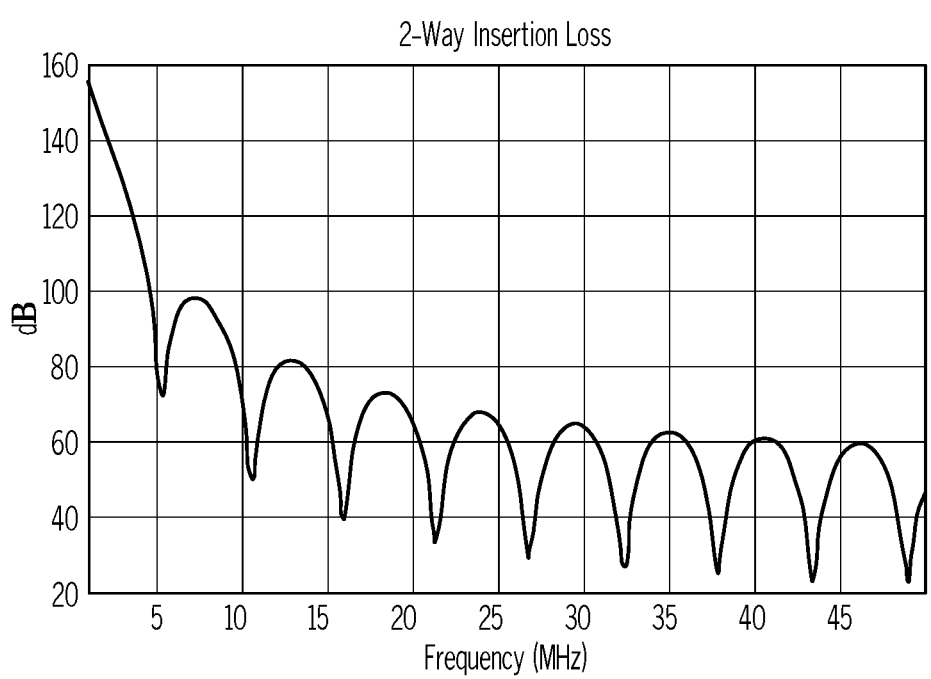

FIG. 34G shows insertion loss into a 50-Ohm system, with no tuning. With tuning and better matching, controller 200 can be configured to provide a 25 MHz drive signal, where system 10 provides a Doppler measurement with high resolution and specificity.

Referring now to FIGS. 35A-B, 36A-B, 37A-B, and 38A-B, sets of perspective and sectional schematic views, respectively, of various user interfaces are illustrated, consistent with the present inventive concepts. User interfaces 550 of FIGS. 35 through 38 each comprise multiple layers that can be configured to function as a display (e.g. a display providing alphanumeric text, images, and/or videos), as well as to record user information, such as "user input information" and/or "user physiologic information".

User input information (also referred to as "user selection information") can include information received from a user comprising one, two or more users. User input information can include information entered into a user interface 550 configured as a touch-screen display. User input information can include information selected from the group consisting of: selection of an icon; activation of a control (e.g. an on, off, start, and/or stop control); keyboard entry (e.g. onscreen keyboard entry); selection and/or sizing of an active area of the screen of user interface 550 (e.g. selection of an area to transition from a sleep mode to an active mode); graphical input data (e.g. a graphic drawn by the user via one or more fingers); "tap information" (e.g. as described hereinbelow); pressure information (e.g. correlating to the force applied by one or more fingers of the user); and combinations of these. Tap information input into user interface 550 by a user can comprise: information representing tapping or other contact of one or more of the user's fingers with user interface 550 (e.g. with one or more exposed surfaces of interface 550). While tap information and other user contact are described herein in reference to a user's one or more fingers, other skin surfaces (e.g. palm, toe, nose, elbow, knee, and the like) shall be considered within the scope of this application. Tap information can comprise touching of interface 550 by multiple fingers with interface 550, simultaneously and/or sequentially (e.g. from a single user or multiple users). Tap information can comprise dragging of one or more of the user's fingers along interface 550 (e.g. to adjust or set a level of a control, to select a portion of the interface 550, and/or to select a portion of an icon, control, and/or other image displayed on interface 550).

User physiologic information recorded by user interface 550 can include physiologic information of one, two, or more users, the information selected from the group consisting of: fingerprint information, pulse oximetry information; blood gas information; blood glucose information; blood pressure information; respiration information; cardiac information; neural firing information (e.g. EEG, LFP, and/or single neuron firing information); and combinations of these.

The user interfaces 550 of FIGS. 35 through 38 can be included in various devices (e.g. in whole or in part, and/or in multiples), such as when user interface 550 is included in one or more user devices 500 described herein. User device 500 can comprise a device selected from the group consisting of: a consumer electronic device (e.g. a cell phone, a tablet, a laptop or desktop computer, a watch such as a smart watch, an exercise and/or other activity-monitoring device, and the like), a medical device (e.g. an infusion device such as an insulin infusion device; a heart rate monitor; a controller for an implanted device such as a pacemaker, defibrillator, and/or other implanted stimulator;), a vehicle (e.g. a car, boat, helicopter, and/or plane); a piece of equipment (e.g. construction equipment and/or excavation equipment); and/or other device in which a user interface 550 can be included.

User interface 550 of FIGS. 35 through 38 can include various layers (e.g. layers comprising one or more materials, and/or layers comprising a functional assembly), such as one, two, or more layers as described hereinbelow. User interface 550 can comprise a "housing layer", such as a layer comprising the housing of the user device 500 into which interface 550 is integrated. User interface 550 can comprise an "x-lines layer" that includes sets of one, two, or more wires in a parallel arrangement, as described herein.

User interface 550 can comprise a "y-lines layer" that includes one, two, or more wires in a parallel arrangement. The wires of the y-lines layer can be angularly offset from the wires in the x-lines layer, such as an angular offset between 10° and 90°. User interface 550 can comprise an "ultrasonic film layer", such as a piezo-material and/or other substrate which can be positioned between the x-lines layer and the y-lines layer, as described herein, such as to cause ultrasound waves to be transmitted and/or received. User interface 550 can comprise an "ultrasound assembly" comprising the x-lines layer, the y-lines layer, and the ultrasonic film layer positioned therebetween. User interface 550 can comprise a "display layer", which can comprise an LCD, OLED, microLED, and/or other display component known to one of skill in the art. User interface 550 can comprise a "substrate layer", which can comprise a substrate material onto which the display layer and/or the ultrasound assembly are mounted (e.g. attached to, deposited on, and/or otherwise manufactured onto). User interface 550 can include a "cover layer", such as a glass or other material (e.g. transparent material) that is configured to protect and/or encapsulate at least a surface of another layer. User interface 550 can include an "adhesive layer" that is configured to bond two layers together (e.g. a layer comprising an adhesive). User interface 550 can comprise an "encapsulation layer", such as a layer comprising glass or other material (e.g. transparent material) can be positioned between the user and the other layers of user interface 550.

The x-lines layer and the y-lines layer can comprise layers with wires (e.g. as described herein), where the wires are positioned relative to each other at a constant distance of separation, and/or at varied distance of separation. A varied distance of separation of the wires can be used to vary the resultant pixel transducer density among different portions of a user interface 550. In some embodiments, higher density transducer portions are configured to record more information (e.g. more user input) than lower density portions, such as is described in reference to FIG. 43 and otherwise herein. In some embodiments, a user interface 550 comprising constant distance of separation between wires can create areas of higher and lower resolutions by selectively applying transmit and receive signals to subsets of the wires, such as is described hereinbelow in reference to FIG. 42.

FIGS. 35 through 40 described hereinbelow illustrate various examples of construction of a user interface, such as user interface 550 and/or 650 described herein. One or more layers of the user interface, and/or components of a single layer, can be attached to another layer or other component via mechanical fasteners and/or adhesives. Alternatively, a layer (e.g. an ultrasound-based sensor 100) can be directly deposited onto another layer (e.g. a display), as described herein.

Figure 35A:
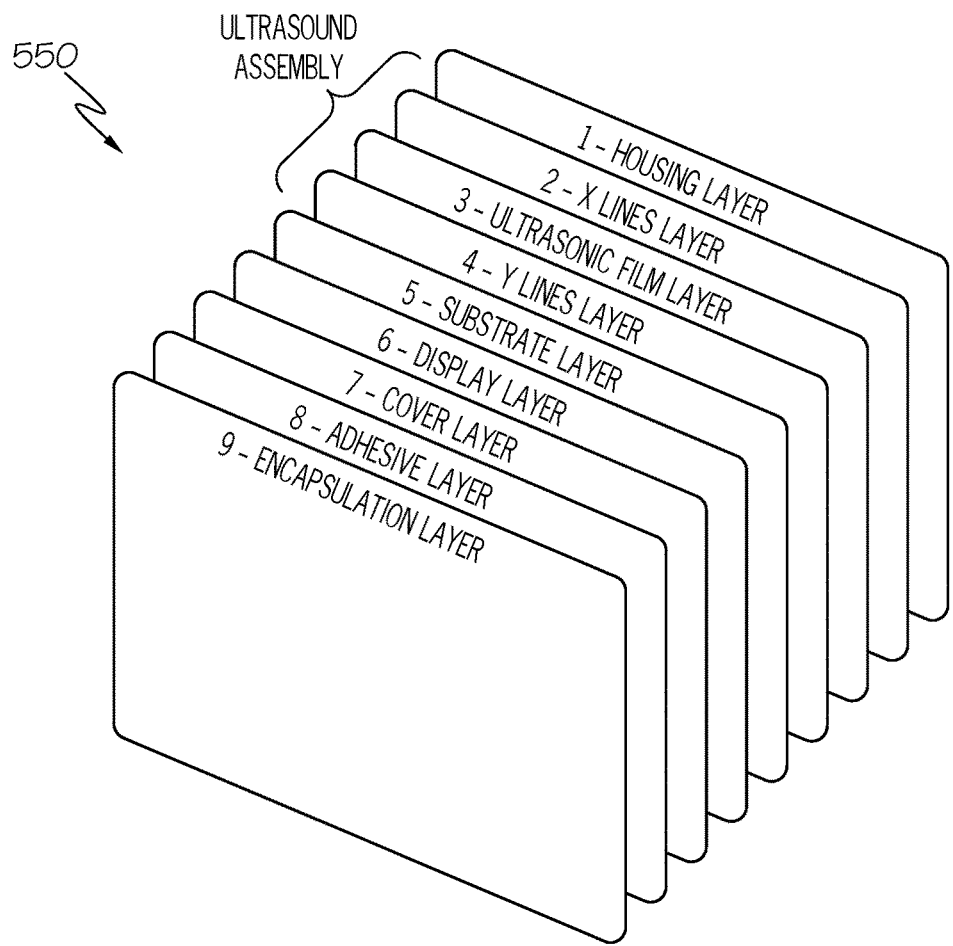
FIGS. 35A through 45B illustrate various schematics, sectional views, perspective views, exploded views, flow charts, and graphs of simulated signals of a system including user classification, consistent with the present inventive concepts.
Figure 35B:
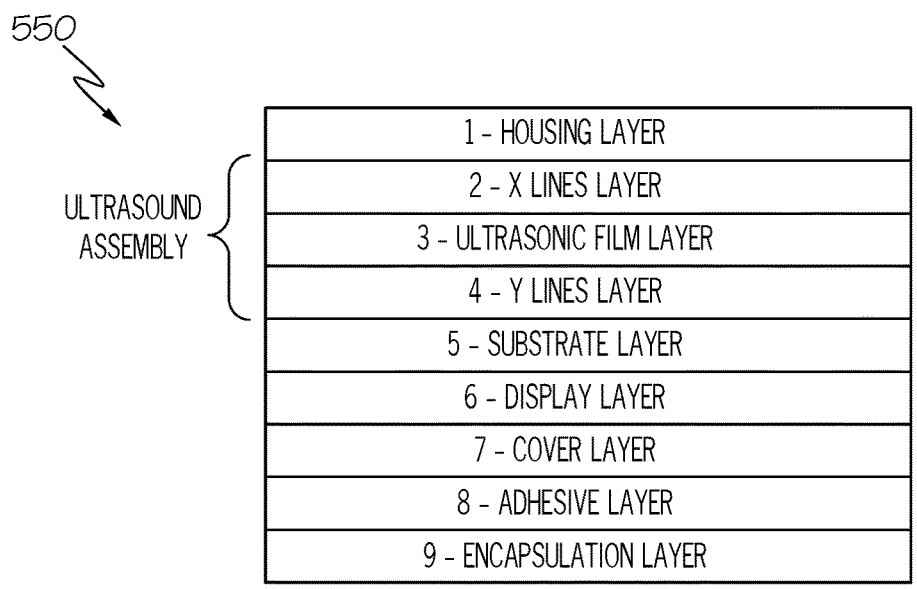

Referring now to FIGS. 35A-B, an exemplary construction of a user interface is illustrated, consistent with the present inventive concepts. User interface 550 of FIGS. 35A-B includes multiple layers (e.g. as described hereinabove) that collectively function to display information to a user, as well as record user information, such as user input information and user physiologic information described hereinabove and otherwise herein. User interface 550 of FIGS. 35A-B comprises a multi-layer construction arranged in the following order (as shown): layer 1 comprising a housing layer; layer 2 comprising an x-lines layer; layer 3 comprising an ultrasonic film layer; layer 4 comprising a y-lines layer; layer 5 comprising a substrate layer; layer 6 comprising a display layer; layer 7 comprising a cover layer; layer 8 comprising an adhesive layer; and layer 9 comprising an encapsulation layer (e.g. a layer of protective glass or plastic).

User interface 550 can include an integrated ultrasound assembly (e.g. configured as a touch sensor) that is positioned behind (from the viewpoint of a user) a display (e.g. an OLED display), as shown in FIGS. 35A-B. This configuration can improve transparency between the display layer and layers positioned on top of the display layer (e.g. layers positioned between the display layer and the user's view, such as the cover layer, adhesive layer, and encapsulation layers shown). This construction of user interface 550 can facilitate modular construction of device 500. Since the ultrasound assembly does not obstruct the user's view to the display, this construction of user interface 550 can be void of transparent electrode material such as indium tin oxide (ITO), such as when the conductors (e.g. the X and/or Y conductors described herein) comprise gold (e.g. providing low resistivity).

Figure 36A:
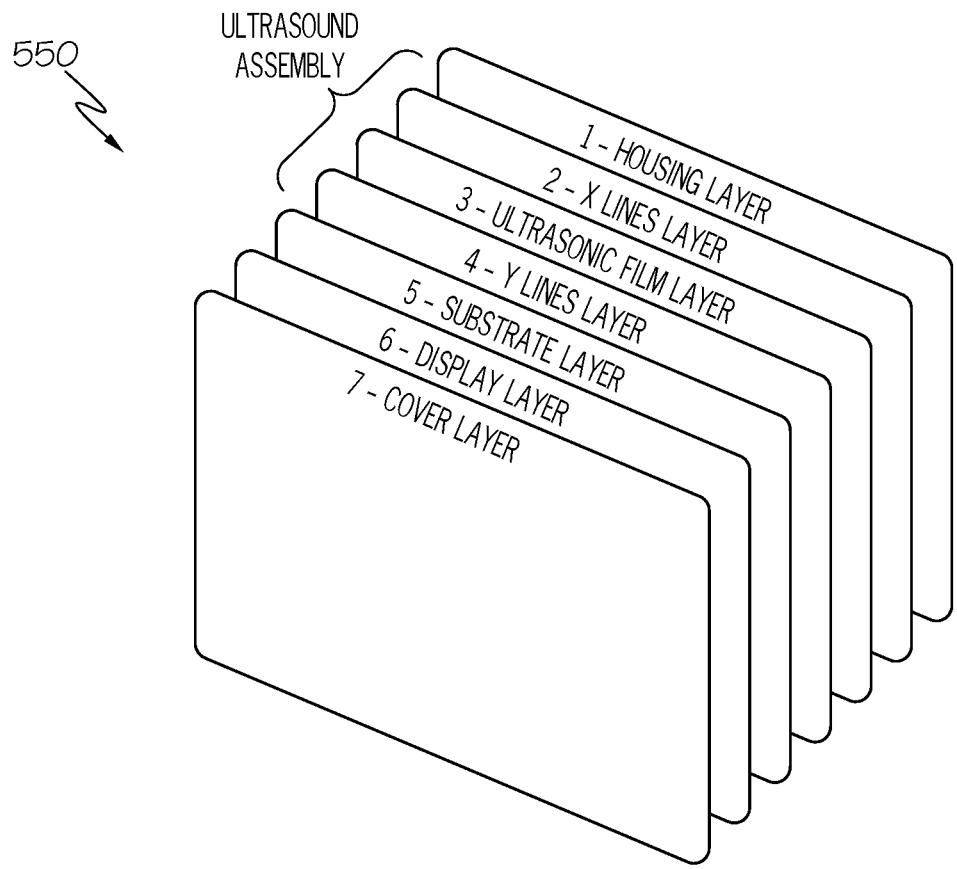
Figure 36B:
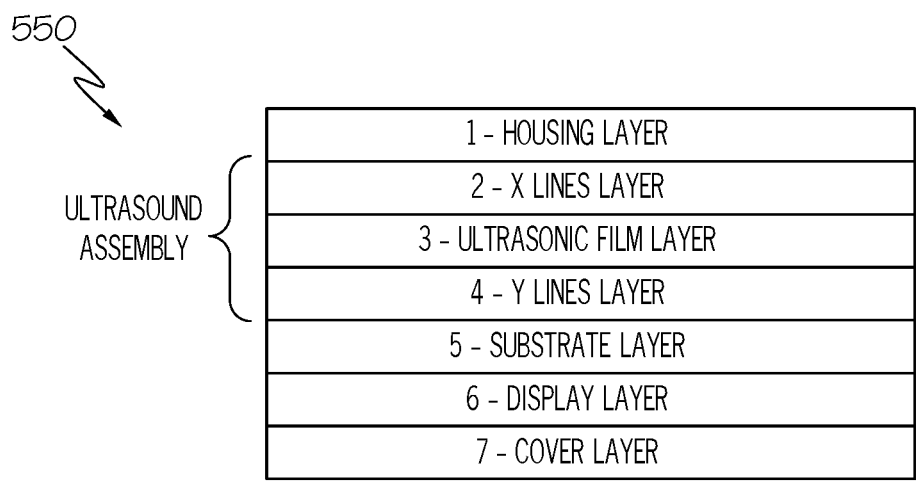

Referring now to FIGS. 36A-B, an exemplary construction of a user interface is illustrated, consistent with the present inventive concepts. User interface 550 of FIGS. 36A-B includes multiple layers (e.g. as described hereinabove) that collectively function to display information to a user, as well as record user information, such as user input information and user physiologic information described hereinabove and otherwise herein. User interface 550 of FIGS. 36A-B comprises a multi-layer construction arranged in the following order (as shown): layer 1 comprising a housing layer; layer 2 comprising an x-lines layer; layer 3 comprising an ultrasonic film layer; layer 4 comprising a y-lines layer; layer 5 comprising a substrate layer; layer 6 comprising a display layer; and layer 7 comprising a cover.

User interface 550 (e.g. as shown in FIGS. 36A-B) can avoid the inclusion of an adhesive layer between the ultrasound assembly (e.g. configured as a touch screen) and the top-most cover layer. Avoidance of an adhesive layer can provide the advantage of avoiding undesired attenuation of ultrasound signals associated with an adhesive layer, as well as avoiding the manufacturing requirements associated with application of an adhesive layer.

Figure 37A:
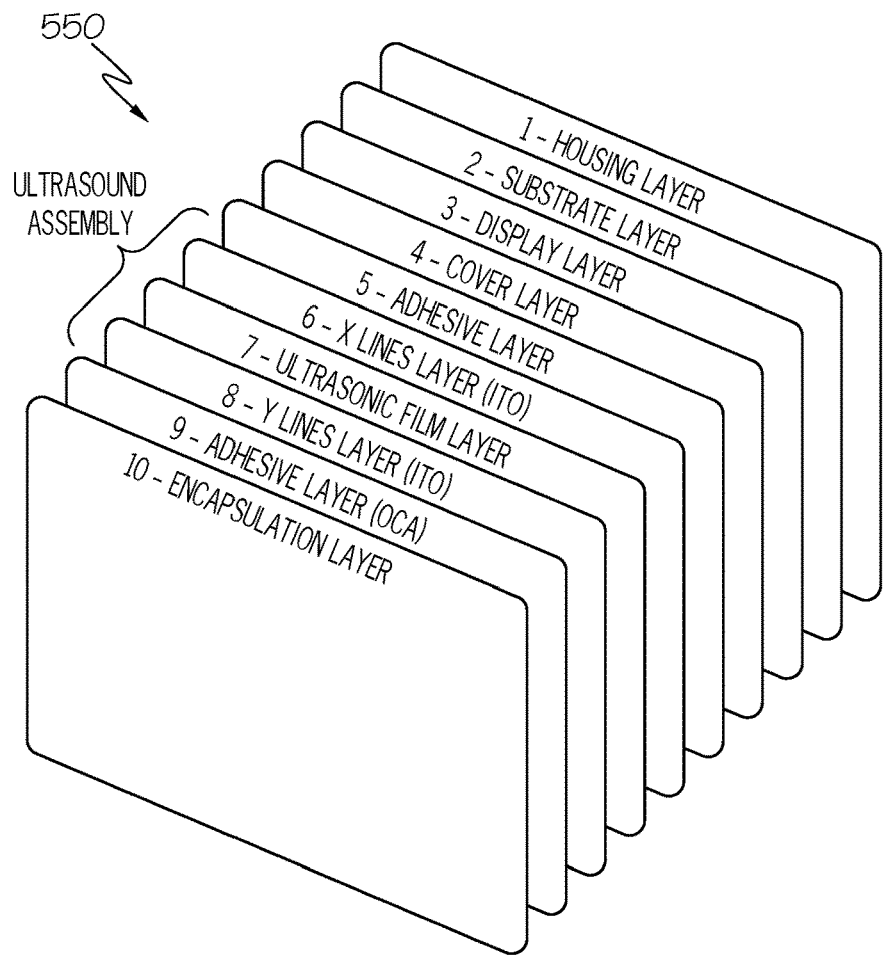
Figure 37B:
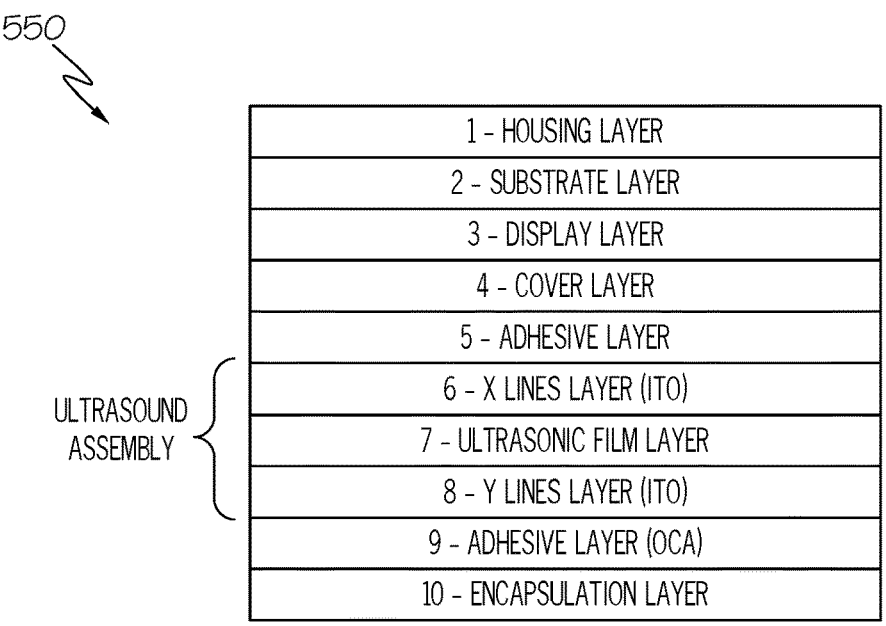

Referring now to FIGS. 37A-B, an exemplary construction of a user interface is illustrated, consistent with the present inventive concepts. User interface 550 of FIGS. 37A-B includes multiple layers (e.g. as described hereinabove) that collectively function to display information to a user, as well as record user information, such as user input information and user physiologic information described hereinabove and otherwise herein. User interface 550 of FIGS. 37A-B comprises a multi-layer construction arranged in the following order (as shown): layer 1 comprising a housing layer; layer 2 comprising a substrate layer; layer 3 comprising a display layer; layer 4 comprising a cover layer; layer 5 comprising an adhesive layer; layer 6 comprising an x-lines layer; layer 7 comprising an ultrasonic film layer; layer 8 comprising a y-lines layer; layer 9 comprising an adhesive layer; and layer 10 comprising an encapsulation layer.

User interface 550 can include an ultrasound assembly (e.g. as shown in FIGS. 37A-B) that avoids the inclusion of a capacitive touch screen between the display layer (e.g. an OLED) and the encapsulation layer. The ultrasound assembly is positioned close to the encapsulation layer, such that the transmit and receive ultrasound signals pass through a reduced number of layers (e.g. reducing acoustic attenuation and/or diffraction).

Referring now to FIGS. 38A-B, an exemplary construction of a user interface is illustrated, consistent with the present inventive concepts. User interface 550 of FIGS. 38A-B includes multiple layers (e.g. as described hereinabove) that collectively function to display information to a user, as well as record user information, such as user input information and user physiologic information described hereinabove and otherwise herein. User interface 550 of FIGS. 38A-B comprises a multi-layer construction arranged in the following order (as shown): layer 1 comprising a cover layer; layer 2 comprising a first display layer; layer 3 comprising a substrate layer; layer 4 comprising an x-lines layer; layer 5 comprising an ultrasonic film layer; layer 6 comprising a y-lines layer; layer 7 comprising a substrate layer; layer 8 comprising a second display layer; and layer 9 comprising a cover layer.

User interface 550 can include an ultrasound assembly (e.g. as shown in FIGS. 38A-B) that is positioned between two display layers (e.g. two back-to-back OLED and/or other displays), such as to record touch of a user via contact with either display with a single ultrasound assembly.

Figure 39:
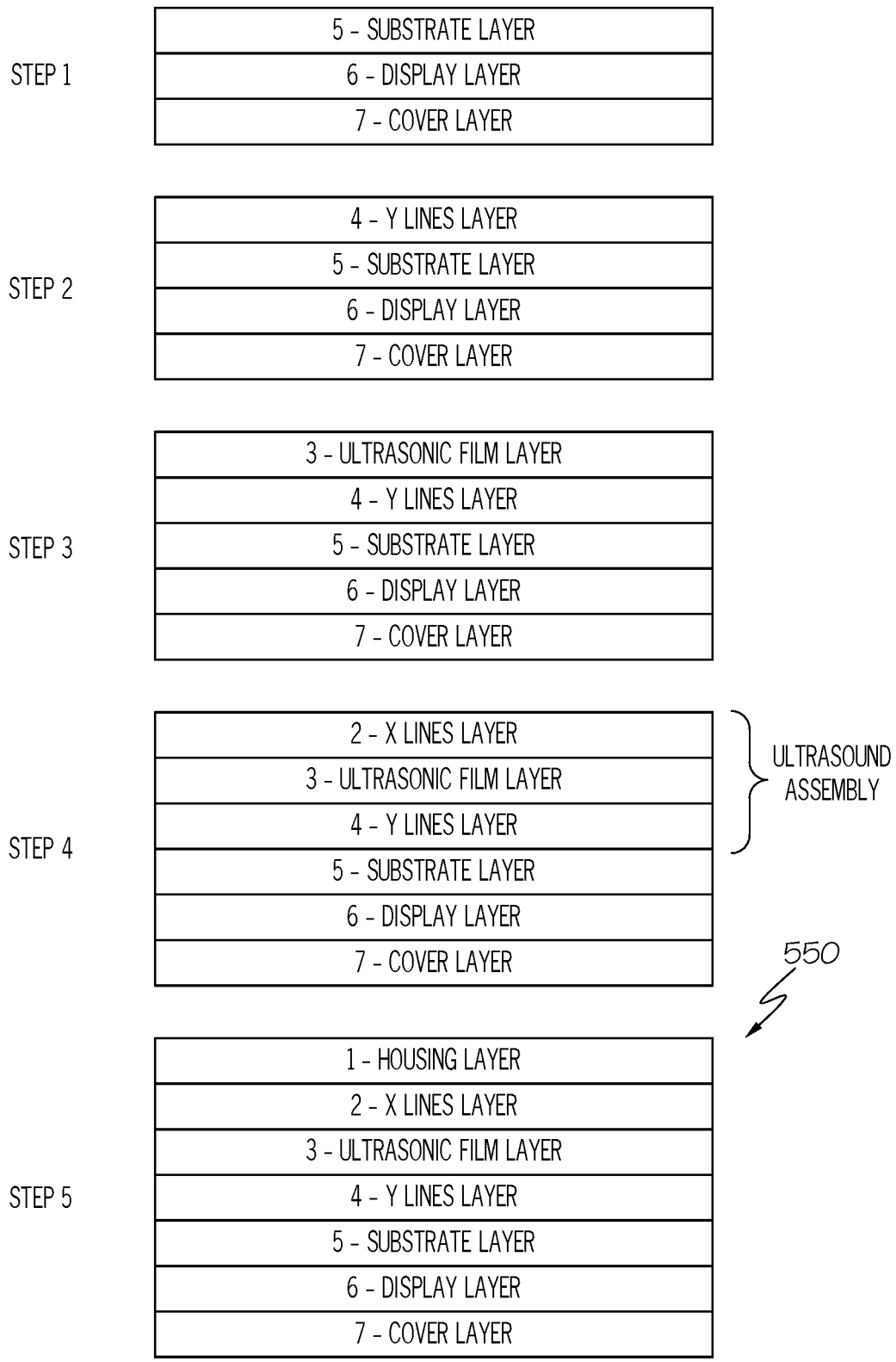

Referring now to FIG. 39, cross sectional images illustrating a manufacturing process for a user interface are illustrated, consistent with the present inventive concepts. In STEP 1, a first assembly is created comprising a substrate layer, a display layer, and a cover layer, each positioned as shown. In STEP 2, a y-lines layer is added to the first assembly, on the substrate layer (opposite the display layer as shown). In STEP 3, an ultrasonic film layer is positioned on the y-lines layer as shown. In STEP 4, an x-lines layer is positioned on the ultrasonic film layer. In STEP 5, a housing can be positioned on the x-lines layer (e.g. a portion of a housing of a user device 500 as described herein).

Figure 40A:
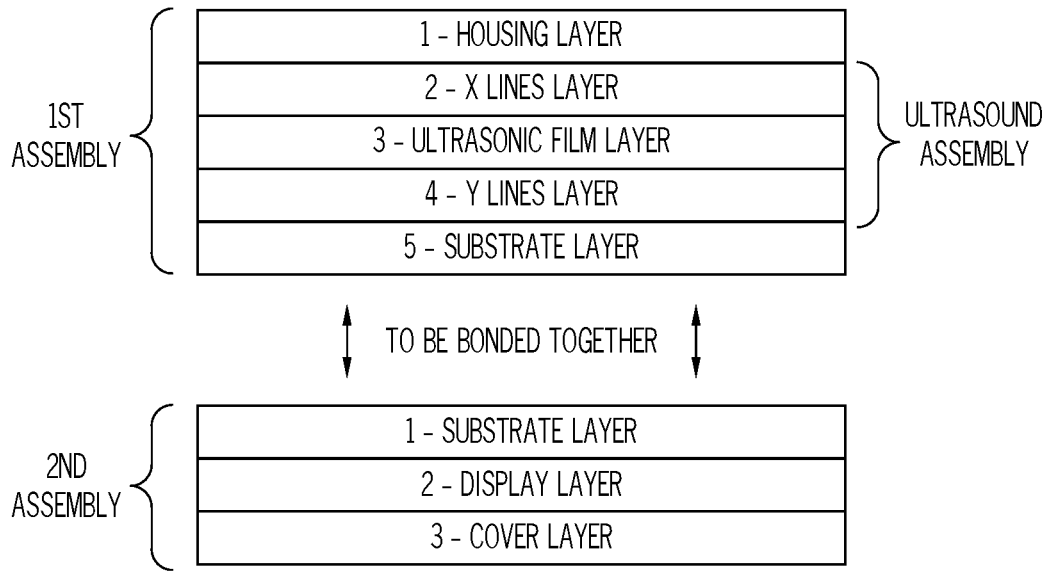
Figure 40B:
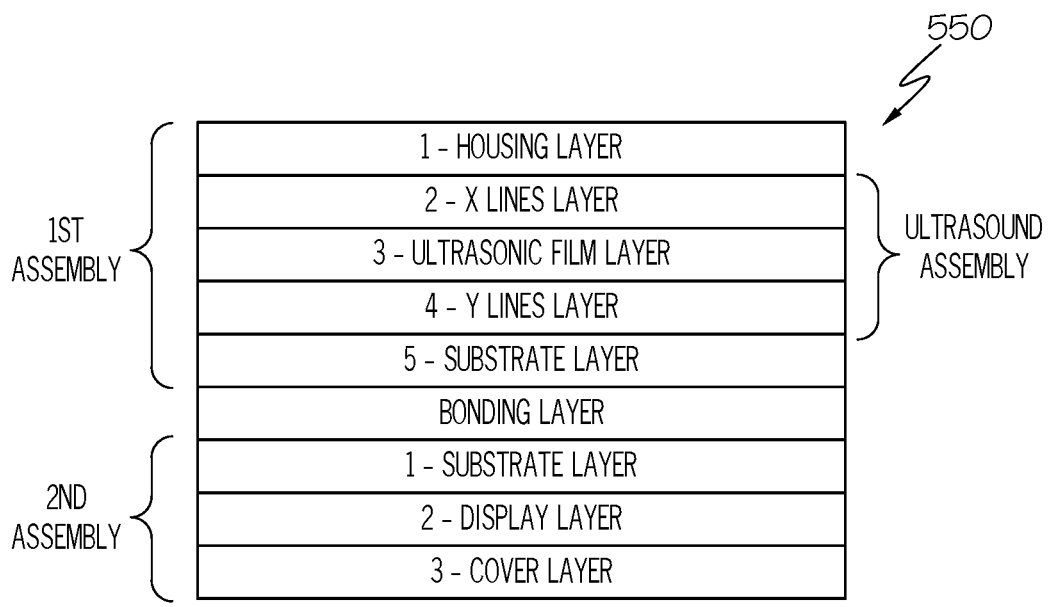

Referring now to FIGS. 40A-B, cross sectional images illustrating a manufacturing process for a user interface are illustrated, consistent with the present inventive concepts. In FIG. 40A two assemblies are illustrated, a first assembly and a second assembly. The first assembly comprises an ultrasound assembly (e.g. an x-lines layer and a y-lines layer with an ultrasonic film layer therebetween), and a substrate later attached to the ultrasound assembly (e.g. attached to the y-lines layer as shown). The first assembly can further comprise a housing layer attached to the ultrasound assembly (e.g. attached to the x-lines layer as shown). The second assembly comprises a display layer, a substrate layer on one side of the display layer and a cover layer on the other side of the display layer. In FIG. 40B, the first assembly and the second assembly have been attached to each through the use of a bonding layer, as shown. The bonding layer can comprise an adhesive layer, as described hereinabove and otherwise herein.

Figure 41:
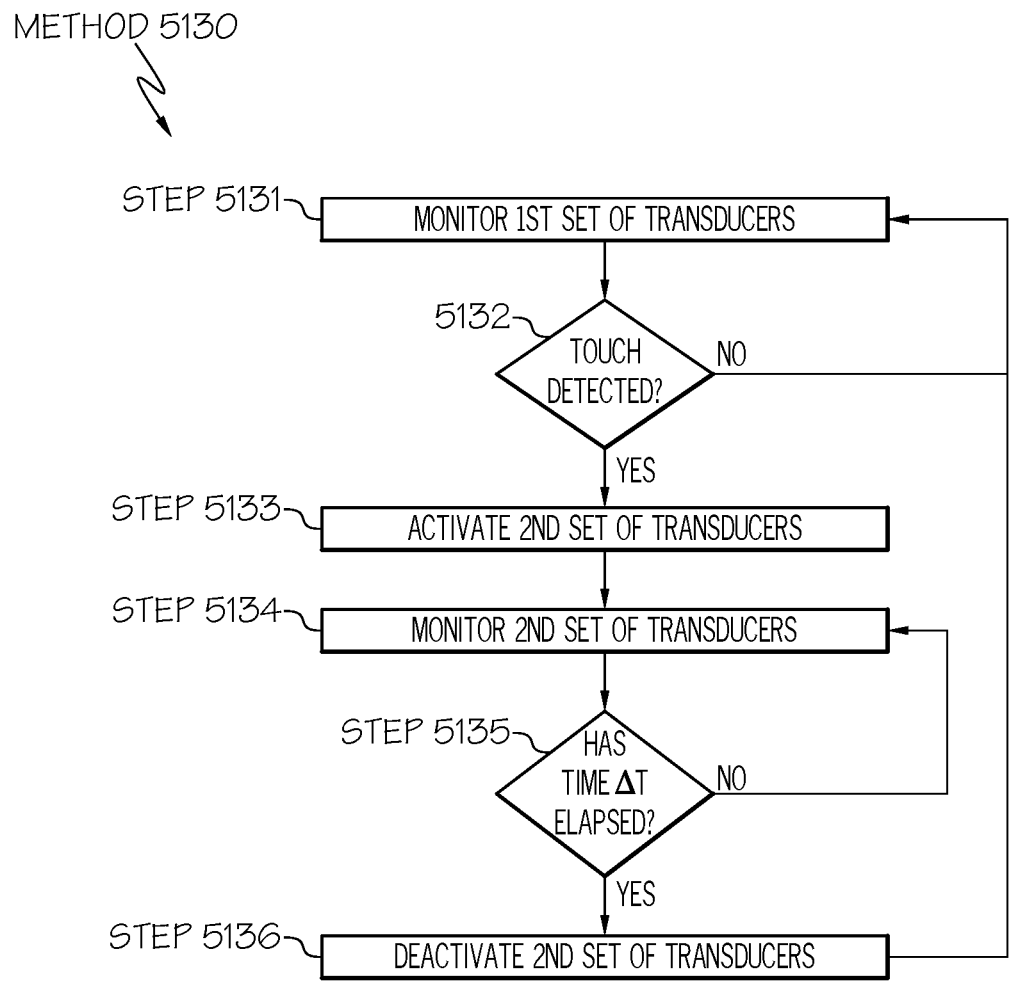

Referring now to FIG. 41, a flow chart of a method for transitioning a device from a low resolution and/or lower power state to a higher resolution and/or higher power state is illustrated, consistent with the present inventive concepts. Method 5130 comprises STEPS 5131 through 5136 as shown, and it is described using system 10 of the present inventive concepts.

In STEP 5131, system 10 is in a first state (e.g. a lower power mode of operation) in which a first set of transducers of a user interface 550 are in an active state (e.g. powered and/or monitored, such as is described herein), while a second set of transducers are in a sleep state (e.g. not powered or otherwise in a low power state). The first set of transducers can comprise a set of ultrasound transducers (e.g. pixel transducers as described herein), and/or the second set of transducers can comprise a set of ultrasound transducers (e.g. pixel transducers as described herein). In some embodiments, the second set of transducers includes all or a portion of the first set of transducers. In some embodiments, the first set of transducers comprise non-ultrasound transducers (e.g. mechanical switches, capacitive switches, and/or magnetic switches), and the second set of transducers comprise ultrasound transducers (e.g. pixel transducers as described herein). The second set of transducers can comprise a larger quantity of transducers than the first set of transducers, and/or the second set of transducers can comprise an arrangement at a higher resolution than the first set of transducers. The second set of transducers can monitor (e.g. detect user contact or other user input) from a larger portion of user interface 550 than is monitored by the first set of transducers.

In STEP 5132, if a tap (e.g. of a finger) and/or other contact ("tap", "touch", and/or "contact" herein) of a user upon interface 550 is detected by the first set of transducers, STEP 5133 is performed, otherwise STEP 5131 is repeated. In STEP 5133, user interface 550 transitions the second set of transducers from a sleep state to an active state, after which STEP 5134 is performed. In some embodiments, the first set of transducers are transitioned into a sleep state in STEP 5133. In other embodiments, the first set of transducers remain active. In some embodiments, power consumption by interface 550 is at least 10%, 20%, 30%, 40%, 50%, 75%, and/or 90% less in the sleep state as compared to the active state. In some embodiments, the first set of transducers comprises a quantity of transducers that is no more than 30%, 20%, 10%, 5%, and/or 2% of the quantity of the second set of transducers.

In STEP 5134, system 10 enters a state in which commands can be received from the second set of transducers (e.g. a set of transducers that can receive user commands from a larger surface area of user interface 550). In some embodiments, commands can also be received from the first set of transducers (e.g. the first set of transducers are not transitioned into a sleep state in STEP 5133). During monitoring of the associated transducers, a time elapsed counter is initiated, in which the time elapsed since the user has last contacted user interface 550 is counted, ΔT shown. Each time user contact with interface 550 is detected, the ΔT resets to zero.

In STEP 5135, if ΔT is above a threshold, STEP 5136 is performed, otherwise STEP 5134 is repeated. In some embodiments, ΔT comprises a time of at least 1 second, such as at least 5, 10, 30, and/or 60 seconds. Alternatively or additionally, ΔT can comprise a time of no more than 10 minutes, such as no more than 5, 3, and/or 2 minutes.

In STEP 5136, the second set of transducers transitions to a sleep state, and method 5130 returns to STEP 5131. If the first set of transducers is not already in an active state, these transducers become active upon the return to STEP 5131.

Figure 42:
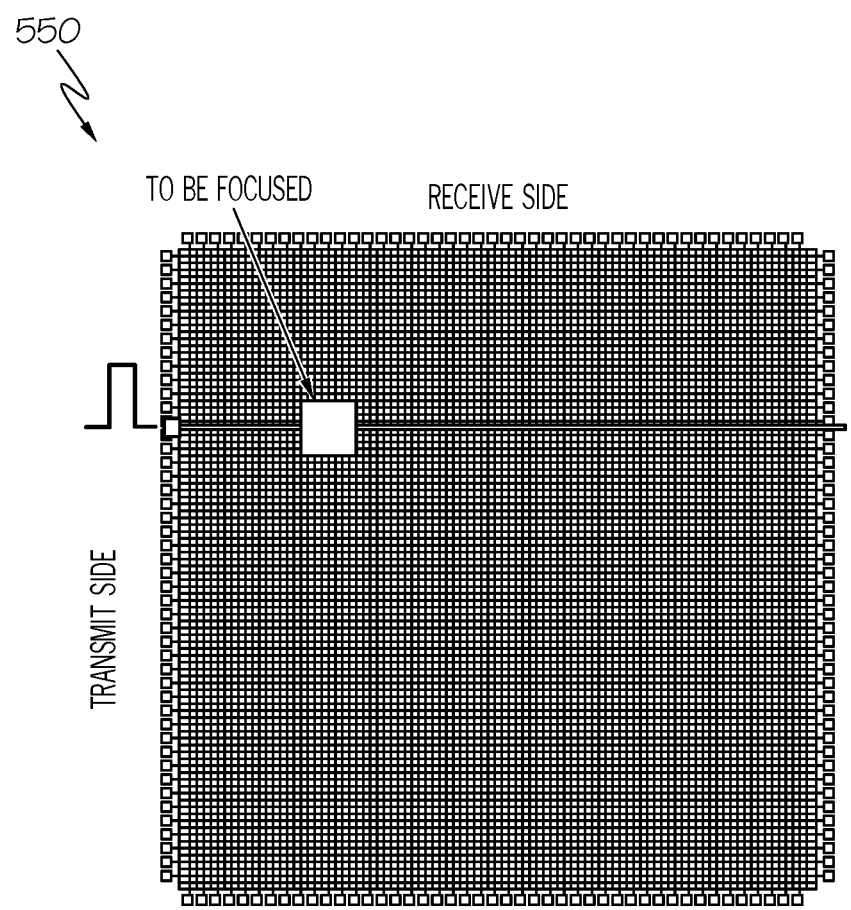

Referring now to FIG. 42, a schematic view of a user interface comprising a homogenous array of pixel transducers is illustrated, consistent with the present inventive concepts. User interface 550 comprises various areas for recording user input information, such as areas that are monitored by ultrasound-based pixel transducers as described herein. These various areas can comprise areas of different resolution for data capture, such as when particular subsets of x-lines and y-lines are selected to transmit and receive, such as to create a sub-portion of the entire array to receive a "focus" (e.g. to be sensed at a high resolution than other areas of the interface).

User interface 550 of FIG. 42 can comprise a layer of x-lines and a layer of y-lines (e.g. separated by an ultrasonic film layer) that are included in an assembly that comprises a display layer (e.g. a display comprising an OLED or other display technology). The user interface 550 can comprise layers that comprise materials such as glass, metal, and/or plastic.

The user interface 550 can comprise an array of pixel transducers that are distributed over a large area, such as a rectangular area of approximately 75 mm by 150 mm or larger, such as a surface an area of at least 10,000 mm², 20,000 mm², and/or 40,000 mm². Addressing of the x-lines and y-lines can be accomplished via electronic componentry (e.g. an ASIC) that multiplexes between the sets of lines, such as when multiplexing between 250 transmit lines and 250 receive lines (i.e. x-lines and y-lines). In some embodiments, user interface 550 comprises a sensor area of 75 mm by 150 mm, and system 10 comprises a single ASIC and is configured to provide a touch resolution of 0.3 mm in one direction (e.g. 250 lines over 75 mm), and 0.6 in the other direction (e.g. 250 lines over 150 mm). Other arrangements of interface 550 dimensions (e.g. length and width dimensions) and quantities of x-lines and y-lines can be included to meet specific needs of users.

In some embodiments, user interface 550 of FIG. 42 includes an ultrasonic film layer comprising PVDF as a piezoelectric layer. In these embodiments, frequency of operation can be selected to be approximately 50 MHz. With the expected bandwidth of the ultrasound assembly, a pulse duration of 40 nsec is achievable and could be used with an attached glass layer with a thickness of 125 μm, or a plastic cover layer with a thickness less than 125 μm. When used with a display (e.g. an OLED or other display) that is thicker than 125 μm, multiple separated echoes can be received.

The ultrasonic film layer (e.g. comprising PVDF) can be epoxied over the entire associated surface area, such as when the metal lines are on the display (e.g. on one side and not on the PVDF), or the lines can be created by applying photoresist to a conductive sheet (e.g. to achieve uniformity).

In some embodiments, an ultrasonic film layer (e.g. comprising PVDF) can be positioned behind a display layer (e.g. behind an OLED or other display). In these embodiments, a device 500 such as a cell phone or other touch screen device, can be void of a capacitive touch sensor, with all user contact recorded through the use of the ultrasound assembly as described herein.

In some embodiments, an ultrasonic film layer (e.g. comprising PVDF) can be positioned on a zinc oxide (ZnO) film, such as when a resolution of at least 300 dpi, 500 dpi, and/or higher is desired. User interface 550 (e.g. sensor 100) can be configured in various arrangements to electrically connect each of the X and Y conductors to the addressing control lines of interfacing circuitry (e.g. one or more ASICs, as described herein). A PVDF layer can be positioned on the ZnO film with an epoxy or another adhesive that provides an insulation layer between the addressing lines of the ZnO film and the PVDF layer.

Figure 42A:
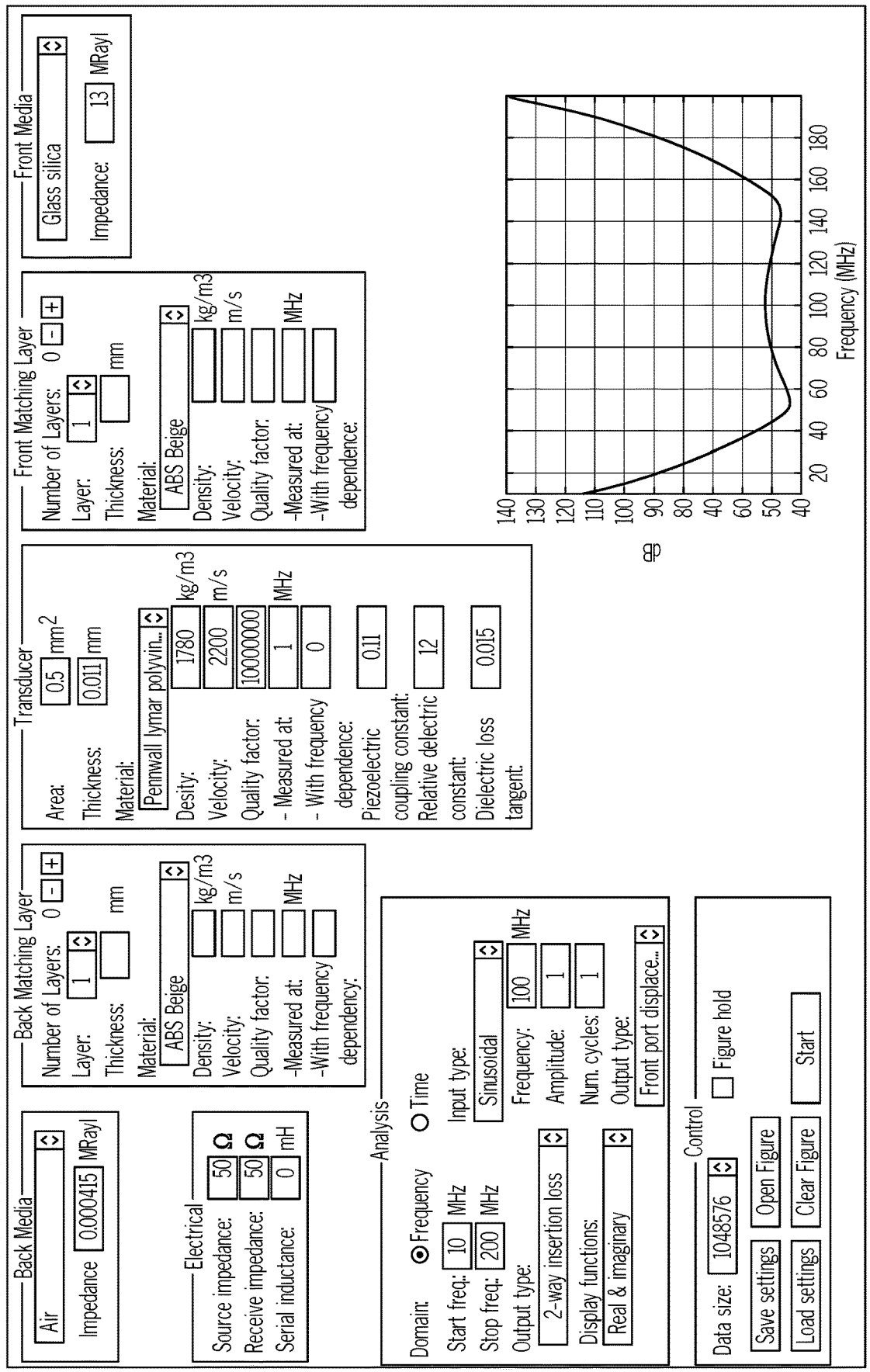

Referring now to FIG. 42A, a display of an analysis of an ultrasound sensor as described hereinabove is illustrated.

Figure 43:
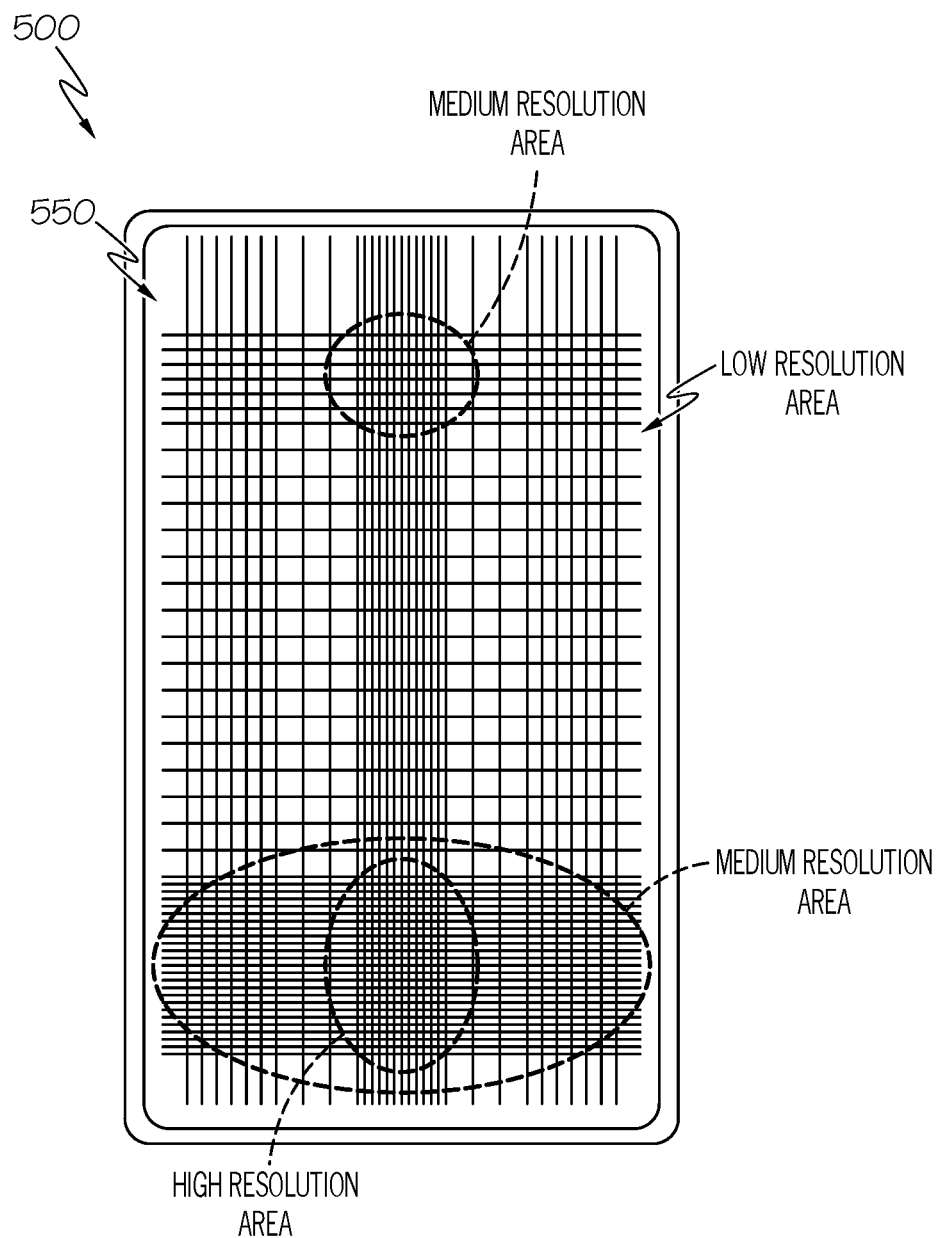

Referring now to FIG. 43, a schematic view of a user interface comprising multiple areas of different resolution is illustrated, consistent with the present inventive concepts. User interface 550 comprises various areas for recording user input information, such as areas that are monitored by ultrasound-based pixel transducers as described herein. These various areas can comprise areas of different resolution for data capture, such as when the areas comprise different densities of pixel transducers (e.g. transducer densities that correlate to the density of x-lines and y-lines of wires as described herein). In FIG. 43, a layer of x-lines and a layer of y-lines are shown where the x-lines and the y-lines have different distances of separation(s) in some areas of user interface 550 than in others. Using this varied separation distance, areas of high resolution (e.g. approximately 400 dpi, 500 dpi, or higher), medium resolution (e.g. approximately 100 dpi to 200 dpi), and low resolution (e.g. approximately 25 dpi to 40 dpi) can be created, as shown.

Figure 44A:
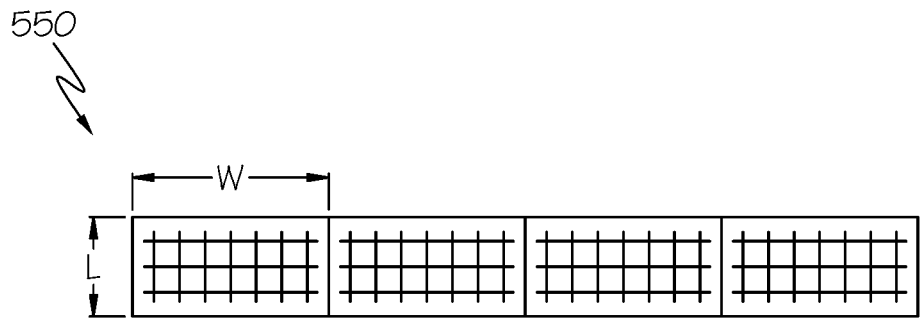
Figure 44B:
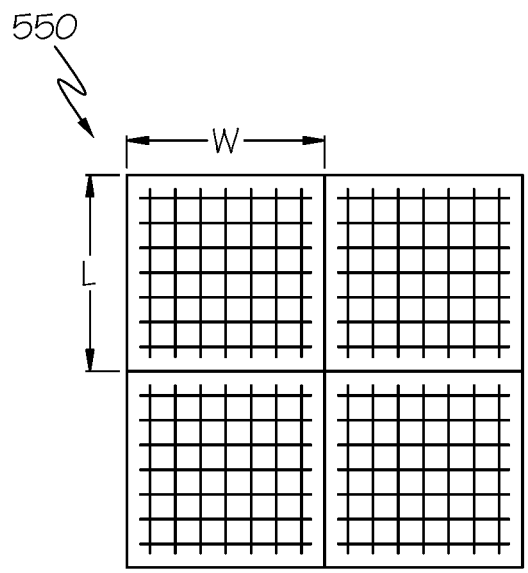
Figure 44C:
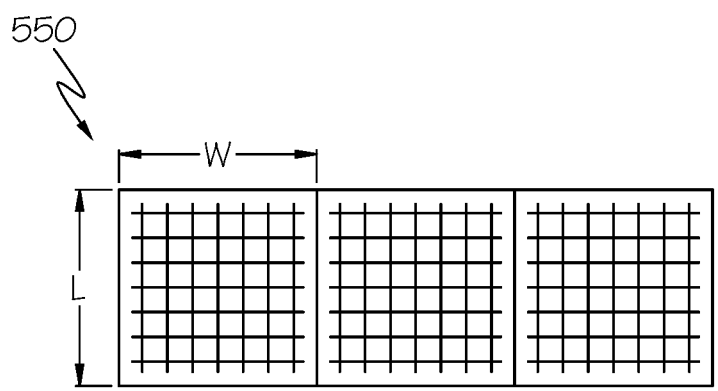

Referring now to FIGS. 44A-C, schematic views of three user interfaces, each including multiple portions, is illustrated, consistent with the present inventive concepts. Each user interface 550 of FIGS. 44A-C can comprise an array of pixel transducers, as described herein. FIGS. 44A-C show a user interface 550 comprising 4, 4, and 3 portions, respectively. It should be understood that configurations of 2 portions, or more than 4 portions (e.g. 6 portions) can be included without departing from the spirit and scope of this application. Each portion can be used by a particular user, and/or any single portion can be used by multiple users.

In FIG. 44A, user interface 550 comprises four portions in a 1 by 4 arrangement as shown. In some embodiments, each portion can be rotated (i.e. folded) relative to a neighboring portion.

In FIG. 44B, user interface 550 comprises four portions in a 2 by 2 arrangement as shown. In some embodiments, the left two portions can be rotated (e.g. in unison) relative to the right two portions, and the top two portions can be rotated (e.g. in unison) relative to the bottom two portions.

In FIG. 44C, a user interface 550 comprises three portions in a 1 by 3 arrangement as shown. In some embodiments, each portion can be rotated relative to a neighboring portion.

The user interface 550 of any of FIGS. 44A-C can comprise a user interface of one, two or more cell phones, and/or one, two or more gaming devices, such as to allow use of the device by multiple users (e.g. users that are identified, differentiated, and/or tracked via fingerprint information).

The user interface 550 of any of FIGS. 44A-C can include an integrated sensor 100 (e.g. an ultrasound-based sensor 100 as described herein), such as when the detection area of sensor 100 is at least 50%, 75%, 85%, and/or 95% of the area of the exposed surface area of user interface 550. In some embodiments, the detection area of sensor 100*b* (e.g. an ultrasound-based sensor as described herein) has an area of at least 10,000 mm$^2$, 40,000 mm$^2$, and/or 1,000,000 mm$^2$, and/or has a major axis of at least 20 cm, 40 cm, and/or 80 cm. The sensor 100 can comprise an array of X and Y conductors (e.g. two sets of at least 128 conductors and/or at least 256 conductors) that are positioned at a uniform density throughout, or the conductors can be positioned to have one or more detection portions that are at a higher density than other portions (e.g. one or more high-density portions used to detect a fingerprint of one or more users of interface 550). In some embodiments, any of the sensors 100 of FIGS. 44A-C can be configured to produce image information (e.g. fingerprint information via two or more user displays as shown), the image information produced via a time shift measurement, such as is described in reference to FIGS. 2 through 19. In some embodiments, each folding portion shown in FIGS. 44A-C comprises at least 128 conductors, or at least 256 conductors (e.g. at equidistant and/or varied density spacing). In some embodiments, a single ASIC of controller 200 interfaces with all the portions of each user interface 550 shown in FIGS. 44A-C. Alternatively, multiple ASICs can be included, such as one ASIC for each screen portion. In some embodiments, one or more of the user interfaces 550 of FIGS. 44A-C can be included in a device 500 comprising a computer, such as a computer used for gaming or other single or multi-user application.

A user interface 550 can comprise one, two, or more portions that are controlled by one, two or more ASICs of controller 200, as described herein. In some embodiments, one or more ASICs provide drive signals (e.g. to X and/or Y conductors) at one frequency to one portion of a user interface 550, and at a different frequency to another portion of user interface 550. Alternatively or additionally, the one, two or more ASICs can differentiate one screen from another using shift measurements, as described herein.

The different portions of the user interfaces 550 of FIGS. 44A-C are illustrated as being rotatably connected along a side of each portion. It should be appreciated that other attachment means between portions, such as cables between discrete displays, can be used.

Figure 45A:
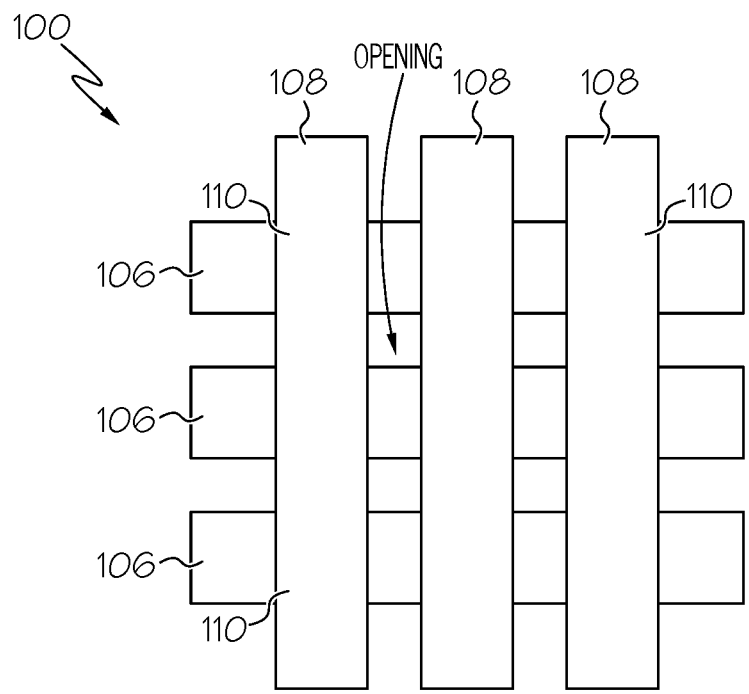
Figure 45B:
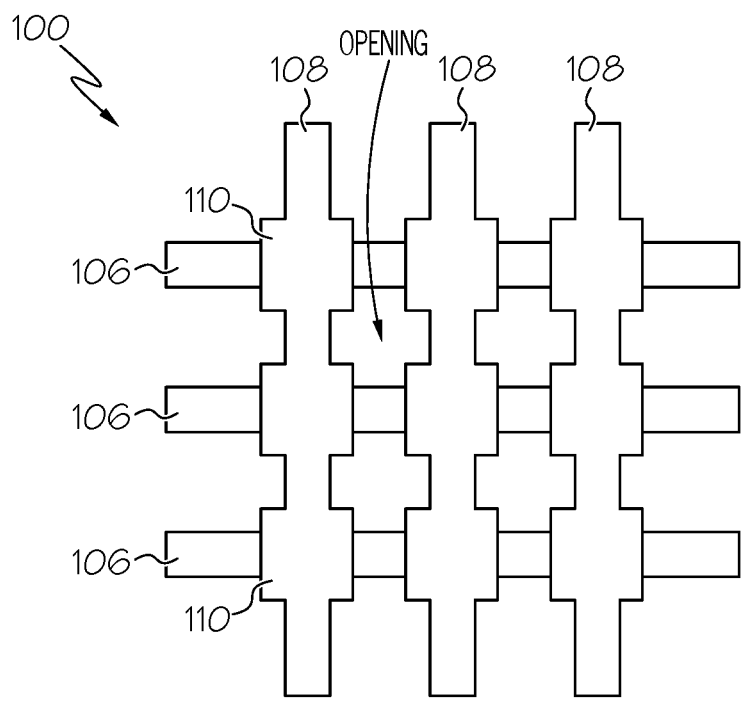

Referring now to FIGS. 45A-B, schematic views of various configurations of row and column electrodes are illustrated, consistent with the present inventive concepts. A portion of sensor 100 including three row electrodes 106, three column electrodes 108, and nine pixel elements 110 (each pixel element 110 positioned at the intersections of electrodes 106 and 108) are shown. It should be appreciated that greater quantities of row and column electrodes (e.g. at least 10, at least 100, at least 200, at least 500, and/or at least 2000) can be similarly configured (e.g. have similar size, proportions, and geometry) without departing from the spirit and scope of this application. In FIG. 45A row electrodes 106 and column electrodes 108 each comprise a constant width, where these widths are approximately equal to the height and width of each pixel element 110. When viewed from the top of sensor 100, "openings" exist between electrodes 106 and 108 as shown (e.g. vertical openings through the gaps between electrodes 106 and 108). These openings can allow light to pass through sensor 100 (e.g. allow a user to visualize a display or other object positioned behind sensor 100). In FIG. 45B, row electrodes 106 and column electrodes 108 each comprise a varied geometry, as shown, where each electrode is wider proximate each pixel element 110, and narrower between pairs of pixel elements 110. In the geometric configuration of FIG. 45B, the openings between electrodes and pixels are larger (have a larger area), allowing more light to pass through sensor 100, such as to allow a user enhanced or otherwise improved visualization of a display or other object positioned behind sensor 100. For example, in FIG. 45A, each electrode can comprise a width of 25 μm, and the portion of the electrode forming each pixel can comprise a height and width of 25 μm, with a pitch of 40 μm (e.g. 15 μm between electrodes). The geometric configuration of FIG. 45A provides an area of 225 μm$^2$ for each opening between conductors. In FIG. 45B, each interconnecting portion of electrodes 106 and 108 (the portion of the electrodes between pixels), can comprise a width of 12.5 μm, while the portion of the electrode forming each pixel can comprise a width of 25 μm (e.g. the same width of electrodes 106 and 108 of FIG. 45A), with a pitch of 40 μm (e.g. the same pitch as sensor 100 of FIG. 45A). The geometric configuration of FIG. 45B provides an area of 600 μm$^2$ for each opening between conductors (e.g. an increase of 2.67 times the opening area of sensor 100 of FIG. 45A).

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A user classification system comprising: a first sensor configured to produce a first sensor signal, the first sensor comprising a multi-platen ultrasound fingerprint sensor comprising: a first platen having a first round-trip propagation time; an array of first pixel transducers adjacent to the first platen; a second platen having a second round-trip propagation time different from the first round-trip propagation time; and an array of second pixel transducers adjacent to the second platen, wherein each of the first pixel transducers are electrically paired with a corresponding second pixel transducer; and a user device comprising: a processor communicably coupled to the first sensor; and a memory storing machine-readable instructions for performing an algorithm, wherein the algorithm is configured to identify a user of the system based on the first sensor signal.

2. The system according to claim 1, wherein the algorithm is configured to perform a signal-processing method comprising determining a time shift between an arrival time of the first sensor signal and a baseline arrival time.

3. The system according to claim 2, wherein the time shift is determined for each of the first pixel transducers.

4. The system according to claim 3, wherein the time shift is determined for each of the second pixel transducers.

5. The system according to claim 1, wherein the algorithm is configured to cause the first sensor to: for each of the first pixel transducers: (i) transmit a first signal ultrasound pulse into the first platen whereby a portion of the first signal ultrasound pulse reflects off of the platen surface to form a first signal echo, (ii) sense the first signal echo, (iii) transmit a first baseline ultrasound pulse into the first platen whereby a portion of the first baseline ultrasound pulse reflects off of the first platen surface to form a first baseline echo, (iv) sense the first baseline echo, and (v) determine a time shift between a first signal arrival time of the first signal echo and a baseline arrival time of the first baseline echo; determine, based on the time shift determined for at least one of the first pixel transducers, if a finger of the user was in contact with the first platen surface while the first signal ultrasound pulse was transmitted and the first signal echo was sensed; and generate, based on the time shift for each first pixel transducer, a fingerprint image of the finger.

6. The system according to claim 5, wherein the algorithm is configured to generate a fingerprint image of the finger based on a time shift determined for each second pixel transducer.

7. The system according to claim 1, further comprising a second sensor configured to produce a second sensor signal, wherein the second sensor comprises a pulse oximetry sensor.

8. The system according to claim 7, wherein the second sensor further comprises a collimator comprising light-absorbing material configured to absorb light at the frequency range of the pulse oximetry sensor, and wherein the collimator is positioned between the first sensor and the second sensor to reduce clutter signals in recordings produced by the second sensor.

9. The system according to claim 1, wherein at least one of the first pixel transducers and/or at least one of the second pixel transducers comprise a Langevin transducer.

10. The system according to claim 1, wherein the algorithm comprises a machine learning, neural network, and/or other artificial intelligence algorithm.

11. The system according to claim 1, wherein the system is configured to perform a user confirmation routine, and wherein the algorithm is configured to detect an attempt at spoofing the user confirmation routine.

12. The system according to claim 1, wherein the system further comprises a wedge platen.

13. The system according to claim 12, wherein the first platen comprises a first portion of the wedge platen and the second platen comprises a second portion of the wedge platen.

14. The system according to claim 1, wherein the array of first pixel transducers comprises a first density of pixel transducers and the array of second pixel transducers comprises a second density of pixel transducers.

15. The system according to claim 14, wherein the first density comprises a higher density than the second density.

16. The system according to claim 1, wherein the user device further comprises a display.

17. The system according to claim 16, wherein the first sensor is positioned behind the display.

18. The system according to claim 17, wherein the first sensor does not include transparent electrode material.

19. The system according to claim 17, wherein the system does not comprise an adhesive layer positioned between the display and the first sensor.

20. The system according to claim 16, wherein the display comprises a touch screen display, and the first sensor further comprises an ultrasound touch sensor.

21. The system according to claim 20, wherein the user device does not include a capacitive touch sensor.

22. The system according to claim 16, wherein the display comprises an encapsulation layer and a display layer, and the first sensor is positioned between the display layer and the encapsulation layer.

23. The system according to claim 22, wherein the encapsulation layer comprises a glass layer, and at least a portion of the first sensor is deposited directly onto the glass layer.

24. The system according to claim 1, wherein the array of first pixel transducers and the array of second pixel transducers are distributed over an area of at least 10,000 $mm^2$.

25. The system according to claim 24, wherein the first sensor signal is produced using time division multiplexing.

26. The system according to claim 24, wherein the first sensor signal is produced using frequency division multiplexing.

* * * * *